(12) United States Patent
Watanabe et al.

(10) Patent No.: US 7,094,770 B2
(45) Date of Patent: Aug. 22, 2006

(54) 3'-OR 2'-HYDROXYMETHYL SUBSTITUTED NUCLEOSIDE DERIVATIVES FOR TREATMENT OF HEPATITIS VIRUS INFECTIONS

(75) Inventors: Kyoichi A. Watanabe, Stone Mountain, GA (US); S. Balakrishna Pai, Chamblee, GA (US)

(73) Assignee: Pharmasset, Ltd., St. Michael (BB)

( * ) Notice: Subject to any disclaimer, the term of this patent is extended or adjusted under 35 U.S.C. 154(b) by 543 days.

(21) Appl. No.: 09/834,596

(22) Filed: Apr. 13, 2001

(65) Prior Publication Data

US 2002/0055483 A1 May 9, 2002

Related U.S. Application Data

(60) Provisional application No. 60/197,068, filed on Apr. 13, 2000, provisional application No. 60/202,663, filed on May 8, 2000.

(51) Int. Cl.
*A01N 43/04* (2006.01)
*A61K 31/70* (2006.01)

(52) U.S. Cl. ............................ 514/49; 514/50; 514/51; 514/52

(58) Field of Classification Search ............ 514/45, 514/46, 47, 48, 49, 50, 51; 536/28.1, 28.2, 536/28.4
See application file for complete search history.

(56) References Cited

U.S. PATENT DOCUMENTS

| | | | |
|---|---|---|---|
| 3,480,613 | A | 11/1969 | Walton et al. |
| 5,534,535 | A | 7/1996 | Townsend et al. |
| 5,905,070 | A | 5/1999 | Schinazi et al. |
| 5,977,061 | A | 11/1999 | Holy et al. |
| 6,004,939 | A | 12/1999 | Chen et al. |
| 6,159,951 | A | 12/2000 | Karpeisky et al. |
| 6,248,878 | B1 | 6/2001 | Matulic-Adamic et al. |
| 6,271,212 | B1 | 8/2001 | Chu et al. |
| 6,340,690 | B1 | 1/2002 | Bachand et al. |
| 6,395,716 | B1 | 5/2002 | Gosselin et al. |
| 6,444,652 | B1 | 9/2002 | Gosselin et al. |
| 6,573,248 | B1 | 6/2003 | Ramasamy et al. |
| 2002/0055483 | A1 | 5/2002 | Watanabe et al. |
| 2002/0147160 | A1 | 10/2002 | Bhat et al. |
| 2003/0008841 | A1 | 1/2003 | Devos et al. |
| 2003/0028013 | A1 | 2/2003 | Wang et al. |
| 2003/0050229 | A1 | 3/2003 | Sommadossi et al. |
| 2003/0083307 | A1 | 5/2003 | Devos et al. |
| 2003/0087873 | A1 | 5/2003 | Stuyver et al. |

FOREIGN PATENT DOCUMENTS

| | | |
|---|---|---|
| GB | 1163103 A | 9/1969 |
| GB | 1209654 A | 10/1970 |
| JP | 06211890 | 2/1994 |
| WO | WO 93/12131 | 6/1993 |
| WO | WO 98/16184 A2 | 4/1998 |
| WO | WO 99/43691 A1 | 9/1999 |
| WO | WO 00/09531 A2 | 2/2000 |
| WO | WO 01/10882 A1 | 2/2001 |
| WO | WO 01/16671 A1 | 3/2001 |
| WO | WO 01/32153 A2 | 5/2001 |
| WO | WO 01/60315 A2 | 8/2001 |

(Continued)

OTHER PUBLICATIONS

McGuigan et al., "Alkyl hydrogen phosphonate derivatives of the anti-HIV agent AZT may be less toxic than the parent nucleoside analogue", Antiviral Chemistry and Chemotherapy, 1994, 5(4), 271-277.*

(Continued)

*Primary Examiner*—James O. Wilson
*Assistant Examiner*—Traviss C. McIntosh, III
(74) *Attorney, Agent, or Firm*—Merchant & Gould

(57) ABSTRACT

The present invention relates to a composition for and a method of treating hepatitis B virus (HBV) infection, hepatitis C virus (HCV) infection, hepatitis D virus (HDV) infection or a proliferative disorder in a patient using an effective amount of a compound selected from the group consisting of formulas [I]–[IV] below and mixtures of two or more thereof:

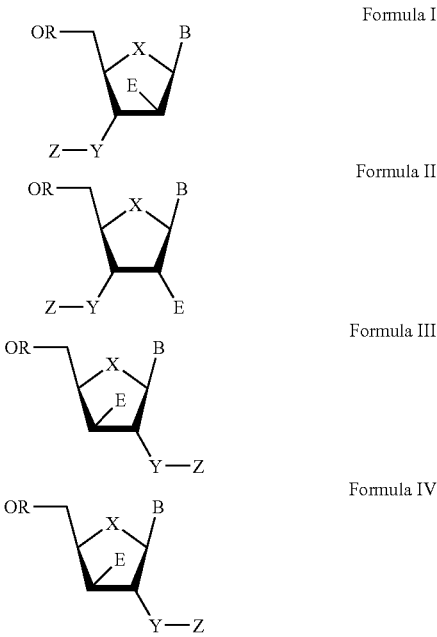

wherein the substituents are as defined herein. Pharmaceutical compositions comprising these compounds in combination with other HBV, HCV, or HDV agents is also disclosed.

42 Claims, No Drawings

FOREIGN PATENT DOCUMENTS

| | | |
|---|---|---|
| WO | WO 01/68663 A1 | 9/2001 |
| WO | WO 01/79246 A2 | 10/2001 |
| WO | WO 01/90121 A2 | 11/2001 |
| WO | WO 01/91737 A2 | 12/2001 |
| WO | WO 01/96353 A2 | 12/2001 |
| WO | WO 02/03997 A1 | 1/2002 |
| WO | WO 02/18404 A2 | 3/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 A2 | 7/2002 |
| WO | WO 02/070533 A2 | 9/2002 |
| WO | WO 02/094289 A1 | 11/2002 |
| WO | WO 02/100415 A2 | 12/2002 |
| WO | WO 03/026589 A2 | 4/2003 |
| WO | WO 03/026675 A1 | 4/2003 |
| WO | WO 03/051899 A1 | 6/2003 |
| WO | WO 03/061385 A1 | 7/2003 |
| WO | WO 03/061576 A2 | 7/2003 |
| WO | WO 03/062255 A2 | 7/2003 |
| WO | WO 03/062256 A1 | 7/2003 |
| WO | WO 03/062257 A1 | 7/2003 |
| WO | WO 03/063771 A2 | 8/2003 |
| WO | WO 03/068162 A2 | 8/2003 |
| WO | WO 03/072757 A2 | 9/2003 |
| WO | WO 03/093290 A2 | 11/2003 |

OTHER PUBLICATIONS

Fedorov, I., et al., XIII International Round Table: Nucleosides, Nucleotides and Their Biological Applications. Montpellier, France, Sep. 6-10, 1998. Poster 35.

Kato, K., et al., XIII International Round Table: Nucleosides, Nucleotides and Their Biological Applications. Montpellier, France, Sep. 6-10, 1998. Poster 49.

Svansson, L., et al., *J. Org. Chem.*, 1991, 56: 2993-97.

Wengel, J., et al., Bioorganic & Medicinal Chemistry, vol. 3, No. 9, pp. 1223-1229, 1995.

Lin, T., et al., J. Med. Chem., 1993, 36:353-62.

Gauvry, N., et al., Tetrahedron 55 (1999) 1321-28.

Sterzyncki, R., et al., Nucleosides & Nucleotides, 10(1-3), 291-94 (1991).

Lee-Ruff, E., et al., J. Med. Chem., 1996, 39:5276-80.

Bamford, M., et al., J. Med. Chem., 1990, 33:2494-2501.

Tino, J., J. Med. Chem, 1993, 36:1221-29.

Brown, B., J. Org. Chem., 1998, 63:8012-18.

Pudlo, J., Nucleosides & Nucleotides, 11(2-4), 279-93 (1992).

Fiandor, J., et al., Nucleosides & Nucleotides, 8(5&6), 1107-8 (1989).

Jeong, L., et al., Nucleosides & Nucleotides, 16(7-9), 1059-62 (1997).

Jorgensen, P., et al., Nucleosides & Nucleotides, 16(7-9), 1063-66 (1997).

Frieden, M., et al., J. Chem. Soc. Perkin Trans I, 1998, 2827-32.

Slusarchyk, W., J. Med Chem., 1992, 35:1799-1806.

Bisacchi, G., et al., J. Med. Chem., 1991, 34:1415-21.

Qiu, Y., et al., J. Med. Chem., 1998, 41:10-23.

Sekiyama, T., J. Med. Chem., 1998, 41:1284-98.

Altmann, K.H., et al., "The Synthesis of 1'-methyl carbocyclic thymidine and its effect on nucleic acid duplex stability", *Synlett, Thieme Verlag, Stuttgart, De*, Oct. 1994, 10, 853-855.

Baginsky, S.G. et al., "Mechanism of action of a pestivirus antiviral compound," *Proc. Nat. Acad. Sci. (USA)* 2000, 97(14), 7981-7986.

Beigelman, L.N., et al, "Dimerization during the acetolysis of 3-O-acetyl-t-O-benzoyl-1,2-O-isopropylidene-3-C-methyl-α-D-ribofruanose. synthesis of 3'-C-methylnucleosides with the β-D-ribo-and α-D-*arabino* configurations", *Carbohydrate Research*, 1988, 181, 77-88.

Beigelman, L.N., et al, "A general method for synthesis of 3'-C-alkylnucleosides", *Nucleic Acids Symp. Ser.*, 1981, 9, 116-119.

Berenguer et al, "Hepatitis B and C Viruses: Molecular Identification and Targeted Antiviral Therapies," *Proceedings of the Association of American Physicians*, 1998, 110(2), 98-112.

Carroll, S.S., et al. "Inhibition of Hepatitis C Virus RNA Replication by 2'-Modified Nucleoside Analogs," *The Journal of Biological Chemistry*, 2003, 278(14), 11979-11984.

Czernecki, S., et al, "Syntheses if Various 3'-Brached 2',3'-Unsaturated Pyrimidine Nucleosides as Potential Anti-HIV Agents," *J. Org. Chem.*, 1992, 57, 7325-7328.

DeFrancesco, R. et al., "Approaching a new era for hepatitis C virus therapy: inhibitors fot eh NS3-4A serine protease and the NS5B RNA-dependent RNA polymerase," *Antiviral Research*, 2003, 58, 1-16.

Faivre-Buet, V., et al, "Synthesis of 1'-Deoxypsicofuranosyl-deoxynucleosides as Potential Anti-HIV Agents," *Nucleosides & Nucleotides*, 1992, 11(7), 1411-1424.

Farkas, J., et al., "Nucleic acid components and their analogues. XCIV. Synthesis of 6-amino-9-(1-deoxy-□-D-psicofuranosyl)purine" *Collect. Czech. Chem. Commun.* 1967, 32, 2663-2667.

Farkas, J., "Nucleic acids components and their analogues. LXXIX. Synthesis of methyl 1-deoxy-D-psicofuranosides substituted at C(1) with haolo atoms or a mercapto group,", *Collect. Czech. Chem. Commun.* 1966, 31, 1535-1543.

Federov, I.I., et al, "3'-C-branched 2'-deoxy-5-methyluridines: Synthesis, enzyme inhibition, and antiviral properties,", *J. Med. Chem.*, 1992, 35, 4567-4575.

Franchetti, P., et al, "2'-C-methyl analogues of selective adenosine receptor agonists: Synthesis and binding studies," *J. Med. Chem.*, 1998, 41, 1708-1715.

Grouiller, A., et al., "Novel p-tolyenesulfonylation and thionocarbonylation of unprotected thymine nucleosides," *Synlett*, 1993, 221-222.

Haraguchi, K., et al, "Preparation and reactions of 2'- and 3'- vinyl bromides of uracil-nucleosides: versatile synthons for anti-HIV agents," *Tetrahedron Letters*, 1991, 32(28), 3391-3394.

Haraguchi, K., et al, Stereoselective synthesis of 1'-C-branched uracil nucleosides from uridine, *Nucleosides & Nucleotides*, 1995, 14, 417-420.

Harry-O'Kuru, et al., "A short, flexible route toward 2'-C-branched ribonucleosides", *J. Org. Chem.* 1997, 62, 1754-1759.

Harry-O'Kuru, R.E., et al., "2'-C-Alkylribonucleosides: Design, Synthesis, and Conformation," *Nucleosides & Nucleotides*, 1997, 16(7-9), 1457-1460.

Hattori, H., et al., "Nucleosides and Nucleotides. 175. Structural requirements of the suga moiety for the antitumor activities of new nucleoside antimetabolites, 1-(3-C-ethynyl-β-D-ribopentofuranosyl)cytosine and -uracil," *J. Med. Chem.*, 1998, 41, 2892-2902.

Hrebabecky, H. et al., "Nucleic acid components and their analogues. CXLIX. Synthesis of pyrimidine nucleosides derived from 1-deoxy-D-psicose," *Collect. Czech. Chem. Commun.* 1972, 37, 2059-2065.

Hrebabecky, H., et al., "Synthesis of 7- and 9β-D-psicofuranosylguanine and their 1'-deoxy derivatives," *Collect. Czech. Chem. Commun.* 1974, 39, 2115-2123.

Iino, T., et a.l, "Nucleosides and Nucleotides. 139. Stereoselective synthesis of (2'S)-2'-C-alkyl-2'-deoxyuridines," *Nucleosides and Nucleotides*, 1996, 15, 169-181.

Itoh, Y., et al., "Divergent and stereocontrolled approach to the synthesis of uracil nucleosides branched at the anomeric position," *J. Org. Chem.*, 1995, 60, 656-662.

Johnson, C.R., et al, 3'-C-trifuloromethyl ribonucleosides, *Nucleosides & Nucleotides*, 1995, 14, 185-194.

Kawana, M., et al, "The deoxygenation of tosylated adenosine derivatives with Grignard reagents," *Nucleic Acids Symp. Ser.*, 1986, 17, 37-40.

Lavaire, S., et al, "3'-deoxy-3'-trifluoromethyl nucleosides: synthesis and antiviral evaluation," *Nucleosides & Nucleotides*, 1998, 17, 2267-2280.

Leyssen, P. et al., "Perspectives for the treatment of infections with Flaviviridae", *Clinical Microbiology Reviews*, Washington, D.C., (Jan. 2000), 13(1), 67-82.

Martin, X., et al., "Intramolecular hydrogen bonding in primary hydroxyl of thymine 1-(1-deoxy-β-D-psicofuranosyl) nucleoside," *Tetrahedron*, 1994, 50, 6689-6694.

Matsuda, A., et al., "Radical deoxygenation of *tert*-alcohols in 2-branched-chain sugar pyrimidine nucleosides: synthesis and antileukemic activity of 2'deoxy-2'(S)-methylcytidine," *Chem. Pharm. Bull.*, 1987, 35, 3967-3970.

Matsuda, A., et al., "Nucleosides and Nucleotides. 94. Radical deoxygenation of *tert*-alcohols in 1-(2-C-alkylpentofuranosyl)pyrimidines: Synthesis of (2'S)-2'-deoxy-2'-C-methylcytidine, an antileukemic nucleoside," *J. Med. Chem.*, 1991, 34, 234-239.

Matsuda, A., et al, "Nucleosides and Nucleotides. 104. Radical and palladium-catalyzed deoxygenation of the allylic alcohol systems in the sugar moiety of pyrimidine nucleosides," *Nucleosides & Nucleotides*, 1992, 11(No. 2/4), 197-226.

Matsuda, A., et al., "Alkyl addition reaction of pyrimidine 2'-ketonucleosides: synthesis of 2'-branched-chain sugar pyrimidine nucleosides (Nucleosides and nucleotides. LXXXI.)," *Chemical & Pharmaceutical Bulletin*, Mar. 1988, 36, 945-953.

Mikhailov, S.N., et al, "Synthesis and properties of 3'-C-methylnucleosides and their phosphoric esters," *Carbohydrate Research*, 1983, 124, 75-96.

Mikhailov, S.N., et al, "Hydrolysis of 2'- and 3'-C-methyluridine 2',3'-cyclid monophosphates and interconversion and dephosphorylation of the resulting 2'- and 3'-monophosphates: comparison with the reactions of uridine monophosphates," *J. Org. Chem.*, 1992, 57, 4122-4126.

Mikhailov, S.N., et al, "Substrate properties of C'-methylnucleoside and C'-methyl-2'-deoxynucleoside 5'-triphosphates in RNA and DNA synthesis reactions catalysed by RNA and DNA polymerases," *Nucleosides & Nucleotides*, 1991, 10, 339-343.

Nutt, R.F., et al., "Branched-chain sugar nucleosides. III. 3'-C-methyladenine," *J. Org. Chem.* 1968, 33, 1789-1795.

Oivanen, M., et al, "Additional evidence for the exceptional mechanism of the acid-catalysed hydrolysis of 4-oxopyrimidine nucleosides: hydrolysis of 1-(1-alkoxyalkyl)uracils. Seconucleosides. 3'-C-alkyl nucleosides and nucleosides 3',5'-cyclic monophosphates," *J. Chem. Soc. Perkin Trans.*, 1994, 2, 309-314.

Ong, S.P., et al, "Synthesis of 3'-C-methyl adenosine and 3'-C-methyluridine diphosphates and their interaction with the ribonucleoside diphosphate reductase from *Corynebacterium nephridii*," *Biochemistry*, 1992, 31, 11210-11215.

Pan-Zhou X-R, et al., "Differential effects of antiretroviral nucleoside analogs on mitochondrial function in HepG2 cells," *Antimicrob Agents Chemother* 2000; 44(No. 3), 496-503.

Rosenthal, A., et al., "Branched-chain sugar nucleosides. Synthesis of 3'-C-ethyl (and 3'-C-butyl)uridine," *Carbohydrate Research*, 1980, 79, 235-242.

Samano, V., et al, "Nucleic acid related compounds. 77.2',3'-didehydro-2',3'-dideosy-2'(and 3')-methylnucleosides via [3,3]-sigmatropic rearrangements of 2'(and 3')-methylene-3'(and 2')-O-thiocarbonyl derivatives and radical reduction of a 2'-chloro-3'-methylene analogue," *Can. J. Chem.*, 1993, 71, 186-191.

Samano, V., et al, "Synthesis and radical-induced ring-opening reactions of 2'-deoxyadenosine-2'-spirocyclopropane and its uridine analogs. Mechanistic probes for ribonucleotide reductases," *J. Am. Chem. Soc.*, 1992, 114, 4007-4008.

Schmidt, C. et al., "The effects of 2'-and 3'-alkyl substituents on oligonucleotide hybridization and stability,", *Biorganic & Medicinal Chemistry Letters*, 1994, 4(No. 16), 1969-1974.

Serafinowski, P.J., et al, "New method for the preparation of some 2'- and 3'-trifluoromethyl-2'-3'-dideoxyuridine derivatives," *Tetrahedron*, 1999, 56(No. 2), 333-339.

Sharma, P.K., et al, "Synthesis of 3'-trifluoromethyl nucleosides as potential antiviral agents," *Nucleosides, Nucleotides and Nucleic Acids*, 2000, 19(No. 4), 757-774.

Sommadossi J-P, et al., "Comparison of cytotoxicity of the (−)- and (+)-enantiomer of 2',3'-dideoxy-3'-thiacytidine in normal human bone marrow progenitor cells," *Biochemical Pharmacology*, 1992; 44:1921-1925.

Sommadossi J-P, et al., "Toxicity of 3'-azido-3'-deoxythymidine and 9-(1,3-dihydroxy-2-propoxymethyl)guanine for normal human hematopoietic progenitor cells in vitro," *Antimicrobial Agents and Chemotherapy*, 1987, 31(No. 3), 452-454.

Tritsch, D., et al., "3'-β-ethynyl and 2'-deoxy-3'-β-ethynyl adenosines: first 3'-β-branched-adenosines substrates of adenosine deaminase," *Bioorganic & Medicinal Chemistry Letters*, 2000, 10, 139-141.

Tunitskaya, V.L., et al, "Substrate properties of C'-methyl UTP derivatives in T7 RNA polymerase reactions. Evidence for N-type NTP conformation," *FEBS Letters*, 1997, 400, 263-266.

Usui, H., et al, "Synthesis of 2'-deoxy-8,2'-ethanoadenosine and 3'-deoxy-8,3'-ethanoadenosine (Nucleosides and Nucleotides. LXIV)," *Chem. Pharm. Bull.*, 1986, 34, 15-23.

Walczak, K., et al, "Synthesis of 1-(3-alkyl-2,3-dideoxy-D-pentofuranosyl)uracils with potential anti-HIV activity," *Acta Chemica Scand.*, 1991, 45, 930-934.

Walton, E., et al, "Branched-chain sugar nucleosides. V. Synthesis and antiviral properties of several branched-chain sugar nucleosides," *J. Med. Chem.*, 1969, 12, 306-309.

Wolfe, M.S., et al, "A concise synthesis of 2'-C-methylribonucleosides," *Tetrahedron Letters*, 1995, 36(No. 42), 7611-7614.

Wu, J.-C., et al, "A new stereospecific synthesis of [3.1.0] bicyclic cyclopropano analog of 2',3'-dideoxyuridine," *Tetrahedron*, 1990, 46, 2587-2592.

Jasko Maxim Vvan I Fedorov et al: "Synthesis, Molecular and Crystal Structure of 3'-N-Alkylamino-3'-Deoxythymidines and some Biochemical Properties of their Phosphorus Esters," *Nucleosides & Nucleotides*, 1995, pp. 23-27, vol. 14, No. 1-2, XP008049088.

Tsibinogin, V. V. et al: "Inhibition of the Replication of Human Hepatitis B Virus," Database CA [Online], Chemical Abstracts Service, Columbus, Ohio, US; 1989, XP002192805.

Matthes, Eckart et al: "Comparative Inhibition of Hepatitis B Virus DNA Polymerase and Cellular DNA Polymerases by Triphosphates of Sugar-Modified 5-Methyldeoxycytidines and of other Nucleoside Analogs," Database CA [Online], Chemical Abstracts Service, Columbus, Ohio, US; 1991, XP002192806.

Victorova Lyubov S et al: "Mode of Inhibition of HIV Reverse Transcriptase-Catalyzed DNA Synthesis by 3'-Amino-3'-Deoxythymidine 5'- Triphosphate," *Nucleosides & Nucleotides*, 1996, pp. 655-667, vol. 15, No. 1-3, XP001062295.

Ueda, Toru et al: "Preparation of 2'-Deoxy-2' (S)-Alkylpyrimidine Nucleosides as Antiviral Agents," Database CA [Online], Chemical Abstracts Service, Columbus, Ohio, US; 1988, XP002192807.

Matsuda, Akira et al: "Preparation of 2'Deoxy-(2' S)-Alkylpyrimidine Nucleosides as Antiviral Agents," Database CA [Online], Chemical Abstracts Service, Columbus, Ohio, US; 1994, XP002192808.

Matthes, E. et al: "Potent Inhibition of Hepatitis B Virus Production in Vitro by Modified Pyrimidine Nucleosides," Database CA [Online], Chemical Abstracts Service, Columbus, Ohio, US; 1990, XP002192809.

Kochetkova, S. V. et al: "Phosphorylation of 3'-Deoxy-3'-Aminothymidine in the Mouse Myeloma p38Ag653 Cell Culture and its Incorporation into DNA," Database CA [Online], Chemical Abstracts Service, Columbus, Ohio, US; 1985, XP002333614.

* cited by examiner

3'-OR 2'-HYDROXYMETHYL SUBSTITUTED NUCLEOSIDE DERIVATIVES FOR TREATMENT OF HEPATITIS VIRUS INFECTIONS

CROSS-REFERENCE TO RELATED APPLICATIONS AND CLAIM FOR BENEFIT

This application claims priority to U.S. provisional patent application Ser. No. 60/197,068, filed on Apr. 13, 2000, and U.S. provisional patent application Ser. No. 60/202,663, filed on May 8, 2000.

FIELD OF THE INVENTION

The present invention relates to a process for preparing a 3'- or 2'-hydroxymethyl substituted nucleoside derivative, and a composition for and a method of treating a hepatitis virus infection or a proliferative disorder using a 3'- or 2'-hydroxymethyl substituted nucleoside derivative. More particularly, the present invention is directed to a composition for and method of treating hepatitis B, C, or D virus or a proliferative disorder such as cancer.

BACKGROUND OF THE INVENTION

This invention relates to a process for preparing a 3'- or 2'-hydroxymethyl substituted nucleoside derivative, compounds and pharmaceutical compositions for, and a method of treating hepatitis virus infections and/or proliferative disorders in patients using 3'-hydroxymethyl and 2'-hydroxymethyl substituted nucleosides and structurally related nucleosides of general formulas [I]–[IV] and their L-nucleoside counterparts.

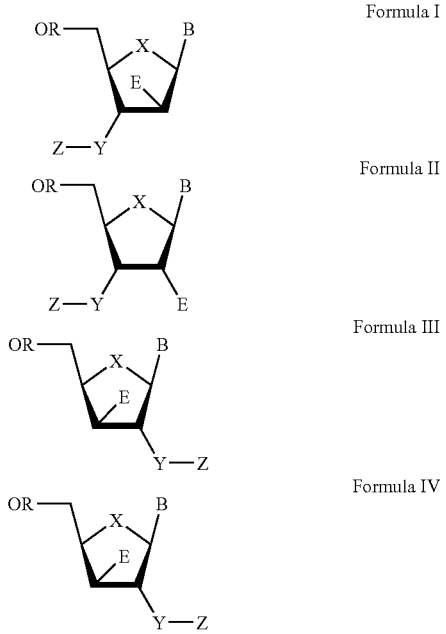

Formula I

Formula II

Formula III

Formula IV wherein the substituents are as defined herein.

Hepatitis B virus (HBV) infection is the most prevalent form of hepatitis and is the second most common infectious disease worldwide. Approximately 5% of the world's population is chronically infected with HBV. The virus is transmitted through blood transfusions, contaminated needles, sexual contact and transmission from mother to child. Moreover, a significant number of people are infected by unknown means.

Carriers of the hepatitis B virus can exhibit various forms of disease, one of which is chronic hepatitis B. Approximately 50% of the carriers show chronic inflammatory changes in the liver and, of these, about 50% have histopathologic changes, which are termed "chronic active hepatitis," which may lead to fibrosis and ultimately to cirrhosis and progressive liver failure. Carriers without chronic inflammatory changes may also develop chronic active hepatitis, while liver cancer develops in about 10 to 30% of hepatitis B carriers. It has been estimated that approximately 4 million carriers of hepatitis B virus die each year from liver cancer or cirrhosis.

HBV, also known as the Dane particle, is a member of the Hepadonaviridae and is a 42 nm complex spherical particle composed of an outer lipoprotein coat (hepatitis B surface antigen HBsAg) and an inner core (hepatitis B core antigen, HBcAg). (Ganem, D., Fundamental Virology, $3^{rd}$ Ed., Lippincott-Raven Pub., Philadelphia, 1996, p. 1199) This core contains partially double stranded DNA of 3.2 kb maintained as a circular structure by 5' cohesive ends. (Chu, C. K., Therapies for Viral Hepatitis, Schinazi, et al., Eds., International Medical Press, 1998) The viral minus strand is full length, while the plus strand is less than full length. The 5' ends of both strands contain short (11 nucleotide) direct repeats. These repeats are involved in priming the synthesis of their respective strands. Remarkably, viral DNA is synthesized in a reverse transcription of an RNA template. (Mason, W. S., Adv. Virus. Res., 1987, 32, 35) Following viral infection, the viral replication cycle begins with translocation of nucleocapsids from the cytoplasm to the nucleus. (Eckart, S. G., J. Virol., 1991, 65, 575) The partially duplex genomic DNA is converted to fully duplex covalently closed supercoiled DNA, which persists as an episomal minichromosome and functions as a reservoir of the viral genome. This feature provides a difficult challenge to therapeutic attack on the virus.

The episomal DNA is transcribed by the host RNA polymerase II and viral proteins are translated from the transcription products. Among the transcripts are full length pregenomic RNAs which are encapsulated by the viral structural proteins together with the viral polymerase. Synthesis of both viral DNA strands by the viral polymerase occurs within these structures. The polymerase contains both a reverse transcriptase and an RNAse H domain. Minus strand synthesis proceeds in two distinct steps (Zolim, F., J. Virol., 1994, 68, 3536). In the first, the polymerase binds to the direct repeat at the 5' end of the pregenomic RNA and serves as a covalent primer for the synthesis of a 4 nucleotide element. The priming hydroxyl group is the side chain of a tyrosine residue on the polymerase and is linked to a dGMP residue. A sequence in the bulge of a stem loop structure in the RNA template serves as the template for this step. This reaction is particular to the virus and is not mimicked in any cellular DNA synthesis reaction. Agents which target this step would have the potential for a high degree of specificity. Following this step the polymerase-nucleotide complex translocates to the other end of the RNA template and complete reverse transcription of the strand takes place. (It has been proposed that there may be proteolytic cleavage of polymerase and RNAse domains away from the portion of the polymerase bound to the tetranucleotide primer. (Bartenschlager, R., EMBO J. 1988, 7, 4185). First strand synthesis is accompanied by the degradation of the RNA in the RNA:DNA hybrid by the RNAse H of the polymerase. Synthesis of the second strand, also mediated by the viral polymerase, is generally incomplete, giving rise to the partially duplex DNA found in the virion.

It is now clear that there are three separate phases in replication and that the first reverse transcription step is of particular interest for therapeutic intervention. It should be noted that an agent that inhibits the reverse transcriptase of other retroviruses does not necessarily have activity against HBV. For example, Zidovudine (or AZT) as its 5'-triphosphate is a potent inhibitor of reverse transcriptase of human immunodeficiency virus and has been widely used in the treatment of HIV-infected patients. However, this agent is inactive against HBV. On the other hand, certain 2'-fluoro-D-arabino nucleosides, such as Fiacitabine (FIAC) and Fialuridine (FIAU), are devoid of activity against HIV although they effectively inhibit replication of HBV.

Hepatitis C virus (HCV), the second major cause of viral hepatitis, is present in an estimated 170 million carriers worldwide, 3.9 million of whom reside in the United States. HCV is considered the most common blood-borne infection in the United States, where it is one of the leading causes for liver transplantation among adults. Most people infected with HCV do not exhibit any acute signs or symptoms of hepatitis. In fact, unless they have a blood test, most people remain unaware that they are infected with HCV for the first 10–20 years.

Aside from direct blood contact, HCV is a very difficult agent to transmit. Maternal-to-fetal transmission is quite low, less than 6% of babies born to infected mothers will carry the virus. Additionally, unlike HBV and human immunodeficiency virus (HIV), evidence of direct sexual transmission of HCV is inconclusive.

HCV is a small, enveloped virus in the Flaviviridae family, with a positive single-stranded RNA genome of ~9.6 kb within the nucleocapsid. The genome contains a single open reading frame (ORF) encoding a polyprotein ofjust over 3,000 amino acids, which is cleaved to generate the mature structural and nonstructural viral proteins. ORF is flanked by 5' and 3' non-translated regions (NTRs) of a few hundred nucleotides in length, which are important for RNA translation and replication. The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase. The junction between NS2 and NS3 is autocatalytically cleaved by the NS2/NS3 protease, while the remaining four junctions are cleaved by the N-terminal serine protease domain of NS3 complexed with NS4A. The NS3 protein also contains the NTP-dependent helicase activity which unwinds duplex RNA during replication. The NS5B protein possesses RNA-dependent RNA polymerase (RDRP) activity, which is essential for viral replication. It is emphasized here that, unlike HBV or HIV, no DNA is involved in the replication of HCV. Recently in in vitro experiments using NS5B, substrate specificity for HCV-RDRP was studied using guanosine 5'-monophosphate (GMP), 5'-diphosphate (GDP), 5'-triphosphate (GTP) and the 5'-triphosphate of 2'-deoxy and 2',3'-dideoxy guanosine (dGTP and ddGTP, respectively). The authors claimed that HCV-RDRP has a strict specificity for ribonucleoside 5'-triphosphates and requires the 2'- and 3'—OH groups. Their experiments suggest that the presence of 2'- and 3'-substituents would be the prerequisite for nucleoside 5'-triphosphates to interact with HCV-RDRP and to act as substrates or inhibitors. The present invention on the development of anti-HCV agents is based on this rationale.

Hepatitis D virus (HDV) is classified separately from other hepatitis viruses, but it is often found in association with hepatitis B virus. The host range of HDV is limited to those species that support the replication of a hepadnavirus capable of supplying a helper function. These include the chimpanzee (hepatitis B virus), the eastern woodchuck (woodchuck hepatitis virus) and possibly the Pekin duck (duck hepatitis virus). The successful replication of HDV is dependent on the replication of the helper hepadnavirus. Inhibition of hepatitis B virus, therefore, should result in inhibition of HDV. Also, while HDV appears to employ the host RNA polymerase, it is not clear if the virus causes some modification of the polymerase enabling it to replicate the HDV genome more efficiently. Thus, nucleosides that inhibit the HBV polymerase or the modified host RNA polymerase would be expected to inhibit the replication of HDV.

The synthesis of some related compounds has been disclosed in the literature (Acton, E. M., et al., J. Med. Chem., 1979; 22:518; Fiandor, J., et al., Nucleosides Nucleotides, 1989; 8:1107; Bamford, M. J., et al., J. Med. Chem., 1990; 23:2494; Svansson, L., et al., J. Org. Chem., 1991; 56:2993; Sterzycki, R. Z., et al., Nucleosides Nucleotides, 1991; 10:291; Svansson, L., et al., Nucleosides Nucleotides, 1992; 11:1353; Kvamstrom, I., et al., Nucleosides Nucleotides, 1992; 11:1367; Tseng, C. K-H., et al., J. Med. Chem., 1991; 34: 343; Lin, T-S., et al., J. Med. Chem., 1993; 36:353; Wengel, J., et al., Bioorg. Med. Chem., 1995; 3:1223; Lee-Ruff, E., et al., J. Med. Chem., 1996; 39:5276; Jorgensen, P. N., et al., Nucleosides Nucleotides, 1997; 16:1063; Jeong, L. S., et al., Nucleosides Nucleotides, 1997; 16:1059;). Moreover, these references also disclose antiviral test results of some of these compounds against herpes virus (HSV) or human immunodeficiency virus (HIV). Only 2',3'-dideoxy-3'-hydroxymethyl-cytidine and adenosine show good activity against HIV and 2',3'-dideoxy-3'-hydroxymethyl-cytidine (Sterzycki, R. Z., et al., Nucleosides Nucleotides, 1991, 10, 291) and 5-bromovinyl-1-(3-deoxy-3-hydroxymethyl-D-arabinofuranosyl)-uracil (Svansson, L., et al., J. Org. Chem., 1991, 56, 2993) are active against HSV.

Although it would not have been expected that an anti-herpes virus agent or anti-HIV agent would also be effective in the treatment of hepatitis, the compounds of the present invention have surprisingly been found to be useful as anti-hepatitis agents. Some of these compounds are particularly favorable in the treatment of hepatitis because they unexpectedly cause less toxic side effects. For example, we discovered that 3'-deoxy-3'-hydroxymethylthymidine, which, though devoid of activity against murine leukemia virus (MuLV), HIV, HSV-1, HSV-2, human cytomegalovirus (HCMV), Varicella zoster virus (VZV) and Epstein Barr virus (EBV)( Sterzycki, R. Z., et al., Nucleosides Nucleotides, 1991, 10, 291), is a potent agent against HBV.

It is therefore an object of the present invention to provide compounds and compositions useful for the treatment of hepatitis.

It is a further object of the present invention to provide a method for treating hepatitis using the compounds of the present invention.

It is another object of the present invention to provide compositions for treating hepatitis comprising the compounds of the present invention in combination with other anti-hepatitis agents.

It is another object of the present invention to provide a method for treating hepatitis using the compounds of the present invention in combination with other anti-hepatitis agents.

It is still another object of the present invention to provide compounds and compositions useful for the treatment of proliferative disorders.

It is still another object of the present invention to provide a method for treating proliferative disorders using the compounds of the present invention.

It is still another object of the present invention to provide a process for preparing 3'- or 2'-hydroxymethyl substituted nucleoside derivatives.

SUMMARY OF INVENTION

The present invention as disclosed herein relates to the compounds of general formulas [I]–[IV], a composition for and a method of treating hepatitis B virus (HBV) in a subject using a nucleoside of general formula [I], and hepatitis C virus (HCV) or hepatitis D virus (HDV) infection using a nucleoside of general formulas [I–IV]:

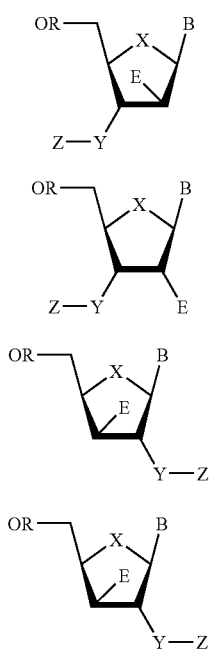

Formula I

Formula II

Formula III

Formula IV wherein:

E is selected from the group consisting of H, OH, OMe, SH, SMe, $NH_2$, NHMe, $N_3$, F, Cl, Br, $CO_2H$, $CO_2$-alkyl, OPh, $OPhNO_2$, NO, $NO_2$, SCN, OCN, NCS, NCO, SOMe, $SO_2Me$;

X is selected from the group consisting of O, S, NH, $CH_2$, CHF, $CF_2$;

Y is selected from the group consisting of $CH_2$, NH, NOH, NMe, NEt, NOMe, CHF, $CF_2$;

Z is selected from the group consisting of H, OH, Ome, SH, SMe, F, Cl, Br, I, $NH_2$, NHMe;

B is a base selected from the group consisting of

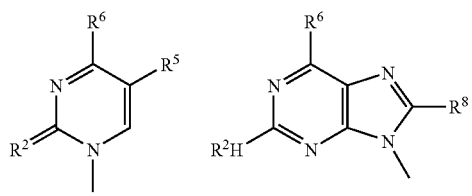

$R^2$ is selected from the group consisting of O, S, NH, NR;

$R^5$ is selected from the group consisting of H, branched or unbranched lower alkyl having 1–5 carbon atoms, F, Cl, Br, I, $CH{=}CH_2$, $CH{=}CHBr$, Ph, Ac, OMe, OPh, NO, $NO_2$, $NH_2$, NHR;

$R^6$ and $R^8$ are the same or different and are independently selected from the group consisting of H, OH, OMe, SH, SMe, F, Cl, Br, I, $NH_2$, NHMe, $NMe_2$;

R is independently selected from the group consisting of

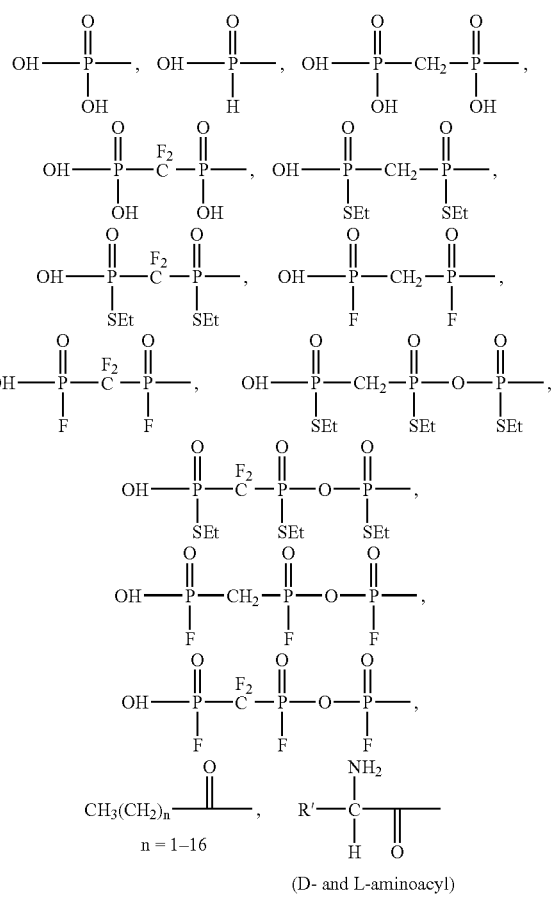

(D- and L-aminoacyl)

Compounds according to the present invention may also be used to treat human immunodeficiency virus (HIV) infection and/or proliferative disorders as well as bacterial infections.

The present invention is also directed to a process for preparing 3'- or 2'-hydroxymethyl substituted nucleoside derivatives.

DETAILED DESCRIPTION

The following terms shall be used to describe the present invention:

The terms "patient" and "host organism" are used throughout the specification to describe an animal, preferably a human, to whom treatment, including prophylactic treatment, with the compounds and pharmaceutical compositions according to the present invention is provided. For treatment of those infections, conditions or disease states which are specific for a specific animal such as a human patient, the terms patient or host refer to that specific animal. In most applications of the present invention, the patient is a human. Veterinary applications, in certain indications, however, are clearly contemplated by the present invention.

The term "therapeutically effective amount" shall mean the administration of at least one compound according to the present invention in an amount or concentration and for period of time including acute, sub-acute or chronic administration, which is effective within the context of its administration for causing an intended effect or physiological outcome in the treatment of HIV, HBV, HCV, HDV, bacterial infection or proliferative disorders such as tumors/cancer. Effective amounts of compounds, according to the present invention, include amounts which are therapeutically effective for delaying the onset of, inhibiting or alleviating the effects of the above disease states. Although effective amounts of compounds, according to the present invention, generally fall within the dosage range of about 0.1 mg/patient kg to about 100 mg/patient kg or more, amounts outside of these ranges, in certain instances, may be used, depending upon the final use of the composition.

As used herein, the term "alkyl" is defined as any straight-chained or branched alkyl, including but not limited to methyl, ethyl, propyl, butyl, pentyl, hexyl, isopropyl, isobutyl, sec-butyl, t-butyl, isopentyl, amyl, and t-pentyl.

The term "acyl" as used herein is defined as the residue of an acid group, including but not limited to acetyl, formyl, propionyl, butyryl, pentanoyl, 3-methylbutyryl, hydrogen succinate, 3-chlorobenzoate, cyclopentyl, cyclohexyl, benzoyl, acetyl, pivaloyl, mesylate, valeryl, caproic, caprylic, capric, lauric, myristic, palmitic, stearic, oleic, amino acids including but not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term "tumor" or "neoplasia" is used to describe the pathological process that results in the formation and growth of a neoplasm, i.e., an abnormal tissue that grows by cellular proliferation more rapidly than normal tissue and continues to grow after the stimuli that initiated the new growth cease. Neoplasia exhibits partial or complete lack of structural organization and functional coordination with the normal tissue, and usually forms a distinct mass of tissue which may be benign (benign tumor) or malignant (carcinoma). The terms "proliferative disorder" and "cancer" are used as general terms to describe any of various types of malignant neoplasms, most of which invade surrounding tissues, may metastasize to several sites, and are likely to recur after attempted removal and to cause death of the patient unless adequately treated. As used herein, the term cancer is subsumed under the term tumor or neoplasia. Cancers, which may be treated using one or more compounds according to the present invention, include stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's leukemia, multiple myeloma leukemias, skin melanoma, acute lymphocytic leukemia, acute myelogenous leukemia, small cell lung cancer, choriocarcinoma, rhabdomyosarcoma, neuroblastoma, mouth/pharynx, esophagus, larynx, melanoma, lymphoma and kidney cancer. Compounds according to the present invention, which are used to treat tumors and/or cancer, are referred to as anti-proliferative.

The term "D-nucleoside" is used to describe a nucleoside compound, according to the present invention, which has a configuration about the nucleoside base/sugar synthon bond which is the same as the configuration of the naturally occurring nucleoside compounds.

The term "L-nucleoside" is used throughout the specification to describe those nucleoside compounds used in the present invention which have an unnatural L-configuration of the sugar synthon moiety in contrast to the natural D-configuration. Certain compounds according to the present invention do not have a D,L distinction.

The term "β-anomer" or "β-nucleoside" is used to describe nucleoside compounds according to the present invention which have a cis-relationship between the base and the 4'-hydroxymethyl group (i.e., a configuration in which the base and 4'-hydroxymethyl group of the sugar are in the same side of the sugar ring).

The term "α-anomer" or "α-nucleoside" is used to describe nucleoside compounds according to the present invention which have a trans-relationship between the base and the 4'-hydroxymethyl group (i.e., a configuration in which the base is oriented in the opposing plane relative to the 4'-hydroxymethyl group of the sugar synthon).

The term pharmaceutically acceptable derivative is used throughout the specification to describe any pharmaceutically acceptable salt or prodrug form (such as an ester, phosphate ester or salt of an ester or a related group) of a nucleoside compound which, upon administration to a patient, provides directly or indirectly the nucleoside compound or an active metabolite of the nucleoside compound. Pharmaceutically acceptable salts forms of the present compounds are also contemplated by the present invention. Pharmaceutically acceptable salts include those derived from pharmaceutically acceptable inorganic or organic bases and acids. Suitable salts include those derived from alkali metals such as potassium and sodium, alkaline earth metals such as calcium and magnesium, and ammonium among numerous other acids well known in the pharmaceutical art.

The term "enantiomerically enriched" is used throughout the specification to describe a nucleoside which includes at least about 95%, preferably at least about 96%, more preferably at least about 97%, even more preferably, at least about 98%, and even more preferably at least about 99% or more of a single enantiomer of that nucleoside. When a nucleoside of a particular configuration (D or L) is referred to in this specification, it is presumed that the nucleoside is an enantiomerically enriched nucleoside, unless otherwise stated.

The invention as described herein includes processes to prepare compounds of formulas [I]–[IV]. In another embodiment, the use of these compounds for the treatment of viral hepatitis (B, C or D), HIV infections and AIDS or abnormal cellular proliferation in humans or other host animals that includes administering an effective amount of a compound of general formulas [I]–[IV] to a patient in need of therapy or preventions. The compounds of this invention either possess anti-viral (anti-HBV, anti-HCV or anti-HDV) activity, anti-HIV activity, antibacterial activity or anti-proliferative activity, or are metabolized to a compound that exhibits such activity. It should be noted that compounds of formula [I]–[IV] may be viewed as sugar ring expanded analogues of the anti-viral antibiotic oxetanocin-G (Presentation 1).

Presentation 1. Structural relationship between oxetanocin and compounds of present invention.

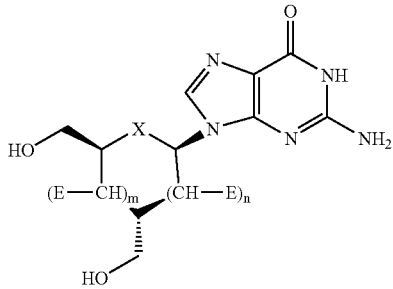

Oxetanocin-G: X=O, n=m=0
Formula I and II: m=0, n=1
Formula III and IV: n=1, m=0

Specifically, this invention provides processes for the preparation of a compound having the structure:

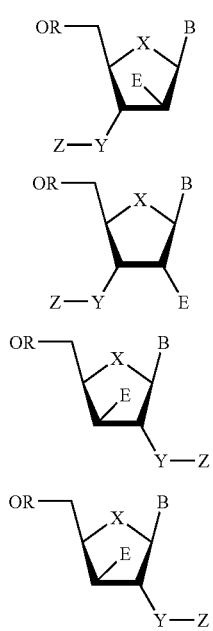

wherein:

E is selected from the group consisting of H, OH, OMe, SH, SMe, $NH_2$, NHMe, $N_3$, F, Cl, Br, $CO_2H$, $CO_2$-alkyl, OPh, $OPhNO_2$, NO, $NO_2$, SCN, OCN, NCS, NCO, SOMe, $SO_2Me$;

X is selected from the group consisting of O, S, NH, $CH_2$, CHF, $CF_2$;

Y is selected from the group consisting of $CH_2$, NH, NOH, NMe, NEt, NOMe, CHF, $CF_2$;

Z is selected from the group consisting of H, OH, Ome, SH, SMe, F, Cl, Br, I, $NH_2$, NHMe;

B is a base selected from the group consisting of

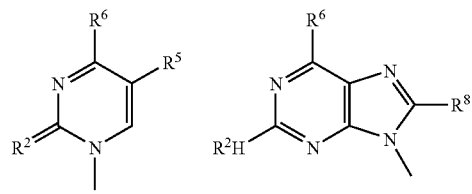

$R^2$ is selected from the group consisting of O, S, NH, NR;

$R^5$ is selected from the group consisting of H, branched or unbranched lower alkyl having 1–5 carbon atoms, F, Cl, Br, I, $CH=CH_2$, $CH=CHBr$, Ph, Ac, OMe, OPh, NO, $NO_2$, $NH_2$, NHR;

$R^6$ and $R^8$ are the same or different and are independently selected from the group consisting of H, OH, OMe, SH, SMe, F, Cl, Br, I, $NH_2$, NHMe, $NMe_2$;

R is independently selected from the group consisting of

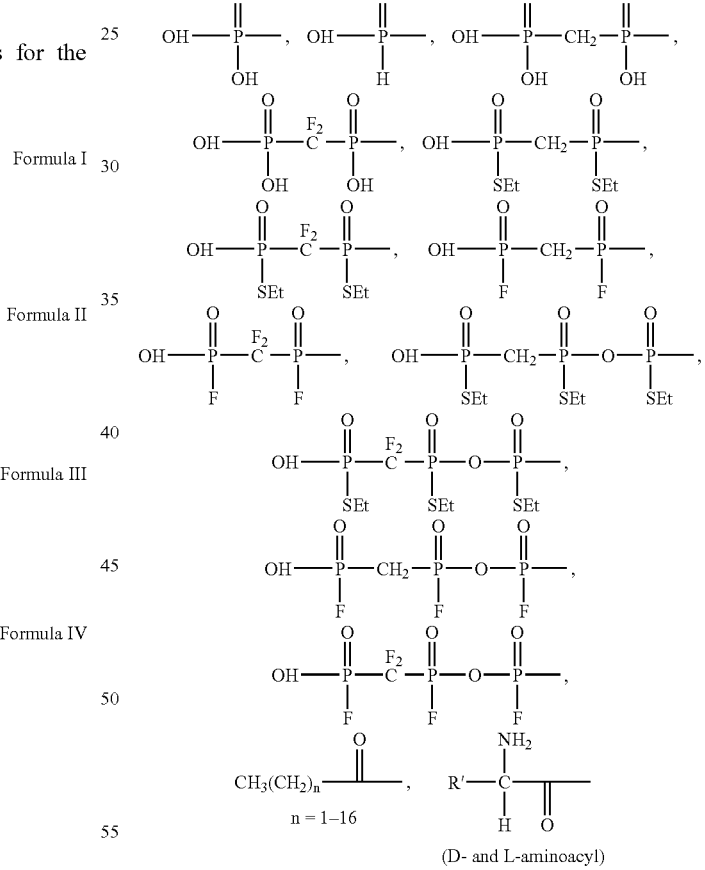

or pharmaceutically acceptable salts or prodrugs thereof.

Pharmaceutical compositions based upon the compounds of the present invention comprise the above-described compounds in a therapeutically effective amount for treating a viral infection such as an HBV, HCV, HDV or HIV infection or a proliferative disease such as a tumor or cancer, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient or host organism (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally administrable form, but certain formulations may be administered via a parenteral, intravenous, intramuscular, transdermal, buccal, subcutaneous, vaginal, suppository or other route. Intravenous and intramulscular formulations are preferably administered in sterile saline. One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.), which are well within the ordinary skill in the art. It is also well within the ordinary artisan's skill to modify the route of administration and dosage regimen of a particular compound in order to manage the pharmacokinetics of the present compounds for maximum beneficial effect in patients.

In certain pharmaceutical dosage forms, the prodrug form of the compounds, especially including acylated (acetylated or other) and ether derivatives, phosphate esters and various salt forms of the present compounds, are preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound in the treatment of viral infections or proliferative diseases.

The amount of compound included within therapeutically active formulations, according to the present invention, is an effective amount for treating the infection or condition, in preferred embodiments, an HBV, HCV, HDV, or HIV infection or a proliferative disease, including cancer. In general, a therapeutically effective amount of the present compound in pharmaceutical dosage form usually ranges from about 0.1 mg/patient kg to about 100 mg/patient kg or more, depending upon the compound used, the condition or infection treated and the route of administration. In the case of proliferative diseases including cancer, the active compound is preferably administered in amounts ranging from about 0.5 mg/patient kg to more than 100 mg/kg of the patient, depending upon the pharmacokinetics of the agent in the patient. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, Q.I.D.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including, but not limited to, water, glycols, oils, alcohols, flavoring agents, preservatives, coloring agents and the like may be used. For solid oral preparations such as powders, tablets, capsules, and for solid preparations such as suppositories, suitable carriers and additives including, but not limited to, starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly impact the bioavailability of the compounds in the patient.

For parenteral formulations, the carrier will usually comprise sterile water or aqueous sodium chloride solution, though other ingredients, including, but not limited to, those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

In particularly preferred embodiments according to the present invention, the compounds and compositions are used to treat, prevent or delay the onset of viral infections of mammals and in particular HBV, HCV, HDV, or HIV infections in humans. Preferably, to treat, prevent or delay the onset of HBV, HCV, HDV or HIV infections, the compositions will be administered in oral dosage form in amounts ranging from about 250 micrograms up to about 500 mg or more at least once a day, preferably, up to four times a day, though it will be recognized by one of ordinary skill in the art that in some instances a lower or higher dosage may be indicated. The present compounds are preferably administered orally, but may be administered parenterally, topically or in suppository form.

The compounds according to the present invention, because of their low toxicity to host cells in certain instances, may be advantageously employed prophylactically to prevent HBV, HCV, HDV or HIV infection or to prevent the occurrence of clinical symptoms associated with the viral infection. Thus, the present invention also encompasses methods for the prophylactic treatment of viral infections, and in particular HBV, HCV, HDV or HIV infections. In this aspect, according to the present invention, the present compositions are used to prevent or delay the onset of an HBV, HCV, HDV or HIV infection. This prophylactic method comprises administration to a patient in need of such treatment, or who is at risk for the development of HBV, HCV, HDV or HIV disease, an amount of a compound according to the present invention effective for alleviating, preventing or delaying the onset of the viral infection. In the prophylactic treatment according to the present invention, it is preferred that the anti-viral compound utilized should be as low in toxicity as possible and preferably non-toxic to the patient. It is particularly preferred in this aspect of the present invention that the compound which is used should be maximally effective against the virus and should exhibit a minimum of toxicity to the patient. In the case of HBV, HCV, HDV and HIV infections, compounds according to the present invention, which may be used to treat these disease states, may be administered within the same dosage range for therapeutic treatment (i.e., about 250 micrograms up to 500 mg or more from one to four times per day for an oral dosage form) as a prophylactic agent to prevent the proliferation of HBV, HCV, HDV or HIV or alternatively, to prolong the onset of an HBV, HCV, HDV or HIV infection, which manifests itself in clinical symptoms.

It has been recognized that drug-resistant variants of HIV, HBV, HCV, and HDV can emerge after prolonged treatment with an antiviral agent. Drug resistance most typically occurs by mutation of a gene that encodes for an enzyme used in the viral lifecycle; in the case of HBV, DNA polymerase, and in the case of HIV, reverse transcriptase, protease, or DNA polymerase. Recently, it has been demonstrated that the efficacy of a drug against HIV or HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Compounds according to the present invention may be administered alone or in combination with other anti-HIV, anti-retrovirus, anti-HBV, anti-HCV, anti-cancer or antibacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data of in vitro and in vivo for a number of antiviral compounds is found in Schinazi, et al., "Mutations in retroviral genes associated with drug resistance," International Antiviral News, Volume 1(4), International Medical Press 1996.

Preferred examples of synthetic nucleosides that can be used in combination or alternation with the compounds disclosed herein for HIV therapy include, but are not limited to (−) or racemic 2-hydroxymethyl-5-(5-fluorocytosin-1-yl)-1,3-oxathiolane (FTC); the (−)-enantiomer of 2-hydroxymethyl-5-(cyostin-1-yl)-1,3-oxathiolane (3TC); carbovir, acyclovir, interferon, AZT, DDI, DDC, D4T, CS-92 (3'-azido-2',3-dideoxy-5-methyl-cytidine), and beta-D-dioxolane nucleosides such as beta-D-dioxolanyl-guanine (DXG), beta-D-dioxolanyl-6-chloropurine (ACP), and abacavir.

Preferred examples of NNRTIs that can be used in combination or alternation with the compounds of the present invention for HIV therapy include, but are not limited to SUSTIVA (DuPont), nevirapine, delavirdine, TMC-120, DMP-266, Loviride, Capravarine and MKC-442 (6-benzyl-1-(ethoxymethyl)-5-isopropyl uracil.

Preferred protease inhibitors that can be used in combination with the compounds of the present invention for HIV therapy include, but are not limited to indinavir, inverase, viracept, norvir, fortovase, agenerase, lopinavir and DMP-450 (DuPont Merck).

Preferred compounds for combination or alternation therapy for the treatment of HBV include FTC (the (−)-enantiomer or the racemate), L-FMAU, interferon, beta-D-dioxolanyl-guanine (DXG), beta-D-dioxolanyl-2,6-diaminopurine (DAPD), beta-D-dioxolanyl-6-chloropurine (ACP), beta-D-dioxolanyl-2-aminopurine (ADP), famciclovir, penciclovir, bis-POM PMEA (adefovir dipivoxil); lobucavir, ganciclovir, ribavarin, lamivudine (3TC), L-thymidine (L-dT), L-2'-deoxycytidine (L-dT), L-2'-deoxycytidine-3', 5'-di-O-valyl (D or L), entecavir (BMS-200475), adefovir, L-D4FC, D-D4FC, and mycophenolic acid (an IMPDH inhibitor).

Other compounds useful in combination or alternation therapy with the compounds of the present invention include interferon, macrokine, heptazyme, ribavarin (D and L), amantadine, ofloxacin, zadaxin and reticulose.

This invention is further illustrated in the Examples which follow. The Examples contained therein are set forth to aid in an understanding of the invention. This section is not intended to, and should not be interpreted to, limit in any way the invention set forth in the claims which follow thereafter.

Preparation of the Compounds

Compounds of formula [I]–[IV], in which X is oxygen, can be synthesized by three routes: (a) from a preformed nucleoside, (b) condensation of a branched sugar with purine or pyrimidine, and (c) combination of the two routes. For example, Bamford et al.(J. Med. Chem., 1990, 23:2494 ) synthesized non-phosphorylated pyrimidine nucleosides of formula [I] in which Y=$CH_2$, Z=OH, $R^5$ is H, $CH_3$, I and (E)-5-(2-bromovinyl), E=H or OH, and $R^2=R^6$=O starting from uracil or thymine O-D-pentofuranoside 2',3'-lyxo-epoxide. Svansson et al.(J. Org. Chem., 1991, 56:2993) prepared a non-phosphorylated methyl 2,3-dideoxy-3-hydroxymethyl-D-ribofuranoside, from which was synthesized the thymine, cytosine and adenine nucleosides via condensation. Pudlo and Townsend (Tetrahedron Letters, 1990, 31:3104) developed a relatively simple method to synthesize non-phosphorylated 5-O-benzoyl-3-benzyloxymethyl-3-deoxy-1,2-O-isopropylidene-α-D-ribofuranose, from which were prepared non-phosphorylated 3-hydroxymethyl analogues of α and β-thymine riboside (Nucleosides Nucleotides, 1992, 11:279) 2'-Deoxygenation of the thymine arabinoside (Bamford, above) or riboside (Pudlo, above) analogue afforded non-phosphorylated 3' -deoxy-3 '-hydroxymethylthymidine.

Our method of synthesis of compounds of formula [I] is illustrated in Scheme 1.

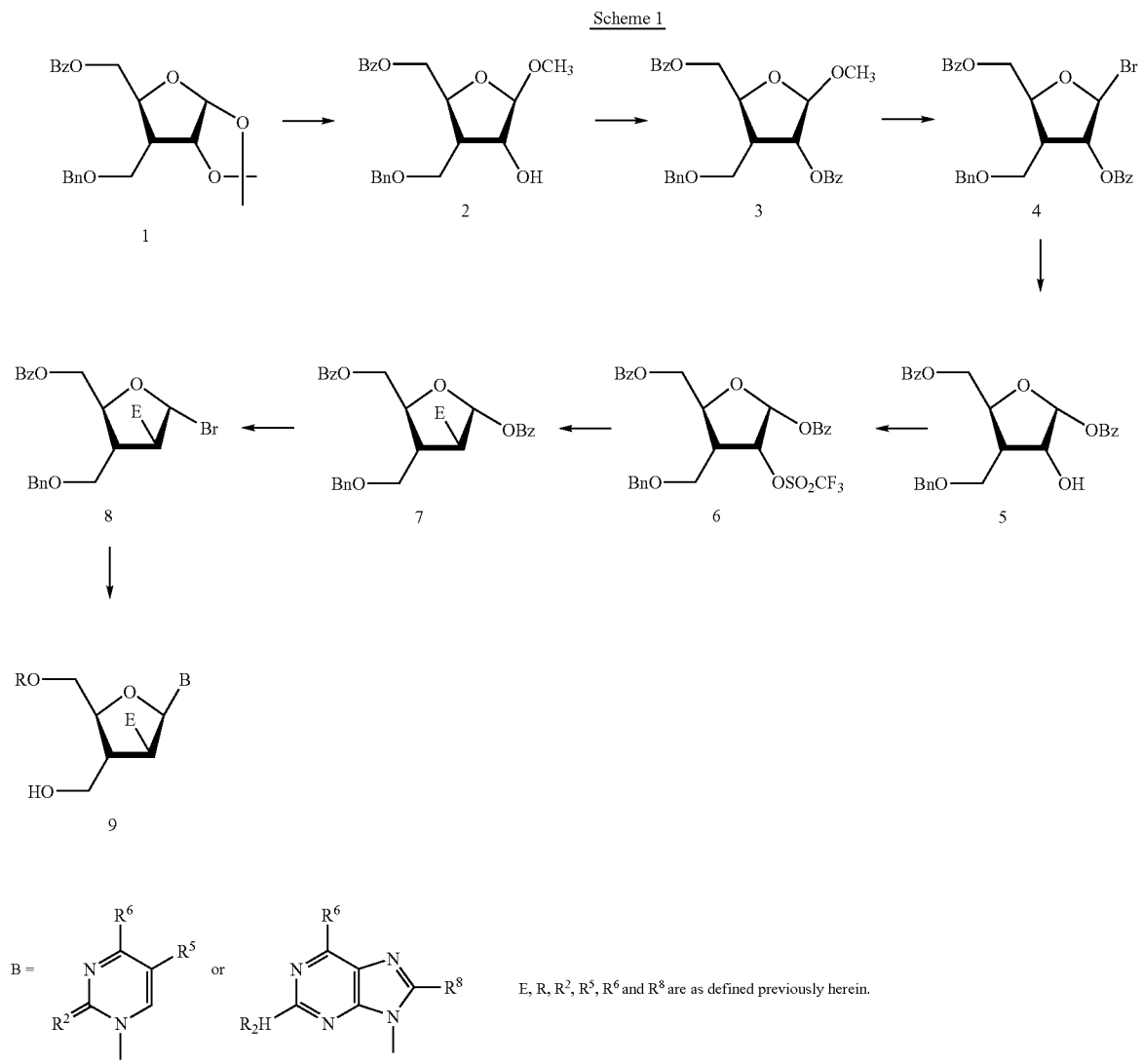

E, R, R², R⁵, R⁶ and R⁸ are as defined previously herein.

The known compound 1 is converted into 2 by the procedure of Pudlo and Townsend. Benzoylation of 2 gives a new compound 3, which is treated with HBr/CH₂Cl₂ to give the bromo derivative 4. Treatment of 4 with mild base causes benzoyl migration to give rise to 5 which is triflylated to 6. Nucleophilic substitution with a halide or other nucleophile, such as azide or cyanide ion, affords the corresponding 2-substituted arabino derivative 7. Alternatively, 5 can be converted into the 2-fluoro-arabino derivative (7, E=F) by the procedure of Tann and Howell (J. Org. Chem., 1985, 50:3644; J. Org. Chem., 1988, 53:85) Due to the presence of the 2-substituent, bromination of 7 gives the α-bromide 8. Since the 2-substituent is electronegative, 8 is rather stable and undergoes mainly $S_N2$ nucleophilic substitution upon condensation with silylated purine or pyrimidine base to give almost exclusively the desired β-nucleoside, which after deprotection affords 9 (R=H). Selective 5'-modification will be discussed later.

Pyrimidine nucleosides of formula II can be synthesized by the procedure in Scheme 2. Compound 3 is condensed with silylated pyrimidine according to Vorbruggen's procedure (J. Org. Chem., 1974, 39:3654; Chem. Ber., 1981, 114:1234; Chem. Ber., 1981, 114:1256). Due to the neighboring group participation of the 2-O-benzoyl group, only the desired β-nucleoside 10 is formed. De-O-benzoylation of 10 with base gives 11, which, upon successive treatment with trityl chloride and mesyl chloride in pyridine, is converted into 12. Base treatment of 12 results in the formation of 2,2'-anhydro-nucleoside 13. Treatment of 13 with a nucleophile, such as halogen, gives the ribo-nucleoside 14. Mild acid treatment of 14 removes the trityl group giving 15, which is converted to the free nucleoside 16 (R=H) by catalytic hydrogenolysis or by treatment with BCl₃ in an inert solvent, such as methylene chloride. Further conversion of 16 (R=H) into 5'-modified nucleosides is discussed later.

Scheme 2

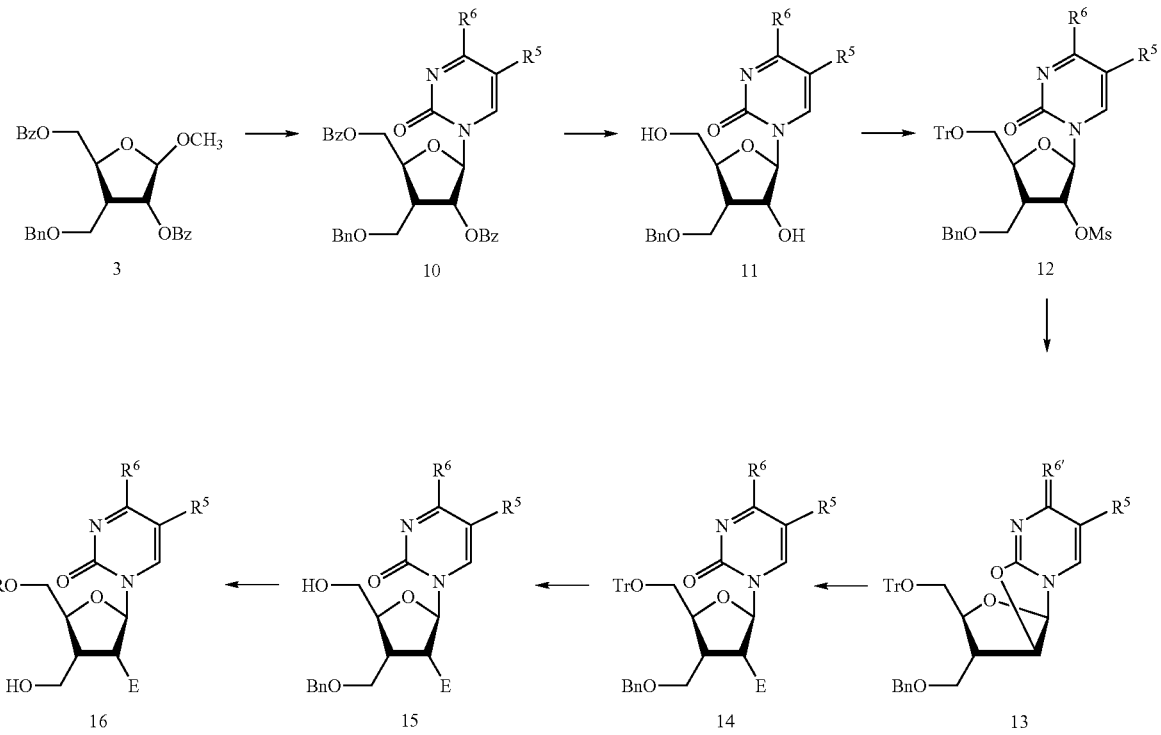

It should be noted that the same chemistry is applicable to the synthesis of L-nucleoside or racemic counterparts starting from the L-sugar derivative or racemate compound corresponding to 1.

Scheme 3 illustrates an example of the synthesis of purine nucleosides of formula II. Compound 4 serves as the starting material, which is treated with sodio derivative of purine base in an inert solvent, such as acetonitrile or nitromethane, according to Kazimierczuk et al. (J. Am. Chem. Soc., 1984, 106:6379) affords the β-nucleoside 17. Saponification of 17 in base gives 18. When $R^8$ is not a participating group, such as OH, SH, NHR (R is methyl, ethyl, isopropyl or benzyl), 18 is treated with mesyl chloride in pyridine to afford the di-O-mesylate 19, which is converted into the 2',5'-di-O-acyl arabino derivative 20 by treatment with alkali metal acylate, such as potassium acetate or sodium benzoate, preferably potassium acetate, in a polar solvent, such as dimethylformamide, dimethylsulfoxide, acetonitrile, hexamethylphosphoric triamide, or nitromethane, preferably dimethylformamide, at a temperature of from 0° C. to 215° C., preferably from 60° C. to 114° C. After saponification of 20, the product is successively treated with trityl chloride and triflyl chloride in pyridine to give 21. Nucleophilic substitution of the triflyloxy group with a halide, azide, sulfide, mercapto, or a like affords the corresponding 2'-substituted ribonucleoside 22. Saponification of 22, followed by hydrogenolysis, gives the desired nucleoside 23 (R=H). Selective 5'-modification will be discussed later.

Scheme 3

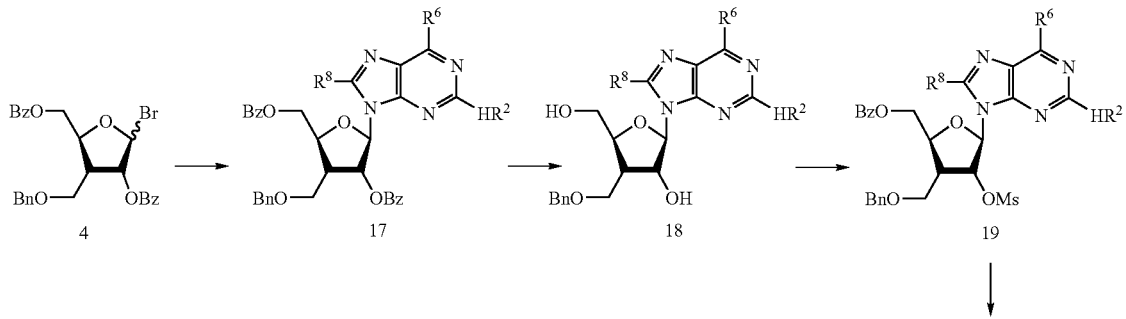

-continued

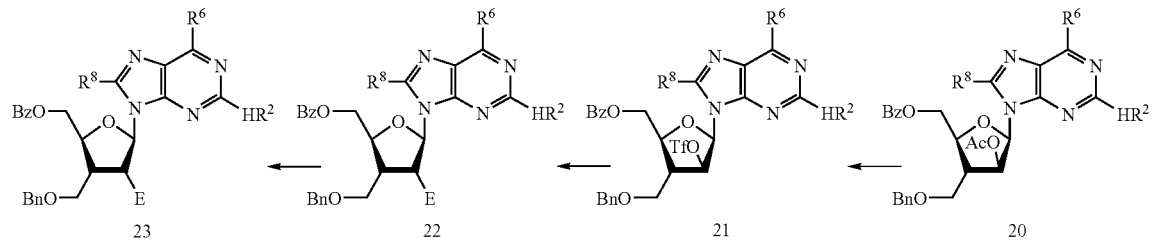

When $R^8$ is OH, SH or NHR (R=methyl, ethyl, isopropyl, or benzyl) in 19, treatment with sodium benzoate in dimethylformamide leads to the formation an 2',8-anhydronucleoside 24 (Scheme 4). Purine nucleosides of formula II, i.e., 22, are prepared from the O-bridged compound 24(O) by treatment with nucleophiles. The S-bridged compound can be converted into the corresponding 2'-deoxy-nucleoside by Raney nickel desulfurization to 22 (E=H), followed by de-blocking.

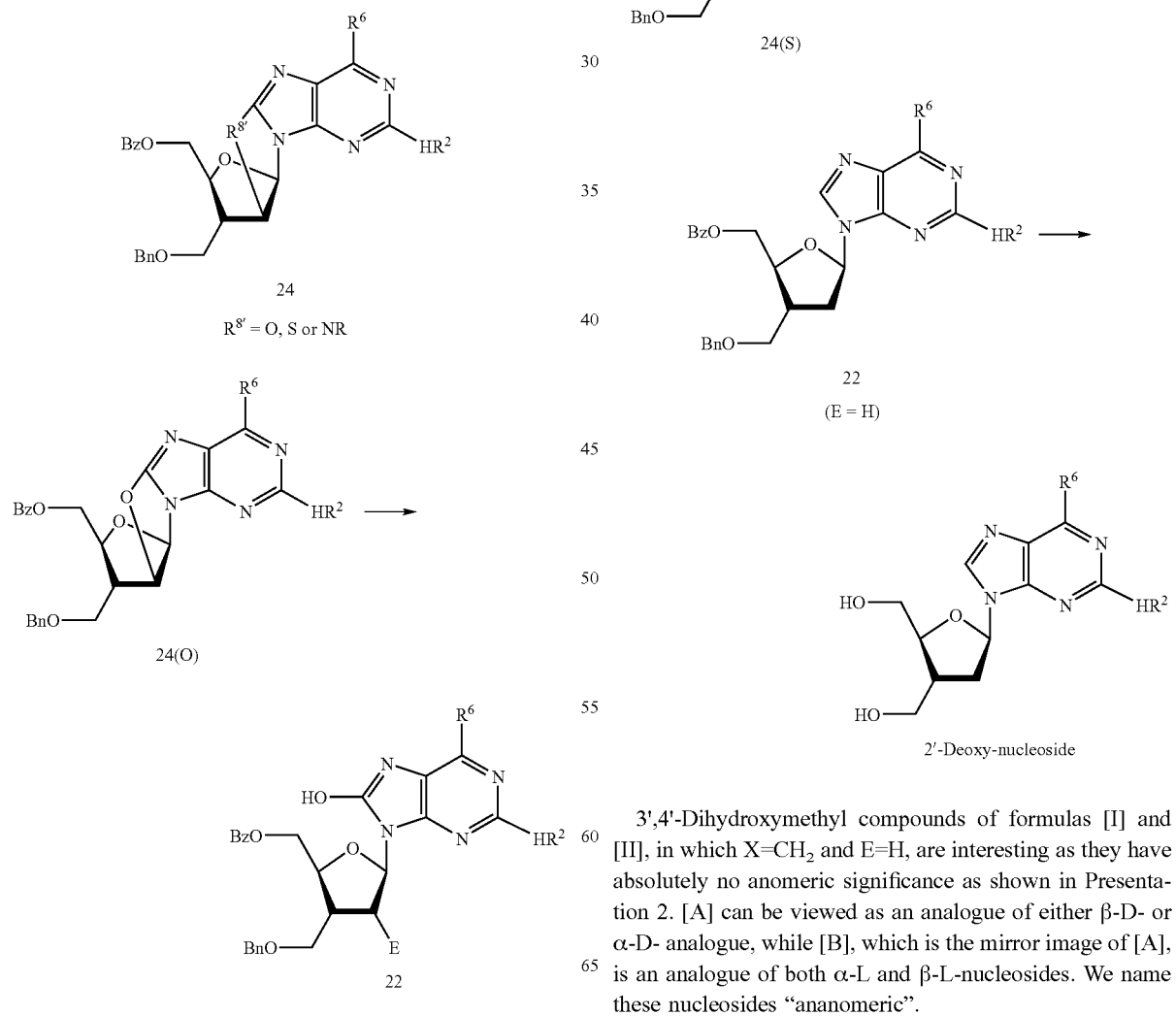

3',4'-Dihydroxymethyl compounds of formulas [I] and [III], in which $X=CH_2$ and E=H, are interesting as they have absolutely no anomeric significance as shown in Presentation 2. [A] can be viewed as an analogue of either β-D- or α-D- analogue, while [B], which is the mirror image of [A], is an analogue of both α-L and β-L-nucleosides. We name these nucleosides "ananomeric".

Presentation 2. Structures of Ananomeric Nucleosides.

Presentation 3. Interesting Structural Features of Carba-nucleosides of Formulas III and IV.

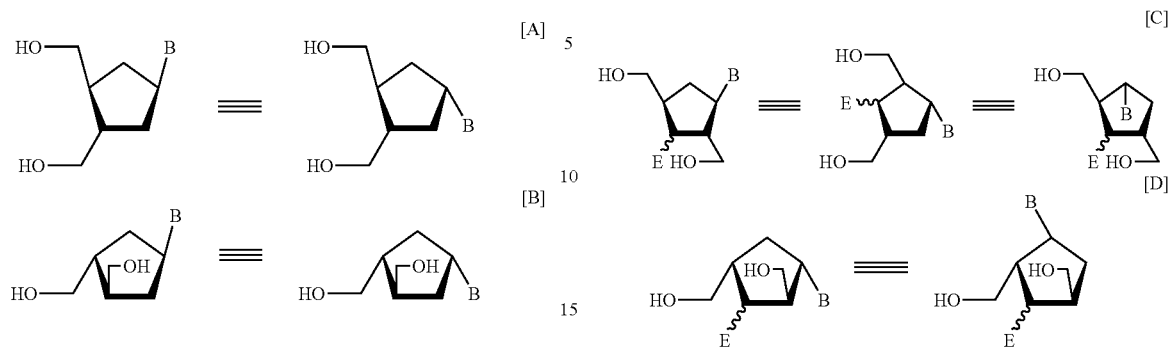

2',4'-Dihydroxymethyl-carba derivatives of formulas III and IV also have interesting structural features: [C] and [D] can be considered as the β-D- and β-L-nucleoside, respectively. They can also be α-isonucleosides (Presentation 3).

A number of chemically intriguing approaches to the carba-nucleosides of formulas I and II can be sought. The following two methods in Schemes 5 and 6 are used for the racemic products.

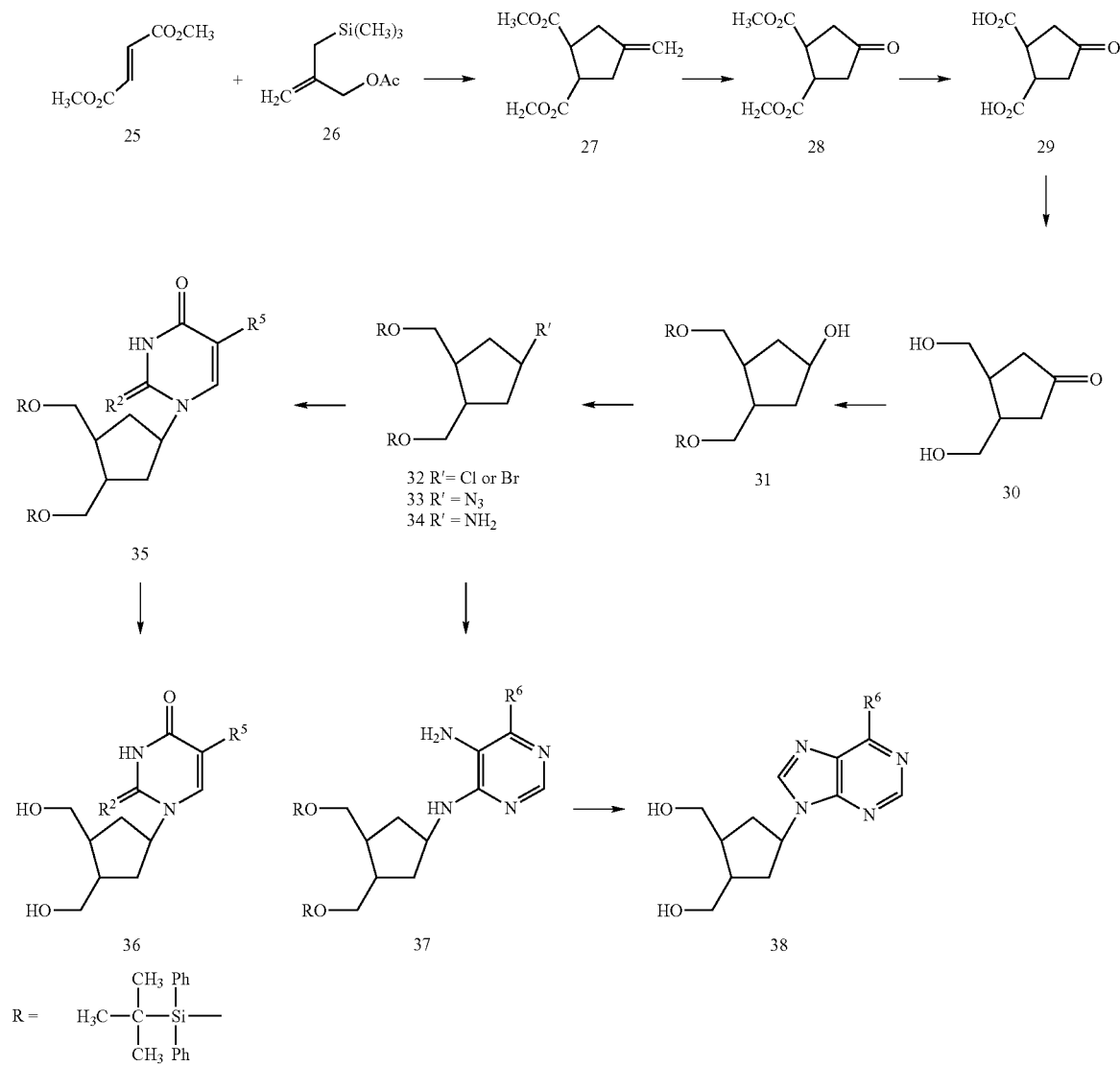

Commercially available reagents 25 and 26 (Scheme 5) are treated with triisopropylphosphine and Pd(OAc)₃ in toluene at reflux temperature to give trans-1,2-methoxycarbonyl-4-methylenecyclopentane (27). Ozonolysis of 27 gives the cyclopentanone 28, which, after saponification to 29, is reduced with diborane in dimethylsulfoxide to give trans-3,5-dihydroxymethylcyclopentanone (30). Treatment of 30 with tert-butyldiphenylsilyl chloride in pyridine, followed by catalytic hydrogenation, affords the cyclopentanol 31, in which C-1 is not chiral due to molecular symmetry. Compound 31 is then converted into the halide 32 by treatment with Vilsmeier-Haack reagent or carbon tetrahalide and triphenylphosphine. Treatment of 32 with NaN₃ gives the azido derivative 33, which, upon reduction affords cyclopentylamine 34. Condensation of 34 with β-ethoxy-N-ethoxycarbonylacrylamide (Wilson, L. J., Synthesis, 1995, 1465) furnish the uracil derivative (35, R²=O, R⁵=H). By using α-methyl-β-methoxyacryloyl isothiocyanate, 2-thiothymine nucleoside (35, R² =S, R=CH₃) is obtained. Deprotection of 35 with fluoride ion gives the free nucleoside 36. Various 5-substituted uracil nucleosides are likewise prepared in a similar manner. For the purine nucleoside synthesis, reaction of 34 with 5-amino-2,4-dichloropyrimidine gives 37 (R⁶=Cl), which is cyclized with triethyl orthoformate and then deprotected to a purine nucleoside (38, R⁶=Cl). Alternatively, reaction of 32 with 5-nitro-2,4-diaminopyrimidine followed by reduction of the product gives 37 (R⁶=NH₂), which is then converted into adenine derivative 38 (R⁶ =NH₂). Various purine nucleoside analogues of formulas I and II are prepared from 37. It should be noted that in the synthesis of racemic compounds 27–38, there is no problem of anomeric configuration.

In an alternate route, the readily available racemic xylo analogue 39 (Scheme 6) is converted into the purine and pyrimidine carba-nucleosides (40) by the known procedures (Shaw, J. Chem. Soc., 1958, 2294; Vince, R., J. Med. Chem., 1984, 27:1358; Cusack, N., J. Chem. Soc., Perkin Trans. I, 1973, 1720) Compound 36 is treated with 2,2-dimethoxypropane in acetone in the presence of catalytic amount of p-toluenesulfonic acid to give the 3',5'-O-isopropylidene derivative 41, which is benzoylated to 42. After acid treatment of 42, the product is tritylated and then oxidized under Bergstrom's conditions (Nucleosides Nucleotides, 1987, 6:53; 1989, 8:1529) to give 43. The ketone 43 is converted into the 3'-methylene nucleoside 44 by Acton's procedure (J. Med. Chem. 1979, 22:518). Hydroboration-oxidation of 44 affords only 3'(α)-hydroxymethyl product 45. Apparently hydride attack occurs exclusively from the least sterically hindered (β)-side. Compound 45 can also be obtained by treatment of 39 with benzyloxymethylene triphenylphosphorane, followed by reduction. Tritylation of 45 followed by O-debenzoylation in base and subsequent deoxygenation by way of xanthate or phenoxythiocarbonate [46, R'=C(S)SMe or C(S)OPh] affords 47. Detritylation of 47 gives the corresponding racemic 2'-deoxynucleoside analogue 36 or 38. Compound 46 in which R is triflyl can be converted to other 2'-modified nucleosides of fromula I and II.

Scheme 6

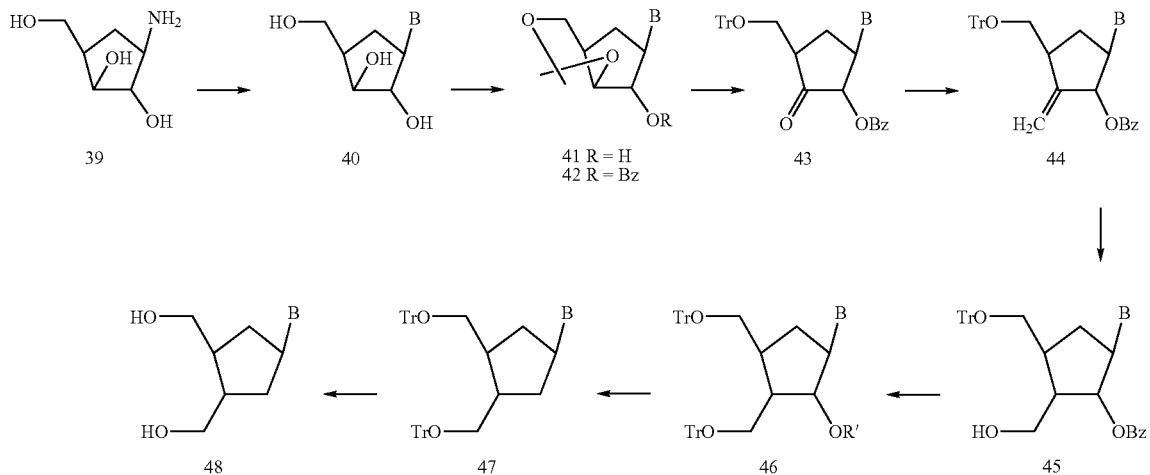

Although optical resolution of the racemate can be effectively performed at the stage of 45 using the Pirkle's method, several routes are developed for the direct synthesis of chiral carba-nucleosides.

L-Arabinolactone (49, Scheme 7) is benzoylated to 50 and then converted into the phosphonate 51 according to Lim and Marquez (Tetrahedron Letters, 1983, 24:5559). Hydrolysis of the hemiketal 51 affords 52, which is oxidized to diketone 53. Subsequent intramolecular Wittig-Horner reaction results in the olefin 54. Reduction of 54 proceeds stereoselectively giving only 55, since the α-side of the carbonyl group and the β-side of the benzoylated hydroxymethyl group are hindered by the presence of neighboring benzoyloxy groups. Chlorination of 55 with thionyl chloride gives the chloride 56 with retention of configuration (characteristics of SOX₂ halogenation). A further treatment of 56 with NaN₃, followed by reduction should afford enantiomerically pure 34. A sequence of reactions from 34 as outlined in Scheme 5 gives the targeted D-nucleoside analogues of Formulas I and II.

Scheme 7

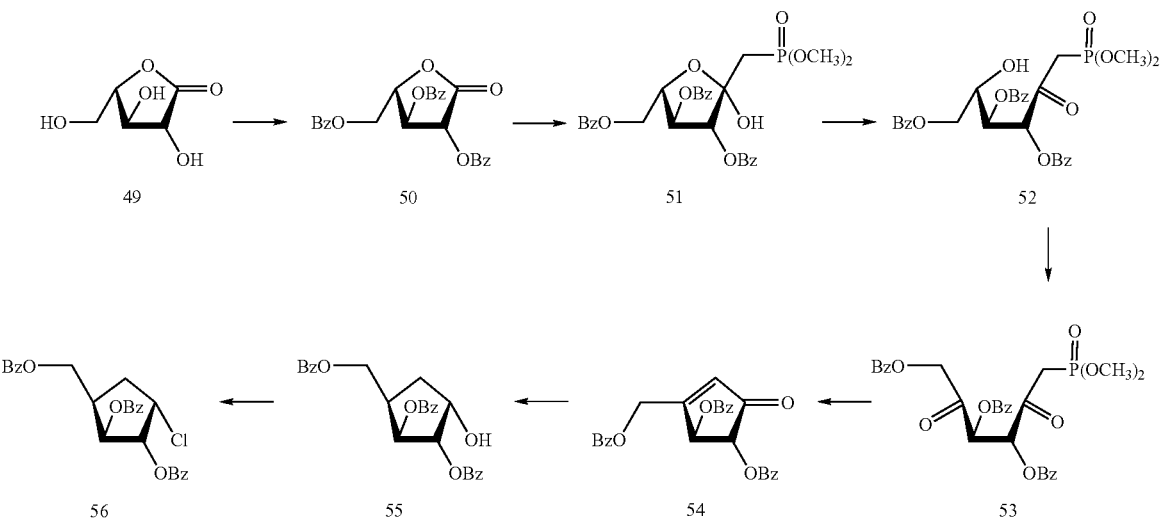

Another alternative is conversion of L-arabinolactone to 5-O-trityl-2,3-di-O-benzoyl-L-arabinolactone (57, Scheme 8), which is treated with lithiobenzyloxymethane to give 58 (stereochemistry of the product is not important at all). Detritylation of 58, then bromination with $CBr_4/PPh_3$ affords 59. Arbuzov reaction with $P(OMe)_3$ gives phosphonate 60, which, upon acid hydrolysis, is converted into the open chain intermediate 61. Intramnolecular Wittig-Horner reaction firnishes the olefin 62. Reduction of 62 proceeds stereoselective manner giving rise to 63 (R=H) which is converted into compounds of formulas I and II via the halogeno intermediate (56 or 64) by procedures described earlier.

Scheme 8

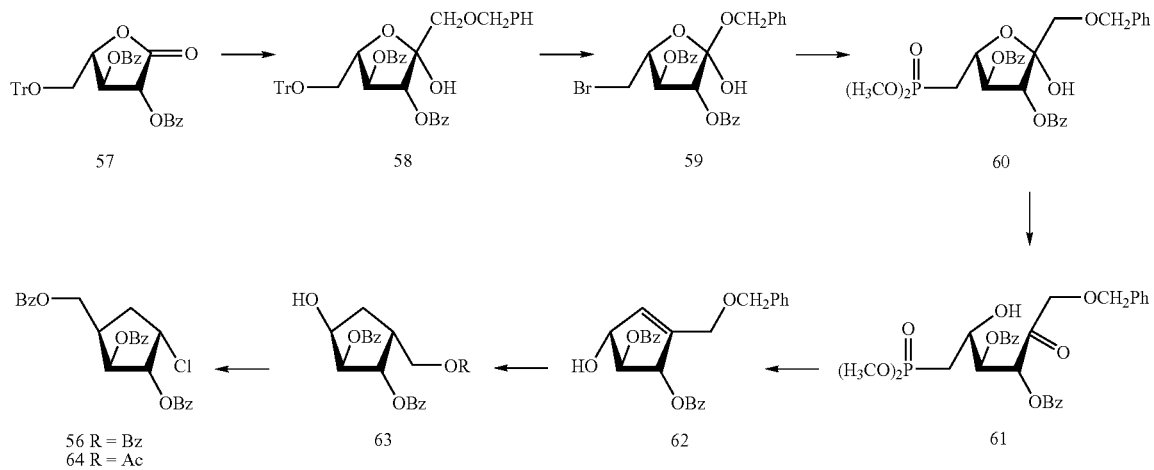

For the synthesis of L-nucleoside counterparts, the starting material is the readily-available tri-O-benzoyl-α-D-arabinose (65, Scheme 9). Swern oxidation of 65 affords tri-O-benzoyl-D-arabinolactone (66). Similar sequence of reactions described for the synthesis of D-nucleosides of formulas [I] and [II] from L-arabinolactone gives the corresponding L-nucleosides.

Scheme 9

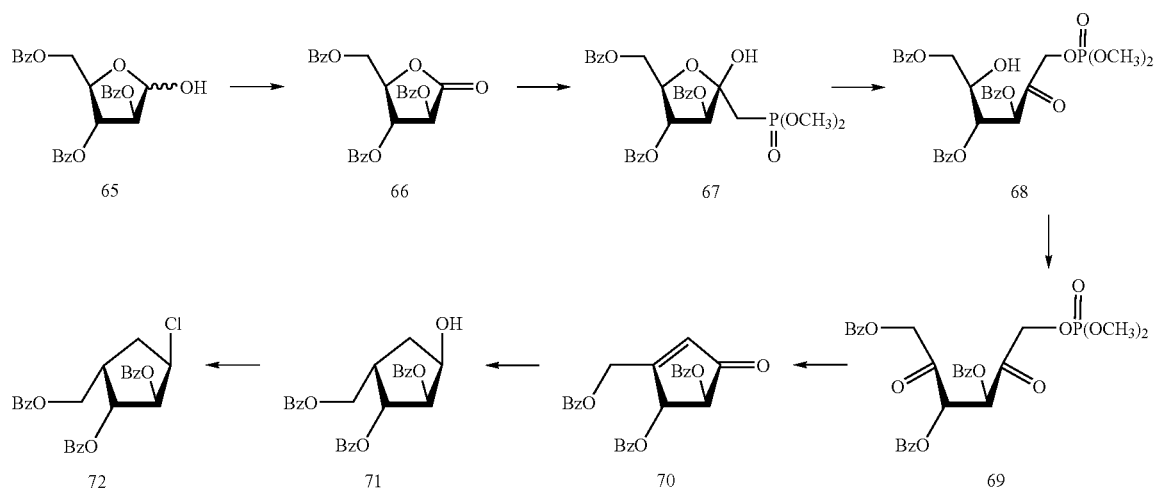

Alternatively, starting from 5-O-trityl-2,3-O-benzoyl-D-arabinolactone (73, Scheme 10), carba-L-nucleosides are synthesized.

E=H, OH, OMe, SH, SMe, $NH_2$, NHMe, N, F, Cl, Br, $CO_2H$, $CO_2Me$, $CO_2Et$, OPh, $OPhNO_2$, NO, $NO_2$, SCN, OCN, NCS, NCO, SOMe, $SO_2Me$

Scheme 10

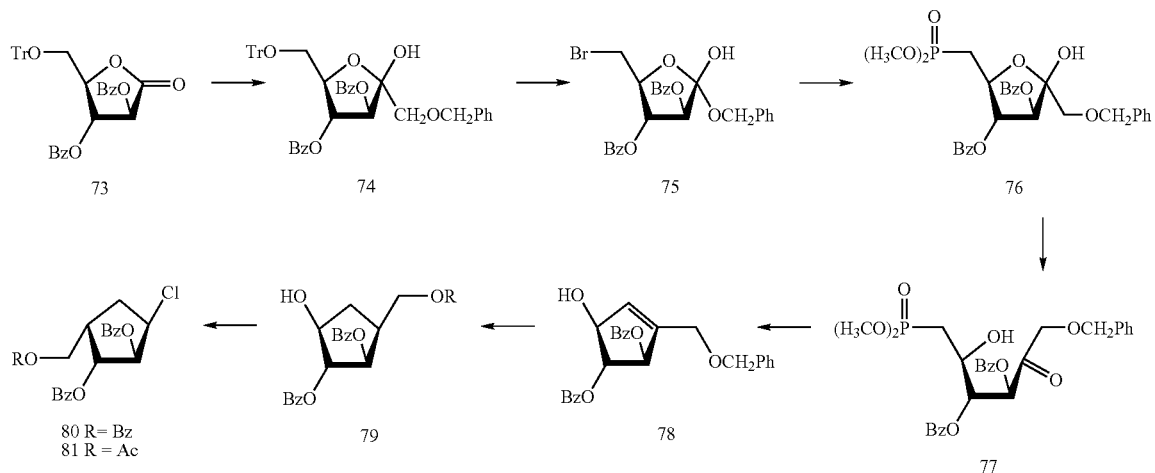

The present invention includes the synthesis of nucleosides with general formula [V] in Presentation 4, which are isomeric to compounds of formulas [I] and [II].

X=O, S, NH, $CH_2$, CHF, $CF_2$
Y=$CH_2$, NH, NOH, NMe, NEt, NOMe, CHF, $CF_2$
Z=H, OH, OMe, SH, SMe, F, Cl, Br, I, $NH_2$, NHMe

FIG. 4. 3'-Hydroxymethyl-xylo-nucleosides

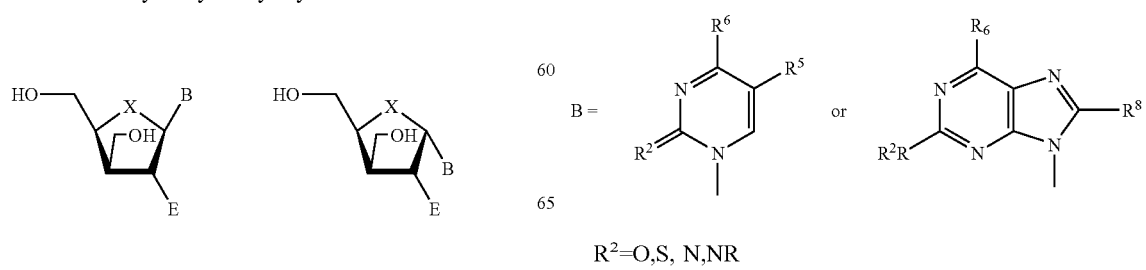

$R^2$=O, S, N, NR

R⁶=H, Me, Et, nPr, iPr, F, Cl, Br, I, CH=CH₂, CH=CHBr, Ph, Ac, OMe, OPh, NO, NO₂, NH₂, NHR

R⁶ and R⁸: Same or different, and H, OH, OMe, SH, SMe, Cl, Br, I, NH₂, NHMe, NMe₂

Of this class of compounds, 2'-deoxy-carba-nucleosides are of particular interest. Such compounds do not have the D and L distinction as shown in Presentation 5. However, there is anomeric configuration the as the all cis-compound [E] (β-nucleoside) is not superimposible to trans-nucleoside [F] (α-nucleoside).

Presentation 5. Nucleosides without D,L Distinction

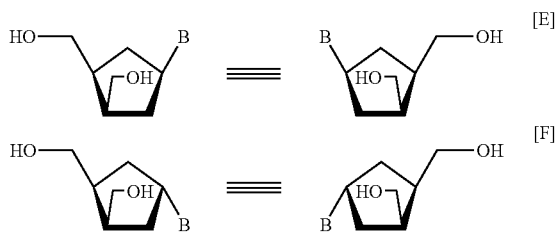

The β-nucleosides [E] is synthesized as shown in Scheme 11. Compound 56 (described in Scheme 7) is readily converted into 82 by treatment with NaN₃ followed by reduction. After saponification, the product 83 is converted into 3,5-O-isopropylidene derivative, and then deoxygenated to 85 by way of 2-phenoxythiocarbonyl derivative 84. After mild acid treatment to remove the isopropylidene group, the product is tritylated to give 86. Oxidation of 86 under Bergstrom's conditions affords 87, which, upon treatment with benzyloxy-methyltriphenylphosphorane, is converted into 88. Hydrogenation of the latter gives the all cis or β-nucleoside exclusively. Apparently the attack of hydride occurs from the least hindered α-side.

The synthesis of trans or α-nucleosides starts with 55, which is converted into the tetrahydropyranyl derivative 90 (Scheme 12). Saponification in base removes benzoyl groups from 90 to give 91, which is then benzylated to 92 with NaH and benzyl halide in tetrahydrofuran. Compound 92 is hydrolyzed in mild acid, and the product 93 is sulfonylated with mesyl chloride, tosyl chloride or triflyl chloride or the like in organic base, such as pyridine in the presence or absence of 4-N,N-dimethylaminopyridine. The product 94 is treated with NaBr in N,N-dimethylformamide to give the β-halogeno derivative 95, which is further converted into the α-azide 96 with NaN₃. This reaction sequence, namely, replacement of the participating benzoyl protecting groups with non-participating benzyl groups is necessary. If the protecting groups in 95 are benzoyl, the next reaction gives the β-azide product by the neighboring group participation instead of the desired α-azide derivative 96. Staudinger reduction of 96 with triphenylphosphine selectively converts the azide into the amine giving rise to 97, which is further converted into nucleosides 98 as described earlier. Catalytic hydrogenation, followed by isopropylidenation with acetone and 2,2-dimethoxypropane in the presence of p-toluenesulfonic acid affords 99, which is deoxygenated to 101 by way of the phenoxythiocarbonyl intermediate 100. De-O-isopropylidenation of 101 with diluted acetic acid, followed by tritylation gives 102. Oxidation of 102 under Swern's conditions with dimethylsolfoxide and oxalyl chloride to give 3'-ketone, which is treated with triphenylbenzyloxymethylenephosphorane to afford 103. Hydrogenation of 103 occurs selectively from the less hindered α-side giving the desired α-nucleoside 104.

Scheme 11

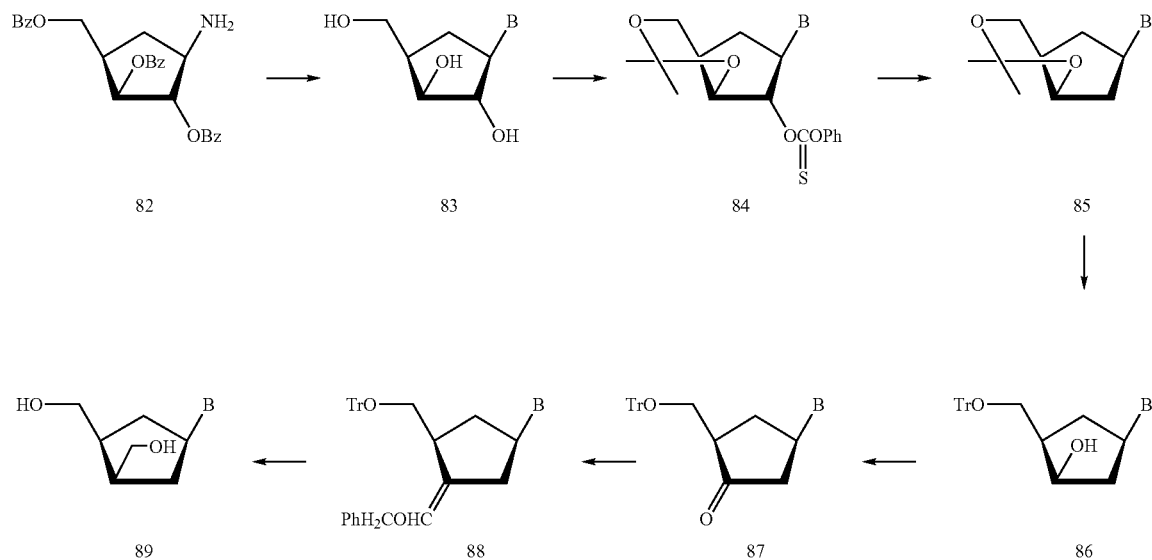

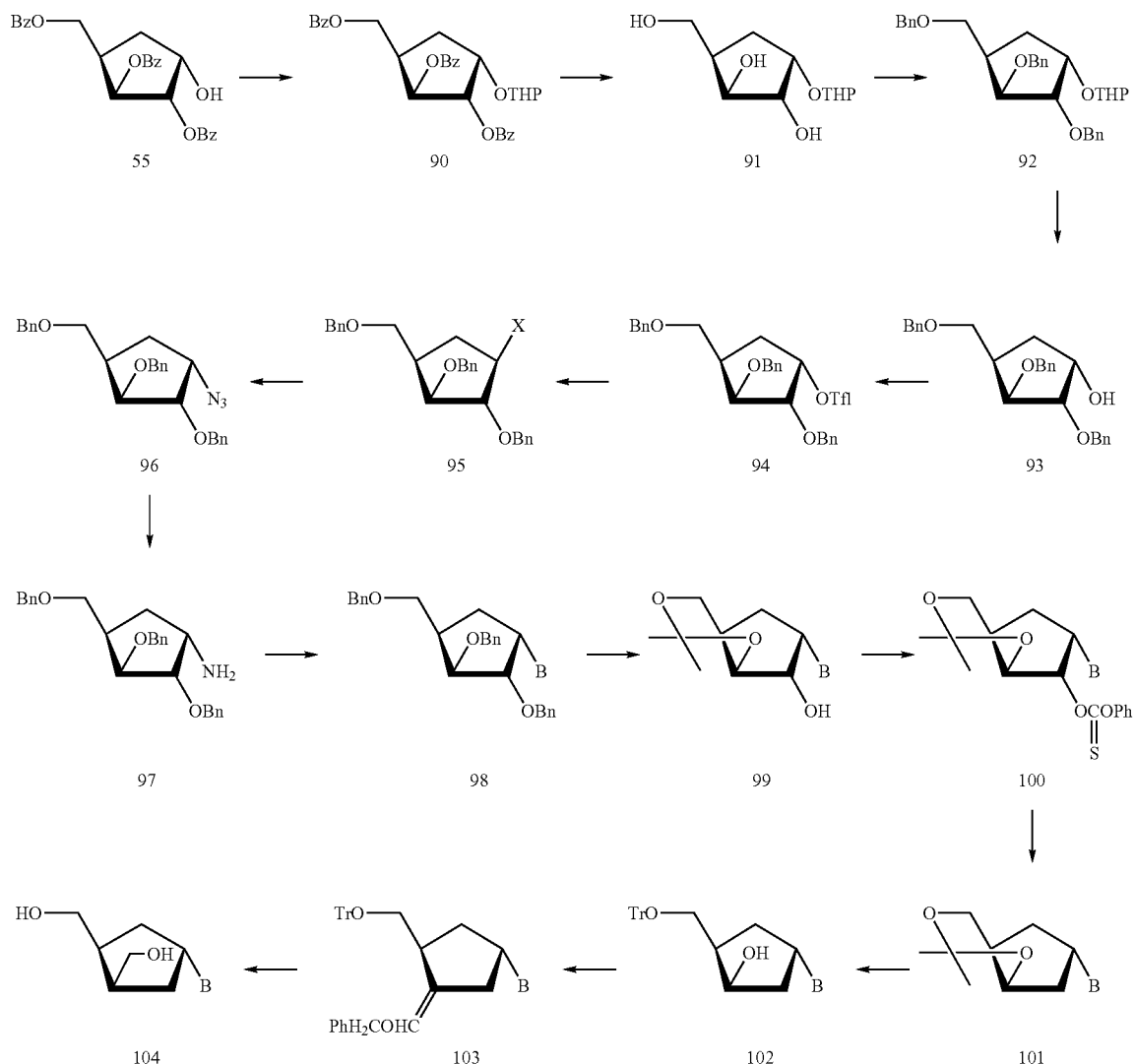

Scheme 12

Stereospecific Synthesis of Nucleoside 5'-monophosphates

Antiviral nucleosides must be converted into their corresponding 5'-triphosphates to exert biological activity. If these nucleosides are very poor substrates for nucleoside kinase(s), they will not exhibit significant activity. However, their synthetic monophosphates may be good substrates for nucleotide kinases, and can be converted into the corresponding triphosphates which are expected to become inhibitors or substrates of polymerases. In many cases, among the three successive phosphorylation steps, the first (catalyzed by nucleoside kinase) is rate limiting, and further conversions to the di- and tri-phosphates are catalyzed by less specific nucleotide kinases. Unfortunately, nucleotides cannot be used as chemotherapeutic agents because there are problems of cell membrane penetration and stability toward hydrolyzing enzymes. It has been demonstrated that the monoester of hydrogenphosphonate (H-phosphonate) or methylphosphonate (Me-phosphonate), which has only one dissociable proton, is a weak acid with pKa of 3–4. Such monoester of phosphonate is much more lipophilic than the corresponding phosphate and should be cell membrane penetrable. The phosphonate analogues are known as more apt for cellular uptake than the parent phosphates. Thus, nucleoside 5'-H-phosphonates are synthesized (see, Scheme 14) as prodrugs, which, after entering the cell, are oxidized to their corresponding 5'-phosphates by biological oxidizing systems, such as cytochrome C.

Pyrimidine β-nucleoside 5'-phosphates

Application of the Mitsunobu reaction to chiral nucleoside 48 affords anhydro-derivative 105 (Scheme 13), which is benzoylated to give 106. After mild alkaline hydrolysis of 106, the product 107 is phosphorylated by the Yoshikawa procedure [$POCl_3$/(MeO)$_3$PO—H$_2$O] or the Roescher-Jastorff procedure [$POCl_3$/pyridine-acetone] to give nucleotide 108. Saponification of the benzoyl group gives the desired β-nucleoside 5'-phosphate (109). Instead of using the benzoyl protecting group, acid labile protecting group, such as tetrahydropyranyl (THP) or trityl group, or dimethyl-t-butylsilyl (DMBS) can also be used.

Scheme 13

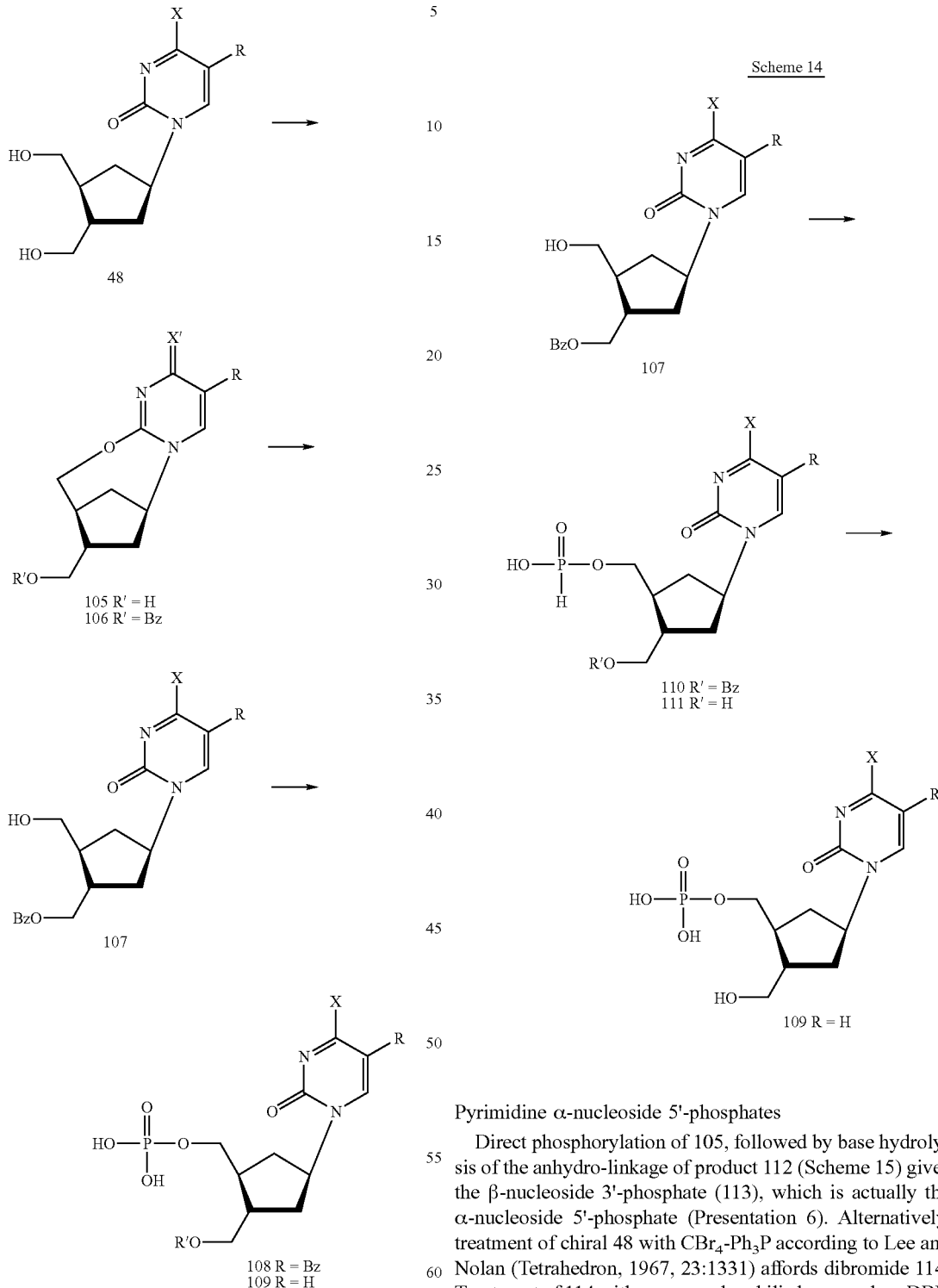

Scheme 14

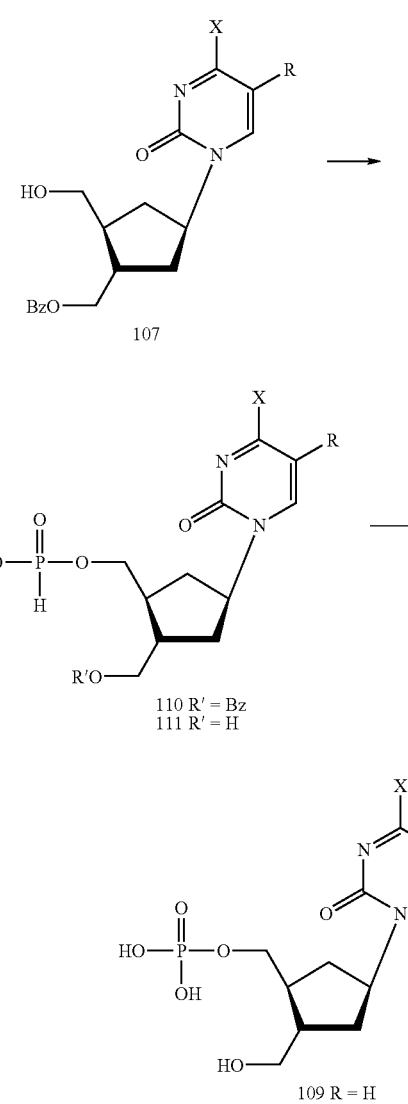

Another method for preparation of β-phosphate (109) is to phosphitylate 107 with tris-(1,1,1,3,3,3-hexafluoro-2-propyl)phosphite to 110 (Scheme 14). After removal of the benzoyl group in base, the product 111 is oxidized to 109 according to Matulic-Adamic, et al. (Nucleosides Nucleotides, 1993, 12:1085). Compound 111 can be viewed as a prodrug of 109.

Pyrimidine α-nucleoside 5'-phosphates

Direct phosphorylation of 105, followed by base hydrolysis of the anhydro-linkage of product 112 (Scheme 15) gives the β-nucleoside 3'-phosphate (113), which is actually the α-nucleoside 5'-phosphate (Presentation 6). Alternatively, treatment of chiral 48 with $CBr_4$-$Ph_3P$ according to Lee and Nolan (Tetrahedron, 1967, 23:1331) affords dibromide 114. Treatment of 114 with a non-nucleophilic base, such as DBU or DBN, in an inert solvent such as DMF, THF, or a like, affords anhydro-nucleoside 115. Treatment of 115 with tribenzylphosphite causes the Arbuzov reaction giving rise to 116, which is hydrogenated to remove benzyl groups affording 113.

Scheme 15

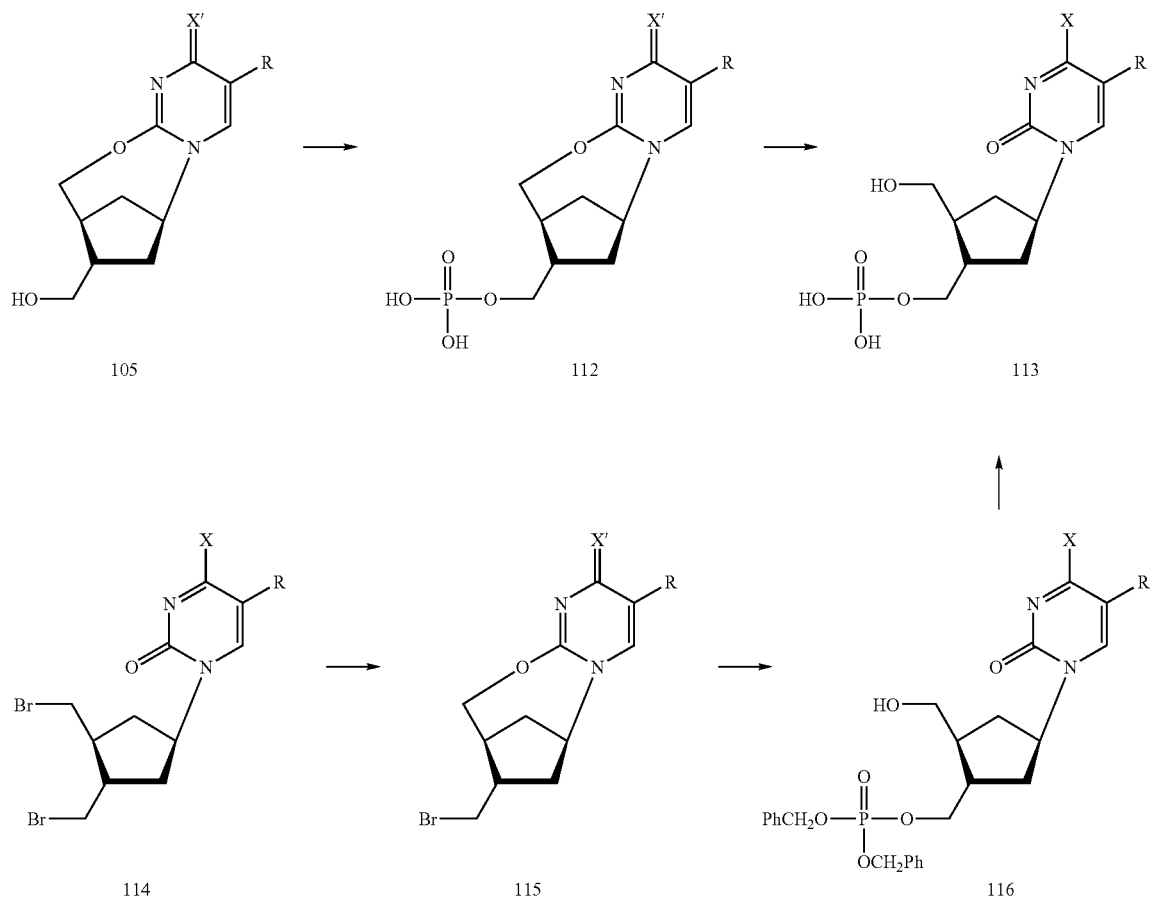

Presentation 6

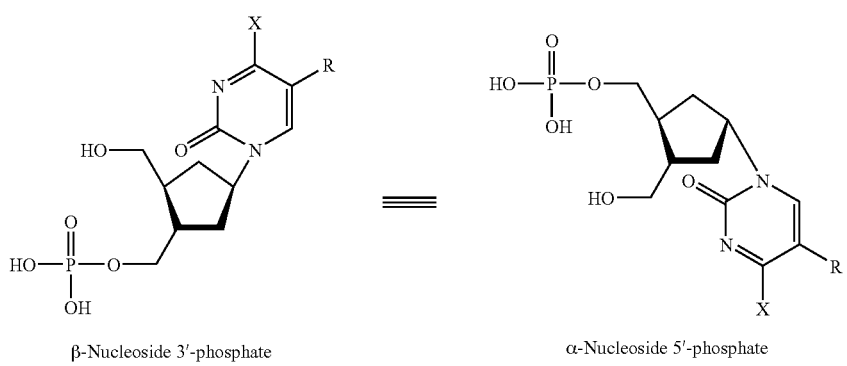

β-Nucleoside 3′-phosphate ≡ α-Nucleoside 5′-phosphate

Purine β-nucleoside 5′-phosphates.

Purine nucleoside is readily converted into the 8-thio-derivative 117 (Scheme 16) via bromination, followed by thiourea treatment. Application of modified Mitsunobu reaction to 117 gives the S-anhydro product 118. After protection of the other primary OH group with a base stable protecting group, such as THP, the product 119 is subjected to mild oxidation with one equivalent of m-chloroperbenzoic acid to convert into sulfoxide 120. Pummerer rearrangement of 120 using benzoic anhydride affords 121. Desulfurization of 121 with Raney nickel to 122, followed by de-O-benzoylation in base gives 123. Phosphorylation of 123 to 124, followed by mild acid treatment furnishes the desired β-D-product 125.

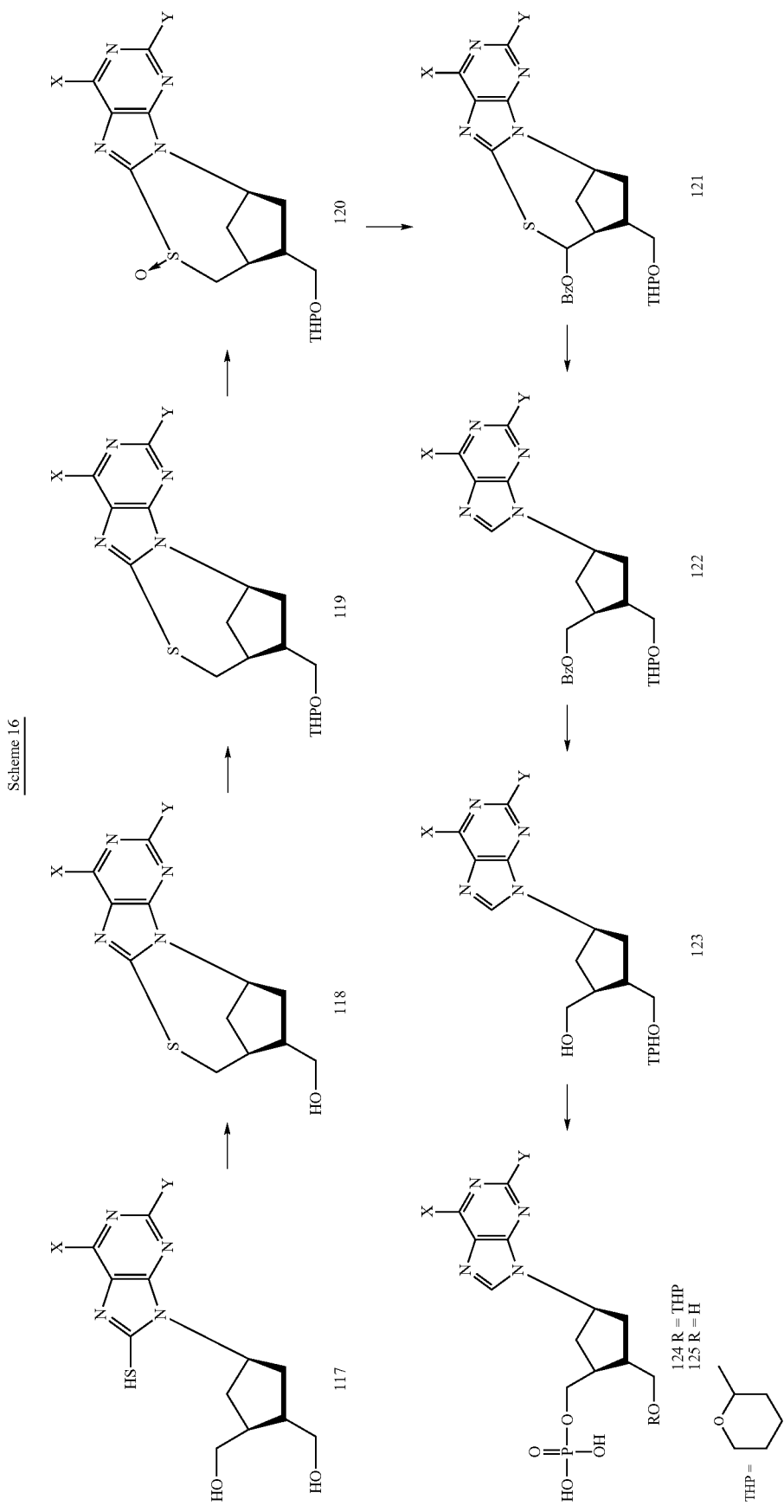

Purine α-nucleoside 5'-phosphates

For the synthesis of α-nucleoside 5'-phosphates, the intermediate 118 is directly phosphorylated to 126 (Scheme 17). Conversion of 126 to the desired cc-nucleotides 130 is achieved via oxidation to 127, followed by Pummerer rearrangement to 128, which is desulfurized to 129 with Raney nickel, and then debenzoylation.

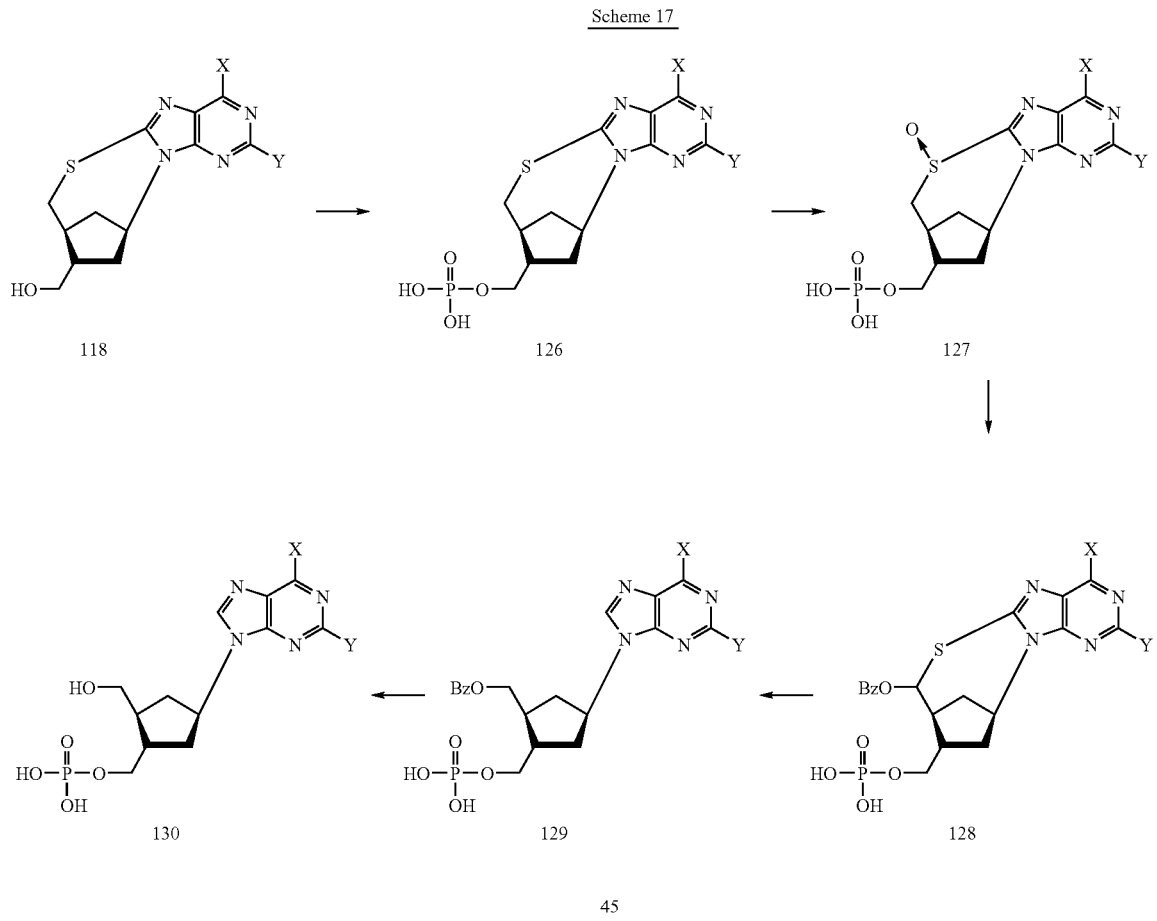

Alternatively, mild acid hydrolysis of 122 affords 131 (Scheme 18). Phosphorylation of 131 to 129, followed by debenzoylation gives 130.

-continued

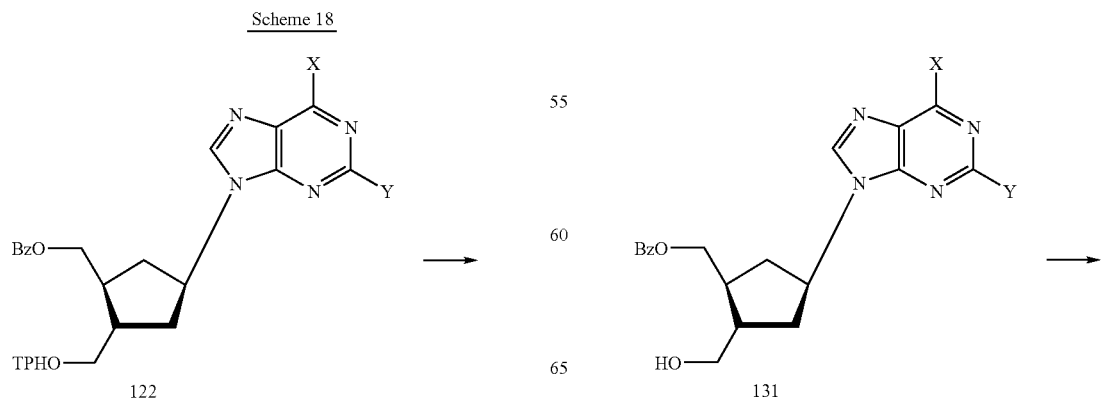

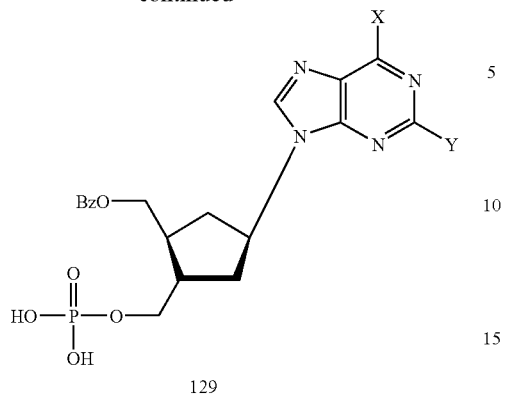

129

Synthesis of Nucleoside 5'-di- and 5'-triphosphates

Nucleoside 5'-monophosphates described above are converted into their corresponding 5'-di- and 5'-triphosphates by methods known in the art.

Synthesis of Enzymatically Stable Analogues of Nucleoside 5'-di- and 5'-triphosphates as Potential Anti-HBV and Anti-HCV Agents.

It is generally known in the art that certain inactive nucleosides become active against the reverse transcriptase of HIV when they are chemically converted into their corresponding 5'-triphosphates. For example, 3'-O-methylthymidine is inactive against HIV while its chemically synthesized 5'-triphosphate is an exceptionally potent inhibitor of HIV reverse transcriptase. This invention deals with the synthesis of methylenebis(phosphonate) based analogues of nucleoside 5'-di- and 5'-triphosphates. The rationale is based on the fact that a synthetic analogue of the important coenzyme, nicotinamide-adenine dinucleotide (NAD) in which the P—O—P is replaced by P—$CH_2$—P is reported to enter the cells. The phosphonate analogues, especially the P—F substituted analogues (Presentation 7) are less polar and less ionic than their parent di- or triphosphates. They therefore enter the cells relatively with ease. Several attempts have been made to develop prodrugs of nucleoside phosphates. However, the strategy of this invention is rather different than others, because the synthetic targets of this invention are not prodrugs but analogues of nucleoside di- and tri-phosphates which are not susceptible to enzymatic hydrolysis.

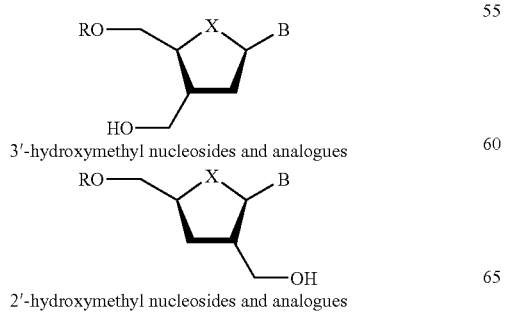

3'-hydroxymethyl nucleosides and analogues

2'-hydroxymethyl nucleosides and analogues

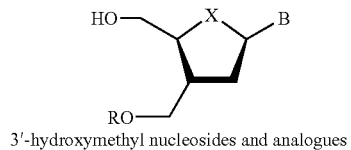

3'-hydroxymethyl nucleosides and analogues

2'-hydroxymethyl nucleosides and analogues

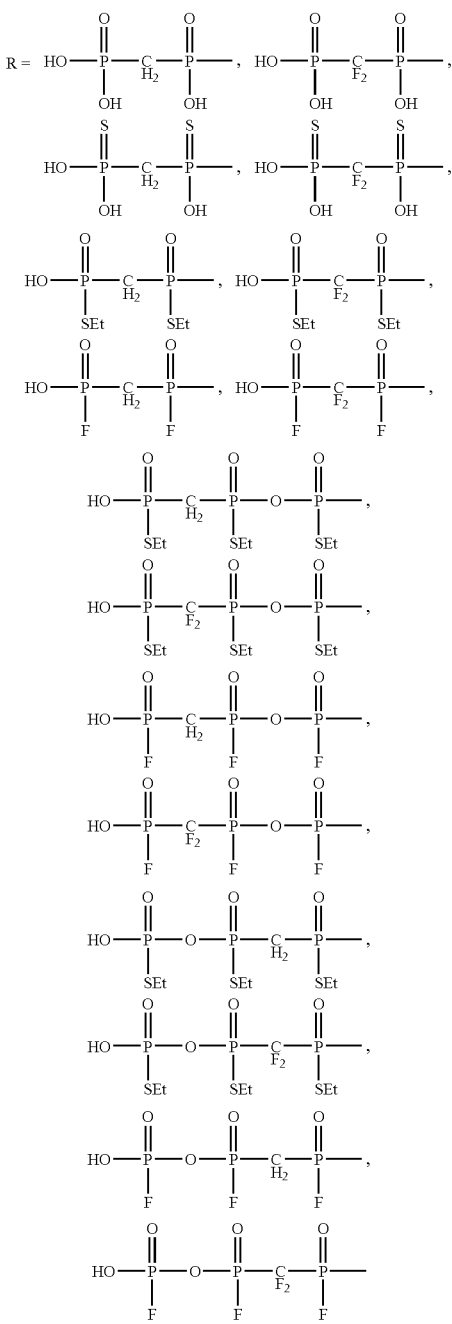

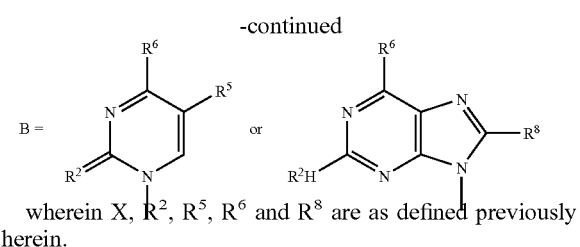

wherein X, $R^2$, $R^5$, $R^6$ and $R^8$ are as defined previously herein.

Scheme 19 illustrates the synthesis of P—F substituted dinucleotide analogues. Addition of sulfur to the known methylenediphosphite tetrachloride (132) produces dithiomethylenebis-(phosphonate) tetrachloride (133), which is hydrolyzed to give 134. Treatment of 107 or 123 with 133 under Yoshikawa-Roeschler's conditions gives the corresponding $P^1$-nucleoside-5'-yl-methylenebis-(thiophosphonate)s 135. Pyrimidine nucleoside 107 is converted into the 5'-sulfonyl derivative 136. When 136 is treated with the tris(tetrabutylammonium) salt of 134 in a polar solvent, such as dimethylsulfoxide gives the corresponding 135. S-Alkylation of 135 to 137, followed by treatment with fluoride ($Bu_4NF$, DAST) gives the protected fluorine substituted derivative 138. After mild deprotection of 138, the desired nucleotide analogue 139 is obtained. These compounds are stable (Sund and Chattopadhyaya, Tetrahedron, 1989, 45:7523; Dabkowski et al., J. Chem. Soc., Perkin Trans. I., 1992, 1447).

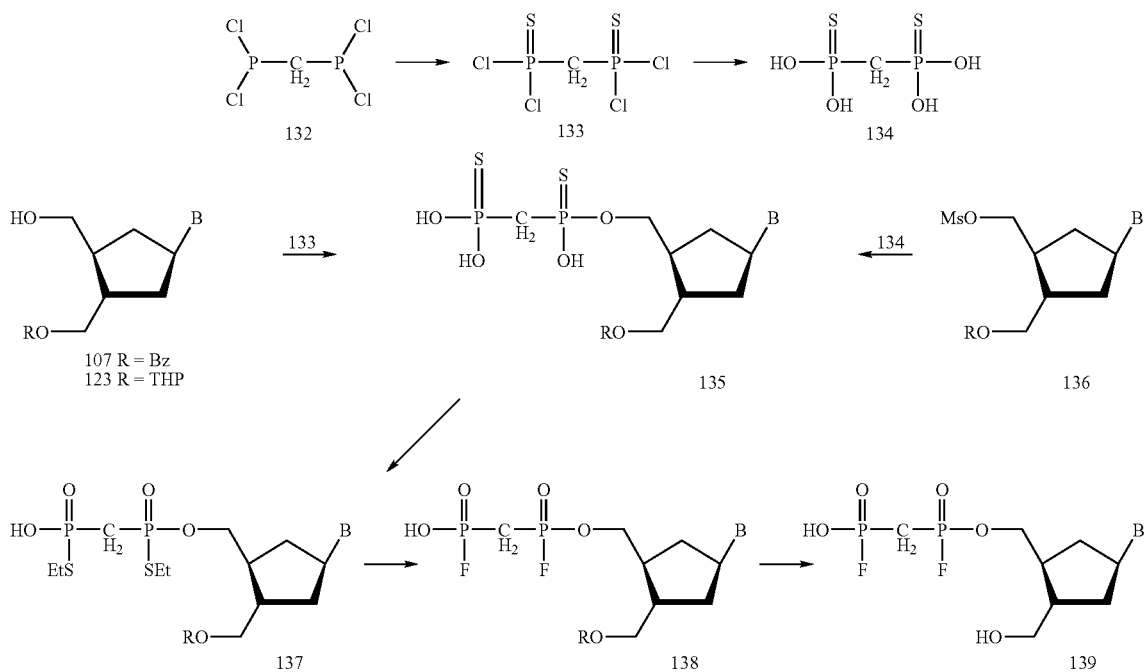

In a similar manner, the α-nucleoside 5'-triphosphate counterparts 144 are prepared starting from 105 and 118 (Scheme 20) or their 5'-O-mesylate 141 via the thiophosphonate 140, S-ethyl 142 and the protected P—F intermediates 143.

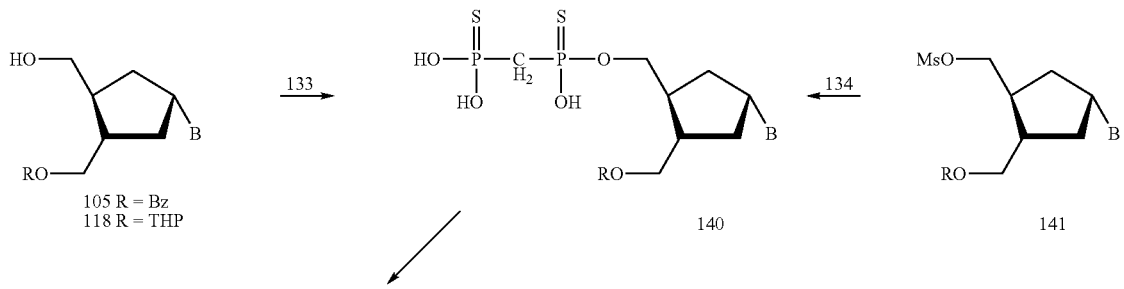

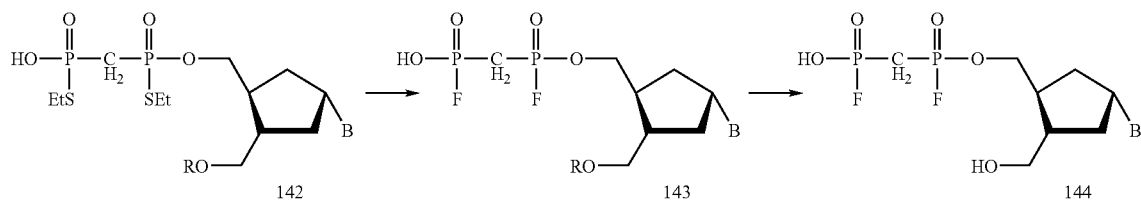

Synthesis of Nucleoside 5'-triphosphate Analogues.

Two types of triphosphate analogues are synthesized in the present invention. As shown in Presentation 8, one type contains an oxygen between α and β phosphorus, and the other between β and γ phosphorus atoms.

Presentation 8

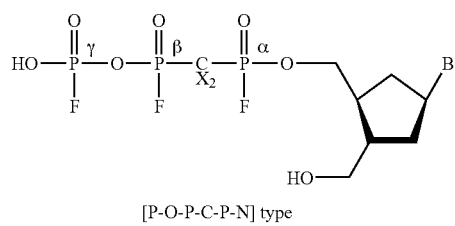

[P-O-P-C-P-N] type

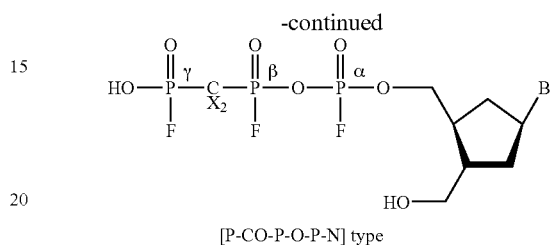

[P-CO-P-O-P-N] type

The starting material for nucleoside triphosphate analogues of [P—O—P—C—P—N] type is 135 (Scheme 21), which is converted into its bis(tetrabutylammonium) salt. Treatment of the salt with 2-(imidazol-1-yl)-4-H-1,3,2-benzodioxaphosphorin-4-one (145), followed by sulfurization gives the corresponding $P^1$-(nucleosid-5-yl)-$P^2$-(thiophosphoryl)methylenebis(dithiophosphonate)s 146. S-Ethylation of 146 with ethyl iodide and potassium carbonate in aqueous solution affords the tri-S-ethyl ester 147, which is treated with DAST to give 148. Alternatively, 137 is directly treated with 146, followed by sulfurization, to give rise to 149. S-Ethylation, followed by DAST treatment affords the desired P—F compound 148.

Scheme 21

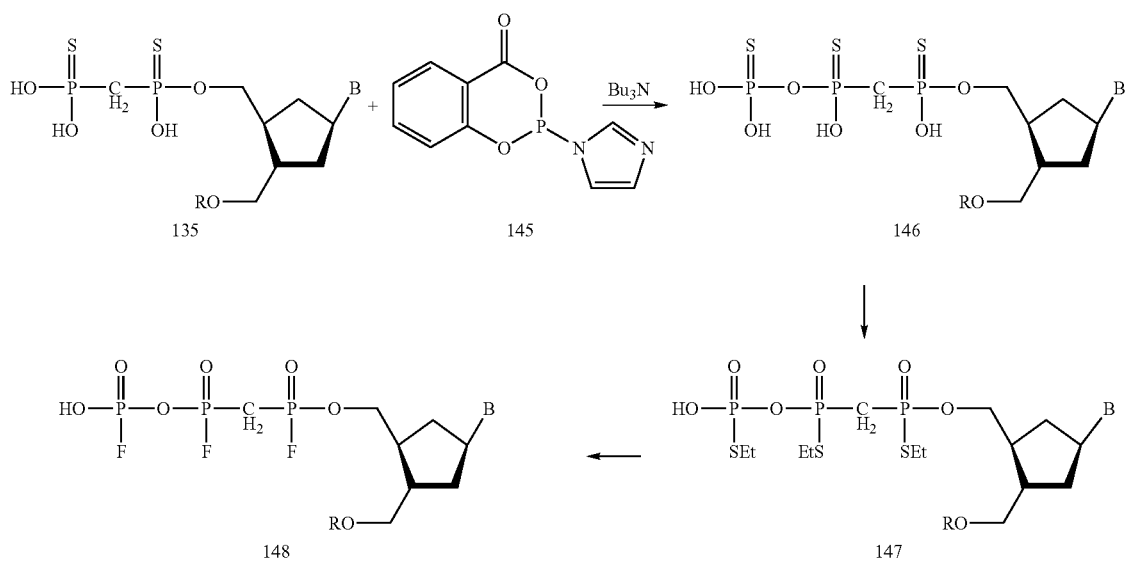

-continued

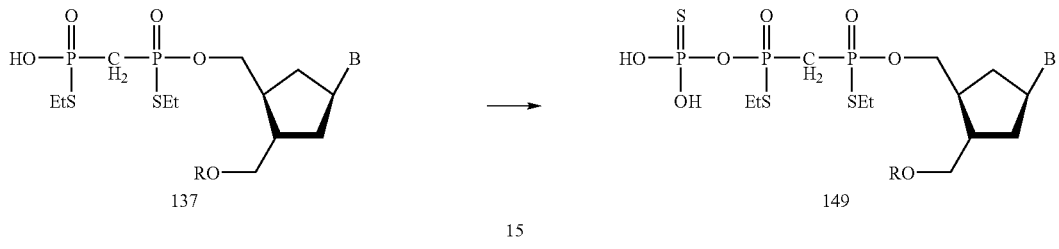

For the synthesis of [P—C—P—O—P—N] type, nucleoside 5'-H-phosphonate, such as 111, serves as the intermediate. Compound 111 is converted into 5'-thiophosphate 150 (Scheme 22) by methods known in the art. After mild alkylation of 150 with ethyl iodide, the product 151 is converted into imidazolide 152. Treatment of 152 with 134 gives 153, which, after S-alkylation to 154, is converted into the desired triphosphate analogue 155.

Scheme 22

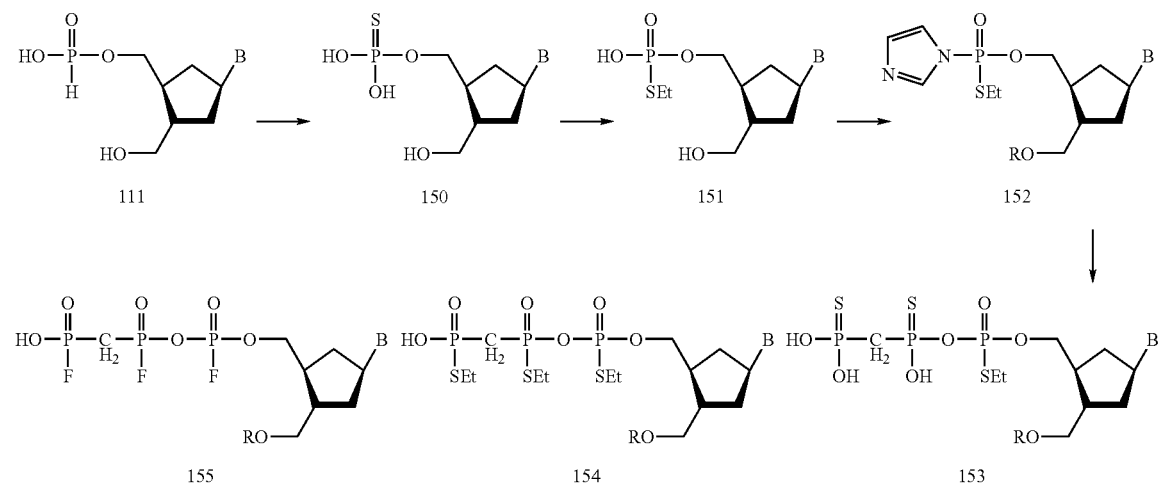

In a similar manner, purine nucleoside triphosphate analogues (both α-D, β-D, α-L and β-L) are synthesized.

In the general formulas [I–IV], wherein X=O, Y=NR and Z=OH, 3'-deoxy-3'-hydroxymethylthymidine (B=thymine, Y=NH) has been synthesized (Schreiber and Ikemoto, Tetrahedron Letters, 1988, 29:321 1). Other nucleosides of this type are prepared in a similar manner. In the present invention, special attention is focused to prepare 2'-β-fluorinated derivatives based on our recent development of a method of stereoselective addition of hydroxylamine derivatives to 2-substituted alkenoates (Zhao et al., J. Am. Chem. Soc., 1999, 12:2456; J. Org. Chem., 1999, 64, 4). Thus, butenolide 156 (Scheme 23) is protected with a base-stable group, such as t-butyldimethylsilyl (TBMS), t-butyldiphenylsilyl (TPMS) or tetrahydropyran (THP), to 157. Treatment of 157 with N-substituted hydroxylamine results in exclusive formation of the arabino compound 158, as the nucleophile attacks the least hindered α-face of 157. The N-hydroxyl group of 158 is protected with TBSCl in dry DMF to give lactone 159, which is reduced with DIBAL in methylene chloride to the corresponding lactol 160. The acetate derivative of 160 does not give the coupling product with silylated bases under Vorbruggen's conditions using TMSOTf as a catalyst. However, glycosyl chloride 161, which is easily prepared by employing mesyl chloride in the presence of trialkylamines (1 equiv. of triethylamine and a catalytic amount of tributylamine), is found to be coupled with silylated pyrimidine bases in an inert solvent, such as methylene chloride, chloroform, dichloroethane, tetrachloroethane, acetonitrile, dimethylformamide or a like, at temperature of from 25° C. to 115° C., preferably between 40° C. and 65° C. Protected nucleosides 162 are generally obtained as an anomeric mixture (α:β =~1:1) in the range of overall 65–70% yields from lactone 159. The two protecting groups are removed to give free nucleoside 163. When these protecting groups are TBMS, they are removed by treatment with tetrabutylammonium fluoride TBAF in dry THF. The α and β anomers are separated by chromatography, and the anomeric configuration of those nucleosides are determined by a well-established rule about the chemical shift of H-4'.

Scheme 23

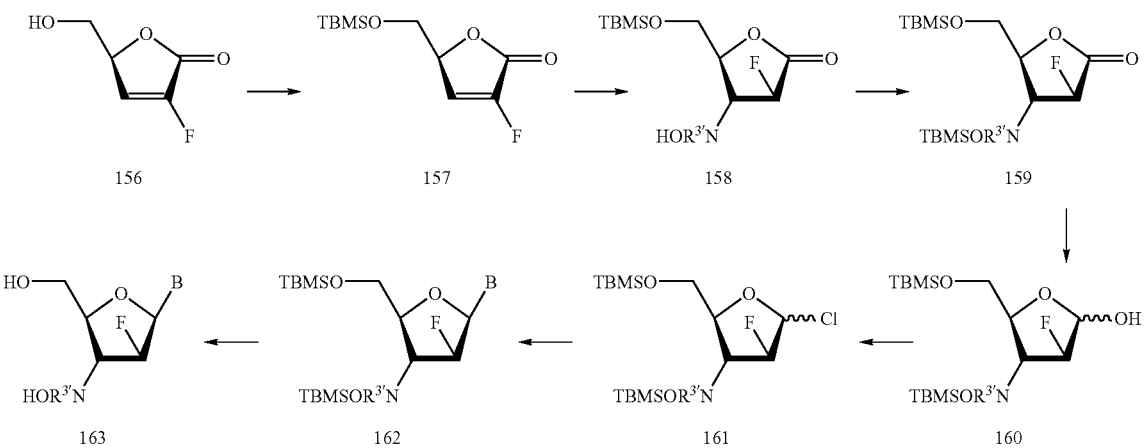

This invention further includes a new and convenient method for making libraries of 3'-N-substituted hydroxy-lamino-nucleosides of 163. For this purpose, 156 is converted into t-butyldiphenyl-silyl (TBPS) protected derivative 164 (Scheme 24) as a readily available common intermediate instead of 157 for the purpose of selective desilylation later in our synthetic route. The concerted addition of N-methylhydroxylamine to 164 under the aforementioned conditions affords adduct 165 as a single isomer, which is converted into glycosyl chloride 168 after successive TBMS-protection to 166, DIBAL reduction to 167, and MsCl chlorination. Intermediate 168 is then reacted with silylated pyrimidines to form protected nucleosides 169 usually as a mixture of anomeric isomers (about 1:1). The O-TBMS group is selectively removed by the use of 48% HF in acetonitrile in nearly quantitative yields to give hydroxylamines 170.

The unique property of hydroxylamine allows the potential replacement of N-methyl functionality, which is an unusual nitrogen-protecting moiety, by other N-alkyl groups. Thus, nucleosides of type 170 are oxidized with an oxidizing agent, such as yellow mercury (II) oxide or DDQ, preferably DDQ to give the corresponding nitrone intermediates 171, in which the N-methyl group of 170 is selectively converted N-methylene. Hydroxylamine is used to efficiently remove the N-methylene group of the nitrones 171 by exchange reactions in an alkanol, such as methanol, ethanol, n-propanol or isopropanol, preferably methanol at a temperature of from 25° C. to 100° C., preferably 40–50° C. to give key intermediates 172. Aliphatic nitrones are easily obtained by coupling of 172 with different carboxaldehydes, including butyraldehyde, isobutyraldehyde and cyclohexan-ecarboxaldehyde in alkanol, such as methanol, ethanol, n-propanol or isopropanol or the like, preferably methanol, to give nitrones 173. The corresponding nitrones are then subjected to the in situ reductions by NaBH$_3$CN to N-alkyl products 174 and overall yields are in the range of 65–93% for the last two steps. The desired nucleosides 175 are finally obtained by the treatment of TBAF in dry THF in 70–96% yields.

Scheme 24

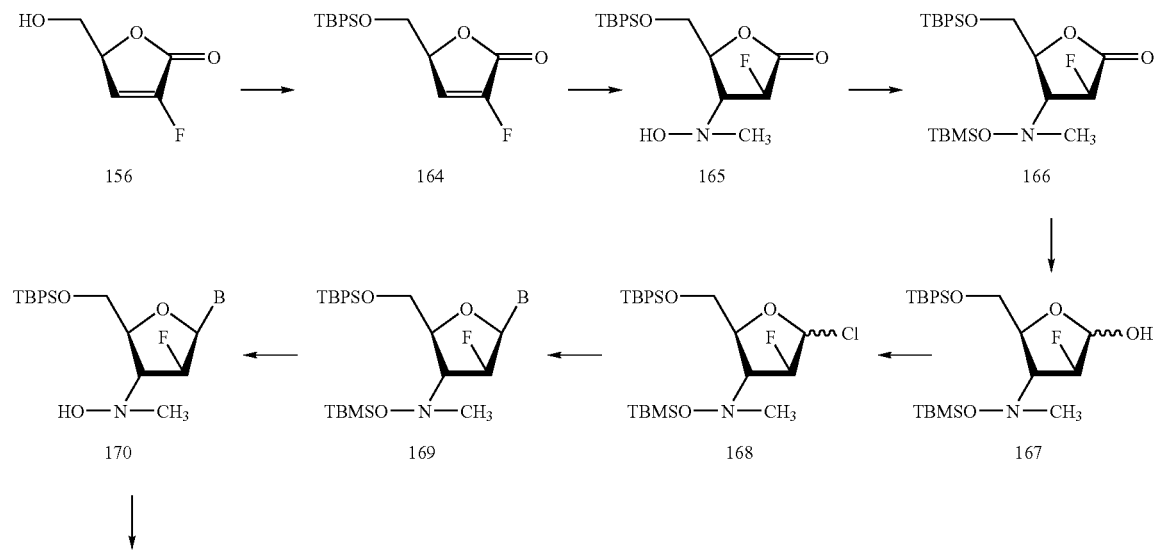

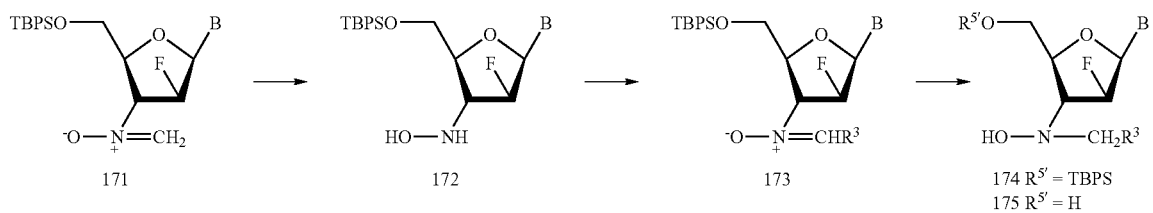

The present invention also includes general methods for stereoselective synthesis of 2'-fluoro-3'-alkylamino-arabinofuranosyl nucleosides by exploitation of the novel hydroxylamine chemistry developed during this invention. Unfortunately, 3'-N-substituted hydroxylamino nucleosides 163, 174 and 175 do not undergo catalytic hydrogenolysis to the corresponding amines. However, when their N-hydroxyl is acylated with a group, such as acetyl, benzoyl, toluoyl, or anisoyl or the like, preferably benzoyl, by treatment with acyl halide, preferably benzoyl chloride, in organic base, such as pyridine or triethylamine or a like, preferably pyridine, the product 176 (Scheme 25) is readily converted into the corresponding N-substituted amino derivatives 177 in high yields by catalytic hydrogenation over 5% Pd—C in alkanol, such as methanol, ethanol, n-propanol or isopropanol, at temperature from 0° C. to 100° C., preferably from 20° C. to 50° C. under a pressure of from 1 to 5 atms, preferably about 1 atm. Deprotection of 177 by treatment with TBAF in THF for 5'-O-TBPS and by saponification for 5'-O-benzoyl protecting group furnishes 3'-(N-substituted amino)-2'-fluoro-2',3'-dideoxy-arabinofuranosyl nucleosides 178. Alternatively, 158 or 165 is acylated, preferably benzoylated, to 179, which is converted into glycosyl halide 181 by way of DIBAL reduction to 180 and sulfonyl halide treatment. After condensation of 181 with silylated bases, the benzoyl protected nucleosides 182 are obtained. In particular, thymidine analogue (182, B=thymine) is formed as an anomeric mixture in an α/β ratio of 2:3, while only the desired β-isomer is produced for cytosine derivative (182, B=cytosine). Compounds 182 are subjected to hydrogenation in the presence of 5% Pd—C to cleave the N-OBz bond. Compounds 177 ($R^3$=CH$_3$) are obtained in very high yields and converted to final nucleosides 178 after treatment with TBAF in THF also in high yields.

Scheme 25

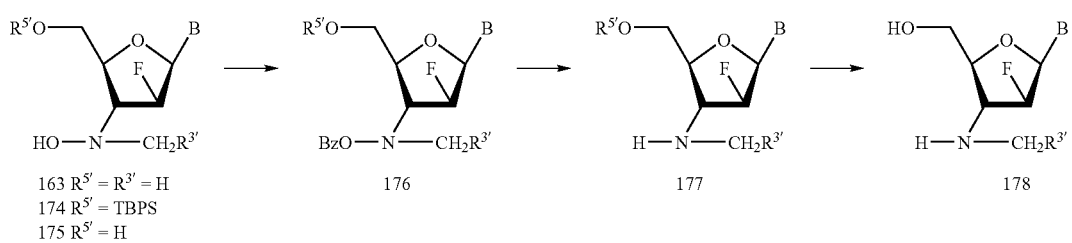

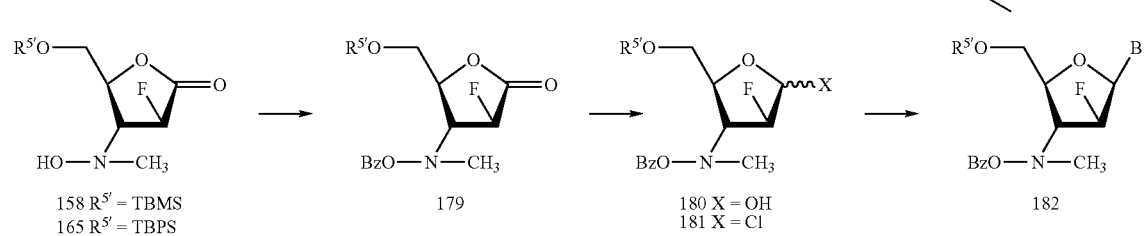

Biological Testing

Cell Culture Assay for Activity of Anti HBV Compounds

We follow the protocol described by Korba and Gerin (Antiviral Res., 1992, 19:55) and Pai et al. (Antimicrobial Agents Chemother., 1996, 40:380) which is used widely in the field. The HepG 2 2.2.15 cells contain a stably integrated HBV genome, the transcript from which serves as a template for viral replication. The cells produce virions which are elaborated into the medium. The production of the virion DNA is monitored by analysis of medium by Southern blotting. Drugs which inhibit viral replication reduce the levels of virion DNA in the medium, relative to controls.

For anti-HBV activity program, three cell culture based assays are used for determining the spectrum of antiviral activity and cytotoxicity of novel nucleosides. Two of these assays, the 2.2.15 cell line and the AD38 cell line, allow for the testing against wild type or nucleoside susceptible virus. The third assay, the AD79 cell line, can test for activity against a known mutant virus with resistance to certain nucleoside analogues such as 3TC (lamivudine). Parallel testing in various cell lines allows for a preliminary assessment of the toxicity of the test compounds. Those compounds that demonstrate anti-HBV activity in cell culture without cytotoxicity are candidates for further testing in animal models.

Protocol

For HepG 2.2.15 Cells:

Confluent cells in 24 well tissue culture dishes are treated with test compounds starting at 1 nM and extending logarithmically to 10 µM (1 nM, 3.2, 10 nM, 32, 100 nM, 1 µM, 10 µM 100 µM). Medium is changed daily every 3 days and DNA extracted from the 3, 6, and 10 9 day samples. The virions are concentrated by polyethylene glycol precipitation (equal volume addition of PEG 8000). After cooling on ice the samples are spun and the pellets treated with SDS and Proteinase K followed by Phenol:Chloroform extraction and ethanol precipitation of the DNA. The DNA is analyzed for HBV sequences by Southern hybridization. The probe used for the analysis is a $^{32}P$ labeled Eco RI fragment from the HBV clone described by Korba et al. 3TC is used as a positive control compound with known activity against HBV.

This assay reflects the amount of viral DNA in the medium. For compounds which are proven to be effective inhibitors against HBV as compared to 3TC the analysis is extended to the viral DNA forms present inside cells. This is done by DNA extraction from cells, followed by electrophoresis and blotting. Analysis of the Southern blot shows the various replicative intermediates and indicates which stage of replication is blocked.

For AD38 and AD79 Cells:

Antiviral activity in AD38 and AD79 cells was determined as described by Ladner et al. (Antivir. Chem. Chemother., 1997, 41:1715). Briefly, cells were plated into a 96-well microtiter plate in the presence of 0.3 µg/ml tetracycline. After three days, the cell monolayers were washed several times with warmed PBS and treated with medium containing various concentrations of inhibitor. At 3 and 6 days after commencement of drug treatment, the cells were washed with PBS and treated with fresh medium containing inhibitor. At 7 days after commencement of drug treatment, the medium was collected from the wells and clarified by centrifugation. The clarified supernatant fluids were assayed for the presence of HBV DNA by dot blot hybridization and phosphorimager analysis. The concentration of compound that reduced the amount of HBV DNA by 50 or 90% ($EC_{50}$ and $EC_{90}$, respectively) was determined by linear regression analysis of the data.

For Cytotoxicity:

We also perform toxicity assays by measuring the inhibition of uptake of neutral red dye by treated cells. These assays are done in 96 well plates. After the standard 10 day treatment regimen medium is removed and PBS containing MTS dye added to each well. After a 2 hour incubation the absorbance of the metabolized product is measured at 490 nm.

Animal Tests

Compounds can be tested in an HBV-transgenic SCID mouse model and determine the in vivo potency and tolerance of the compounds. Additional testing in woodchuck hepatitis model is also available. Compounds that demonstrate both in vitro and in vivo anti-HBV activity are candidates for further preclinical development. The compounds (chosen on the basis of activity determined in the in vitro assay) are tested in the woodchuck model.

Briefly, woodchucks, chronically infected with woodchuck hepatitis virus, are administered compounds intraperitoneally for 14 days. In separate trials, compounds are administered orally. The effect on virus production is monitored by analysis of serum samples for viral DNA and viral surface antigen. Levels of viral DNA are also determined in liver biopsies. Additionally, compounds are tested in chimpanzees infected with HCV for their effect on virus production and clinical hepatitis. Briefly, chimpanzees previously infected with HCV are tested orally with compound for 7–28 days. HCV RNA in blood is measured and liver biopsies are analyzed. Also, SCID mice transfected with human PBMC and infected with HIV can be used to test the anti-HIV activity of compounds.

Hepatitis D Methodology

Hepatitis D virus infection can be studied in the chimpanzee woodchucks and Pekin ducks using procedures well known in the art.

For Anti HIV Evaluation

Human PBM cells from healthy donors, seronegative for HIV-1 and HBV, are isolated by a single-step Ficoll-Hypaque discontinuous gradient centrifugation and propagated as described previously (Schinazi et al., Antimicrobial Agents Chemother., 1990, 34:1061; 1992, 36:2423; 1993, 37:875). Compounds are screened for activity against HIV-1 and cytotoxicity by a protocol reported previously reported by Schinazi, et al. The prototype strain of HIV-1LAI obtained from the Centers for Disease Control and Prevention, Atlanta, Ga., is used as the standard virus for the studies in human PBM cells.

EXAMPLES

Example 1

5-O-[tert-Butyldimethylsilyl-2,3-dideoxy-2-fluoro-3-(N-hydroxy-N-methylamino)]-arabino-1,4-lactone (158, $R^3$=H): To a solution of N-methylhydroxylamine hydrochloride (12.53 g, 150 mmol) in ethanol (300 mL) is added NaOEt (10.20 g, 150 mmol) portionwise. The resulting mixture is stirred at room temperature for 10 minutes and 2-fluorobutenolide 157 (7.38 g, 30 mmol) is then added. The resulting solution is refluxed for 5 hours and then concentrated under reduced pressure. 100 mL of water is added to the residue and the resulting solution is extracted with methylene chloride. The organic layer is washed with brine, dried over $Na_2SO_4$, filtrated, and concentrated. The residue is purified by flash column chromatography over silica gel eluting with 25% EtOAc/petroleum ether to give lactone 158 (6.08 g, 69%) as an oil. $^1$H NMR (CDCl$_3$) δ 6.30 (bs, 1H, OH), 5.53 (dd, J=7.2 and 51.4 Hz, 1H, H-2), 4.51 (dt, J=7.2 and 2.4 Hz, 1H, H-4), 3.85 (m, 3H, H-3 and H-5), 2.78 (S, 3H, NCH$_3$), 0.89 (s, 9H, t-Bu), 0.08 (s, 6H, 2SiCH$_3$). $^{13}$C NMR (CDCl$_3$) δ 88.1, 84.3, 79.4, 79.3, 69.2, 68.8, 62.4, 47.5, 26.3, −4.8, −4.9. Anal. Calcd for $C_{12}H_{24}FNO_4Si$: C, 49.12; H, 8.24; N, 4.77. Found: C, 49.23; H, 8.30; N, 4.81.

Example 2

5-O-{tert-Butyldimethylsilyl-2,3-dideoxy-2-fluoro-3-[N-(tert-butyldimethylsilyloxy)-N-methylamino]}-arabino-1,4-lactone (159): A mixture of 158 (5.50 g, 18.7 mmol), TBSCl (3.10 g, 20.6 mmol) and imidazole (2.80 g, 41.2 mmol) in anhydrous DMF (90 mL) is stirred under argon atmosphere at room temperature overnight. After addition of water, the resulting mixture is extracted with methylene chloride. The organic layer is washed with brine, dried over $Na_2SO_4$, filtrated, and concentrated. The residue is purified with flash column chromatography over silica gel eluting with 5% EtOAc/petroleum ether to give compound 3(7.10g, 93%) as an oil. $^1$H NMR (CDCl$_3$)δ 5.50 (br, 1H, H-2), 4.38(bs, 1H, H-4), 3.80 (m, 3H, H-3 and H-5), 2.69 (s, 3H, NCH$_3$), 0.85 (s, 18H, 2t-Bu), 0.08 (m, 12H, 4SiCH$_3$). $^{13}$C NMR (CDCl$_3$) δ 78.6, 78.5, 70.1, 69.7, 61.1, 47.7, 26.4, 26.3, 18.8, 18.2, −3.9, −4.1, −4.8,−4.9.

Example 3

5-O-{tert-Butyldimethylsilyl-2,3-dideoxy-2-fluoro-3-[N-(tert-butyldimethylsilyloxy)-N-methylamino]}-arabino-1,4-lactol (160): To a solution of compound 159 (5.45 g, 13.5 mmol) in dry $CH_2Cl_2$ (80 mL) at −78° C. is added DIBAL (14.9 mL, 1.0 M in hexane) in an argon atmosphere. The reaction mixture is stirred at −78° C. for 1 hour, and quenched with methanol (10 mL) and followed by saturated NH$_4$Cl. After the resulting solution is warmed 3to room temperature, solid materials are removed by filtration over Celite and the filtrate is extracted with methylene chloride. The organic layer is washed with brine, dried over $Na_2SO_4$, filtrated, and concentrated to give the crude lactol 160 (5.07 g) as a colorless oil which was directly used in the next step without further purification.

Example 4

General procedure for synthesis of 5'-O-tert-butyldimethylsilyl-2', 3'-dideoxy-2'-fluoro-3'-[N-(O-tert-butyldimethylsiloxy)-N-methylamino]-D-arabinofuranosyl nucleosides (162): To a solution of crude lactol 160 (0.409 g, 1 mmol), Et$_3$N (0.162 g, 1.6 mmol) and n-Bu$_3$N (0.037 g, 0.2 mmol) in dry $CH_2Cl_2$ (1 mL) at −40° C. is added MsCl (0.149 g, 1.3 mmol) dropwise in an argon atmosphere. After stirring at room temperature for 1 hour, the resulting mixture is diluted with methylene chloride, washed with water, brine, dried over $Na_2SO_4$, filtrated, and concentrated to give crude chloro sugar 161 as a yellowish oil which is used in glycosylation without further purification.

A mixture of TMS-protected base (3 mmol) and the crude chloro sugar 161 in ethanol free chloroform (5 mL) is refluxed overnight. After the addition of water, the resulting mixture is extracted with methylene chloride. The organic layer is washed with brine, dried over $Na_2SO_4$, filtrated, and concentrated. The residue is purified on a silica gel column eluting with 25–50% EtOAc/petroleum ether to give the protected nucleosides 162.

{5'-O-tert-Butyldimethylsilyl-2',3'-dideoxy-2'-fluoro-3'-[N-(O-tert-butyldimethylsiloxy)-N-methylamino]-D-arabinofuranosyl}uracil (162, B=uracil): The uridine derivative (68% total) 162 (B=U) is obtained as an anomeric mixture, which is partially separated by silica gel column chromatography as white solids. 162β (B=uracil): $^1$H NMR (CDCl$_3$) δ 10.00 (bs, 1H, NH), 7.63 (d, J=7.3 Hz, 1H, H-6), 6.09 (dd, J=3.7 and 17.6 Hz, 1H, H-1'), 5.66 (d, J=8.1 Hz, 1H, H-5), 5.55 (br, 1H, H-2'), 3.80 (m, 3H, H-4' and H-5'), 3.50 (dd, J=5.1 and 26.3 Hz, 1H, H-3'), 2.69 (s, 3H, NCH$_3$), 0.88 (s, 18H, 2t-Bu), 0.15 (m, 12H, 4SiCH$_3$). $^{13}$C NMR (CDCl$_3$) δ 164.1, 150.7, 141.8, 101.9, 85.1, 84.9, 74.5, 74.1, 62.8, 47.7, 26.5, 26.4, 18.8, 18.2, −3.8, −4.0, −4.8, −4.9. 162a (B=U): $^1$H NMR (CDCl$_3$) δ 9.50 (s, 1H, NH), 7.35 (d, J=8.1 Hz, 1H, H-6), 6.17 (dd, J=3.9 and 14.6Hz, 1H, H-1'), 5.75 (d, J=8.1 Hz, 1H, H-5), 5.55 (br, 1H, H-2'), 4.23 (bs, 1H, H-4'), 3.88 (dd, J=2,6 and 11.4 Hz, 1H, H-5'), 3.74 (dd, J=3.4 and 11.4 Hz, 1H, H-5'), 3.62 (dt, J=5.4 and 25.0 Hz, 1H, H-3'), 2.68 (s, 3H, NCH$_3$), 0.90 (s, 9H, t-Bu), 0.87 (s, 9H, t-Bu), 0.15 (m, 12H, 4SiCH$_3$). $^{13}$C NMR (CDCl$_3$) δ 163.8, 150.7, 139.8, 103.3, 90.2, 89.8, 82.5, 82.4, 74.4, 74.0, 47.9, 26.5, 26.4, 18.9, 18.2, −3.9, −4.0, −4.7, −4.8.

In a similar manner but using the corresponding silyated bases, the following nucleosides are prepared:

1-{5'-O-tert-Butyldimethylsilyl-2',3'-dideoxy-2'-fluoro-3'-[N-(O-tert-1-butyldimethylsiloxy)-N-1-methylamino]-β-D-arabinofuranosyl}thymine, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-fluorouracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-chlorouracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-bromouracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-iodouracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}5-ethyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-n-propyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5i-propyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5(E-2-bromovinyl)uracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-vinyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-carboxyuracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-ethoxycarbonyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-aminocarbonyluracil, 1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-cyanouracil,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-phenyluracil,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-benzyluracil,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}cytosine,
1-{5'-O-tert-Butyldimethylsilyl-2',3'-dideoxy-2'-fluoro-3'-[N-(O-tert-butyldimethylsiloxy)-N-methylamino]-β-D-arainofuranosyl}-5-fluorocytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-chlorocytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-bromocytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5iodocytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-ethylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-n-propylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-i-propylsytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-(E-2-bromovinyl)cytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-vinylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-carboxycytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-ethoxycarbonylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-aminocarbonylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-cyanocytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-phenylcytosine,
1-{5'-O-tert-Butyldimethylsilyl-2',3'-dideoxy-2'-fluoro-3'-[N-(O-tert-butyldimethylsiloxy)-N-methylamino]-β-D-arabinofuranosyl}-5-benzylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}thymine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-fluorouracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-chlorouracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-bromourcil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-iodourcil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-ethyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-n-propyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-i-propyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-(E-2-bromovinyl)uracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-vinyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-carboxyuracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-ethoxycarbonyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-aminocarbonyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-cyanouracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-phenyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-benzyluracil,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}cytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-fluorocytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-chlorocytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-bromocytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-iodocytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-ethylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-n-propylcyosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-i-propylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-(E-2-bromovinyl)cytosine, 1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-vinylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-carboxycytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-ethoxycarbonylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-aminocarbonylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-cyanocytosine,
1-{5'-O-tert-Butyldimethylsilyl-2',3'-dideoxy-2'-fluoro-3'-[N-(Otert-butyldimethylsiloxy)-N-methylamino]-α-D-arabinofuranosyl}-5-phenylcytosine,
1-{5'-O-tert-Butyldimethylsilyl-2',3'-dideoxy-2'-fluoro-3'-[N-(O-tert-butyldimethylsiloxy)-N-methylamino]-α-D-arabinofuranosyl}-5-benzylcytosine, Example 5

2',3'-Dideoxy-2'-fluoro-3'-(N-hydroxy-N-methylamino)-D-arabinofuranosyl nucleosides (163): Protected nucleosides 162 are separately treated with TBAF (2.5 eq) in dry THF. After stirring at room temperature for 2 hours, the resulting mixture is directly transferred to silica gel column for purification without evaporation.

[2,3-Dideoxy-2-fluoro-3-(N-hydroxy-N-methylamino)-D-arabinofuranosyl]-5-fluorouracil]-5-fluorourcil (163, B=FU): An anomieric mixture of 163 (B=5-fluorouracil) is obtained from as white solids (99%) from the corresponding 162. The anoners are partially separated by flash column chromatography over silica gel. 163β: $^1$H NMR (CD$_3$OD) δ 8.08 (dd, J=1.8 and 6.9 Hz, 1H, H-6), 6.04 (ddd, J=1.6, 3.9 and 18.0 Hz, 1H, H-1'), 5.45 (dt, J=1.8 and 52.8 Hz, 1H, H-2'), 4.15 (m, 1H, H-4'), 3.92 (dd, J=2.8 and 12.4 Hz, 1H, H-5'), 3.76 (dd, J=4.4 and 12.4 Hz, 1H, H-5'), 3.48 (ddd, J=1.7, 6.2 and 27.1 Hz, 1H, H-3'), 2.72 (s, 3H, NCH$_3$). $^{13}$C NMR (CD$_3$OD) δ 150.7, 143.8, 139.2, 128.1, 127.4, 95.1, 91.4, 86.5, 86.2, 81.5, 74.6, 74.1, 63.1, 47.4. Anal. Calcd for C$_{10}$H$_{13}$F$_2$N$_3$O$_5$·0.6 H$_2$O: C, 39.50; H, 4.7; N, 13.82. Found: C, 39.23; H, 4.70; N, 13.99. 163α: $^1$H NMR (CD$_3$OD) δ 7.87 (d, J=6.6 Hz, 1H, H-6), 6.10 (dt, J=1.6 and 5.8 H, 1H, H1'), 5.46 (dt, J=2.3 and 50.9 Hz, 1H, H-2'), 4.51 (m, 1H, H-4'), 3.80 (dd, J=4.0 and 11.8 Hz, 1H, H-5'), 3.70 (dd, J=5.3 and 12.1 Hz, 1H, H-5'), 3.43 (ddd, J=2.6, 5.1 and 24.5 Hz, 1H, H-3'), 2.70 (s, 3H, NCH$_3$). $^{13}$C NMR (CD$_3$OD) δ 163.6, 151.0, 144.2, 139.6, 126.9, 126.2, 100.2, 96.5, 92.8, 92.0, 86.0, 75.7, 75.3, 64.2, 47.6. Anal. Calcd for C$_{10}$H$_{13}$F$_2$N$_3$O$_5$·0.2 H$_2$O: C, 40.46; H, 4.55; N, 14.16. Found: C, 40.61; H, 4.37; N, 14.43.

In a similar manner but using the corresponding silyated bases, the following nucleosides are prepared:
1-[2',3'-Dideoxy-2'-fluoro-3'-(N-hydroxy-N-methylamino)-β-D-arabinofuranosyl]thymine,
1-[2',3'-Dideoxy-2'-fluoro-3'-(N-hydroxy-N-methylamino)-β-D-arabinofuranosyl]uracil,
1-[2',3'-Dideoxy-2'-fluoro-3'-(N-hydroxy-N-methylamino)-β-D-arabinofuranosyl]-5-chlorouracil,
1-[2',3'-Dideoxy-2'-fluoro-3'-(N-hydroxy-N-methylamino)-β-D-arabinofuranosyl]-5-bromouracil,
1-[2',3'-Dideoxy-2'-fluoro-3'-(N-hydroxy-N-methylamino)-β-D-arabinofuranosyl]-5-iodouracil,
1-[2',3'-Dideoxy-2'-fluoro-3'-(N-hydroxy-N-methylamino)-β-D-arabinofuranosyl]-5-ethyluracil,
1-[2',3'-Dideoxy-2'-fluoro-3'-(N-hydroxy-N-methylamino)-β-D-arabinofranosyl]-5-n-propyluracil,
1-[2',3'-Dideoxy-2'-fluoro-3'-(N-hydroxy-N-methylamino)-β-D-arabinofuranosyl]-5-i-propyluracil,
1-[2',3'-Dideoxy-2'-fluoro-3'-(N-hydroxy-N-methylamino)-β-D-arabinofuranosyl]-5-(E-2-bromo-vinyl)uracil,
1-[2',3'-Dideoxy-2'-fluoro-3'-(N-hydroxy-N-methylamino)-β-D-arabinofuranosyl-]5-vinyluracil,
1-[2',3'-Dideoxy-2'-fluoro-3'-(N-hydroxy-N-methylamino)-β-D-arabinofuranosyl]-5-carboxyuracil,
1-[2',3'-Dideoxy-2'-fluoro-3'-(N-hydroxy-N-methylamino)-β-D-arabinofuranosyl]-5-ethoxycarbonyluracil,
1-[2',3'-Dideoxy-2'-fluoro-3'-(N-hydroxy-N-methylamino)-β-D-arabinofuranosyl]-5-aminocarbonyluracil,
1-[2',3'-Dideoxy-2'-fluoro-3'-(N-hydroxy-N-methylamino)-β-D-arabinofuranosyl]-5-cyanouracil,
1-[2',3'-Dideoxy-2'-fluoro-3'-(N-hydroxy-N-methylamino)-β-D-arabinofuranosyll-5-phenyluracil,
1-[2',3'-Dideoxy-2'-fluoro-3'-(N-hydroxy-N-methylamino)-β-D-arabinofuranosyl]-5-benzyluracil,
1-[2',3'-Dideoxy-2'-fluoro-3'-(N-hydroxy-N-methylamino)-β-D-arabinofuranosyl]cytosine,
1-[2',3'-Dideoxy-2'-fluoro-3'-(N-hydroxy-N-methylamino)-β-D-arabinofuranosyl]-5-fluorocytosine,
1-[2',3'-Dideoxy-2'-fluoro-3'-(N-hydroxy-N-methylamino-β-D-arabinofuranosyl]-5-chlorocytosine,
1-[2',3'-Dideoxy-2'-fluoro-3'-(N-hydroxy-N-methylamino]-β-D-arabinofuranosyl]-5-bromocytosine,
1-[2',3'-Dideoxy-2'-fluoro-3'-(N-hydroxy-N-methylamino]-β-D-arabinofuranosyl]-5-iodocytosine,
1-[2',3'-Dideoxy-2'-fluoro-3'-(N-hydroxy-N-methylamino]-β-D-arabinofuranosyl]-5-ethylcytosine,
1-[2',3'-Dideoxy-2'-fluoro-3'-(N-hydroxy-N-methylamino)-β-D-arabinofuranosyl]-5-n-propylcytosine,
1-[2',3'-Dideoxy-2'-fluoro-3'-(N-hydroxy-N-methylamino]-β-D-arabinofuranosyl]-5-i-propylcytosine,
1-[2',3'-Dideoxy-2'-fluoro-3'-(N-hydroxy-N-methylamino]-β-D-arabinofuranosyl]-5-(E-2-bromovinyl)cytosine,
1-[2',3'-Dideoxy-2'-fluoro-3'-(N-hydroxy-N-methylanino]-β-D-arabinofuranosyll-vinylcytosine,
1-[2',3'-Dideoxy-2'-fluoro-3'-(N-hydroxy-N-methylamino]-β-D-arabinofuranosyl]-carboxycytosine,
1-[2',3'-Dideoxy-2'-fluoro-3'-(N-hydroxy-N-methylamino]-β-D-arabinofuranosyl]-5-ethoxycarbonyl-cytosine,
1-[2',3'-Dideoxy-2'-fluoro-3'-(N-hydroxy-N-methylamino]-β-D-arabinofuranosyl]-5-aminocarbonyl-cytosine,
1-[2',3'-Dideoxy-2'-fluoro-3'-(N-hydroxy-N-methylamino]-β-D-arabinofuranosyl]-5-cyanocytosine,
1-[2',3'-Dideoxy-2'-fluoro-3'-(N-hydroxy-N-methylamino]-β-D-arabinofuranosyl-5-phenylcytosine,
1-[2',3'-Dideoxy-2'-fluoro-3'-(N-hydroxy-N-methylamino)-β-D-arabinofuranosyl]-5-benzylcytosine,
1-[2',3'-Dideoxy-2'-fluoro-3'-(N-hydroxy-N-methylamino)-α-D-arabinofuranosyl]thymine,
1-[2',3'-Dideoxy-2'-fluoro-3'-(N-hydroxy-N-methylamino)-α-D-arabinofuranosyl]-5-fluorouracil,
1-[2',3'-Dideoxy-2'-fluoro-3'-(N-hydroxy-N-methylamino)-α-D-arabinofuranosyl]-5-chlorouracil,
1-[2',3'-Dideoxy-2'-fluoro-3'-(N-hydroxy-N-methylamino)-α-D-arabinofuranosyl]-5-bromouracil,
1-[2',3'-Dideoxy-2'-fluoro-3'-(N-hydroxy-N-methylamino)-α-D-arabinofuranosyl]-5-iodouracil,
1-[2',3'-Dideoxy-2'-fluoro-3'-(N-hydroxy-N-methylamino)-α-D-arabinofuranosyl]ethyluracil, 1-[2',3'-Dideoxy-2'-fluoro-3'-(N-hydroxy-N-methylamino)-
α-D-arabinofuranosyl]-5-n-propyluracil,
1-[2',3'-Dideoxy-2'-fluoro-3'-(N-hydroxy-N-methylamino)-
α-D-arabinofuranosyl]-5-i-propyluracil,
1-[2',3'-Dideoxy-2'-fluoro-3'-(N-hydroxy-N-methylamino)-
α-D-arabinofuranosyl]-5-(E-2-bromovinyl)-uracil,
1-[2',3'-Dideoxy-2'-fluoro-3'-(N-hydroxy-N-methylamino)-
α-D-arabinofuranosyl]-5-vinyluracil,
1-[2',3'-Dideoxy-2'-fluoro-3'-(N-hydroxy-N-methylamino)-
α-D-arabinofuranosyl]-5-carboxyuracil,
1-[2',3'-Dideoxy-2'-fluoro-3'-(N-hydroxy-N-methylamino)-
α-D-arabinofuranosyl]-5-ethoxycarbonyl-uracil,
1-[2',3'-Dideoxy-2'-fluoro-3'-(N-hydroxy-N-methylamino)-
α-D-arabinofuranosyl]-5-aminocarbonyl-uracil,
1-[2',3'-Dideoxy-2'-fluoro-3'-(N-hydroxy-N-methylamino)-
α-D-arabinofuranosyl -5-cyanouracil,
1-[2',3'-Dideoxy-2'-fluoro-3'-(N-hydroxy-N-methylamino)-
α-D-arabinofuranosyl]-5-phenyluracil,
1-[2',3'-Dideoxy-2'-fluoro-3'-(N-hydroxy-N-methylamino)-
α-D-arabinofuranosyl]-5-benzyluracil,
1-[2',3'-Dideoxy-2'-fluoro-3'-(N-hydroxy-N-methylamino)-
α-D-arabinofuranosyl]-cytosine,
1-[2',3'-Dideoxy-2'-fluoro-3'-(N-hydroxy-N-methylamino)-
α-D-arabnofuranosyl]-5-fluorocytosine,
1-[2',3'-Dideoxy-2'-fluoro-3'-(N-hydroxy-N-methylamino)-
α-D-arabinofuranosyl]-5-chlorocytosine,
1-[2',3'-Dideoxy-2'-fluoro-3'-(N-hydroxy-N-methylamino)-
α-D-arabinofiuranosyl]-5-bromocytosine,
1-[2',3'-Dideoxy-2'-fluoro-3'-(N-hydroxy-N-methylamino)-
α-D-arbinofuranosyl]-5-iodocytosine,
1-[2',3'-Dideoxy-2'-fluoro-3'-(N-hydroxy-N-methylamino)-
α-D-arabinofuranosyl]-5-ethylcytosine,
1-[2',3'-Dideoxy-2'-fluoro-3'-(N-hydroxy-N-methylamino)-
α-D-arabinofuranosyl]-5 -n-propylcytosine,
1-[2',3'-Dideoxy-2'-fluoro-3'-(N-hydroxy-N-methylamino)-
α-D-rabinofuranosyl]-5-i-propylcytosine,
1-[2',3'-Dideoxy-2'-fluoro-3'-(N-hydroxy-N-methylamino)-
α-D-arabinofuranosyl]-5-(E-2-bromovinyl)cytosine,
1-[2',3'-Dideoxy-2'-fluoro-3'-(N-hydroxy-N-methylamino)-
α-D-arabinofuranosyl]-5-vinylcytosine,
1-[2',3'-Dideoxy-2'-fluoro-3'-(N-hydroxy-N-methylamino)-
α-D-arabinofuranosyl]-5-carboxycytosine,
1-[2',3'-Dideoxy-2'-fluoro-3'-(N-hydroxy-N-methylamino)-
α-D-arabinofuranosyl]-5-ethoxycarbonyl-cytosine,
1-[2',3'-Dideoxy-2'-fluoro-3'-(N-hydroxy-N-methylamino]-
α-D-arabinofuranosyl]-5-aminocarbonyl-cytosine,
1-[2',3'-Dideoxy-2'-fluoro-3'-(N-hydroxy-N-methylamino]-
α-D-arabinofuranosyl}-5-cyanocytosine,
1-[2',3'-Dideoxy-2'-fluoro-3'-(N-hydroxy-N-methylamino)-
α-D-arabinofuranosyl]-5-phenylcytosine,
1-[2',3'-Dideoxy-2'-fluoro-3'-(N-hydroxy-N-methylamino)-
α-D-arabinofuranosyl]-5-benzylcytosine, Example 6

5—[tert-Butyldiphenylsilyl-2,3-dideoxy-2-fluoro-3-(N-hydroxy-N-methylamino)]-arabino-1,4-lactone (164): In a similar manner to prepare compound 157, compound 164 is prepared from 156 as an oil (65% yield). $^1$H NMR (CDCl$_3$) δ 7.69 (m, 4H, arom.), 7.42 (m, 6H, arom.), 5.92 (bs, 1H, OH), 5.57 (dd, J=7.3 and 50.9 Hz, 1H, H-2), 4.51 (m, 1H, H-4), 3.95 (m, 3H, H-3 and H-5), 2.78 (s, 3H, NCH$_3$), 1.08 (s, 9H, t-Bu). $^{13}$C NMR (CDCl$_3$) δ 170.4, 170.0, 136.2, 136.0, 133., 132.9, 130.4, 128.3, 88.1, 84.2, 79.3, 79.1, 69.4, 69.1, 63.3, 47.5, 27.3, 19.9.

Example 7

5-O-{tert-Butyldiphenylsilyl-2,3-dideoxy-2-fluoro-3-[N-(tert-butyldimethylsilyloxy)-N-methylamino]}-arabino-1,4-lactone (166): In a similar manner to prepare compound 157, compound 166 is prepared from 164 as an oil (89% yield). $^1$H NMR (CDCl$_3$) δ 7.71 (m, 4H, arom.), 7.45 (m, 6H, arom.), 4.47 (bs, 1H, H-4), 3.95 (m, 3H, H-3 and H-5), 2.72 (s, 3H, NCH$_3$), 1.09 (s, 9H, t-Bu), 0.90 (s, 9H, t-Bu), 0.12 (m, 6H, 2SiCH$_3$). $^{13}$C NMR (CDCl$_3$) δ 170.4, 170.0, 136.2, 36.0, 133.3, 132.9, 130.4, 128.3, 78.7, 78.6, 70.4, 70.0, 62.5, 47.8, 27.3, 26.5, 19.9, 18.3, −3.9, −4.0.

Example 8

{5-O-tert-Butyldiphenylsilyl-2,3-dideoxy-2-fluoro-3-[N-(tert-butyldimethylsiloxy)-N-methylamino]-D-arabinofuranosyl}uracil (169,B=uracil): In a similar manner to prepare compounds 160, compound 169 (B=uracil) is prepared from 166 (3 steps) as an anomeric mixture which is separated by silica gel column chromatography as white solids (68% from 166). β-anomer: $^1$H NMR (CDCl$_3$) δ 10.12 (bs, 1H, NH), 7.70 (m, 4H, arom.), 7.45 (m, 7H, arom. and H-6),6.12 (dd, J=4.0 and 18.7 Hz, 1H, H-1'), 5.58 (d, J=8.4 Hz, 1H, H-5), 3.95 (m, 3H, H-4' and H-5'), 3.63 (dd, J=5.6 and 26.3 Hz, 1H, H-3'), 2.69 (s, 3H, NCH$_3$), 1.11(s, 9H, t-Bu), 0.93 (s, 9H, t-Bu), 0.18 (m, 6H, 2SiCH$_3$). $^{13}$C NMR (CDCl$_3$) δ 164.2, 150.9, 141.8, 136.1, 136.0, 133.5, 133.3, 130.4, 128.3, 102.0, 85.2, 84.9, 74.8, 74.3, 47.8, 47.7, 27.4, 26.6, 19.9, 19.3, −3.7, −4.0. α-anomer: $^1$H NMR (CDCl$_3$) δ 9.88 (s, 1H, NH), 7.71 (m, 4H, arom.), 7.42 (m, 7H, arom. and H-6), 6.25 (dd, J=3.7 and 14.6 Hz, 1H, H-1'), 5.78 (d, J=8.0 Hz, 1H, H-5), 4.32 (bs, 1H, H-4'), 3.89 (m, 2H, H-5'), 3.68 (dd, J=4.3 and 6.4 Hz, 1H, H-3'), 2.65 (s, 3H, NCH$_3$), 1.12 (s, 9H, t-Bu), 0.88 (s, 9H, t-Bu), 0.12 (m, 6H, 2SiCH$_3$). $^{13}$C NMR (CDCl$_3$) δ 163.9, 150.8, 139.9, 136.1, 136.0, 133.5, 133.3, 130.3, 128.3, 103.3, 90.3, 89.6, 82.6, 82.4, 74.6, 74.2, 64.8, 47.9, 27.4, 26.6, 26.5, 19.9, 18.3, −3.9.

In a similar manner but using the corresponding silyated bases, the following nucleosides are prepared:
1-{5'-O-tert-Butyldiphenylsilyl-2',3'-dideoxy-2'-fluoro-3'-[N-(tert-butyldimethylsiloxy)-N-methylamino]-β-D-arabinofuranosyl}thymine,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-fluorouracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-chlorouracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-bromouracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-iodouracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}5-ethyluracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-n-propyluracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-i-propyluracil,
1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-(E-2-bromovinyl)uracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-vinyluracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-carboxyuracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-ethoxycarbonyluracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-aminocarbonyluracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-cyanouracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-phenyluracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-benzyluracil, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}cytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-fluorocytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-cholorocytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-bromocytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-iodocytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-ethylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-n-propylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-i-propylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-(E-2-bromovinyl)cytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-vinylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-carboxycytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-ethoxycarbonylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-aminocarbonylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-cyanocytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-phenylcytosine, 1-{5'-O-tert-Butyldiphenylsilyl-2',3'-dideoxy-2'-fluoro-3'-[N-(tert-butyldimethylsiloxy)-N-methylamino]-β-D-arabinofuranosyl}-5-benzylcytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}thymine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-fluorouracil, 1-{5'-O-tert-Butyldiphenylsilyt-2',3'-dideoxy-2'-fluoro-3'-[N-(tert-butyldimethylsiloxy)-N-methylamino]-α-D-arabinofuranosyl}-5-chlorouracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-bromouracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-iodouracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-ethyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-n-propyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-i-propyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-(E-2-bromovinyl)uracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-vinyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-carboxyuracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-ethoxycarbonyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-aminocarbonyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-cyanouracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-phenyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-benzyluracil, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}cytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-fluorocytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5chlorocytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-bromocytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-iodocytosine, 1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-ethylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-n-propylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-i-propylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-(E-2-bromovinyl)cytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-vinylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-carboxycytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-ethoxycarbonylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-aminocarbonylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-cyanocytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-phenylcytosine,
1-{5'-O-tert-Butyldiphenylsilyl-2',3'-dideoxy-2'-fluoro-3'-[N-(tert-butyldimethylsiloxy)-N-methylamino]-α-D-arabinofuranosyl}-5-benzylcytosine, Example 9

General procedure for synthesis of 5'-O-tert-butyldiphenylsilyl-2',3'-dideoxy-2'-fluoro-3'-(N-hydroxy-N-methylamino)-D-arabinofuranosyl nucleosides (170): To a solution of (169) (1 mmol) in acetonitrile (10 mL) is added 48% HF in water (0.036 mL). The resulting mixture is stirred at room temperature for 1 hour, and then water (10 mL) is added. The resulting solution is extracted with methylene chloride. The organic layer is washed with saturated NaHCO$_3$ and brine, dried over Na$_2$SO$_4$, filtrated, concentrated to give the crude products, which are further purified by flash column chromatography over silica gel.

[5-O-tert-Butyldiphenylsilyl-2,3-dideoxy-2-fluoro-3-(N-hydroxy-N-methylamino)-β-D-arabinofuranosyl]-5-fluorouracil (170-b, B=5-fluorouracil): This compound is prepared from 169 (B=5-fluorouracil) as white solids (97% total): $^1$H NMR (CDCl$_3$) δ 7.72 (m, 4H, arom.), 7.40 (m, 7H, arom. and H-6), 6.14 (d, J=17.7 Hz, 1H, H1'), 5.49 (dd, J=1.7 and 52.9 Hz, 1H, H-2'), 4.30 (m, 1H, H-4'), 3.98 (m, 2H, H-5'), 3.6 (dd, J=5.0 and 26.6 Hz, 1H, H-3'), 2.71 (s, 3H, NCH$_3$), 1.11 (s, 9H, t-Bu). $^{13}$C NMR (CDCl$_3$) δ 158.3, 157.7, 149.7, 142.9, 138.2, 136.1, 136.0, 133.3, 133.2, 130.5, 128.4, 126.8, 126.1, 94.7, 90.9, 85.6, 85.2, 79.7, 73.7, 73.3, 64.2, 46.8, 27.4, 19.9.

In a similar manner but using the corresponding 3'-(O-tert-butyldimethylsilyloxy-N-methylamino) nucleosides, the following nucleosides are prepared:
1-[5'-O-tert-Butyldiphenylsilyl-2',3'-dideoxy-2'-fluoro-3'-(N-hydroxy-N-methylamino)-β-D-arabinofuranosyl] thymine,
1-[5'-O-tert-Butyldiphenylsilyl-2',3'-dideoxy-2'-fluoro-3'-(N-hydroxy-N-methylamino)-β-D-arabinofuranosyl] uracil,
1-[5'-O-tert-Butyldiphenylsilyl-2',3'-dideoxy-2'-fluoro-3'-(N-hydroxy-N-methylamino)-β-D-arabinofuranosyl]-5-chlorouracil,
1-[5'-O-tert-Butyldiphenylsilyl-2',3'-dideoxy-2'-fluoro-3'-(N-hydroxy-N-methylamino)-β-D-arabinofuranosyl]-5-bromouracil,
1-[5'-O-tert-Butyldiphenylsilyl-2',3'-dideoxy-2'-fluoro-3'-(N-hydroxy-N-methylamino)-β-D-arabinofuranosyl]-5-iodouracil,
1-[5'-O-tert-Butyldiphenylsilyl-2',3'-dideoxy-2'-fluoro-3'-(N-hydroxy-N-methylamino)-β-D-arabinofuranosyl]-5-ethyluracil,
1-[5'-O-tert-Butyldiphenylsilyl-2',3'-dideoxy-2'-fluoro-3'-(N-hydroxy-N-methylamino)-β-D-arabinofuranosyl]-5-n-propyluracil,
1-[5'-O-tert-Butyldiphenylsilyl-2',3'-dideoxy-2'-fluoro-3'-(N-hydroxy-N-methylamino)-β-D-arabinofuranosyl]-5-i-propyluracil,
1-[5'-O-tert-Butyldiphenylsilyl-2',3'-dideoxy-2'-fluoro-3'-(N-hydroxy-N-methylamino)-β-D-arabinofuranosyl]-5-(E-2-bromovinyl)uracil,
1-[5'-O-tert-Butyldiphenylsilyl-2',3'-dideoxy-2'-fluoro-3'-(N-hydroxy-N-methylamino)-β-D-arabinofuranosyl]-5-vinyluracil,
1-[5'-O-tert-Butyldiphenylsilyl-2',3'-dideoxy-2'-fluoro-3'-(N-hydroxy-N-methylamino)-β-D-arabinofuranosyl]-5-carboxyuracil,
1-[5'-O-tert-Butyldiphenylsilyl-2',3'-dideoxy-2'-fluoro-3'-(N-hydroxy-N-methylamino)-β-D-arabinofuranosyl]-5-ethoxycarbonyluracil,
1-[5'-O-tert-Butyldiphenylsilyl-2',3'-dideoxy-2'-fluoro-3'-(N-hydroxy-N-methylamino)-β-D-arabinofuranosyl]-5-aminocarbonyluracil,
1-[5'-O-tert-Butyldiphenylsilyl-2',3'-dideoxy-2'-fluoro-3'-(N-hydroxy-N-methylamino)-β-D-arabinofuranosyl]-5-cyanouracil,
1-[5'-O-tert-Butyldiphenylsilyl-2',3'-dideoxy-2'-fluoro-3'-(N-hydroxy-N-methylamino)-β-D-arabinofuranosyl]-5-phenyluracil,
1-[5'-O-tert-Butyldiphenylsilyl-2',3'-dideoxy-2'-fluoro-3'-(N-hydroxy-N-methylamino)-β-D-arabinofuranosyl]-5-benzyluracil,
1-[5'-O-tert-Butyldiphenylsilyl-2',3'-dideoxy-2'-fluoro-3'-(N-hydroxy-N-methylamino)-β-D-arabinofuranosyl]-5-cytosine,
1-[5'-O-tert-Butyldiphenylsilyl-2',3'-dideoxy-2'-fluoro-3'-(N-hydroxy-N-methylamino)-β-D-arabinofuranosyl]-5-fluorocytosine,
1-[5'-O-tert-Butyldiphenylsilyl-2',3'-dideoxy-2'-fluoro-3'-(N-hydroxy-N-methylamino)-β-D-arabinofuranosyl]-5-chlorocytosine,
1-[5'-O-tert-Butyldiphenylsilyl-2',3'-dideoxy-2'-fluoro-3'-(N-hydroxy-N-methylamino)-β-D-arabinofuranosyl]-5-bromocytosine,
1-[5'-O-tert-Butyldiphenylsilyl-2',3'-dideoxy-2'-fluoro-3'-(N-hydroxy-N-methylamino)-β-D-arabinofuranosyl]-5-iodocytosine,
1-[5'-O-tert-Butyldiphenylsilyl-2',3'-dideoxy-2'-fluoro-3'-(N-hydroxy-N-methylamino)-β-D-arabinofuranosyl]-5-ethylcytosine,
1-[5'-O-tert-Butyldiphenylsilyl-2',3'-dideoxy-2'-fluoro-3'-(N-hydroxy-N-methylamino)-β-D-arabinofuranosyl]-5-n-propylcytosine, 1-[5'-O-tert-Butyldiphenylsilyl-2',3'-dideoxy-2'-fluoro-3'-(N-hydroxy-N-methylamino)-β-D-arabinofuranosyl]-5-cyanouracil,
1-[5'-O-tert-Butyldiphenylsilyl-2',3'-dideoxy-2'-fluoro-3'-(N-hydroxy-N-methylamino)-β-D-arabinofuranosyl]-5-phenyluracil,
1-[5'-O-tert-Butyldiphenylsilyl-2',3'-dideoxy-2'-fluoro-3'-(N-hydroxy-N-methylamino)-β-D-arabinofuranosyl]-5-benzyluracil,
1-[5'-O-tert-Butyldiphenylsilyl-2',3'-dideoxy-2'-fluoro-3'-(N-hydroxy-N-methylamino)-β-D-arabinofuranosyl]cytosine,
1-[5'-O-tert-Butyldiphenylsilyl-2',3'-dideoxy-2'-fluoro-3'-(N-hydroxy-N-methylamino)-β-D-arabinofuranosyl]-5-fluorocytosine,
1-[5'-O-tert-Butyldiphenylsilyl-2',3'-dideoxy-2'-fluoro-3'-(N-hydroxy-N-methylamino)-β-D-arabinofuranosyl]-5-chlorocytosine,
1-[5'-O-tert-Butyldiphenylsilyl-2',3'-dideoxy-2'-fluoro-3'-(N-hydroxy-N-methylamino)-β-D-arabinofuranosyl]-5-bromocytosine,
1-[5'-O-tert-Butyldiphenylsilyl-2',3'-dideoxy-2'-fluoro-3'-(N-hydroxy-N-methylamino)-β-D-arabinofuranosyl]-5-iodocytosine,
1-[5'-O-tert-Butyldiphenylsilyl-2',3'-dideoxy-2'-fluoro-3'-(N-hydroxy-N-methylamino)-β-D-arabinofuranosyl]-5-ethylcytosine,
1-[5'-O-tert-Butyldiphenylsilyl-2',3'-dideoxy-2'-fluoro-3'-(N-hydroxy-N-methylamino)-β-D-arabinofuranosyl]-5-n-propylcytosine,
1-[5'-O-tert-Butyldiphenylsilyl-2',3'-dideoxy-2'-fluoro-3'-(N-hydroxy-N-methylamino)-β-D-arabinofuranosyl]-5-i-propylcytosine,
1-[5'-O-tert-Butyldiphenylsilyl-2',3'-dideoxy-2'-fluoro-3'-(N-hydroxy-N-methylamino)-β-D-arabinofuranosyl]-5-(E-2-bromovinyl)cytosine,
1-[5'-O-tert-Butyldiphenylsilyl-2',3'-dideoxy-2'-fluoro-3'-(N-hydroxy-N-methylamino)-β-D-arabinofuranosyl]-5-vinylcytosine,
1-[5'-O-tert-Butyldiphenylsilyl-2',3'-dideoxy-2'-fluoro-3'-(N-hydroxy-N-methylamino)-β-D-arabinofuranosyl]-5-carboxycytosine,
1-[5'-O-tert-Butyldiphenylsilyl-2',3'-dideoxy-2'-fluoro-3'-(N-hydroxy-N-methylamino)-β-D-arabinofuranosyl]-5-ethoxycarbonylcytosine,
1-[5'-O-tert-Butyldiphenylsilyl-2',3'-dideoxy-2'-fluoro-3'-(N-hydroxy-N-methylamino)-β-D-arabinofuranosyl]-5-aminocarbonylcytosine,
1-[5'-O-tert-Butyldiphenylsilyl-2',3'-dideoxy-2'-fluoro-3'-(N-hydroxy-N-methylamino)-β-D-arabinofuranosyl]-5-cyanocytosine,
1-[5'-O-tert-Butyldiphenylsilyl-2',3'-dideoxy-2'-fluoro-3'-(N-hydroxy-N-methylamino)-β-D-arabinofuranosyl]-5-phenylcytosine,
1-[5'-O-tert-Butyldiphenylsilyl-2',3'-dideoxy-2'-fluoro-3'-(N-hydroxy-N-methylamino)-β-D-arabinofuranosyl]-5-benzylcytosine,
1-[5'-O-tert-Butyldiphenylsilyl-2',3'-dideoxy-2'-fluoro-3'-(N-hydroxy-N-methylamino)-β-D-arabinofuranosyl]thymine,
1-[5'-O-tert-Butyldiphenylsilyl-2',3'-dideoxy-2'-fluoro-3'-(N-hydroxy-N-methylamino)-α-D-arabinofuranosyl]-5-fluorouracil,
1-[5'-O-tert-Butyldiphenylsilyl-2',3'-dideoxy-2'-fluoro-3'-(N-hydroxy-N-methylamino)-α-D-arabinofuranosyl]-5-chlorouracil,
1-[5'-O-tert-Butyldiphenylsilyl-2',3'-dideoxy-2'-fluoro-3'-(N-hydroxy-N-methylamino)-α-D-arabinofuranosyl]-5-bromouracil,
1-[5'-O-tert-Butyldiphenylsilyl-2',3'-dideoxy-2'-fluoro-3'-(N-hydroxy-N-methylamino)-α-D-arabinofuranosyl]-5-iodouracil,
1-[5'-O-tert-Butyldiphenylsilyl-2',3'-dideoxy-2'-fluoro-3'-(N-hydroxy-N-methylamino)-α-D-arabinofuranosyl]-5-ethyluracil,
1-[5'-O-tert-Butyldiphenylsilyl-2',3'-dideoxy-2'-fluoro-3'-(N-hydroxy-N-methylamino)-α-D-arabinofuranosyl]-5-n-propyluracil,
1-[5'-O-tert-Butyldiphenylsilyl-2',3'-dideoxy-2'-fluoro-3'-(N-hydroxy-N-methylamino)-α-D-arabinofuranosyl]-5-i-propyluracil,
1-[5'-O-tert-Butyldiphenylsilyl-2',3'-dideoxy-2'-fluoro-3'-(N-hydroxy-N-methylamino)-α-D-arabinofuranosyl]-5-(E-2-bromovinyl)uracil,
1-[5'-O-tert-Butyldiphenylsilyl-2',3'-dideoxy-2'-fluoro-3'-(N-hydroxy-N-methylamino)-α-D-arabinofuranosyl]-5-vinyluracil,
1-[5'-O-tert-Butyldiphenylsilyl-2',3'-dideoxy-2'-fluoro-3'-(N-hydroxy-N-methylamino)-α-D-arabinofuranosyl]-5-carboxyuracil,
1-[5'-O-tert-Butyldiphenylsilyl-2',3'-dideoxy-2'-fluoro-3'-(N-hydroxy-N-methylamino)-α-D-arabinofuranosyl]-5-ethoxycarbonyluracil,
1-[5'-O-tert-Butyldiphenylsilyl-2',3'-dideoxy-2'-fluoro-3'-(N-hydroxy-N-methylamino)-α-D-arabinofuranosyl]-5-aminocarbonyluracil,
1-[5'-O-tert-Butyldiphenylsilyl-2',3'-dideoxy-2'-fluoro-3'-(N-hydroxy-N-methylamino)-α-D-arabinofuranosyl]-5-cyanouracil,
1-[5'-O-tert-Butyldiphenylsilyl-2',3'-dideoxy-2'-fluoro-3'-(N-hydroxy-N-methylamino)-α-D-arabinofuranosyl]-5-phenyluracil,
1-[5'-O-tert-Butyldiphenylsilyl-2',3'-dideoxy-2'-fluoro-3'-(N-hydroxy-N-methylamino)-α-D-arabinofuranosyl]-5-benzyluracil,
1-[5'-O-tert-Butyldiphenylsilyl-2',3'-dideoxy-2'-fluoro-3'-(N-hydroxy-N-methylamino)-α-D-arabinofuranosyl]cytosine,
1-[5'-O-tert-Butyldiphenylsilyl-2',3'-dideoxy-2'-fluoro-3'-)N-hydroxy-N-methylamino)-α-D-arabinofuranosyl]-5-fluorocytosine,
1-[5'-O-tert-Butyldiphenylsilyl-2',3'-dideoxy-2'-fluoro-3'-(N-hydroxy-N-methylamino)-α-D-arabinofuranosyl]-5-chlorocytosine,
1-[5'-O-tert-Butyldiphenylsilyl-2',3'-dideoxy-2'-fluoro-3'-(N-hydroxy-N-methylamino)-α-D-arabinofuranosyl]-5-bromocytosine,
1-[5'-O-tert-Butyldiphenylsilyl-2',3'-dideoxy-2'-fluoro-3'-(N-hydroxy-N-methylamino)-α-D-arabinofuranosyl]-5-iodocytosine,
1-[5'-O-tert-Butyldiphenylsilyl-2',3'-dideoxy-2'-fluoro-3'-(N-hydroxy-N-methylamino)-α-D-arabinofuranosyl]-5-ethylcytosine,
1-[5'-O-tert-Butyldiphenylsilyl-2',3'-dideoxy-2'-fluoro-3'-(N-hydroxy-N-methylamino)-α-D-arabinofuranosyl]-5-n-propylcytosine,
1-[5'-O-tert-Butyldiphenylsilyl-2',3'-dideoxy-2'-fluoro-3'-(N-hydroxy-N-methylamino)-α-D-arabinofuranosyl]-5-i-propylcytosine,
1-[5'-O-tert-Butyldiphenylsilyl-2',3'-dideoxy-2'-fluoro-3'-(N-hydroxy-N-methylamino)-α-D-arabinofuranosyl]-5-(E-2-bromovinyl)cytosine, 1-[5'-O-tert-Butyldiphenylsilyl-2',3'-dideoxy-2'-fluoro-3'-(N-hydroxy-N-methylamino)-α-D-arabinofuranosyl]-5-vinylcytosine, 1-[5'-O-tert-Butyldiphenylsilyl-2',3'-dideoxy-2'-fluoro-3'-(N-hydroxy-N-methylamino)-α-D-arabinofuranosyl]-5-carboxycytosine, 1-[5'-O-tert-Butyldiphenylsilyl-2',3'-dideoxy-2'-fluoro-3'-(N-hydroxy-N-methylamino)-α-D-arabinofuranosyl]-5-ethoxycarbonylcytosine, 1-[5'-O-tert-Butyldiphenylsilyl-2',3'-dideoxy-2'-fluoro-3'-(N-hydroxy-N-methylamino)-α-D-arabinofuranosyl]-5-aminocarbonylcytosine, 1-[5'-O-tert-Butyldiphenylsilyl-2',3'-dideoxy-2'-fluoro-3'-(N-hydroxy-N-methylamino)-α-D-arabinofuranosyl]-5-cyanocytosine, 1-[5'-O-tert-Butyldiphenylsilyl-2',3'-dideoxy-2'-fluoro-3'-(N-hydroxy-N-methylamino)-α-D-arabinofuranosyl]-5-phenylcytosine, 1-[5'-O-tert-Butyldiphenylsilyl-2',3'-dideoxy-2'-fluoro-3'-(N-hydroxy-N-methylamino)-α-D-arabinofuranosyl]-5-benzylcytosine, Example 10

General procedure for synthesis of 5'-O-tert-butyldiphenylsilyl-2',3'-dideoxy-2'-fluoro-3'-(N-hydroxyamino)-D-arabinofuranosyl nucleosides (172): To a solution of 170 (1 mmol) in methylene chloride (10 mL) is added a solution of DDQ (0.272 g, 1.2 mmol) in methylene chloride (10 mL) in portion. After the resulting mixture is stirred at room temperature for 30 minutes, it is diluted with methylene chloride (10 mL). The organic solution is washed successively with saturated NaHCO$_3$, brine and water, dried over Na$_2$SO$_4$, filtrated, and concentrated to give crude nitrone, which is purified by a short column over silica gel eluting with 10% methanol in methylene chloride.

To the residue nitrone is added methanol (10 mL) and NH$_2$OH.HCl (0.104 g, 1.5 mmol). The resulting mixture is warmed to 50° C. and stirred for 1 hour. After evaporation of methanol, the residue is dissolved in methylene chloride (20 mL). The organic solution is washed with brine, dried over Na$_2$SO$_4$, filtrated, and concentrated to give crude product which is purified by flash column chromatography over silica gel.

[5-O-tert-Butyldiphenylsilyl-2,3-dideoxy-2-β-fluoro-3-(N-hydroxyamino)-β-D-arabinofuranosyl]-5-fluorouracil (172b, 5-flurouracil): This is prepared from corresponding 170b as a white solid (53% for 2 steps): $^1$H NMR (CDCl$_3$) δ 7.72–7.31 (m, 12H, arom., H-6, OH), 6.17 (d, J=18.7 Hz, 1H, H-1'), 5.35 (d, J=53.0 Hz, 1H, H-2'), 3.95 (m, 4H, H-3', H-4' and H-5'), 1.11 (s, 9H, t-Bu). $^{13}$C NMR (CDCl$_3$) δ 158.2, 157.7, 149.7, 143.0, 138.3, 136.1, 136.0, 133.2, 130.5, 128.4, 126.7, 125.9, 95.5, 91.7, 85.7, 85.5, 80.6, 68.1, 67.6, 64.0, 27.4, 19.8.

In a similar manner but using the corresponding 3'-(N-hydroxy-N-methylamino) nucleosides, the following nucleosides are prepared:

1-[5'-O-tert-Butyldiphenylsilyl-2',3'-dideoxy-2'-fluoro-3'-(N-hydroxyamino)-β-D-arabinofluranosyl]-thymine, 1-[5'-O-tert-Butyldiphenylsilyl-2',3'-dideoxy-2'-fluoro-3'-(N-hydroxylamino)-β-D-arabinofuranosyl]-uracil, 1-[5'-O-tert-Butyldiphenylsilyl-2',3'-dideoxy-2'-fluoro-3'-(N-hydroxylamino)-β-D-arabinofuranosyl]-5-chlorouracil, 1-[5'-O-tert-Butyldiphenylsilyl-2',3'-dideoxy-2'-fluoro-3'-(N-hydroxylamino)-β-D-arabinofuranosyl]-5-bromouracil, 1-[5'-O-tert-Butyldiphenylsilyl-2',3'-dideoxy-2'-fluoro-3'-(N-hydroxylamino)-β-D-arabinofuranosyl]-5-iodouracil, 1-[5'-O-tert-Butyldiphenylsilyl-2',3'-dideoxy-2'-fluoro-3'-(N-hydroxylamino)-β-D-arabinofuranosyl]-5-ethyluracil, 1-[5'-O-tert-Butyldiphenylsilyl-2',3'-dideoxy-2'-fluoro-3'-(N-hydroxylamino)-β-D-arabinofuranosyl]-5-n-propyluracil, 1-[5'-O-tert-Butyldiphenylsilyl-2',3'-dideoxy-2'-fluoro-3'-(N-hydroxylamino)-β-D-arabinofuranosyl]-5-i-propyluracil, 1-[5'-O-tert-Butyldiphenylsilyl-2',3'-dideoxy-2'-fluoro-3'-(N-hydroxylamino)-β-D-arabinofuranosyl]-5-(E-2-bromovinyl)uracil, 1-[5'-O-tert-Butyldiphenylsilyl-2',3'-dideoxy-2'-fluoro-3'-(N-hydroxylamino)-β-D-arabinofuranosyl]-5-vinyluracil, 1-[5'-O-tert-Butyldiphenylsilyl-2',3'-dideoxy-2'-fluoro-3'-(N-hydroxylamino)-β-D-arabinofuranosyl]-5-carboxyuracil, 1-[5'-O-tert-Butyldiphenylsilyl-2',3'-dideoxy-2'-fluoro-3'-(N-hydroxylamino)-β-D-arabinofuranosyl]-5-ethoxycarbonyluracil, 1-[5'-O-tert-Butyldiphenylsilyl-2',3'-dideoxy-2'-fluoro-3'-(N-hydroxylamino)-β-D-arabinofuranosyl]-5-aminocarbonyluracil, 1-[5'-O-tert-Butyldiphenylsilyl-2',3'-dideoxy-2'-fluoro-3'-(N-hydroxylamino)-β-D-arabinofuranosyl]-5-cyanouracil, 1-[5'-O-tert-Butyldiphenylsilyl-2',3'-dideoxy-2'-fluoro-3'-(N-hydroxylamino)-β-D-arabinofuranosyl]-5-phenyluracil, 1-[5'-O-tert-Butyldiphenylsilyl-2',3'-dideoxy-2'-fluoro-3'-(N-hydroxylamino)-β-D-arabinofuranosyl]-5-benzyluracil, 1-[5'-O-tert-Butyldiphenylsilyl-2',3'-dideoxy-2'-fluoro-3'-(N-hydroxylamino)-β-D-arabinofuranosyl]-5-cytosine, 1-[5'-O-tert-Butyldiphenylsilyl-2',3'-dideoxy-2'-fluoro-3'-(N-hydroxylamino)-β-D-arabinofuranosyl]-5-flurocytosine, 1-[5'-O-tert-Butyldiphenylsilyl-2',3'-dideoxy-2'-fluoro-3'-(N-hydroxylamino)-β-D-arabinofuranosyl]-5-chlorocytosine, 1-[5'-O-tert-Butyldiphenylsilyl-2',3'-dideoxy-2'-fluoro-3'-(N-hydroxylamino)-β-D-arabinofuranosyl]-5-bromocytosine, 1-[5'-O-tert-Butyldiphenylsilyl-2',3'-dideoxy-2'-fluoro-3'-(N-hydroxylamino)-β-D-arabinofuranosyl]-5-iodocytosine, 1-[5'-O-tert-Butyldiphenylsilyl-2',3'-dideoxy-2'-fluoro-3'-(N-hydroxylamino)-β-D-arabinofuranosyl]-5-ethylcytosine, 1-[5'-O-tert-Butyldiphenylsilyl-2',3'-dideoxy-2'-fluoro-3'-(N-hydroxylamino)-β-D-arabinofuranosyl]-5-n-propylcytosine, 1-[5'-O-tert-Butyldiphenylsilyl-2',3'-dideoxy-2'-fluoro-3'-(N-hydroxylamino)-β-D-arabinofuranosyl]-5-i-propylcytosine, 1-[5'-O-tert-Butyldiphenylsilyl-2',3'-dideoxy-2'-fluoro-3'-(N-hydroxylamino)-β-D-arabinofuranosyl]-5-(E-2-bromovinyl)cytosine, 1-[5'-O-tert-Butyldiphenylsilyl-2',3'-dideoxy-2'-fluoro-3'-(N-hydroxylamino)-β-D-arabinofuranosyl]-5-vinylcytosine, 1-[5'-O-tert-Butyldiphenylsilyl-2',3'-dideoxy-2'-fluoro-3'-(N-hydroxylamino)-β-D-arabinofuranosyl]-5-carboxycytosine, 1-[5'-O-tert-Butyldiphenylsilyl-2',3'-dideoxy-2'-fluoro-3'-(N-hydroxylamino)-β-D-arabinofuranosyl]-5-ethoxycarbonylcytosine,
1-[5'-O-tert-Butyldiphenylsilyl-2',3'-dideoxy-2'-fluoro-3'-(N-hydroxylamino)-β-D-arabinofuranosyl]-5-aminocarbonylcytosine,
1-[5'-O-tert-Butyldiphenylsilyl-2',3'-dideoxy-2'-fluoro-3'-(N-hydroxylamino)-β-D-arabinofuranosyl]-5-cyanocytosine,
1-[5'-O-tert-Butyldiphenylsilyl-2',3'-dideoxy-2'-fluoro-3'-(N-hydroxylanino)-β-D-arabinofuranosyl]-5-phenylcytosine,
1-[5'-O-tert-Butyldiphenylsilyl-2',3'-dideoxy-2'-fluoro-3'-(N-hydroxylamino)-β-D-arabinofuranosyl]-5-benzylcytosine,
1-[5'-O-tert-Butyldiphenylsilyl-2',3'-dideoxy-2'-fluoro-3'-(N-hydroxylamino)-α-D-arabinofuranosyl]thymine,
1-[5'-O-tert-Butyldiphenylsilyl-2',3'-dideoxy-2'-fluoro-3'-(N-hydroxylamino)-α-D-arabinofuranosyl]-5-fluorouracil,
1-[5'-O-tert-Butyldiphenylsilyl-2',3'-dideoxy-2'-fluoro-3'-(N-hydroxylamino)-α-D-arabinofuranosyl]-5-chlorouracil,
1-[5'-O-tert-Butyldiphenylsilyl-2',3'-dideoxy-2'-fluoro-3'-(N-hydroxylamino)-α-D-arabinofuranosyl]-5-bromouracil,
1-[5'-O-tert-Butyldiphenylsilyl-2',3'-dideoxy-2'-fluoro-3'-(N-hydroxylamino)-α-D-arabinofuranosyl]-5-iodouracil,
1-[5'-O-tert-Butyldiphenylsilyl-2',3'-dideoxy-2'-fluoro-3'-(N-hydroxylamino)-α-D-arabinofuranosyl]-5-ethyluracil,
1-[5'-O-tert-Butyldiphenylsilyl-2',3'-dideoxy-2'-fluoro-3'-(N-hydroxylamino)-α-D-arabinofuranosyl]-5-n-propyluracil,
1-[5'-O-tert-Butyldiphenylsilyl-2',3'-dideoxy-2'-fluoro-3'-(N-hydroxylamino)-α-D-arabinofuranosyl]-5-i-propyluracil,
1-[5'-O-tert-Butyldiphenylsilyl-2',3'-dideoxy-2'-fluoro-3'-(N-hydroxylamino)-α-D-arabinofuranosyl]-5-(E-2-bromovinyl)uracil,
1-[5'-O-tert-Butyldiphenylsilyl-2',3'-dideoxy-2'-fluoro-3'-(N-hydroxylamino)-α-D-arabinofuranosyl]-5-vinyluracil,
1-[5'-O-tert-Butyldiphenylsilyl-2',3'-dideoxy-2'-fluoro-3'-(N-hydroxylamino)-α-D-arabinofuranosyl]-5-carboxyuracil,
1-[5'-O-tert-Butyldiphenylsilyl-2',3'-dideoxy-2'-fluoro-3'-(N-hydroxylamino)-α-D-arabinofuranosyl]-5-ethoxycarbonyluracil,
1-[5'-O-tert-Butyldiphenylsilyl-2',3'-dideoxy-2'-fluoro-3'-(N-hydroxylamino)-α-D-arabinofuranosyl]-5-aminocarbonyluracil,
1-[5'-O-tert-Butyldiphenylsilyl-2',3'-dideoxy-2'-fluoro-3'-(N-hydroxylamino)-α-D-arabinofuranosyl]-5-cyanouracil,
1-[5'-O-tert-Butyldiphenylsilyl-2',3'-dideoxy-2'-fluoro-3'-(N-hydroxylamino)-α-D-arabinofuranosyl]-5-phenyluracil,
1-[5'-O-tert-Butyldiphenylsilyl-2',3'-dideoxy-2'-fluoro-3'-(N-hydroxylamino)-α-D-arabinofuranosyl]-5-benzyluracil,
1-[5'-O-tert-Butyldiphenylsilyl-2',3'-dideoxy-2'-fluoro-3'-(N-hydroxylamino)-α-D-arabinofuranosyl]cytosine,
1-[5'-O-tert-Butyldiphenylsilyl-2',3'-dideoxy-2'-fluoro-3'-)N-hydroxylamino)-α-D-arabinofuranosyl]-5-flurocytosine,
1-[5'-O-tert-Butyldiphenylsilyl-2',3'-dideoxy-2'-fluoro-3'-(N-hydroxylamino)-α-D-arabinofuranosyl]-5-chlorocytosine,
1-[5'-O-tert-Butyldiphenylsilyl-2',3'-dideoxy-2'-fluoro-3'-(N-hydroxylamino)-α-D-arabinofuranosyl]-5-bromocytosine,
1-[5'-O-tert-Butyldiphenylsilyl-2',3'-dideoxy-2'-fluoro-3'-(N-hydroxylamino)-α-D-arabinofuranosyl]-5-iodocytosine,
1-[5'-O-tert-Butyldiphenylsilyl-2',3'-dideoxy-2'-fluoro-3'-(N-hydroxylanino)-α-D-arabinofuranosyl]-5-ethylcytosine,
1-[5'-O-tert-Butyldiphenylsilyl-2',3'-dideoxy-2'-fluoro-3'-(N-hydroxylamino)-α-D-arabinofuranosyl]-5-n-propylcytosine,
1-[5'-O-tert-Butyldiphenylsilyl-2',3'-dideoxy-2'-fluoro-3'-(N-hydroxylamino)-α-D-arabinofuranosyl]-5-i-propylcytosine,
1-[5'-O-tert-Butyldiphenylsilyl-2',3'-dideoxy-2'-fluoro-3'-(N-hydroxylamino)-α-D-arabinofuranosyl]-5-(E-2-bromovinyl)cytosine,
1-[5'-O-tert-Butyldiphenylsilyl-2',3'-dideoxy-2'-fluoro-3'-(N-hydroxylamino)-α-D-arabinofuranosyl]-5-vinylcytosine,
1-[5'-O-tert-Butyldiphenylsilyl-2',3'-dideoxy-2'-fluoro-3'-(N-hydroxylamino)-α-D-arabinofuranosyl]-5-carboxycytosine,
1-[5'-O-tert-Butyldiphenylsilyl-2',3'-dideoxy-2'-fluoro-3'-(N-hydroxylamino)-α-D-arabinofuranosyl]-5-ethoxycarbonylcytosine,
1-[5'-O-tert-Butyldiphenylsilyl-2',3'-dideoxy-2'-fluoro-3'-(N-hydroxylamino)-α-D-arabinofuranosyl]-5-aminocarbonylcytosine,
1-[5'-O-tert-Butyldiphenylsilyl-2',3'-dideoxy-2'-fluoro-3'-(N-hydroxylamino)-α-D-arabinofuranosyl]-5-cyanocytosine,
1-[5'-O-tert-Butyldiphenylsilyl-2',3'-dideoxy-2'-fluoro-3'-(N-hydroxylamino)-α-D-arabinofuranosyl]-5-phenylcytosine,
1-[5'-O-tert-Butyldiphenylsilyl-2',3'-dideoxy-2'-fluoro-3'-(N-hydroxylamino)-α-D-arabinofuranosyl]-5-benzylcytosine, Example 11

General procedure for synthesis of 5'-O-tert-butyldiphenylsilyl-2',3'-dideoxy-2'-fluoro-3'-(N-hydroxy-N-substituted amino)-D-arabinofuranosyl nucleosides (174): To a solution of 172 (1 eq) in methanol is added an aldehyde (1.2 eq). The resulting mixture is stirred at room temperature for 10 minuntes. NaBH$_3$CN (2 eq) is then added in portion. The reaction is continuously stirred at room temperature for 10 mininutes. After concentration of the mixture to dryness, the residue is dissolved in methylene chloride. The organic solution is washed with brine, dried over Na$_2$SO$_4$, filtrated, and concentrated to give the crude product which is purified by flash column chromatography over silica gel.

[5-O-tert-Butyldiphenylsilyl-2,3-dideoxy-2-fluoro-3-(N-hydroxy-N-butylamino)-β-D-arabinofuranosyl]uracil (174, B=uracil, $R^{3'}$=n-C$_3$H$_7$): This compound is prepared from 172 (B=uracil) as a white solid (93% for 2 steps): $^1$H NMR (CDCl$_3$) δ 10.58 (bs, 1H, NH), 7.69 (m, 5H, arom. and H-6), 7.40 (m, 6H, arom.), 7.11 (bs, 1H, OH), 6.20 (dd, J=3.4 and 18.5 Hz, 1H, H1'), 5.56 (d, J=8.2 Hz, 1H, H-5), 5.50 (dd, J=3.2 and 52.7 Hz, 1H, H-2'), 4.28 (m, 1H, H-4'), 3.92 (m, 3H, H-3' and H-5'), 2.81 (m, 2H, NCH$_2$), 1.67–0.88 (m, 16H, t-Bu, CH$_3$ and 2CH$_2$). $^{13}$C NMR (CDCl$_3$) δ 164.4, 150.9, 142.3, 136.1, 136.0, 133.6, 133.3, 130.4, 128.3, 112.8, 101.9, 94.6, 90.9, 85.4, 85.0, 79.4, 72.5, 72.0, 64.2, 58.9, 29.6, 27.4, 20.9, 19.9, 14.6.

[5-O-tert-Butyldiphenylsilyl-2,3-dideoxy-2-fluoro-3-(N-hydroxy-N-iso-butylamino)-β-D-arabinofuranosyl]uracil (174, B=uracil, $R^{3'}$=i-$C_3H_7$): This compound is prepared from 172 (B=uracil) as a white solid (92% for 2 steps): $^1$H NMR (CDCl$_3$) δ 10.16 (bs, 1H, NH), 7.69 (m, 5H, arom. and H-6), 7.41 (m, 6H, arom.), 6.51 (bs, 1H, OH), 6.19 (dd, J=3.2 and 18.7 Hz, 1H, H1'), 5.58 (d, J. 8.1 Hz, 1H, H-5), 5.45 (m, 1H, H-2'), 4.27 (m, 1H, H-4'), 4.04 (dd, J=3.0 and 11.6 Hz, 1H, H-5'), 3.88 (dd, J=3.0 and 11.0 Hz, 1H, H-5'), 3.69 (dd, J=5.0 and 26.4 Hz, 1H, H-3'), 2.55 (d, J=7.0 Hz, 2H, NCH$_2$), 1.91 (m, 1H, CH), 1.11 (s, 9H, t-Bu), 0.94 (dd, J=1.8 and 6.6 Hz, 6H, 2CH$_3$). $^3$C NMR (CDCl$_3$) δ 164.2, 150.8, 142.1, 136.1, 136.0, 133.5, 133.3, 130.5, 130.4, 128.3, 102.0, 94.9, 91.2, 85.5, 85.1, 79.3, 73.2, 72.7, 66.9, 64.3, 27.5, 26.7, 21.3, 19.9.

[5-O-tert-Butyldiphenylsilyl-2,3-dideoxy-2-fluoro-3-(N-hydroxy-N-cyclohexylmethylamino)-β-D-arabinofuranosyl]uracil (174, B=uracil, $R^{3'}$=cyclohexyl): This compound is prepared from 172 (B=uracil) as a white solid (88% for 2 steps): $^1$H NMR (CDCl$_3$) δ 9.89 (bs, 1H, NH), 7.53 (m, 11H, arom. and H-6), 6.25 (bs, 1H, OH), 6.17 (dd, J=3.7 and 18.8 Hz, 1H, H-1'), 5.56 (d, J=8.3 Hz, 1H, H-5), 5.42 (m, 1H, H-2'), 4.22 (m, 1H, H-4'), 4.02 (dd, J=3.0 and 11.1 Hz, 1H, H-5'), 3.87 (dd, J=3.3 and 11.3 Hz, 1H, H-5'), 3.69 (dd, J=4.4 and 27.1 Hz, 1H, H-3'), 2.59 (d, J=6.7 Hz, 2H, NCH$_2$), 1.85–0.79 (m, 11H, CH, 5CH$_2$), 1.09 (s, 9H, t-Bu). $^{13}$C NMR (CDCl$_3$) δ 164.1, 150.9, 142.1, 136.1, 136.0, 133.5, 133.3, 130.4, 128.3, 112.8, 102.0, 94.8, 91.0, 85.4, 85.1, 79.3, 73.0, 72.5, 65.8, 64.2, 36.1, 32.2, 27.5, 27.3, 26.6, 19.9.

[5-O-tert-Butyldiphenylsilyl-2,3-dideoxy-2-fluoro-3-(N-hydroxy-N-iso-butylamino)-β-D-arabinofuranosyl]-5-flurouracil (174, B=5-fluorouracil, $R^{3'}$=i-$C_3H_7$): This compound is prepared from 172 (B=5-fluorouracil) as a white solid (65% for 2 steps): $^1$H NMR (CDCl$_3$) δ 10.34 (bs, 1H, NH), 7.71 (m, 5H, arom. and H-6), 7.43 (m, 6H, arom.), 6.30 (bs, 1H, OH), 6.13 (d, J=18.0 Hz, 1H, H1'), 5.45 (dd, J=2.4 and 52.1 Hz, 1H, H-2'), 4.28 (m, 1H, H-4'), 4.02 (dd, J=3.6 and 11.4 Hz, 1H, H-5'), 3.84 (dd, J=3.3 and 11.4 Hz, 1H, H-5'), 3.64 (dd, J=5.0 and 27.0 Hz, 1H, H-3'), 2.50 (d, J=6.7 Hz, 2H, NCH$_2$), 1.89 (m, 1H, CH), 1.11 (s, 9H, t-Bu), 0.92 (dd, J=2.5 and 6.6 Hz, 6H, 2CH$_3$). $^{13}$C NMR (CDCl$_3$) δ 157.9, 157.4, 149.5, 142.9, 138.2, 136.1, 136.0, 133.3, 130.5, 128.3, 126.6, 126.0, 95.1, 91.4, 85.7, 85.4, 79.4, 73.2, 72.7, 66.7, 64.2, 27.4, 26.6, 21.2, 19.8.

[5-O-tert-Butyldiphenylsilyl-2,3-dideoxy-2-fluoro-3-(N-hydroxy-N-iso-butylamino)-α-D-arabinofuranosyl]-5-fluorouracil (174, B=5-fluorouracil): This compound is prepared from the α-anomer of 172 (B=5-fluorouracil) as a white solid (83% for 2 steps): $^1$H NMR (CDCl$_3$) δ10.46 (bs, 1H, NH), 7.55 (m, 11H, arom. and H-6), 6.62 (bs, 1H, OH), 6.00 (d, J=14.6 Hz, 1H, H-1'), 5.62 (d, J=49.1 Hz, 1H, H-2'), 4.49 (m, 1H, H-4'), 3.84 (m, 2H, H-5'), 3.64 (m, 1H, H-3'), 2.51 (d, J=6.4 Hz, 2H, NCH$_2$), 1.9 (m, 1H, CH), 1.10 (s, 9H, t-Bu), 0.90 (dd, J=2.3 and 6.6 Hz, 6H, 2CH$_3$). $^{13}$C NMR (CDCl$_3$) δ 158.5, 158.1, 149.2, 142.5, 137.8, 136.1, 133.4, 130.4, 128.3, 126.5, 125.8, 99.5, 95.9, 92.6, 91.8, 84.9, 74.1, 73.6, 67.5, 65.1, 27.4, 26.4, 21.3, 19.8.

In addition, 5'-O-tert-butyldiphenylsilyl-2',3'-dideoxy-2'-fluoro-3'-(N-hydroxylamino)-D-arabinofuranosyl nucleosides (172) are converted into the corresponding 5'-O-tert-butyldiphenylsilyl-2',3'-dideoxy-2'-fluoro-3'-(N-hydroxyl-N-substituted amino)-D-arabinofuranosyl nucleosides (174) using the following aldehydes: n-valeraldehyde, caproaldehyde, heptaldehyde, n-caprylaldehyde, n-pelargonaldehyde, palmitaldehyde, stearaldehyde, phenylacetaldehyde, benzaldehyde, o-tolualdehyde, m-tolualdehyde, p-tolualdehyde, salicylaldehyde, p-hydroxybenzaldehyde, anisaldehyde, vanillin, piperonal, geranial and cinnamaldehyde.

Example 12

2',3'-Dideoxy-2'-β-fluoro-3'-(N-hydroxy-N-substituted amino)-D-arabinofuranosyl nucleosides (175): To a solution of protected nucleosides 174 in dry THF is added a solution of TBAF (1.2 eq) in THF. After stirring at room temperature for 1 hour, the resulting mixture is directly transferred onto a silica gel column for purification without evaporation.

1-[2,3-Dideoxy-2-fluoro-3-(N-hydroxy-N-butylamino)-β-D-arabinofuranosyl]uracil (175, B=uracil, $R^{3'}$=n-$C_3H_7$): This compound is prepared from the corresponding 174 as a white solid (93%): $^1$H NMR (CD$_3$OD) δ 7.86 (dd, J=2.0 and 8.1 Hz, 1H, H-6), 6.06 (dd, J=3.7 and 18.7 Hz, 1H, H-1'), 5.69 (d, J=8.1 Hz, 1H, H-5) 5.43 (ddd, J=1.5, 3.7 and 53.1 Hz, 1H, H-2'), 4.19 (m, 1H, H-4'), 3.90 (dd, J=2.9 and 12.4 Hz, 1H, H-5'), 3.75 (dd, J=4.72 and 12.4 Hz, 1H, H-5'), 3.52 (ddd, J=1.5, 6.1 and 27.5 Hz, 1H, H-3'), 2.79 (m, 2H, NCH$_2$), 1.48 (m, 4H, 2 CH$_2$), 0.95 (t, J=7.1 Hz, 3H, CH3). 13C NMR (CD3OD) (166.3, 152.2, 143.9, 143.8, 102.1, 95.4, 91.6, 86.6, 86.3, 81.3, 81.2, 74.0, 73.5, 63.3, 59.6, 31.1, 21.7, 14.8. Anal. Calcd for $C_{13}H_{20}FN_3O_5.0.5H_2O$: C, 47.85; H, 6.49; N, 12.88. Found: C, 48.00; H, 6.62; N, 12.97.

[2,3-Dideoxy-2-fluoro-3-(N-hydroxy-N-isobutylamino)-β-D-arabinofuranosyl]uracil (175, B=uracil, R3'=i-$C_3H_7$): This compound is prepared from the corresponding 174 as a white solid (94%): $^1$H NMR (CD$_2$OD) δ 7.86 (dd, J=2.0 and 8.1 Hz, 1H, H-6), 6.06 (dd, J=3.7 and 18.6 Hz, 1H, H1'), 5.69 (d, J=8.1 Hz, 1H, H-5), 5.43 (ddd, J=1.6, 3.8 and 53.2 Hz, 1H, H-2'), 4.18 (m, 1H, H-4'), 3.83 (ddd, J=2.8, 12.2 and 29.4 Hz, 2H, H-5'), 3.48 (ddd, J=1.5, 6.1 and 27.4 Hz, 1H, H-3'), 2.67 (dd, J=6.2 and 12.1 Hz, 1H, NCH$_2$), 2.46 (dd, J=7.6 and 12.2 Hz, 1H, NCH$_2$), 1.90 (m, 1H, CH), 0.95 (m, 6H, 2 CH$_3$). $^{13}$C NMR (CD$_2$OD) δ 166.3, 152.2, 143.8, 102.1, 95.4, 91.7, 86.6, 86.3, 81.3, 74.3, 73.9, 67.9, 63.4, 27.7. 21.5, 21.4. Anal. Calcd for $C_{13}H_{20}FN_3O_5.0.2H_2O$: C, 48.65; H, 6.41; N, 13.09. Found: C, 48.61; H, 6.65; N, 12.93.

1-[2,3-Dideoxy-2-β-fluoro-3-(N-hydroxy-N-cyclohexanemethylamino)-β-D-arabinofuranosyl]uracil (175, B=uracil, $R^{3'}$=cyclohexyl): This compound is prepared from the corresponding 174 as a white solid (85%): $^1$H NMR (CD$_3$OD) δ 7.86 (dd, J=2.0 and 8.1 Hz, 1H, H-6), 6.05 (dd, J=3.8 and 18.6 Hz, 1H, H1'), 5.68 (d, J=8.1 Hz, 1H, H-5), 5.41 (ddd, J=1.6, 3.8 and 53.2 Hz, 1H, H-2'), 4.17 (m, 1H, H-4'), 3.90 (dd, J=3.2 and 12.4 Hz, 1H, H-5'), 3.74 (dd, J=4.6 and 12.2 Hz, 1H, H-5'), 3.46 (ddd, J=1.7, 6.3 and 27.4 Hz, 1H, H-3'), 2.68 (dd, J=5.6 and 12.1 Hz, 1H, NCH$_2$), 2.51 (dd, J=7.4 and 12.5 Hz, 1H, NCH$_2$), 1.98–0.81 (m, 11H, CH, 5 CH$_2$). $^{13}$C NMR (CD$_3$OD) δ 166.3, 152.2, 143.8, 102.0, 95.4, 91.7, 86.6, 86.3, 81.4, 81.3, 74.4, 73.9, 66.7, 63.4, 37.2, 33.0, 28.3, 27.6. Anal. Calcd for $C_{16}H_{24}FN_3O_5$: C, 53.77; H, 6.77; N, 11.76. Found: C, 53.57; H, 6.75; N, 12.06.

1-[2,3-dideoxy-2-fluoro-3-(N-hydroxy-N-iso-butylamino)-β-D-arabinofuranosyl]-5-fluoro-uracil (175, B=5-fluorouracil, $R^3$=i-$C_3H_7$): This compound is prepared from corresponding 174 as a white solid (76%): $^1$H NMR (CD$_2$OD) δ 8.08 (dd, J=1.8 and 6.8 Hz, 1H, H-6), 6.04 (ddd, J=1.7, 3.9 and 18.0 Hz, 1H, H-1'), 5.44 (ddd, J=1.7, 3.7 and 53.1 Hz, 1H, H-2'), 4.18 (m, 1H, H-4'), 3.92 (dd, J=3.6 and 12.6 Hz, 1H, H-5'), 3.75 (dd, J=4.4 and 12.4 Hz, 1H, H-5'), 3.51 (ddd, J=1.7, 6.2 and 27.4 Hz, 1H, H-3'), 2.67 (dd, J=6.2 and 12.8 Hz, 1H, NCH$_2$), 2.46 (dd, J=7.7 and 12.4 Hz, 1H, NCH$_2$), 1.89 (m, 1H, CH), 0.97 (d, J=2.2 Hz, 3H, CH$_3$), 0.94

(d, J=2.2 Hz, 3H, CH₃). ¹³C NMR (CD₂OD) δ 159.8, 150.8, 143.8, 139.2, 128.1, 127.4, 95.4, 91.6, 86.6, 86.3, 81.5, 81.4, 74.0, 73.6, 67.9, 63.1, 27.7, 21.4, 21.3. Anal. Calcd for C₁₃H₁₉F₂N₃O₅.0.5 H₂O: C, 45.48; H, 5.87; N, 12.24. Found: C, 45.60: H, 5.55; N, 12.17.

1-[2,3-Dideoxy-2-β-fluoro-3-(N-hydroxy-N-iso-butylamino)-α-D-arabinofuranosyl]-5-fluoro-uracil (175, a-anomer, B=5-fluorouracil, R³'=i-C₃H₇): This compound is prepared from corresponding a-anomer of 174 as a white solid (70%): ¹H NMR (CD₂OD) δ 7.89 (d, J=6.7 Hz, 1H, H-6), 6.09 (d, J=15.6 Hz, 1H, H1'), 5.45 (dt, J=1.9 and 50.5 Hz, 1H, H-2'), 4.54 (m, 1H, H-4'), 3.74 (m, 2H, H-5'), 3.44 (ddd, J=2.0, 4.6 and 24.6 Hz, 1H, H-3'), 2.57 (dd, J=6.2 and 12.5 Hz, 1H, NCH₂), 2.46 (dd, J=7.5 and 12.4 Hz, 1H, NCH₂), 1.93 (m, 1H, CH), 0.93 (dd, J=4.6 and 6.6 Hz, 6H, 2 CH₃). ¹³C NMR (CD₃OD) δ 160.0, 159.5, 151.0, 144.2, 139.5, 127.0, 126.3, 100.5, 96.9, 93.0, 92.2, 86.3, 86.2, 75.2, 74.7, 68.1, 64.2, 27.6, 21.4, 21.3. Anal. Calcd for C₁₃H₁₉F₂N₃O₅.0.4 H₂O: C, 45.59; H, 5.83; N, 12.27. Found: C, 45.85; H, 5.59; N, 12.58.

By using the same procedure but from the corresponding 5'-O-(tert-butyldiphenylsilyl) nucleosides, the following compounds are synthesized:

1-[2',3'-Dideoxy-2'-fluoro-3'-(N-hydroxy-N-pentylamino)-β-D-arabinofuranosyl]thymine,
1-[2',3'-Dideoxy-2'-fluoro-3'-(N-hydroxy-N-pentylamino)-β-D-arabinofuranosyl]uracil,
1-[2',3'-Dideoxy-2'-fluoro-3'-(N-hydroxy-N-pentylamino)-β-D-arabinofuranosyl]-5-chlorouracil,
1-[2',3'-Dideoxy-2'-fluoro-3'-(N-hydroxy-N-pentylamino)-β-D-arabinofiuranosyl]-5-bromouracil,
1-[2',3'-Dideoxy-2'-fluoro-3'-(N-hydroxy-N-pentylamino)-β-D-arabinofuranosyl]-5-iodouracil,
1-[2',3'-Dideoxy-2'-fluoro-3'-(N-hydroxy-N-pentylamino)-β-D-arabinofuranosyl]-5-ethyluracil,
1-[2',3'-Dideoxy-2'-fluoro-3'-(N-hydroxy-N-pentylamino)-β-D-arabinofuranosyl]-5-n-propyluracil,
1-[2',3'-Dideoxy-2'-fluoro-3'-(N-hydroxy-N-pentylamino)-β-D-arabinofuranosyl]-5-i-propyluracil,
1-[2',3'-Dideoxy-2'-fluoro-3'-(N-hydroxy-N-pentylamino)-β-D-arabinofuranosyl]-5-(E-2-bromo-vinyl)uracil,
1-[2',3'-Dideoxy-2'-fluoro-3'-(N-hydroxy-N-pentylamino)-β-D-arabinofaranosyl]-5-vinyluracil,
1-[2',3'-Dideoxy-2'-fluoro-3'-(N-hydroxy-N-pentylamino)-β-D-arabinofuranosyl]-5-carboxyuracil,
1-[2',3'-Dideoxy-2'-fluoro-3'-(N-hydroxy-N-pentylamino)-β-D-arabinofuranosyl]-5-ethoxycarbonyluracil,
1-[2',3'-Dideoxy-2'-fluoro-3'-(N-hydroxy-N-pentylamino)-β-D-arabinofuranosyl]-5-aminocarbonyluracil,
1-[2',3'-Dideoxy-2'-fluoro-3'-(N-hydroxy-N-pentylamino)-β-D-arabinofuranosyl]-5-cyanouracil,
1-[ 2',3'-Dideoxy-2'-fluoro-3'-(N-hydroxy-N-pentylamino)-β-D-arabinofuranosyl]-5-phenyluracil,
1-[2',3'-Dideoxy-2'-fluoro-3'-(N-hydroxy-N-pentylamino)-β-D-arabinofuranosyl]-5-benzyluracil,
1-[2',3'-Dideoxy-2'-fluoro-3'-(N-hydroxy-N-pentylamino)-β-D-arabinofuranosyl]-cytosine,
1-[2',3'-Dideoxy-2'-fluoro-3'-(N-hydroxy-N-pentylamino)-β-D-arabinofuranosyl]-5-fluorocytosine,
1-[2',3'-Dideoxy-2'-fluoro-3'-(N-hydroxy-N-pentylamino]-β-D-arabinofuranosyl]-5-chlorocytosine,
1-[2',3'-Dideoxy-2'-fluoro-3'-(N-hydroxy-N-pentylamino]-β-D-arabinofuranosyl]-5-bromocytosine,
1-[2',3'-Dideoxy-2'-fluoro-3'-(N-hydroxy-N-pentylamino]-β-D-arabinofuranosyl]-5-iodocytosine,
1-[2',3'-Dideoxy-2'-fluoro-3'-(N-hydroxy-N-pentylamino]-β-D-arabinofuranosyl]-5-ethylcytosine,
1-[2',3'-Dideoxy-2'-fluoro-3'-(N-hydroxy-N-pentylamino)-β-D-arabinofuranosyl]-5-n-propylcytosine,
1-[2',3'-Dideoxy-2'-fluoro-3'-(N-hydroxy-N-pentylamino)-β-D-arabinofuranosyl]-5-i-propylcytosine,
1-[2',3'-Dideoxy-2'-fluoro-3'-(N-hydroxy-N-pentylamino)-β-D-arabinofuranosyl]-5-(E-2-bromovinyl)cytosine,
1-[2',3'-Dideoxy-2'-fluoro-3'-(N-hydroxy-N-pentylamino)-β-D-arabinofuranosyl]-5-vinylcytosine,
1-[2',3'-Dideoxy-2'-fluoro-3'-(N-hydroxy-N-pentylamino)-β-D-arabinofuranosyl]-5-carboxycytosine,
1-[2',3'-Dideoxy-2'-fluoro-3'-(N-hydroxy-N-pentylamino)-β-D-arabinofuranosyl]-5-ethoxycarbonylcytosine,
1-[2',3'-Dideoxy-2'-fluoro-3'-(N-hydroxy-N-pentylamino]-β-D-arabinofiuranosyl]-5-aminocarbonylcytosine,
1-[2',3'-Dideoxy-2'-fluoro-3'-(N-hydroxy-N-pentylamino]-β-D-arabinofuranosyl]-5-cyanocytosine,
1-[2',3'-Dideoxy-2'-fluoro-3'-(N-hydroxy-N-pentylamino)-β-D-arabinofuranosyl]-5-phenylcytosine,
1-[2',3'-Dideoxy-2'-fluoro-3'-(N-hydroxy-N-pentylamino)-β-D-arabinofuranosyl]-5-benzylcytosine,
1-[2',3'-Dideoxy-2'-fluoro-3'-(N-hydroxy-N-pentylamino)-α-D-arabinofuranosyl]thymine,
1-[2',3'-Dideoxy-2'-fluoro-3'-(N-hydroxy-N-pentylamino)-α-D-arabinofuranosyl]-5-fluorouracil,
1-[2',3'-Dideoxy-2'-fluoro-3'-(N-hydroxy-N-pentylamino)-α-D-arabinofuranosyl]-5-chlorouracil,
1-[2',3'-Dideoxy-2'-fluoro-3'-(N-hydroxy-N-pentylamino)-α-D-arabinofuranosyl]-5-bromouracil,
1-[2',3'-Dideoxy-2'-fluoro-3'-(N-hydroxy-N-pentylamino)-α-D-arabinofuranosyl]-5-iodouracil,
1-[2',3'-Dideoxy-2'-fluoro-3'-(N-hydroxy-N-pentylamino)-α-D-arabinofuranosyl]-5-ethyluracil,
1-[2',3'-Dideoxy-2'-fluoro-3'-(N-hydroxy-N-pentylamino)-α-D-arabinofuranosyl]-5-n-propyluracil,
1-[2',3'-Dideoxy-2'-fluoro-3'-(N-hydroxy-N-pentylamino)-α-D-arabinofuranosyl]-5-i-propyluracil,
1-[2',3'-Dideoxy-2'-fluoro-3'-(N-hydroxy-N-pentylamino)-α-D-arabinofuranosyl]-5-(E-2-bromovinyl)uracil,
1-[2',3'-Dideoxy-2'-fluoro-3'-(N-hydroxy-N-pentylamino)-α-D-arabinofuranosyl]-5-vinyluracil,
1-[2',3'-Dideoxy-2'-fluoro-3'-(N-hydroxy-N-pentylamino)-α-D-arabinofuranosyl]-5-carboxyuracil,
1-[2',3'-Dideoxy-2'-fluoro-3'-(N-hydroxy-N-pentylamino)-α-D-arabinofuranosyl]-5-ethoxycarbonyluracil,
1-[2',3'-Dideoxy-2'-fluoro-3'-(N-hydroxy-N-pentylamino)-α-D-arabinofuranosyl]-5-aminocarbonyluracil,
1-[2',3'-Dideoxy-2'-fluoro-3'-(N-hydroxy-N-pentylamino)-α-D-arabinofuranosyl}-5-cyanouracil,
1-[2',3'-Dideoxy-2'-fluoro-3'-(N-hydroxy-N-pentylamino)-α-D-arabinofuranosyl]-5-phenyluracil,
1-[2',3'-Dideoxy-2'-fluoro-3'-(N-hydroxy-N-pentylamino)-α-D-arabinofuranosyl]-5-benzyluracil,
1-[2',3'-Dideoxy-2'-fluoro-3'-(N-hydroxy-N-pentylamino)-α-D-arabinofuranosyl]cytosine,
1-[2',3'-Dideoxy-2'-fluoro-3'-(N-hydroxy-N-pentylamino)-α-D-arabinofuranosyl]-5-fluorocytosine,
1-[2',3'-Dideoxy-2'-fluoro-3'-(N-hydroxy-N-pentylamino)-α-D-arabinofuranosyl]-5-chlorocytosine,
1-[2',3'-Dideoxy-2'-fluoro-3'-(N-hydroxy-N-pentylamino)-α-D-arabinofuranosyl]-5-bromocytosine,
1-[2',3'-Dideoxy-2'-fluoro-3'-(N-hydroxy-N-pentylamino)-α-D-arabinofuranosyl]-5-iodocytosine,
1-[2',3'-Dideoxy-2'-fluoro-3'-(N-hydroxy-N-pentylamino)-α-D-arabinofuranosyl]-5-ethylcytosine,
1-[2',3'-Dideoxy-2'-fluoro-3'-(N-hydroxy-N-pentylamino)-α-D-arabinofuranosyl]-5-n-propylcytosine, 1-[2',3'-Dideoxy-2'-fluoro-3'-(N-hydroxy-N-pentylamino)-α-D-arabinofuranosyl]-5-i-propylcytosine,
1-[2',3'-Dideoxy-2'-fluoro-3'-(N-hydroxy-N-pentylamino)-α-D-arabinofuranosyl]-5-(E-2-bromovinyl)cytosine,
1-[2',3'-Dideoxy-2'-fluoro-3'-(N-hydroxy-N-pentylanino)-α-D-arabinofuranosyl]-5-vinylcytosine,
1-[2',3'-Dideoxy-2'-fluoro-3'-(N-hydroxy-N-pentylamino)-α-D-arabinofuranosyl]-5-carboxycytosine,
1-[2',3'-Dideoxy-2'-fluoro-3'-(N-hydroxy-N-pentylamino)-α-D-arabinofuranosyl]-5-ethoxycarbonylcytosine,
1-[2',3'-Dideoxy-2'-fluoro-3'-(N-hydroxy-N-pentylamino)-α-D-arabinofuranosyl]-5-aminocarbonylcytosine,
1-[2',3'-Dideoxy-2'-fluoro-3'-(N-hyrdoxy-N-pentylamino]-α-D-arabinofaranosyll-5-cyanocytosine,
1-[2',3'-Dideoxy-2'-fluoro-3'-(N-hydroxy-N-pentylamino)-α-D-arabinofuranosyl]-5-phenylcytosine,
1-[2',3'-Dideoxy-2'-fluoro-3'-(N-hydroxy-N-pentylamino)-α-D-arabinofuranosyl]-5-benzylcytosine,
1-[2',3'-Dideoxy-2'-fluoro-3'-(N-hydroxy-N-hexylamino)-β-D-arabinofuranosyl]thymine,
1-[2',3'-Dideoxy-2'-fluoro-3'-(N-hydroxy-N-hexylamino)-β-D-arabinofuranosyl]uracil,
1-[2',3'-Dideoxy-2'-fluoro-3'-(N-hydroxy-N-hexylamino)-β-D-arabinofuranosyl]-5-chlorouracil,
1-[2',3'-Dideoxy-2'-fluoro-3'-(N-hydroxy-N-hexylamino)-β-D-arabinofuranosyl]-5-bromouracil,
1-[2',3'-Dideoxy-2'-fluoro-3'-(N-hydroxy-N-hexylamino)-β-D-arabinofuranosyl]-5-iodouracil,
1-[2',3'-Dideoxy-2'-fluoro-3'-(N-hydroxy-N-hexylamino)-β-D-arabinofuranosyl]-5-ethyluracil,
1-[2',3'-Dideoxy-2'-fluoro-3'-(N-hydroxy-N-hexylamino)-β-D-arabinofuranosyl]-5-n-propyluracil,
1-[2',3'-Dideoxy-2'-fluoro-3'-(N-hydroxy-N-hexylamino)-β-D-arabinofuranosyl]-5-i-propyluracil,
1-[2',3'-Dideoxy-2'-fluoro-3'-(N-hydroxy-N-hexylamino)-β-D-arabinofuranosyl]-5-(E-2-bromovinyl)uracil,
1-[2',3'-Dideoxy-2'-fluoro-3'-(N-hydroxy-N-hexylamino)-β-D-arabinofuranosyl]-5-vinyluracil,
1-[2',3'-Dideoxy-2'-fluoro-3'-(N-hydroxy-N-hexylamino)-β-D-arabinofuranosyl]-5-carboxyuracil,
1-[2',3'-Dideoxy-2'-fluoro-3'-(N-hydroxy-N-hexylamino)-β-D-arabinofuranosyl]-5-ethoxycarbonyluracil,
1-[2',3'-Dideoxy-2'-fluoro-3'-(N-hydroxy-N-hexylamino)-β-D-arabinofuranosyl]-5-aminocarbonyluracil,
1-[2',3'-Dideoxy-2'-fluoro-3'-(N-hydroxy-N-hexylamino)-β-D-arabinofuranosyl]-5-cyanouracil,
1-[2',3'-Dideoxy-2'-fluoro-3'-(N-hydroxy-N-hexylamino)-β-D-arabinofuranosyl]-5-phenyluracil,
1-[2',3'-Dideoxy-2'-fluoro-3'-(N-hydroxy-N-hexylamino)-β-D-arabinofuranosyl]-5-benzyluracil,
1-[2',3'-Dideoxy-2'-fluoro-3'-(N-hydroxy-N-hexylamino)-β-D-arabinofuranosyl]cytosine,
1-[2',3'-Dideoxy-2'-fluoro-3'-(N-hydroxy-N-hexylamino)-β-D-arabinofuranosyl]-5-fluorocytosine,
1-[2',3'-Dideoxy-2'-fluoro-3'-(N-hydroxy-N-hexylamino]-β-D-arabinofuranosyl}-5-chlorocytosine,
1-[2',3'-Dideoxy-2'-fluoro-3'-(N-hydroxy-N-hexylamino]-β-D-arabinofuranosyl]-5-bromocytosine,
1-[2',3'-Dideoxy-2'-fluoro-3'-(N-hydroxy-N-hexylamino]-β-D-arabinofuranosyl]-5-iodocytosine,
1-[2',3'-Dideoxy-2'-fluoro-3'-(N-hydroxy-N-hexylamino]-β-D-arabinofuranosyl-5-ethylcytosine,
1-[2',3'-Dideoxy-2'-fluoro-3'-(N-hydroxy-N-hexylamino]-β-D-arabinofuranosyl]-5-n-propylcytosine,
1-[2',3'-Dideoxy-2'-fluoro-3'-(N-hydroxy-N-hexylamino]-β-D-arabinofuranosyl]-5-i-propylcytosine,
1-[2',3'-Dideoxy-2'-fluoro-3'-(N-hydroxy-N-hexylamino]-β-D-arabinofuranosyl]-5-(E-2-bromovinyl)cytosine,
1-[2',3'-Dideoxy-2'-fluoro-3'-(N-hydroxy-N-hexylamino]-β-D-arabinofuranosyl]-5-vinylcytosine,
1-[2',3'-Dideoxy-2'-fluoro-3'-(N-hydroxy-N-hexylamino]-β-D-arabinofuranosyl]-5-ethoxycarbonylcytosine,
1-[2',3'-Dideoxy-2'-fluoro-3'-(N-hydroxy-N-hexylamino]-β-D-arabinofuranosy]-5-aminocarbonylcytosine,
1-[2',3'-Dideoxy-2'-fluoro-3'-(N-hydroxy-N-hexylamino]-β-D-arabinofuranosyl]-5-cyanocytosine,
1-[2',3'-Dideoxy-2'-fluoro-3'-(N-hydroxy-N-hexylamino]-β-D-arabinofuranosyl]-5-phenylcytosine,
1-[2',3'-Dideoxy-2'-fluoro-3'-(N-hydroxy-N-hexylamino)-β-D-arabinofuranosyl]-5-benzylcytosine,
1-[2',3'-Dideoxy-2'-fluoro-3'-(N-hydroxy-N-hexylamino)-β-D-arabinofuranosyl]-thymine,
1-[2',3'-Dideoxy-2'-fluoro-3'-(N-hydroxy-N-hexylamino)-β-D-arabinofuranosyl]-5-fluorouracil,
1-[2',3'-Dideoxy-2'-fluoro-3'-(N-hydroxy-N-hexylamino)-β-D-arabinofuranosyl]-5-chlorouracil,
1-[2',3'-Dideoxy-2'-fluoro-3'-(N-hydroxy-N-hexylamino)-β-D-arabinofuranosyl]-5-bromouracil,
1-[2',3'-Dideoxy-2'-fluoro-3'-(N-hydroxy-N-hexylamino)-β-D-arabinofuranosyl]-5-iodouracil,
1-[2',3'-Dideoxy-2'-fluoro-3'-(N-hydroxy-N-hexylamino)-β-D-arabinofuranosyl]-5-ethyluracil,
1-[2',3'-Dideoxy-2'-fluoro-3'-(N-hydroxy-N-hexylamino)-β-D-arabinofuranosyl]-5-n-propyluracil,
1-[2',3'-Dideoxy-2'-fluoro-3'-(N-hydroxy-N-hexylamino)-β-D-arabinofuranosyl]-5-i-propyluracil,
1-[2',3'-Dideoxy-2'-fluoro-3'-(N-hydroxy-N-hexylamino)-α-D-arabinofuranosyl]-5-(E-2-bromovinyl)-uracil,
1-[2',3'-Dideoxy-2'-fluoro-3'-(N-hydroxy-N-hexylamino)-α-D-arabinofuranosyl]-5-vinyluracil,
1-[2',3'-Dideoxy-2'-fluoro-3'-(N-hydroxy-N-hexylamino)-α-D-arabinofuranosyl]-5-carboxyuracil,
1-[2',3'-Dideoxy-2'-fluoro-3'-(N-hydroxy-N-hexylamino)-α-D-arabinofuranosyl]-5-ethoxycarbonyluracil,
1-[2',3'-Dideoxy-2'-fluoro-3'-(N-hydroxy-N-hexylamino)-α-D-arabinofuranosyl]-5-aminocarbonyluracil,
1-[2',3'-Dideoxy-2'-fluoro-3'-(N-hydroxy-N-hexylamino)-α-D-arabinofuranosyl]-5-cyanouracil,
1-[2',3'-Dideoxy-2'-fluoro-3'-(N-hydroxy-N-hexylamino)-α-D-arabinofuranosyl]-5-phenyluracil,
1-[2',3'-Dideoxy-2'-fluoro-3'-(N-hydroxy-N-hexylarino)-α-D-arabinofuranosyl]-5-benzyluracil,
1-[2',3'-Dideoxy-2'-fluoro-3'-(N-hydroxy-N-hexylamino)-α-D-arabinofuranosyl]cytosine,
1-[2',3'-Dideoxy-2'-fluoro-3'-(N-hydroxy-N-hexylamino)-α-D-arabinofuranosyl]-5-fluorocytosine,
1-[2',3'-Dideoxy-2'-fluoro-3'-(N-hydroxy-N-hexylamino)-α-D-arabinofuranosyl]-5-chlorocytosine,
1-[2',3'-Dideoxy-2'-fluoro-3'-(N-hydroxy-N-hexylamino)-α-D-arabinofuranosyl]-5-bromocytosine,
1-[2',3'-Dideoxy-2'-fluoro-3'-(N-hydroxy-N-hexylamino)-α-D-arabinofuranosyl]-5-iodocytosine,
1-[2',3'-Dideoxy-2'-fluoro-3'-(N-hydroxy-N-hexylamino)-α-D-arabinofiranosyl]-5-ethylcytosine,
1-[2',3'-Dideoxy-2'-fluoro-3'-(N-hydroxy-N-hexylamino)-α-D-arabinofuranosyl]-5-n-propylcytosine,
1-[2',3'-Dideoxy-2'-fluoro-3'-(N-hydroxy-N-hexylamino)-α-D-arabinofuranosyl]-5-i-propylcytosine,
1-[2',3'-Dideoxy-2'-fluoro-3'-(N-hydroxy-N-hexylamino)-α-D-arabinofuranosyl]-5-(E-2-bromovinyl)cytosine,
1-[2',3'-Dideoxy-2'-fluoro-3'-(N-hydroxy-N-hexylamino)-α-D-arabinofuranosyl]-5-vinylcytosine, 1-[2',3'-Dideoxy-2'-fluoro-3'-(N-hydroxy-N-hexylamino)-α-D-arabinofuranosyl]-5-carboxycytosine,
1-[2',3'-Dideoxy-2'-fluoro-3'-(N-hydroxy-N-hexylamino)-α-D-arabinofaranosyl]-5-ethoxycarbonylcytosine,
1-[2',3'-Dideoxy-2'-fluoro-3'-(N-hydroxy-N-hexylamino]-α-D-arabinofuranosyl]-5-aminocarbonylcytosine,
1-[2',3'-Dideoxy-2'-fluoro-3'-(N-hydroxy-N-hexylamnino]-α-D-arabinofuranosyl}-5-cyanocytosine,
1-[2',3'-Dideoxy-2'-fluoro-3'-(N-hydroxy-N-hexylamino)-α-D-arabinofuranosyl]-5-phenylcytosine,
1-[2',3'-Dideoxy-2'-fluoro-3'-(N-hydroxy-N-hexylamino)-α-D-arabinofuranosyl]-5-benzylcytosine,
1-[2',3'-Dideoxy-2'-fluoro-3'-(N-hydroxy-N-heptylamino)-β-D-arabinofuranosyl]thymine,
1-[2',3'-Dideoxy-2'-fluoro-3'-(N-hydroxy-N-heptylamino)-β-D-arabinofuranosyl]uracil,
1-[2',3'-Dideoxy-2'-fluoro-3'-(N-hydroxy-N-heptylamino)-β-D-arabinofuranosyl]-5-chlorouracil,
1-[2',3'-Dideoxy-2'-fluoro-3'-(N-hydroxy-N-heptylamino)-β-D-arabinofuranosyl]-5-bromouracil,
1-[2',3'-Dideoxy-2'-fluoro-3'-(N-hydroxy-N-heptylamino)-β-D-arabinofuranosyl]-5-iodouracil,
1-[2',3'-Dideoxy-2'-fluoro-3'-(N-hydroxy-N-heptylamino)-β-D-arabinofuranosyl]-5-ethyluracil,
1-[2',3'-Dideoxy-2'-fluoro-3'-(N-hydroxy-N-heptylamino)-β-D-arabinofuranosyl]-5-n-propyluracil,
1-[2',3'-Dideoxy-2'-fluoro-3'-(N-hydroxy-N-heptylamino)-β-D-arabinofuranosyl]-5-i-propyluracil,
1-[2',3'-Dideoxy-2'-fluoro-3'-(N-hydroxy-N-heptylamino)-β-D-arabinofuranosyl]-5-(E-2-bromovinyl)-uracil,
1-[2',3'-Dideoxy-2'-fluoro-3'-(N-hydroxy-N-heptylamino)-β-D-arabinofuranosyl]-5-vinyluracil,
1-[2',3'-Dideoxy-2'-fluoro-3'-(N-hydroxy-N-heptylamino)-β-D-arabinofuranosyl]-5-carboxyuracil,
1-[2',3'-Dideoxy-2'-fluoro-3'-(N-hydroxy-N-heptylamino)-β-D-arabinofuranosyl]-5-ethoxycarbonyluracil,
1-[2',3'-Dideoxy-2'-fluoro-3'-(N-hydroxy-N-heptylamino)-β-D-arabinofuranosyl]-5-aminocarbonyluracil,
1-[2',3'-Dideoxy-2'-fluoro-3'-(N-hydroxy-N-heptylamino)-β-D-arabinofuranosyl]-5-cyanouracil,
1-[2',3'-Dideoxy-2'-fluoro-3'-(N-hydroxy-N-heptylamino)-β-D-arabinofuranosyl]-5-phenyluracil,
1-[2',3'-Dideoxy-2'-fluoro-3'-(N-hydroxy-N-heptylamino)-β-D-arabinofuranosyl]-5-benzyluracil,
1-[2',3'-Dideoxy-2'-fluoro-3'-(N-hydroxy-N-heptylanino)-β-D-arabinofuranosyl]-cytosine,
1-[2',3'-Dideoxy-2'-fluoro-3'-(N-hydroxy-N-heptylamino)-β-D-arabinoftiranosyl]-5-fluorocytosine,
1-[2',3'-Dideoxy-2'-fluoro-3'-(N-hydroxy-N-heptylamino]-β-D-arabinofuranosyl]-5-chlorocytosine,
1-[2',3'-Dideoxy-2'-fluoro-3'-(N-hydroxy-N-heptylamino]-β-D-arabinofuranosyl]-5-bromocytosine,
1-[2',3'-Dideoxy-2'-fluoro-3'-(N-hydroxy-N-heptylamino]-β-D-arabinofuranosyl]-5-iodocytosine,
1-[2',3'-Dideoxy-2'-fluoro-3'-(N-hydroxy-N-heptylamino]-β-D-arabinofuranosyl]-5-ethylcytosine,
1-[2',3'-Dideoxy-2'-fluoro-3'-(N-hydroxy-N-heptylamino)-β-D-arabinofuranosyl]-5-n-propylcytosine,
1-[2',3'-Dideoxy-2'-fluoro-3'-(N-hydroxy-N-heptylamino]-β-D-arabinofuranosyl]-5-i-propylcytosine,
1-[2',3'-Dideoxy-2'-fluoro-3'-(N-hydroxy-N-heptylamino)-β-D-arabinofuranosyl]-5-(E-2-bromovinyl)cytosine,
1-[2',3'-Dideoxy-2'-fluoro-3'-(N-hydroxy-N-heptylamino]-β-D-arabinofuranosyl]-5-vinylcytosine,
1-[2',3'-Dideoxy-2'-fluoro-3'-(N-hydroxy-N-heptylamino)-β-D-arabinofuranosyl]-5-carboxycytosine,
1-[2',3'-Dideoxy-2'-fluoro-3'-(N-hydroxy-N-heptylamino]-β-D-arabinofuranosyl]-5-ethoxycarbonylcytosine,
1-[2',3'-Dideoxy-2'-fluoro-3'-(N-hydroxy-N-heptylamino]-β-D-arabinofaranosyl]-5-aminocarbonyl-cytosine,
1-[2',3'-Dideoxy-2'-fluoro-3'-(N-hydroxy-N-heptylamino]-β-D-arabinofuranosyl]-5-cyanocytosine,
1-[2',3'-Dideoxy-2'-fluoro-3'-(N-hydroxy-N-heptylamino)-β-D-arabinofuranosyl]-5-phenylcytosine,
1-[2',3'-Dideoxy-2'-fluoro-3'-(N-hydroxy-N-heptylamino)-β-D-arabinofuranosyl]-5-benzylcytosine,
1-[2',3'-Dideoxy-2'-fluoro-3'-(N-hydroxy-N-heptylamino)-α-D-arabinofuranosyl]thymine,
1-[2',3'-Dideoxy-2'-fluoro-3'-(N-hydroxy-N-heptylamino)-α-D-arabinofuranosyl]-5-fluorouracil,
1-[2',3'-Dideoxy-2'-fluoro-3'-(N-hydroxy-N-heptylamino)-α-D-arabinofuranosyl]-5-chlorouracil,
1-[2',3'-Dideoxy-2'-fluoro-3'-(N-hydroxy-N-heptylamino)-α-D-arabinofuranosyl]-5-bromouracil,
1-[2',3'-Dideoxy-2'-fluoro-3'-(N-hydroxy-N-heptylamino)-α-D-arabinofuranosyl]-5-iodouracil,
1-[2',3'-Dideoxy-2'-fluoro-3'-(N-hydroxy-N-heptylamino)-α-D-arabinofuranosyl]-5-ethyluracil,
1-[2',3'-Dideoxy-2'-fluoro-3'-(N-hydroxy-N-heptylamino)-α-D-arabinofuranosyl]-5-n-propyluracil,
1-[2',3'-Dideoxy-2'-fluoro-3'-(N-hydroxy-N-heptylamino)-α-D-arabinofuranosyl]-5-i-propyluracil,
1-[2',3'-Dideoxy-2'-fluoro-3'-(N-hydroxy-N-heptylamino)-α-D-arabinofuranosyl]-5-(E-2-bromovinyl)uracil,
1-[2',3'-Dideoxy-2'-fluoro-3'-(N-hydroxy-N-heptylamino)-α-D-arabinofuranosyl]-5-vinyluracil,
1-[2',3'-Dideoxy-2'-fluoro-3'-(N-hydroxy-N-heptylamino)-α-D-arabinofuranosyl]-5-carboxyuracil,
1-[2',3'-Dideoxy-2'-fluoro-3'-(N-hydroxy-N-heptylamino)-α-D-arabinofuranosyl]-5-ethoxycarbonyluracil,
1-[2',3'-Dideoxy-2'-fluoro-3'-(N-hydroxy-N-heptylamino)-α-D-arabinofuranosyl]-5-aminocarbonyluracil,
1-[2',3'-Dideoxy-2'-fluoro-3'-(N-hydroxy-N-heptylamino)-α-D-arabinofuranosyl]-5-cyanouracil,
1-[2',3'-Dideoxy-2'-fluoro-3'-(N-hydroxy-N-heptylamino)-α-D-arabinofuranosyl]-5-phenyluracil,
1-[2',3'-Dideoxy-2'-fluoro-3'-(N-hydroxy-N-heptylamino)-α-D-arabinofuranosyl]-5-benzyluracil,
1-[2',3'-Dideoxy-2'-fluoro-3'-(N-hydroxy-N-heptylamino)-α-D-arabinofuranosyl]-cytosine,
1-[2',3'-Dideoxy-2'-fluoro-3'-(N-hydroxy-N-heptylamino)-α-D-arabinofuranosyl]-5-fluorocytosine,
1-[2',3'-Dideoxy-2'-fluoro-3'-(N-hydroxy-N-heptylamino)-α-D-arabinofuranosyl]-5-chlorocytosine,
1-[2',3'-Dideoxy-2'-fluoro-3'-(N-hydroxy-N-heptylamino)-α-D-arabinofuranosyl]-5-bromocytosine,
1-[2',3'-Dideoxy-2'-fluoro-3'-(N-hydroxy-N-heptylamino)-α-D-arabinofuranosyl]-5-iodocytosine,
1-[2',3'-Dideoxy-2'-fluoro-3'-(N-hydroxy-N-heptylamino)-α-D-arabinofuranosyl]-5-ethylcytosine,
1-[2',3'-Dideoxy-2'-fluoro-3'-(N-hydroxy-N-heptylamino)-α-D-arabinofuranosyl]-5-n-propylcytosine,
1-[2',3'-Dideoxy-2'-fluoro-3'-(N-hydroxy-N-heptylamino)-α-D-arabinofuranosyl]-5-i-propylcytosine,
1-[2',3'-Dideoxy-2'-fluoro-3'-(N-hydroxy-N-heptylamino)-α-D-arabinofuranosyl-5-(E-2-bromovinyl)cytosine,
1-[2',3'-Dideoxy-2'-fluoro-3'-(N-hydroxy-N-heptylamino)-α-D-arabinofuranosyl]-5-vinylcytosine,
1-[2',3'-Dideoxy-2'-fluoro-3'-(N-hydroxy-N-heptylamino)-α-D-arabinofuranosyl]-5-carboxycytosine,
1-[2',3'-Dideoxy-2'-fluoro-3'-(N-hydroxy-N-heptylamino)-α-D-arabinofuranosyl]-5-ethoxycarbonyl-cytosine, 1-[2',3'-Dideoxy-2'-fluoro-3'-(N-hydroxy-N-heptylamino]-α-D-arabinofuranosyl]-5-aminocarbonylcytosine,
1-[2',3'-Dideoxy-2'-fluoro-3'-(N-hydroxy-N-heptylamino]-α-D-arabinofuranosyl]-5-cyanocytosine,
1-[2',3'-Dideoxy-2'-fluoro-3'-(N-hydroxy-N-heptylamino)-α-D-arabinofuranosyl]-5-phenylcytosine,
1-[2',3'-Dideoxy-2'-fluoro-3'-(N-hydroxy-N-octylamino)-β-D-arabinofuranosyl]thymine,
1-[2',3'-Dideoxy-2'-fluoro-3'-(N-hydroxy-N-octylamino)-β-D-arabinofuranosyl]uracil,
1-[2',3'-Dideoxy-2'-fluoro-3'-(N-hydroxy-N-octylamino)-β-D-arabinofuranosyl]-5-chlorouracil,
1-[2',3'-Dideoxy-2'-fluoro-3'-(N-hydroxy-N-octylamino)-β-D-arabinofuranosyl]-5-bromouracil,
1-[2',3'-Dideoxy-2'-fluoro-3'-(N-hydroxy-N-octylamino)-β-D-arabinofuranosyl]-5-iodouracil,
1-[2',3'-Dideoxy-2'-fluoro-3'-(N-hydroxy-N-octylamino)-β-D-arabinofuranosyl]-5-ethyluracil,
1-[2',3'-Dideoxy-2'-fluoro-3'-(N-hydroxy-N-octylamino)-β-D-arabinofuranosyl]-5-n-propyluracil,
1-[2',3'-Dideoxy-2'-fluoro-3'-(N-hydroxy-N-octylamino)-β-D-arabinofuranosyl]-5-i-propyluracil,
1-[2',3'-Dideoxy-2'-fluoro-3'-(N-hydroxy-N-octylamino)-β-D-arabinofuranosyl]-5-(E-2-bromo-vinyl)uracil,
1-[2',3'-Dideoxy-2'-fluoro-3'-(N-hydroxy-N-octylamino)-β-D-arabinofuranosyl]-5-vinyluracil,
1-[2',3'-Dideoxy-2'-fluoro-3'-(N-hydroxy-N-octylamino)-β-D-arabinofuranosyl]-5-carboxyuracil,
1-[2',3'-Dideoxy-2'-fluoro-3'-(N-hydroxy-N-octylamino)-β-D-arabinofuranosyl]-5-ethoxycarbonyluracil,
1-[2',3'-Dideoxy-2'-fluoro-3'-(N-hydroxy-N-octylamino)-β-D-arabinofuranosyl]-5-aminocarbonyluracil,
1-[2',3'-Dideoxy-2'-fluoro-3'-(N-hydroxy-N-octylamino)-β-D-arabinofuranosyl]-5-cyanouracil,
1-[2',3'-Dideoxy-2'-fluoro-3'-(N-hydroxy-N-octylamino)-β-D-arabinofuranosyl]-5-phenyluracil,
1-[2',3'-Dideoxy-2'-fluoro-3'-(N-hydroxy-N-octylamino)-β-D-arabinofuranosyl]-5-benzyluracil,
1-[2',3'-Dideoxy-2'-fluoro-3'-(N-hydroxy-N-octylamino)-β-D-arabinofuranosyl]cytosine,
1-[2',3'-Dideoxy-2'-fluoro-3'-(N-hydroxy-N-octylamino)-β-D-arabinofuranosyl]-5-fluorocytosine,
1-[2',3'-Dideoxy-2'-fluoro-3'-(N-hydroxy-N-octylamino]-β-D-arabinofuranosyl-5-chlorocytosine,
1-[2',3'-Dideoxy-2'-fluoro-3'-(N-hydroxy-N-octylamino]-β-D-arabinofuranosyl]-5-bromocytosine,
1-[2',3'-Dideoxy-2'-fluoro-3'-(N-hydroxy-N-octylamino]-β-D-arabinofuranosyl]-5-iodocytosine,
1-[2',3'-Dideoxy-2'-fluoro-3'-(N-hydroxy-N-octylamino]-β-D-arabinofuranosyl]-5-ethylcytosine,
1-[2',3'-Dideoxy-2'-fluoro-3'-(N-hydroxy-N-octylamino]-β-D-arabinofuranosyl]-5-n-propylcytosine,
1-[2',3'-Dideoxy-2'-fluoro-3'-(N-hydroxy-N-octylamino]-β-D-arabinofuranosyl]-5-i-propylcytosine,
1-[2',3'-Dideoxy-2'-fluoro-3'-(N-hydroxy-N-octylamino]-β-D-arabinofuranosyl]-5-(E-2-bromovinyl)cytosine,
1-[2',3'-Dideoxy-2'-fluoro-3'-(N-hydroxy-N-octylamino]-β-D-arabinofuranosyl]-5-vinylcytosine,
1-[2',3'-Dideoxy-2'-fluoro-3'-(N-hydroxy-N-octylamino]-β-D-arabinofuranosyl]-5-carboxycytosine,
1-[2',3'-Dideoxy-2'-fluoro-3'-(N-hydroxy-N-octylamino]-β-D-arabinofuranosyl]-5-ethoxycarbonylcytosine,
1-[2',3'-Dideoxy-2'-fluoro-3'-(N-hydroxy-N-octylamino]-β-D-arabinofuranosyl]-5-aminocarbonylcytosine,
1-[2',3'-Dideoxy-2'-fluoro-3'-(N-hydroxy-N-octylamino]-β-D-arabinofuranosyl]-5-cyanocytosine,
1-[2',3'-Dideoxy-2'-fluoro-3'-(N-hydroxy-N-octylamino)-β-D-arabinofuranosyl]-5-phenylcytosine,
1-[2',3'-Dideoxy-2'-fluoro-3'-(N-hydroxy-N-octylamino)-β-D-arabinofuranosyl]-5-benzylcytosine,
1-[2',3'-Dideoxy-2'-fluoro-3'-(N-hydroxy-N-octylamino)-α-D-arabinofuranosyl]thymine,
1-[2',3'-Dideoxy-2'-fluoro-3'-(N-hydroxy-N-octylamino)-α-D-arabinofuranosyl]-5-fluorouracil,
1-[2',3'-Dideoxy-2'-fluoro-3'-(N-hydroxy-N-octylamino)-α-D-arabinofuranosyl]-5-chlorouracil,
1-[2',3'-Dideoxy-2'-fluoro-3'-(N-hydroxy-N-octylamino)-α-D-arabinofuranosyl]-5-bromouracil,
1-[2',3'-Dideoxy-2'-fluoro-3'-(N-hydroxy-N-octylamino)-α-D-arabinofuranosyl]-5-iodouracil,
1-[2',3'-Dideoxy-2'-fluoro-3'-(N-hydroxy-N-octylamino)-α-D-arabinofuranosyl]-5-ethyluracil,
1-[2',3'-Dideoxy-2'-fluoro-3'-(N-hydroxy-N-octylamino)-α-D-arabinofuranosyl]-5-n-propyluracil,
1-[2',3'-Dideoxy-2'-fluoro-3'-(N-hydroxy-N-octylamino)-α-D-arabinofuranosyl]-5-i-propyluracil,
1-[2',3'-Dideoxy-2'-fluoro-3'-(N-hydroxy-N-octylamino)-α-D-arabinofuranosyl]-5-(E-2-bromovinyl)uracil,
1-[2',3'-Dideoxy-2'-fluoro-3'-(N-hydroxy-N-octylamino)-α-D-arabinofuranosyl]-5-vinyluracil,
1-[2',3'-Dideoxy-2'-fluoro-3'-(N-hydroxy-N-octylanino)-α-D-arabinofuranosyl]-5-carboxyuracil,
1-[2',3'-Dideoxy-2'-fluoro-3'-(N-hydroxy-N-octylamino)-α-D-arabinofuranosyl]-5-ethoxycarbonyluracil,
1-[2',3'-Dideoxy-2'-fluoro-3'-(N-hydroxy-N-octylamino)-α-D-arabinofuranosyl]-5-aminocarbonyluracil,
1-[2',3'-Dideoxy-2'-fluoro-3'-(N-hydroxy-N-octylamino)-α-D-arabinofuranosyl}-5-cyanouracil,
1-[2',3'-Dideoxy-2'-fluoro-3'-(N-hydroxy-N-octylamino)-α-D-arabinofuranosyl]-5-phenyluracil,
1-[2',3'-Dideoxy-2'-fluoro-3'-(N-hydroxy-N-octylamino)-α-D-arabinofuranosyl]-5-benzyluracil,
1-[2',3'-Dideoxy-2'-fluoro-3'-(N-hydroxy-N-octylamino)-α-D-arabinofuranosyl]cytosine,
1-[2',3'-Dideoxy-2'-fluoro-3'-(N-hydroxy-N-octylamino)-α-D-arabinofuranosyl]-5-fluorocytosine,
1-[2',3'-Dideoxy-2'-fluoro-3'-(N-hydroxy-N-octylamino)-α-D-arabinofranosyl]-5-chlorocytosine,
1-[2',3'-Dideoxy-2'-fluoro-3'-(N-hydroxy-N-octylamino)-α-D-arabinofuranosyl]-5-bromocytosine,
1-[2',3'-Dideoxy-2'-fluoro-3'-(N-hydroxy-N-octylamino)-α-D-arabinofuranosyl]-5-iodocytosine,
1-[2',3'-Dideoxy-2'-fluoro-3'-(N-hydroxy-N-octylamino)-α-D-arabinofuranosyl]-5-ethylcytosine,
1-[2',3'-Dideoxy-2'-fluoro-3'-(N-hydroxy-N-octylamino)-α-D-arabinofuranosyl]-5-n-propylcytosine,
1-[2',3'-Dideoxy-2'-fluoro-3'-(N-hydroxy-N-octylamino)-α-D-arabinofuranosyl]-5-i-propylcytosine,
1-[2',3'-Dideoxy-2'-fluoro-3'-(N-hydroxy-N-octylamino)-α-D-arabinofuranosyl]-5-(E-2-bromovinyl)cytosine,
1-[2',3'-Dideoxy-2'-fluoro-3'-(N-hydroxy-N-octylamino)-α-D-arabinofuranosyl]-5-vinylcytosine,
1-[2',3'-Dideoxy-2'-fluoro-3'-(N-hydroxy-N-octylamino)-α-D-arabinofuranosyl]-5-carboxycytosine,
1-[2',3'-Dideoxy-2'-fluoro-3'-(N-hydroxy-N-octylamino)-α-D-arabinofuranosyl]-5-ethoxycarbonylcytosine,
1-[2',3'-Dideoxy-2'-fluoro-3'-(N-hydroxy-N-octylamino]-α-D-arabinofuranosyl]-5-aminocarbonylcytosine,
1-[2',3'-Dideoxy-2'-fluoro-3'-(N-hydroxy-N-octylamino)-α-D-arabinofuranosyl}-5-cyanocytosine,
1-[2',3'-Dideoxy-2'-fluoro-3'-(N-hydroxy-N-octylamino)-α-D-arabinofuranosyl]-5-phenylcytosine, 1-[2',3'-Dideoxy-2'-fluoro-3'-(N-hydroxy-N-octylamino)-α-D-arabinofuranosyl]-5-benzylcytosine,
1-[2',3'-Dideoxy-2'-fluoro-3'-(N-hydroxy-N-nonylamino)-β-D-arabinofuranosyl]thymine,
1-[2',3'-Dideoxy-2'-fluoro-3'-(N-hydroxy-N-nonylamino)-β-D-arabinofuranosyl]uracil,
1-[2',3'-Dideoxy-2'-fluoro-3'-(N-hydroxy-N-nonylamino)-β-D-arabinofuranosyl]-5-chlorouracil,
1-[2',3'-Dideoxy-2'-fluoro-3'-(N-hydroxy-N-nonylamino)-β-D-arabinofuranosyl]-5-bromouracil,
1-[2',3'-Dideoxy-2'-fluoro-3'-(N-hydroxy-N-nonylamino)-β-D-arabinofuranosyl]-5-iodouracil,
1-[2',3'-Dideoxy-2'-fluoro-3'-(N-hydroxy-N-nonylamino)-β-D-arabinofuranosyl]-5-ethyluracil,
1-[2',3'-Dideoxy-2'-fluoro-3'-(N-hydroxy-N-nonylamino)-β-D-arabinofuranosyl]-5-n-propyluracil,
1-[2',3'-Dideoxy-2'-fluoro-3'-(N-hydroxy-N-nonylamino)-β-D-arabinofuranosyl]-5-i-propyluracil,
1-[2',3'-Dideoxy-2'-fluoro-3'-(N-hydroxy-N-nonylamino)-β-D-arabinofuranosyl]-5-(E-2-bromovinyl)uracil,
1-[2',3'-Dideoxy-2'-fluoro-3'-(N-hydroxy-N-nonylamino)-β-D-arabinofuranosyl]-5 -vinyluracil,
1-[2',3'-Dideoxy-2'-fluoro-3'-(N-hydroxy-N-nonylamino)-β-D-arabinofuranosyl]-5-carboxyuracil,
1-[2',3'-Dideoxy-2'-fluoro-3'-(N-hydroxy-N-nonylamino)-β-D-arabinofuranosyl]-5-ethoxycarbonyluracil,
1-[2',3'-Dideoxy-2'-fluoro-3'-(N-hydroxy-N-nonylamino)-β-D-arabinofuranosyl]-5-aminocarbonyluracil,
1-[2',3'-Dideoxy-2'-fluoro-3'-(N-hydroxy-N-nonylamino)-β-D-arabinofuranosyl]-5-cyanouracil,
1-[2',3'-Dideoxy-2'-fluoro-3'-(N-hydroxy-N-nonylamino)-β-D-arabinofuranosyl]-5-phenyluracil,
1-[2',3'-Dideoxy-2'-fluoro-3'-(N-hydroxy-N-nonylamino)-β-D-arabinofuranosyl]-5-benzyluracil,
1-[2',3'-Dideoxy-2'-fluoro-3'-(N-hydroxy-N-nonylamino)-β-D-arabinofuranosyl]cytosine,
1-[2',3'-Dideoxy-2'-fluoro-3'-(N-hydroxy-N-nonylamino)-β-D-arabinofuranosyl]-5-fluorocytosine,
1-[2',3'-Dideoxy-2'-fluoro-3'-(N-hydroxy-N-nonylamino]-β-D-arabinofuranosyl}-5-chlorocytosine,
1-[2',3'-Dideoxy-2'-fluoro-3'-(N-hydroxy-N-nonylamino]-β-D-arabinofuranosyl]-5-bromocytosine,
1-[2',3'-Dideoxy-2'-fluoro-3'-(N-hydroxy-N-nonylamino]-β-D-arabinofuranosyl]-5-iodocytosine,
1-[2',3'-Dideoxy-2'-fluoro-3'-(N-hydroxy-N-nonylamino]-β-D-arabinofuranosyl]-5-ethylcytosine,
1-[2',3'-Dideoxy-2'-fluoro-3'-(N-hydroxy-N-nonylamino)-β-D-arabinofuranosyl]-5-n-propylcytosine,
1-[2',3'-Dideoxy-2'-fluoro-3'-(N-hydroxy-N-nonylamino]-β-D-arabinofuranosyl]-5-i-propylcytosine,
1-[2',3'-Dideoxy-2'-fluoro-3'-(N-hydroxy-N-nonylamino]-β-D-arabinofuranosyl]-5-(E-2-bromovinyl)cytosine,
1-[2',3'-Dideoxy-2'-fluoro-3'-(N-hydroxy-N-nonylamino]-β-D-arabinofuranosyl]-5-vinylcytosine,
1-[2',3'-Dideoxy-2'-fluoro-3'-(N-hydroxy-N-nonylamino]-β-D-arabinofuranosyl]-5-carboxycytosine,
1-[2',3'-Dideoxy-2'-fluoro-3'-(N-hydroxy-N-nonylamino]-β-D-arabinofuranosyl]-5-ethoxycarbonylcytosine,
1-[2',3'-Dideoxy-2'-fluoro-3'-(N-hydroxy-N-nonylamino]-β-D-arabinofuranosyl]-5-aminocarbonylcytosine,
1-[2',3'-Dideoxy-2'-fluoro-3'-(N-hydroxy-N-nonylamino]-β-D-arabinofuranosyl]-5-cyanocytosine,
1-[2',3'-Dideoxy-2'-fluoro-3'-(N-hydroxy-N-nonylamino]-β-D-arabinofuranosyl]-5-phenylcytosine,
1-[2',3'-Dideoxy-2'-fluoro-3'-(N-hydroxy-N-nonylamino)-β-D-arabinofuranosyl]-5-benzylcytosine,
1-[2',3'-Dideoxy-2'-fluoro-3'-(N-hydroxy-N-nonylamino)-α-D-arabinofuranosyl]thymine,
1-[2',3'-Dideoxy-2'-fluoro-3'-(N-hydroxy-N-nonylamino)-α-D-arabinofiranosyl]-5-fluorouracil,
1-[2',3'-Dideoxy-2'-fluoro-3'-(N-hydroxy-N-nonylamino)-α-D-arabinofuranosyl)-5-chlorouracil,
1-[2',3'-Dideoxy-2'-fluoro-3'-(N-hydroxy-N-nonylamino)-α-D-arabinofuranosyl]-5-bromouracil,
1-[2',3'-Dideoxy-2'-fluoro-3'-(N-hydroxy-N-nonylamino)-α-D-arabinofuranosyl]-5-iodouracil,
1-[2',3'-Dideoxy-2'-fluoro-3'-(N-hydroxy-N-nonylamino)-α-D-arabinofuranosyl-5-ethyluracil,
1-[2',3'-Dideoxy-2'-fluoro-3'-(N-hydroxy-N-nonylamino)-α-D-arabinofuranosyl]-5-n-propyluracil,
1-[2',3'-Dideoxy-2'-fluoro-3'-(N-hydroxy-N-nonylamino)-α-D-arabinofuranosyl]-5-i-propyluracil,
1-[2',3'-Dideoxy-2'-fluoro-3'-(N-hydroxy-N-nonylamino)-α-D-arabinofuranosyl]-5-(E-2-bromovinyl)-uracil,
1-[2',3'-Dideoxy-2'-fluoro-3'-(N-hydroxy-N-nonylamino)-α-D-arabinofuanosyl]-5-vinyluracil,
1-[2',3'-Dideoxy-2'-fluoro-3'-(N-hydroxy-N-nonylamino)-α-D-arabinofuranosyl]-5-carboxyuracil,
1-[2',3'-Dideoxy-2'-fluoro-3'-(N-hydroxy-N-nonylamino)-α-D-arabinofuranosyl]-5-ethoxycarbonyl-uracil,
1-[2',3'-Dideoxy-2'-fluoro-3'-(N-hydroxy-N-nonylamino)-α-D-arabinofuranosyl]-5-aminocarbonyl-uracil,
1-[2',3'-Dideoxy-2'-fluoro-3'-(N-hydroxy-N-nonylamino)-α-D-arabinofuranosyl]-5-cyanouracil,
1-[2',3'-Dideoxy-2'-fluoro-3'-(N-hydroxy-N-nonylamino)-α-D-arabinofuranosyl]-5-phenyluracil,
1-[2',3'-Dideoxy-2'-fluoro-3'-(N-hydroxy-N-nonylamino)-α-D-arabinofuranosyl]-5-benzyluracil,
1-[2',3'-Dideoxy-2'-fluoro-3'-(N-hydroxy-N-nonylamino)-α-D-arabinofuranosyl]cytosine,
1-[2',3'-Dideoxy-2'-fluoro-3'-(N-hydroxy-N-nonylamino)-α-D-arabinofuranosyl]-5-fluorocytosine,
1-[2',3'-Dideoxy-2'-fluoro-3'-(N-hydroxy-N-nonylamino)-α-D-arabinofuranosyl]-5-chlorocytosine,
1-[2',3'-Dideoxy-2'-fluoro-3'-(N-hydroxy-N-nonylamino)-α-D-arabinofuranosyl]-5-bromocytosine,
1-[2',3'-Dideoxy-2'-fluoro-3'-(N-hydroxy-N-nonylamino)-α-D-arabinofuranosyl]-5-iodocytosine,
1-[2',3'-Dideoxy-2'-fluoro-3'-(N-hydroxy-N-nonylamino)-α-D-arabinofuranosyl]-5-ethylcytosine,
1-[2',3'-Dideoxy-2'-fluoro-3'-(N-hydroxy-N-nonylamino)-α-D-arabinofuranosyl]-5-n-propylcytosine,
1-[2',3'-Dideoxy-2'-fluoro-3'-(N-hydroxy-N-nonylamino)-α-D-arabinofuranosyl]-5-i-propylcytosine,
1-[2',3'-Dideoxy-2'-fluoro-3'-(N-hydroxy-N-nonylamino)-α-D-arabinofuranosyl-5-(E-2-bromovinyl)cytosine,
1-[2',3'-Dideoxy-2'-fluoro-3'-(N-hydroxy-N-nonylamino)-α-D-arabinofuranosyl]-5-vinylcytosine,
1-[2',3'-Dideoxy-2'-fluoro-3'-(N-hydroxy-N-nonylamino)-α-D-arabinofuranosyl]-5-carboxycytosine,
1-[2',3'-Dideoxy-2'-fluoro-3'-(N-hydroxy-N-nonylamino)-α-D-arabinofuranosyl]-5-ethoxycarbonyl-cytosine,
1-[2',3'-Dideoxy-2'-fluoro-3'-(N-hydroxy-N-nonylamino]-α-D-arabinofuranosyl]-5-aminocarbonyl-cytosine,
1-[2',3'-Dideoxy-2'-fluoro-3'-(N-hydroxy-N-nonylamino]-α-D-arabinofuranosyl}-5-cyanocytosine,
1-[2',3'-Dideoxy-2'-fluoro-3'-(N-hydroxy-N-nonylamino)-α-D-arabinofuranosyl]-5-phenylcytosine,
1-[2',3'-Dideoxy-2'-fluoro-3'-(N-hydroxy-N-nonylamino)-α-D-arabinofuranosyl]-5-benzylcytosine,
1-[2',3'-Dideoxy-2'-fluoro-3'-(N-hydroxy-N-hexadecanylamino)-β-D-arabinofuranosyl]thymine, 1-[2',3'-Dideoxy-2'-fluoro-3'-(N-hydroxy-N-hexadecany-lamino)-β-D-arabinofuranosyl]uracil,
1-[2',3'-Dideoxy-2'-fluoro-3'-(N-hydroxy-N-hrxadecany-lamino)-β-D-arabinofuranosyl]-5-chlorouracil,
1-[2',3'-Dideoxy-2'-fluoro-3'-(N-hydroxy-N-hexadecany-lamino)-β-D-arabinofuranosyl]-5-bromouracil,
1-[2',3'-Dideoxy-2'-fluoro-3'-(N-hydroxy-N-hexadecany-lamino)-β-D-arabinofuranosyl]-5-iodouracil,
1-[2',3'-Dideoxy-2'-fluoro-3'-(N-hydroxy-N-hexadecany-lamino)-β-D-arabinofuranosyl]-5-ethyluracil,
1-[2',3'-Dideoxy-2'-fluoro-3'-(N-hydroxy-N-hexadecany-lamino)-β-D-arabinofuranosyl]-5-n-propyluracil,
1-[2',3'-Dideoxy-2'-fluoro-3'-(N-hydroxy-N-hexadecany-lamino)-β-D-arabinofuranosyl]-5-i-propyluracil
1-[2',3'-Dideoxy-2'-fluoro-3'-(N-hydroxy-N-hexadecany-lamino)-β-D-arabinofuranosyl]-5-(E-2-bromo-vinyl) uracil,
1-[2',3'-Dideoxy-2'-fluoro-3'-(N-hydroxy-N-hexadecany-lamino)-β-D-arabinofuranosyl]-5-vinyluracil,
1-[2',3'-Dideoxy-2'-fluoro-3'-(N-hydroxy-N-hexadecany-lamino)-β-D-arabinofuranosyl]-5-carboxyuracil,
1-[2',3'-Dideoxy-2'-fluoro-3'-(N-hydroxy-N-hexadecany-lamino)-β-D-arabinofuranosyl]-5-ethoxycarbonyluracil,
1-[2',3'-Dideoxy-2'-fluoro-3'-(N-hydroxy-N-hexadecany-lamino)-β-D-arabinofuranosyl]-5-aminocarbonyl-uracil,
1-[2',3'-Dideoxy-2'-fluoro-3'-(N-hydroxy-N-hexadecany-lamino)-β-D-arabinofuranosyl]-5-cyanouracil,
1-[2',3'-Dideoxy-2'-fluoro-3'-(N-hydroxy-N-hexadecany-lamino)-β-D-arabinofuranosyl]5phenyluracil,
1-[2',3'-Dideoxy-2'-fluoro-3'-(N-hydroxy-N-hexadecany-lamino)-β-D-arabinofuranosyl]-5-benzyluracil,
1-[2',3'-Dideoxy-2'-fluoro-3'-(N-hydroxy-N-hexadecany-lamino)-β-D-arabinofuranosyl]cytosine,
1-[2',3'-Dideoxy-2'-fluoro-3'-(N-hydroxy-N-hexadecany-lamino)-β-D-arabinofuranosyl]-5-fluorocytosine,
1-[2',3'-Dideoxy-2'-fluoro-3'-(N-hydroxy-N-hexadecany-lamino]-β-D-arabinofuranosyl]-5-chlorocytosine,
1-[2',3'-Dideoxy-2'-fluoro-3'-(N-hydroxy-N-hexadecany-lamino]-β-D-arabinofuranosyl}-5-bromocytosine,
1-[2',3'-Dideoxy-2'-fluoro-3'-(N-hydroxy-N-hexadecany-lamino]-β-D-arabinofuranosyl]-5-iodocytosine,
1-[2',3'-Dideoxy-2'-fluoro-3'-(N-hydroxy-N-hexadecany-lamino]-β-D-arabinofuranosyl]-5-ethylcytosine,
1-[2',3'-Dideoxy-2'-fluoro-3'-(N-hydroxy-N-hexadecany-lamino)-β-D-arabinofuranosyl]-5-n-propylcytosine,
1-[2',3'-Dideoxy-2'-fluoro-3'-(N-hydroxy-N-hexadecany-lamino]-β-D-arabinofuranosyl]-5-i-propylcytosine,
1-[2',3'-Dideoxy-2'-fluoro-3'-(N-hydroxy-N-hexadecany-lamino]-β-D-arabinofuranosyl]-5-(E-2-bromovinyl)cytosine,
1-[2',3'-Dideoxy-2'-fluoro-3'-(N-hydroxy-N-hexadecany-lamino]-β-D-arabinofuranosyl]-5-vinylcytosine,
1-[2',3'-Dideoxy-2'-fluoro-3'-(N-hydroxy-N-hexadecany-lamino]-β-D-arabinofuranosyl]-5-carboxycytosine,
1-[2',3'-Dideoxy-2'-fluoro-3'-(N-hydroxy-N-hexadecany-lamino]-β-D-arabinofuranosyl]-5-ethoxycarbonylcytosine,
1-[2',3'-Dideoxy-2'-fluoro-3'-(N-hydroxy-N-hexadecany-lamino]-β-D-arabinofuranosyl]-5-aminocarbonylcytosine,
1-[2',3'-Dideoxy-2'-fluoro-3'-(N-hydroxy-N-hexadecany-lamino]-β-D-arabinofuranosyl]-5-cyanocytosine,
1-[2',3'-Dideoxy-2'-fluoro-3'-(N-hydroxy-N-hexadecany-lamino)-β-D-arabinofuranosyl]-5-phenylcytosine,
1-[2',3'-Dideoxy-2'-fluoro-3'-(N-hydroxy-N-hexadecany-lamino)-β-D-arabinofuranosyl]-5-benzylcytosine,
1-[2',3'-Dideoxy-2'-fluoro-3'-(N-hydroxy-N-hexadecany-lamino)-α-D-arabinofuranosyl]thymine,
1-[2',3'-Dideoxy-2'-fluoro-3'-(N-hydroxy-N-hexadecany-lamino)-α-D-arabinofuranosyl]uracil,
1-[2',3'-Dideoxy-2'-fluoro-3'-(N-hydroxy-N-hexadecany-lamino)-α-D-arabinofuranosyl]-5-chlorouracil,
1-[2',3'-Dideoxy-2'-fluoro-3'-(N-hydroxy-N-hexadecany-lamino)-α-D-arabinofuranosyl]-5-bromouracil,
1-[2',3'-Dideoxy-2'-fluoro-3'-(N-hydroxy-N-hexadecany-lamino)-α-D-arabinofuranosyl]-5-iodouracil,
1-[2',3'-Dideoxy-2'-fluoro-3'-(N-hydroxy-N-hexadecany-lamino)-α-D-arabinofuranosyl]-5-ethyluracil,
1-[2',3'-Dideoxy-2'-fluoro-3'-(N-hydroxy-N-hexadecany-lamino)-α-D-arabinofuranosyl]-5-n-propyluracil,
1-[2',3'-Dideoxy-2'-fluoro-3'-(N-hydroxy-N-hexadecany-lamino)-α-D-arabinofuranosyl]-5-i-propyluracil
1-[2',3'-Dideoxy-2'-fluoro-3'-(N-hydroxy-N-hexadecany-lamino)-α-D-arabinofuranosyl]-5-(E-2-bromovinyl) uracil,
1-[2',3'-Dideoxy-2'-fluoro-3'-(N-hydroxy-N-hexadecany-lamino)-α-D-arabinofuranosyl]-5-vinyluracil,
1-[2',3'-Dideoxy-2'-fluoro-3'-(N-hydroxy-N-hexadecany-lamino)-α-D-arabinofuranosyl]-5-carboxyuracil,
1-[2',3'-Dideoxy-2'-fluoro-3'-(N-hydroxy-N-hexadecany-lamino)-α-D-arabinofuranosyl]-5-ethoxycarbonyluracil,
1-[2',3'-Dideoxy-2'-fluoro-3'-(N-hydroxy-N-hexadecany-lamino)-α-D-arabinofuranosyl]-5-aminocarbonyluracil,
1-[2',3'-Dideoxy-2'-fluoro-3'-(N-hydroxy-N-hexadecany-lamino)-α-D-arabinofuranosyl]-5-cyanouracil,
1-[2',3'-Dideoxy-2'-fluoro-3'-(N-hydroxy-N-hexadecany-lamino)-α-D-arabinofuranosyl]-5-phenyluracil,
1-[2',3'-Dideoxy-2'-fluoro-3'-(N-hydroxy-N-hexadecany-lamino)-α-D-arabinofuranosyl]-5-benzyluracil
1-[2',3'-Dideoxy-2'-fluoro-3'-(N-hydroxy-N-hexadecany-lamino)-α-D-arabinofuranosyl]-cytosine,
1-[2',3'-Dideoxy-2'-fluoro-3'-(N-hydroxy-N-hexadecany-lamino)-α-D-arabinofuranosyl]-5-fluorocytosine,
1-[2',3'-Dideoxy-2'-fluoro-3'-(N-hydroxy-N-hexadecany-lamino]-α-D-arabinofuranosyl}-5-chlorocytosine,
1-[2',3'-Dideoxy-2'-fluoro-3'-(N-hydroxy-N-hexadecany-lamino]-α-D-arabinofuranosyl]-5-bromocytosine,
1-[2',3'-Dideoxy-2'-fluoro-3'-(N-hydroxy-N-hexadecany-lamino]-α-D-arabinofuranosyl]-5-iodocytosine,
1-[2',3'-Dideoxy-2'-fluoro-3'-(N-hydroxy-N-hexadecany-lamino]-α-D-arabinofuranosyl]-5-ethylcytosine,
1-[2',3'-Dideoxy-2'-fluoro-3'-(N-hydroxy-N-hexadecany-lamino)-α-D-arabinofuranosyl]-5-n-propylcytosine,
1-[2',3'-Dideoxy-2'-fluoro-3'-(N-hydroxy-N-hexadecany-lamino]-α-D-arabinofuranosyl]-5-i-propylcytosine,
1-[2',3'-Dideoxy-2'-fluoro-3'-(N-hydroxy-N-hexadecany-lamino]-α-D-arabinofuranosyl]-5-(E-2-bromovinyl)cytosine,
1-[2',3'-Dideoxy-2'-fluoro-3'-(N-hydroxy-N-hexadecany-lamino]-α-D-arabinofuranosyl]-5-vinylcytosine,
1-[2',3'-Dideoxy-2'-fluoro-3'-(N-hydroxy-N-hexadecany-lamino]-α-D-arabinofuranosyl]-5-carboxycytosine,
1-[2',3'-Dideoxy-2'-fluoro-3'-(N-hydroxy-N-hexadecany-lamino]-α-D-arabinofuranosyl]-5-ethoxycarbonyl-cytosine,
1-[2',3'-Dideoxy-2'-fluoro-3'-(N-hydroxy-N-hexadecany-lamino]-α-D-arabinofuranosyl]-5-aminocarbonyl-cytosine,
1-[2',3'-Dideoxy-2'-fluoro-3'-(N-hydroxy-N-hexadecany-lamino]-α-D-arabinofuranosyl]-5-cyanocytosine,
1-[2',3'-Dideoxy-2'-fluoro-3'-(N-hydroxy-N-hexadecany-lamino)-α-D-arabinofuranosyl]-5-phenylcytosine, 1-[2',3'-Dideoxy-2'-fluoro-3'-(N-hydroxy-N-hexadecanylamino)-α-D-arabinofuranosyl]-5-benzylcytosine,
1-[2',3'-Dideoxy-2'-fluoro-3'-(N-hydroxy-N-octadecanylamino)-β-D-arabinofuranosyl]thymine,
1-[2',3'-Dideoxy-2'-fluoro-3'-(N-hydroxy-N-octadecanylamino)-β-D-arabinofuranosyl]uracil,
1-[2',3'-Dideoxy-2'-fluoro-3'-(N-hydroxy-N-octadecanylamino)-β-D-arabinofuranosyl]-5-chlorouracil,
1-[2',3'-Dideoxy-2'-fluoro-3'-(N-hydroxy-N-octadecanylamino)-β-D-arabinofuranosyl]-5-bromouracil,
1-[2',3'-Dideoxy-2'-fluoro-3'-(N-hydroxy-N-octadecanylamino)-β-D-arabinofuranosyl]-5-iodouracil,
1-[2',3'-Dideoxy-2'-fluoro-3'-(N-hydroxy-N-octadecanylamino)-β-D-arabinofuranosyl]-5-ethyluracil,
1-[2',3'-Dideoxy-2'-fluoro-3'-(N-hydroxy-N-octadecanylamino)-β-D-arabinofuranosyl]-5-n-propyluracil,
1-[2',3'-Dideoxy-2'-fluoro-3'-(N-hydroxy-N-octadecanylamino)-β-D-arabinofuranosyl]-5-i-propyluracil
1-[2',3'-Dideoxy-2'-fluoro-3'-(N-hydroxy-N-octadecanylamino)-β-D-arabinofuranosyl]-5-(E-2-bromo-vinyl)uracil,
1-[2',3'-Dideoxy-2'-fluoro-3'-(N-hydroxy-N-octadecanylamino)-β-D-arabinofuranosyl]-5-vinyluracil,
1-[2',3'-Dideoxy-2'-fluoro-3'-(N-hydroxy-N-octadecanylamino)-β-D-arabinofuranosyl]-5-carboxyuracil,
1-[2',3'-Dideoxy-2'-fluoro-3'-(N-hydroxy-N-octadecanylamino)-β-D-arabinofuranosyl]-5-ethoxycarbonyl-uracil,
1-[2',3'-Dideoxy-2'-fluoro-3'-(N-hydroxy-N-octadecanylamino)-β-D-arabinofuranosyl]-5-aminocarbonyl-uracil,
1-[2',3'-Dideoxy-2'-fluoro-3'-(N-hydroxy-N-octadecanylamino)-β-D-arabinofuranosyl]-5-cyanouracil,
1-[2',3'-Dideoxy-2'-fluoro-3'-(N-hydroxy-N-octadecanylamino)-β-D-arabinofuranosyl]-5-phenyluracil,
1-[2',3'-Dideoxy-2'-fluoro-3'-(N-hydroxy-N-octadecanylamino)-β-D-arabinofuranosyl]-5-benzyluracil,
1-[2',3'-Dideoxy-2'-fluoro-3'-(N-hydroxy-N-octadecanylamino)-β-D-arabinofuranosyl]cytosine,
1-[2',3'-Dideoxy-2'-fluoro-3'-(N-hydroxy-N-octadecanylamino)-β-D-arabinofuranosyl]-5-fluorocytosine,
1-[2',3'-Dideoxy-2'-fluoro-3'-(N-hydroxy-N-octadecanylamino]-β-D-arabinofuranosyl}-5-chlorocytosine,
1-[2',3'-Dideoxy-2'-fluoro-3'-(N-hydroxy-N-octadecanylamino)-β-D-arabinofuranosyl]-5-bromocytosine,
1-[2',3'-Dideoxy-2'-fluoro-3'-(N-hydroxy-N-octadecanylamino)-β-D-arabinofuranosyl]-5-iodocytosine,
1-[2',3'-Dideoxy-2'-fluoro-3'-(N-hydroxy-N-octadecanylamino)-β-D-arabinofuranosyl]-5-ethylcytosine,
1-[2',3'-Dideoxy-2'-fluoro-3'-(N-hydroxy-N-octadecanylamino)-β-D-arabinofuranosyl]-5-n-propylcytosine,
1-[2',3'-Dideoxy-2'-fluoro-3'-(N-hydroxy-N-octadecanylamino)-β-D-arabinofuranosyl]-5-i-propylcytosine,
1-[2',3'-Dideoxy-2'-fluoro-3'-(N-hydroxy-N-octadecanylamino]-β-D-arabinofuranosyl]-5-(E-2-bromovinyl)cytosine,
1-[2',3'-Dideoxy-2'-fluoro-3'-(N-hydroxy-N-octadecanylamino]-β-D-arabinofuranosyl]-5-vinylcytosine,
1-[2',3'-Dideoxy-2'-fluoro-3'-(N-hydroxy-N-octadecanylamino]-β-D-arabinofuranosyl]-5-carboxycytosine,
1-[2',3'-Dideoxy-2'-fluoro-3'-(N-hydroxy-N-octadecanylamino]-β-D-arabinofuranosyl]-5-ethoxycarbonylcytosine,
1-[2',3'-Dideoxy-2'-fluoro-3'-(N-hydroxy-N-octadecanylamino]-β-D-arabinofuranosyl]-5-aminocarbonylcytosine,
1-[2',3'-Dideoxy-2'-fluoro-3'-(N-hydroxy-N-octadecanylamino]-β-D-arabinofuranosyl]-5-cyanocytosine,
1-[2',3'-Dideoxy-2'-fluoro-3'-(N-hydroxy-N-octadecanylamino)-β-D-arabinofuranosyl]-5-phenylcytosine,
1-[2',3'-Dideoxy-2'-fluoro-3'-(N-hydroxy-N-octadecanylamino)-β-D-arabinofuranosyl]-5-benzylcytosine,
1-[2',3'-Dideoxy-2'-fluoro-3'-(N-hydroxy-N-octadecanylamino)-α-D-arabinofuranosyl]thymine,
1-[2',3'-Dideoxy-2'-fluoro-3'-(N-hydroxy-N-octadecanylamino)-α-D-arabinofuranosyl]uracil,
1-[2',3'-Dideoxy-2'-fluoro-3'-(N-hydroxy-N-octadecanylamino)-α-D-arabinofuranosyl]-5-chlorouracil,
1-[2',3'-Dideoxy-2'-fluoro-3'-(N-hydroxy-N-octadecanylamino)-α-D-arabinofuranosyl]-5-bromouracil,
1-[2',3'-Dideoxy-2'-fluoro-3'-(N-hydroxy-N-octadecanylamino)-α-D-arabinofuranosyl]-5-iodouracil,
1-[2',3'-Dideoxy-2'-fluoro-3'-(N-hydroxy-N-octadecanylamino)-α-D-arabinofuranosyl]-5-ethyluracil,
1-[2',3'-Dideoxy-2'-fluoro-3'-(N-hydroxy-N-octadecanylamino)-α-D-arabinofuranosyl]-5-n-propyluracil,
1-[2',3'-Dideoxy-2'-fluoro-3'-(N-hydroxy-N-octadecanylamino)-α-D-arabinofuranosyl]-5-i-propyluracil
1-[2',3'-Dideoxy-2'-fluoro-3'-(N-hydroxy-N-octadecanylamino)-α-D-arabinofuranosyl]-5-(E-2-bromo-vinyl)uracil,
1-[2',3'-Dideoxy-2'-fluoro-3'-(N-hydroxy-N-octadecanylamino)-α-D-arabinofuranosyl]-5-vinyluracil,
1-[2',3'-Dideoxy-2'-fluoro-3'-(N-hydroxy-N-octadecanylamino)-α-D-arabinofuranosyl]-5-carboxyuracil,
1-[2',3'-Dideoxy-2'-fluoro-3'-(N-hydroxy-N-octadecanylamino)-α-D-arabinofuranosyl]-5-ethoxycarbonyluracil,
1-[2',3'-Dideoxy-2'-fluoro-3'-(N-hydroxy-N-octadecanylamino)-α-D-arabinofuranosyl]-5-aminocarbonyluracil,
1-[2',3'-Dideoxy-2'-fluoro-3'-(N-hydroxy-N-octadecanylamino)-α-D-arabinofuranosyl]-5-cyanouracil,
1-[2',3'-Dideoxy-2'-fluoro-3'-(N-hydroxy-N-octadecanylamino)-α-D-arabinofuranosyl]-5-phenyluracil,
1-[2',3'-Dideoxy-2'-fluoro-3'-(N-hydroxy-N-octadecanylamino)-α-D-arabinofuranosyl]-5-benzyluracil,
1-[2',3'-Dideoxy-2'-fluoro-3'-(N-hydroxy-N-octadecanylamino)-α-D-arabinofuranosyl]cytosine,
1-[2',3'-Dideoxy-2'-fluoro-3'-(N-hydroxy-N-octadecanylamino)-α-D-arabinofuranosyl]-5-fluorocytosine,
1-[2',3'-Dideoxy-2'-fluoro-3'-(N-hydroxy-N-octadecanylamino]-α-D-arabinofuranosyl}-5-chlorocytosine,
1-[2',3'-Dideoxy-2'-fluoro-3'-(N-hydroxy-N-octadecanylamino)-α-D-arabinofuranosyl]-5-bromocytosine,
1-[2',3'-Dideoxy-2'-fluoro-3'-(N-hydroxy-N-octadecanylamino)-α-D-arabinofuranosyl]-5-iodocytosine,
1-[2',3'-Dideoxy-2'-fluoro-3'-(N-hydroxy-N-octadecanylamino]-α-D-arabinofuranosyl]-5-ethylcytosine,
1-[2',3'-Dideoxy-2'-fluoro-3'-(N-hydroxy-N-octadecanylamino)-α-D-arabinofuranosyl]-5-n-propylcytosine,
1-[2',3'-Dideoxy-2'-fluoro-3'-(N-hydroxy-N-octadecanylamino]-α-D-arabinofuranosyl]-5-i-propylcytosine,
1-[2',3'-Dideoxy-2'-fluoro-3'-(N-hydroxy-N-octadecanylamino]-α-D-arabinofuranosyl]-5-(E-2-bromovinyl)cytosine,
1-[2',3'-Dideoxy-2'-fluoro-3'-(N-hydroxy-N-octadecanylamino]-α-D-arabinofuranosyl]-5-vinylcytosine,
1-[2',3'-Dideoxy-2'-fluoro-3'-(N-hydroxy-N-octadecanylamino]-α-D-arabinofuranosyl]-5-carboxycytosine,
1-[2',3'-Dideoxy-2'-fluoro-3'-(N-hydroxy-N-octadecanylamino]-α-D-arabinofuranosyl]-5-ethoxycarbonylcytosine,
1-[2',3'-Dideoxy-2'-fluoro-3'-(N-hydroxy-N-octadecanylamino]-α-D-arabinofuranosyl]-5-aminocarbonylcytosine, 1-[2',3'-Dideoxy-2'-fluoro-3'-(N-hydroxy-N-octadecany-lamino]-α-D-arabinofuranosyl]-5-cyanocytosine,
1-[2',3'-Dideoxy-2'-fluoro-3'-(N-hydroxy-N-octadecany-lamino)-α-D-arabinofuranosyl]-5-phenylcytosine,
1-[2',3'-Dideoxy-2'-fluoro-3'-(N-hydroxy-N-octadecany-lamino)-α-D-arabinofuranosyl]-5-benzylcytosine,
1-[2',3'-Dideoxy-2'-fluoro-3'-(N-hydroxy-N-phenethy-lamino)-β-D-arabinofuranosyl]thymine,
1-[2',3'-Dideoxy-2'-fluoro-3'-(N-hydroxy-N-phenethy-lamino)-β-D-arabinofuranosyl]uracil,
1-[2',3'-Dideoxy-2'-fluoro-3'-(N-hydroxy-N-phenethy-lamino)-β-D-arabinofuranosyl]-5-chlorouracil,
1-[2',3'-Dideoxy-2'-fluoro-3'-(N-hydroxy-N-phenethy-lamino)-β-D-arabinofuranosyl]-5-bromouracil,
1-[2',3'-Dideoxy-2'-fluoro-3'-(N-hydroxy-N-phenethy-lamino)-β-D-arabinofuranosyl]-5-iodouracil,
1-[2',3'-Dideoxy-2'-fluoro-3'-(A-hydroxy-N-phenethy-lamino)-β-D-arabinofuranosyl]-5-ethyluracil
1-[2',3'-Dideoxy-2'-fluoro-3'-(N-hydroxy-N-phenethy-lamino)-β-D-arabinofuranosyl]-5-n-propyluracil,
1-[2',3'-Dideoxy-2'-fluoro-3'-(N-hydroxy-N-phenethy-lamino)-β-D-arabinofuranosyl]-5-i-propyluracil,
1-[2',3'-Dideoxy-2'-fluoro-3'-(N-hydroxy-N-phenethy-lamino)-β-D-arabinofuranosyl-5-(E-2-bromo-vinyl)uracil,
1-[2',3'-Dideoxy-2'-fluoro-3'-(N-hydroxy-N-phenethy-lamino)-β-D-arabinofuranosyl]-5-vinyluracil,
1-[2',3'-Dideoxy-2'-fluoro-3'-(N-hydroxy-N-phenethy-lamino)-β-D-arabinofuranosyl]-5-carboxyuracil,
1-[2',3'-Dideoxy-2'-fluoro-3'-(N-hydroxy-N-phenethy-lamino)-β-D-arabinofuranosyl]-5-ethoxycarbonyl-uracil,
1-[2',3'-Dideoxy-2'-fluoro-3'-(N-hydroxy-N-phenethy-lamino)-β-D-arabinofuranosyl]-5-aminocarbonyl-uracil,
1-[2',3'-Dideoxy-2'-fluoro-3'-(N-hydroxy-N-phenethy-lamino)-β-D-arabinofuranosyl]-5-cyanouracil,
1-[2',3'-Dideoxy-2'-fluoro-3'-(N-hydroxy-N-phenethy-lamino)-β-D-arabinofuranosyl]-5-phenyluracil,
1-[2',3'-Dideoxy-2'-fluoro-3'-(N-hydroxy-N-phenethy-lamino)-β-D-arabinofuranosyl]-5-benzyluracil,
1-[2',3'-Dideoxy-2'-fluoro-3'-(N-hydroxy-N-phenethy-lamino)-β-D-arabinofuranosyl]cytosine,
1-[2',3'-Dideoxy-2'-fluoro-3'-(N-hydroxy-N-phenethy-lamino)-β-D-arabinofuranosyl]-5-fluorocytosine,
1-[2',3'-Dideoxy-2'-fluoro-3'-(N-hydroxy-N-phenethy-lamino]-β-D-arabinofuranosyl}-5-chlorocytosine,
1-[2',3'-Dideoxy-2'-fluoro-3'-(N-hydroxy-N-phenethy-lamino)-β-D-arabinofuranosyl]-5-bromocytosine,
1-[2',3'-Dideoxy-2'-fluoro-3'-(N-hydroxy-N-phenethy-lamino)-β-D-arabinofuranosyl]-5-iodocytosine,
1-[2',3'-Dideoxy-2'-fluoro-3'-(N-hydroxy-N-phenethy-lamino)-β-D-arabinofuranosyl]-5-ethylcytosine,
1-[2',3'-Dideoxy-2'-fluoro-3'-(N-hydroxy-N-phenethy-lamino)-β-D-arabinofuranosyl]-5-n-propylcytosine,
1-[2',3'-Dideoxy-2'-fluoro-3'-(N-hydroxy-N-phenethy-lamino)-β-D-arabinofuranosyl]-5-i-propylcytosine,
1-[2',3'-Dideoxy-2'-fluoro-3'-(N-hydroxy-N-phenethy-lamino)-β-D-arabinofuranosyl]-5-[E-(2-bromovinyl)]cytosine,
1-[2',3'-Dideoxy-2'-fluoro-3'-(N-hydroxy-N-phenethy-lamino)-β-D-arabinofuranosyl]-5-vinylcytosine,
1-[2',3'-Dideoxy-2'-fluoro-3'-(N-hydroxy-N-phenethy-lamino)-β-D-arabinofuranosyl]-5-carboxycytosine,
1-[2',3'-Dideoxy-2'-fluoro-3'-(N-hydroxy-N-phenethy-lamino)-β-D-arabinofuranosyl]-5-ethoxycarbonylcytosine,
1-[2',3'-Dideoxy-2'-fluoro-3'-(N-hydroxy-N-phenethy-lamino)-β-D-arabinofuranosyl]-5-aminocarbonyl-cytosine,
1-[2',3'-Dideoxy-2'-fluoro-3'-(N-hydroxy-N-phenethy-lamino)-β-D-arabinofuranosyl]-5-ethyluracil,
1-[2',3'-Dideoxy-2'-fluoro-3'-(N-hydroxy-N-phenethy-lamino)-β-D-arabinofuranosyl]-5-n-propyluracil,
1-[2',3'-Dideoxy-2'-fluoro-3'-(N-hydroxy-N-phenethy-lamino)-β-D-arabinofuranosyl]-5-i-propyluracil,
1-[2',3'-Dideoxy-2'-fluoro-3'-(N-hydroxy-N-phenethy-lamino)-β-D-arabinofuranosyl]-5-(E-2-bromo-vinyl)uracil,
1-[2',3'-Dideoxy-2'-fluoro-3'-(N-hydroxy-N-phenethy-lamino)-β-D-arabinofuranosyl]-5-vinyluracil,
1-[2',3'-Dideoxy-2'-fluoro-3'-(N-hydroxy-N-benzylamino]-α-D-arabinofuranosyl]-5-cyanocytosine,
1-[2',3'-Dideoxy-2'-fluoro-3'-(N-hydroxy-N-benzylamino)-α-D-arabinofuranosyl]-5-phenylcytosine,
1-[2',3'-Dideoxy-2'-fluoro-3'-(N-hydroxy-N-benzylamino)-α-D-arabinofuranosyl]-5-benzylcytosine,
1-{2',3'-Dideoxy-2'-fluoro-3'-[N-hydroxy-N-(o-methylben-zylamino)]-α-D-arabinofuranosyl}-5-ethoxycarbonyluracil,
1-{2',3'-Dideoxy-2'-fluoro-3'-[N-hydroxy-N-(o-methylben-zylamino)]-α-D-arabinofuranosyl}-5-aminocarbonyluracil,
1-{2',3'-Dideoxy-2'-fluoro-3'-[N-hydroxy-N-(o-methylben-zylamino)]-α-D-arabinofuranosyl}-5-cyanouracil,
1-{2',3'-Dideoxy-2'-fluoro-3'-[N-hydroxy-N-(o-methylben-zylamino)]-α-D-arabinofuranosyl}-5-phenyluracil,
1-{2',3'-Dideoxy-2'-fluoro-3'-[N-hydroxy-N-(o-methylben-zylamino)]-α-D-arabinofuranosyl}-5-benzyluracil,
1-{2',3'-Dideoxy-2'-fluoro-3'-[N-hydroxy-N-(o-methylben-zylamino)]-α-D-arabinofuranosyl}-cytosine,
1-{2',3'-Dideoxy-2'-fluoro-3'-[N-hydroxy-N-(o-methylben-zylamino)]-α-D-arabinofuranosyl}-5-fluorocytosine,
1-{2',3'-Dideoxy-2'-fluoro-3'-[N-hydroxy-N-(o-methylben-zylamino)]-α-D-arabinofuranosyl}-5-chlorocytosine,
1-{2',3'-Dideoxy-2'-fluoro-3'-[N-hydroxy-N-(o-methylben-zylanino)]-α-D-arabinofuranosyl}-5-bromocytosine,
1-{2',3'-Dideoxy-2'-fluoro-3'-[N-hydroxy-N-(o-methylben-zylamino)]-α-D-arabinofuranosyl}-5-iodocytosine,
1-{2',3'-Dideoxy-2'-fluoro-3'-[N-hydroxy-N-(o-methylben-zylamino)]-α-D-arabinofuranosyl}-5-ethylcytosine,
1-{2',3'-Dideoxy-2'-fluoro-3'-[N-hydroxy-N-(o-methylben-zylamino)]-α-D-arabinofuranosyl}-5-n-propylcytosine,
1-{2',3'-Dideoxy-2'-fluoro-3'-[N-hydroxy-N-(o-methylben-zylamino)]-α-D-arabinofuranosyl}-5-i-propylcytosine,
1-{2',3'-Dideoxy-2'-fluoro-3'-[N-hydroxy-N-(o-methylben-zylamino)]-α-D-arabinofuranosyl}-5-(E-2-bromovinyl)cytosine,
1-{2',3'-Dideoxy-2'-fluoro-3'-[N-hydroxy-N-(o-methylben-zylamino)]-α-D-arabinofuranosyl}-5-vinylcytosine,
1-{2',3'-Dideoxy-2'-fluoro-3'-[N-hydroxy-N-(o-methylben-zylamino)]-α-D-arabinofuranosyl}-5-carboxycytosine,
1-{2',3'-Dideoxy-2'-fluoro-3'-[N-hydroxy-N-(o-methylben-zylamino)]-α-D-arabinofuranosyl}-5-ethoxycarbonylcytosine,
1-{2',3'-Dideoxy-2'-fluoro-3'-[N-hydroxy-N-(o-methylben-zylamino)]-α-D-arabinofuranosyl}-5-aminocarbonylcytosine,
1-{2',3'-Dideoxy-2'-fluoro-3'-[N-hydroxy-N-(o-methylben-zylamino)]-α-D-arabinofuranosyl}-5-cyanocytosine,
1-{2',3'-Dideoxy-2'-fluoro-3'-[N-hydroxy-N-(o-methylben-zylamino)]-α-D-arabinofuranosyl}-5-phenylcytosine,
1-{2',3'-Dideoxy-2'-fluoro-3'-[N-hydroxy-N-(o-methylben-zylamino)]-α-D-arabinofuranosyl}-5-benzylcytosine, 1-{2',3'-Dideoxy-2'-fluoro-3'-[N-hydroxy-N-(m-methylbenzylamino)]-β-D-arabinofuranosyl}-thymine,
1-{2',3'-Dideoxy-2'-fluoro-3'-[N-hydroxy-N-(m-methylbenzylamino)]-β-D-arabinofuranosyl}uracil,
1-{2',3'-Dideoxy-2'-fluoro-3'-[N-hydroxy-N-(m-methylbenzylamino)]-β-D-arabinofuranosyl}-5-chlorouracil,
1-{2',3'-Dideoxy-2'-fluoro-3'-[N-hydroxy-N-(m-methylbenzylamino)]-β-D-arabinofuranosyl}-5-bromouracil,
1-{2',3'-Dideoxy-2'-fluoro-3'-[N-hydroxy-N-(m-methylbenzylamino)]-β-D-arabinofuranosyl}-5-iodouracil,
1-{2',3'-Dideoxy-2'-fluoro-3'-[N-hydroxy-N-(m-methylbenzylamino)]-β-D-arabinofuranosyl}-5-ethyluracil,
1-{2',3'-Dideoxy-2'-fluoro-3'-[N-hydroxy-N-(m-methylbenzylamino)]β-D-arabinofuranosyl}-5-n-propyluracil,
1-{2',3'-Dideoxy-2'-fluoro-3'-[N-hydroxy-N-(m-methylbenzylamino)]-β-D-arabinofuranosyl}-5-i-propyluracil,
1-{2',3'-Dideoxy-2'-fluoro-3'-[N-hydroxy-N-(m-methylbenzylamino)]-β-D-arabinofuranosyl}-5-(E-2-bromo-vinyl)uracil,
1-{2',3'-Dideoxy-2'-fluoro-3'-[N-hydroxy-N-(m-methylbenzylamino)]-β-D-arabinofuranosyl}-5-vinyluracil,
1-{2',3'-Dideoxy-2'-fluoro-3'-[N-hydroxy-N-(m-methylbenzylamino)]-β-D-arabinofuranosyl}-5-carboxyuracil,
1-{2',3'-Dideoxy-2'-fluoro-3'-[N-hydroxy-N-(m-methylbenzylamino)]-β-D-arabinofuranosyl}-5-ethoxycarbonyluracil,
1-{2',3'-Dideoxy-2'-fluoro-3'-[N-hydroxy-N-(m-methylbenzylamino)]-β-D-arabinofuranosyl}-5-aminocarbonyluracil,
1-{2',3'-Dideoxy-2'-fluoro-3'-[N-hydroxy-N-(m-methylbenzylamino)]-β-D-arabinofuranosyl}-5-cyanouracil,
1-{2',3'-Dideoxy-2'-fluoro-3'-[N-hydroxy-N-(m-methylbenzylamino)]-β-D-arabinofuranosyl}-5-phenyluracil,
1-{2',3'-Dideoxy-2'-fluoro-3'-[N-hydroxy-N-(m-methylbenzylamino)]-β-D-arabinofuranosyl}-5-benzyluracil,
1-{2',3'-Dideoxy-2'-fluoro-3'-[N-hydroxy-N-(m-methylbenzylamino)]-β-D-arabinofuranosyl}-cytosine,
1-{2',3'-Dideoxy-2'-fluoro-3'-[N-hydroxy-N-(m-methylbenzylamino)]-β-D-arabinofuranosyl]-5-fluorocytosine,
1-{2',3'-Dideoxy-2'-fluoro-3'-[N-hydroxy-N-(m-methylbenzylamino)]-β-D-arabinofuranosyl}-5-chlorocytosine,
1-{2',3'-Dideoxy-2'-fluoro-3'-[N-hydroxy-N-(n-methylbenzylamino)]-β-D-arabinofuranosyl}-5-bromocytosine,
1-{2',3'-Dideoxy-2'-fluoro-3'-[N-hydroxy-N-(m-methylbenzylamino)]-β-D-arabinofuranosyl}-5-iodocytosine,
1-{2',3'-Dideoxy-2'-fluoro-3'-[N-hydroxy-N-(m-methylbenzylamino)]-β-D-arabinofuranosyl}-5-ethylcytosine,
1-{2',3'-Dideoxy-2'-fluoro-3'-[N-hydroxy-N-(m-methylbenzylamino)]-β-D-arabinofuranosyl}-5-n-propylcytosine,
1-{2',3'-Dideoxy-2'-fluoro-3'-[N-hydroxy-N-(m-methylbenzylamino)]-β-D-arabinofuranosyl}-5-i-propylcytosine,
1-{2',3'-Dideoxy-2'-fluoro-3'-[N-hydroxy-N-(m-methylbenzylamino)]-β-D-arabinofuranosyl}-5-(E-2-bromovinyl)cytosine,
1-{2',3'-Dideoxy-2'-fluoro-3'-[N-hydroxy-N-(m-methylbenzylamino)]-β-D-arabinofuranosyl}-5-vinylcytosine,
1-{2',3'-Dideoxy-2'-fluoro-3'-[N-hydroxy-N-(m-methylbenzylamino)]-β-D-arabinofuranosyl}-5-carboxycytosine,
1-{2',3'-Dideoxy-2'-fluoro-3'-[N-hydroxy-N-(m-methylbenzylamino)]-β-D-arabinofuranosyl}-5-ethoxycarbonyl-cytosine,
1-{2',3'-Dideoxy-2'-fluoro-3'-[N-hydroxy-N-(m-methylbenzylamino)]-β-D-arabinofuranosyl}-5-aminocarbonylcytosine,
1-{2',3'-Dideoxy-2'-fluoro-3'-[N-hydroxy-N-(m-methylbenzylamino)]-β-D-arabinofuranosyl}-5-cyanocytosine,
1-{2',3'-Dideoxy-2'-fluoro-3'-[N-hydroxy-N-(m-methylbenzylamino)]-β-D-arabinofuranosyl}-5-phenylcytosine,
1-{2',3'-Dideoxy-2'-fluoro-3'-[N-hydroxy-N-(m-methylbenzylamino)]-β-D-arabinofuranosyl}-5-benzylcytosine,
1-{2',3'-Dideoxy-2'-fluoro-3'-[N-hydroxy-N-(m-methylbenzylamino)]-α-D-arabinofuranosyl}-thymine,
1-{2',3'-Dideoxy-2'-fluoro-3'-[N-hydroxy-N-(m-methylbenzylamino)]-α-D-arabinofuranosyl}-uracil,
1-{2',3'-Dideoxy-2'-fluoro-3'-[N-hydroxy-N-(m-methylbenzylamino)]-α-D-arabinofuranosyl}-5-chlorouracil,
1-{2',3'-Dideoxy-2'-fluoro-3'-[N-hydroxy-N-(m-methylbenzylamino)]-α-D-arabinofuranosyl}-5-bromouracil,
1-{2',3'-Dideoxy-2'-fluoro-3'-[N-hydroxy-N-(m-methylbenzylamino)]-α-D-arabinofuranosyl}-5-iodouracil,
1-{2',3'-Dideoxy-2'-fluoro-3'-[N-hydroxy-N-(m-methylbenzylamino)]-α-D-arabinofuranosyl}-5-ethyluracil,
1-{2',3'-Dideoxy-2'-fluoro-3'-[N-hydroxy-N-(m-methylbenzylamino)]-α-D-arabinofuranosyl}-5-n-propyluracil,
1-{2',3'-Dideoxy-2'-fluoro-3'-[N-hydroxy-N-(m-methylbenzylamino)]-α-D-arabinofuranosyl}-5-i-propyluracil,
1-{2',3'-Dideoxy-2'-fluoro-3'-[N-hydroxy-N-(m-methylbenzylamino)]-α-D-arabinofuranosyl}-5-(E-2-bromo-vinyl)uracil,
1-{2',3'-Dideoxy-2'-fluoro-3'-[N-hydroxy-N-(m-methylbenzylamino)]-α-D-arabinofuranosyl}-5-vinyluracil,
1-{2',3'-Dideoxy-2'-fluoro-3'-[N-hydroxy-N-(m-methylbenzylamino)]-α-D-arabinofuranosyl}-5-carboxyuracil,
1-{2',3'-Dideoxy-2'-fluoro-3'-[N-hydroxy-N-(m-methylbenzylamino)]-α-D-arabinofuranosyl}-5-ethoxycarbonyluracil,
1-{2',3'-Dideoxy-2'-fluoro-3'-[N-hydroxy-N-(m-methylbenzylamino)]-α-D-arabinofuranosyl}-5-aminocarbonyluracil,
1-{2',3'-Dideoxy-2'-fluoro-3'-[N-hydroxy-N-(m-methylbenzylamino)]-α-D-arabinofuranosyl}-5-cyanouracil,
1-{2',3'-Dideoxy-2'-fluoro-3'-[N-hydroxy-N-(m-methylbenzylamino)]-α-D-arabinofuranosyl}-5-phenyluracil,
1-{2',3'-Dideoxy-2'-fluoro-3'-[N-hydroxy-N-(m-methylbenzylamino)]-β-D-arabinofuranosyl}-5-benzyluracil,
1-{2',3'-Dideoxy-2'-fluoro-3'-[N-hydroxy-N-(m-methylbenzylamino)]-α-D-arabinofuranosyl}-cytosine,
1-{2',3'-Dideoxy-2'-fluoro-3'-[N-hydroxy-N-(m-methylbenzylamino)]-α-D-arabinofuranosyl]-5-fluorocytosine,
1-{2',3'-Dideoxy-2'-fluoro-3'-[N-hydroxy-N-(m-methylbenzylamino)]-α-D-arabinofuranosyl}-5-chlorocytosine,
1-{2',3'-Dideoxy-2'-fluoro-3'-[N-hydroxy-N-(m-methylbenzylamino)]-α-D-arabinofuranosyl}-5-bromocytosine,
1-{2',3'-Dideoxy-2'-fluoro-3'-[N-hydroxy-N-(m-methylbenzylamino)]-α-D-arabinofuranosyl}-5-iodocytosine,
1-{2',3'-Dideoxy-2'-fluoro-3'-[N-hydroxy-N-(m-methylbenzylamino)]-α-D-arabinofuranosyl}-5-ethylcytosine,
1-{2',3'-Dideoxy-2'-fluoro-3'-[N-hydroxy-N-(m-methylbenzylamino)]-α-D-arabinofuranosyl}-5-n-propylcytosine,
1-{2',3'-Dideoxy-2'-fluoro-3'-[N-hydroxy-N-(m-methylbenzylamino)]-α-D-arabinofuranosyl}-5-i-propylcytosine,
1-{2',3'-Dideoxy-2'-fluoro-3'-[N-hydroxy-N-(m-methylbenzylamino)]-α-D-arabinofuranosyl}-5-(E-2-bromovinyl)cytosine,
1-{2',3'-Dideoxy-2'-fluoro-3'-[N-hydroxy-N-(m-methylbenzylamino)]-α-D-arabinofuranosyl}-5-vinylcytosine,
1-{2',3'-Dideoxy-2'-fluoro-3'-[N-hydroxy-N-(m-methylbenzylamino)]-α-D-arabinofuranosyl}-5-carboxycytosine,
1-{2',3'-Dideoxy-2'-fluoro-3'-[N-hydroxy-N-(m-methylbenzylamino)]-α-D-arabinofuranosyl}-5-ethoxycarbonyl-cytosine, 1-{2',3'-Dideoxy-2'-fluoro-3'-[N-hydroxy-N-(m-methylbenzylamino)]-α-D-arabinofuranosyl}-5-aminocarbonyl-cytosine,
1-{2',3'-Dideoxy-2'-fluoro-3'-[N-hydroxy-N-(m-methylbenzylamino)]-α-D-arabinofuranosyl}-5-cyanocytosine,
1-{2',3'-Dideoxy-2'-fluoro-3'-[N-hydroxy-N-(m-methylbenzylamino)]-α-D-arabinofuranosyl}-5-phenylcytosine,
1-{2',3'-Dideoxy-2'-fluoro-3'-[N-hydroxy-N-(m-methylbenzylamino)]-α-D-arabinofuranosyl}-5-benzylcytosine,
1-{2',3'-Dideoxy-2'-fluoro-3'-[N-hydroxy-N-(p-methylbenzylamino)]-β-D-arabinofuranosyl}-thymine,
1-{2',3'-Dideoxy-2'-fluoro-3'-[N-hydroxy-N-(p-methylbenzylamino)]-β-D-arabinofuranosyl}uracil,
1-{2',3'-Dideoxy-2'-fluoro-3'-[N-hydroxy-N-(p-methylbenzylamino)]-β-D-arabinofuranosyl}-5-chlorouracil,
1-{2',3'-Dideoxy-2'-fluoro-3'-[N-hydroxy-N-(p-methylbenzylamino)]-β-D-arabinofuranosyl}-5-bromouracil,
1-{2',3'-Dideoxy-2'-fluoro-3'-[N-hydroxy-N-(p-methylbenzylamino)]-β-D-arabinofuranosyl}-5-iodouracil,
1-{2',3'-Dideoxy-2'-fluoro-3'-[N-hydroxy-N-(p-methylbenzylamino)]-β-D-arabinofuranosyl}-5-ethyluracil,
1-{2',3'-Dideoxy-2'-fluoro-3'-[N-hydroxy-N-(p-methylbenzylamino)]-β-D-arabinofuranosyl}-5-n-propyluracil,
1-{2',3'-Dideoxy-2'-fluoro-3'-[N-hydroxy-N-(p-methylbenzylamino)]-β-D-arabinofuranosyl}-5-i-propyluracil,
1-{2',3'-Dideoxy-2'-fluoro-3'-[N-hydroxy-N-(p-methylbenzylamino)]-β-D-arabinofuranosyl}-5-(E-2-bromo-vinyl)uracil,
1-{2',3'-Dideoxy-2'-fluoro-3'-[N-hydroxy-N-(p-methylbenzylamino)]-β-D-arabinofuranosyl}-5-vinyluracil,
1-{2',3'-Dideoxy-2'-fluoro-3'-[N-hydroxy-N-(p-methylbenzylamino)]-β-D-arabinofuranosyl}-5-carboxyuracil,
1-{2',3'-Dideoxy-2'-fluoro-3'-[N-hydroxy-N-(p-methylbenzylamino)]-β-D-arabinofuranosyl}-5-ethoxycarbonyl-uracil,
1-{2',3'-Dideoxy-2'-fluoro-3'-[N-hydroxy-N-(p-methylbenzylamino)]-β-D-arabinofuranosyl}-5-aminocarbonyl-uracil,
1-{2',3'-Dideoxy-2'-fluoro-3'-[N-hydroxy-N-(p-methylbenzylamino)]-β-D-arabinofuranosyl}-5-cyanouracil,
1-{2',3'-Dideoxy-2'-fluoro-3'-[N-hydroxy-N-(p-methylbenzylamino)]-β-D-arabinofuranosyl}-5-phenyluracil,
1-{2',3'-Dideoxy-2'-fluoro-3'-[N-hydroxy-N-(p-methylbenzylamino)]-β-D-arabinofuranosyl}-5-benzyluracil,
1-{2',3'-Dideoxy-2'-fluoro-3'-[N-hydroxy-N-(p-methylbenzylamino)]-β-D-arabinofuranosyl}-cytosine,
1-{2',3'-Dideoxy-2'-fluoro-3'-[N-hydroxy-N-(p-methylbenzylamino)]-β-D-arabinofuranosyl]-5-fluorocytosine,
1-{2',3'-Dideoxy-2'-fluoro-3'-[N-hydroxy-N-(p-methylbenzylamino)]-β-D-arabinofuranosyl}-5-chlorocytosine,
1-{2',3'-Dideoxy-2'-fluoro-3'-[N-hydroxy-N-(p-methylbenzylamino)]-β-D-arabinofuranosyl}-5-bromocytosine,
1-{2',3'-Dideoxy-2'-fluoro-3'-[N-hydroxy-N-(p-methylbenzylamnino)]-β-D-arabinofuranosyl}-5-iodocytosine,
1-{2',3'-Dideoxy-2'-fluoro-3'-[N-hydroxy-N-(p-methylbenzylamino)]-β-D-arabinofuranosyl}-5-ethylcytosine,
1-{2',3'-Dideoxy-2'-fluoro-3'-[N-hydroxy-N-(p-methylbenzylamino)]-β-D-arabinofuranosyl}-5-n-propylcytosine,
1-{2',3'-Dideoxy-2'-fluoro-3'-[N-hydroxy-N-(p-methylbenzylamino)]-β-D-arabinofuranosyl}-5-i-propylcytosine,
1-{2',3'-Dideoxy-2'-fluoro-3'-[N-hydroxy-N-(p-methylbenzylamino)]-β-D-arabinofuranosyl}-5-(E-2-bromovinyl)cytosine,
1-{2',3'-Dideoxy-2'-fluoro-3'-[N-hydroxy-N-(p-methylbenzylamino)]-β-D-arabinofuranosyl}-5-vinylcytosine,
1-{2',3'-Dideoxy-2'-fluoro-3'-[N-hydroxy-N-(p-methylbenzylamino)]-β-D-arabinofuranosyl}-5-carboxycytosine,
1-{2',3'-Dideoxy-2'-fluoro-3'-[N-hydroxy-N-(p-methylbenzylamino)]-β-D-arabinofuranosyl}-5-ethoxycarbonyl-cytosine,
1-{2',3'-Dideoxy-2'-fluoro-3'-[N-hydroxy-N-(p-methylbenzylamino)]-β-D-arabinofuranosyl}-5-aminocarbonyl-cytosine,
1-{2',3'-Dideoxy-2'-fluoro-3'-[N-hydroxy-N-(p-methylbenzylamino)]-β-D-arabinofuranosyl}-5-cyanocytosine,
1-{2',3'-Dideoxy-2'-fluoro-3'-[N-hydroxy-N-(p-methylbenzylamino)]-β-D-arabinofuranosyl}-5-phenylcytosine,
1-{2',3'-Dideoxy-2'-fluoro-3'-[N-hydroxy-N-(p-methylbenzylamino)]-β-D-arabinofuranosyl]-5-benzylcytosine,
1-{2',3'-Dideoxy-2'-fluoro-3'-[N-hydroxy-N-(p-methylbenzylamino)]-α-D-arabinofuranosyl}-thymine,
1-{2',3'-Dideoxy-2'-fluoro-3'-[N-bydroxy-N-(p-methylbenzylamino)]-α-D-arabinofuranosyl}- uracil,
1-{2',3'-Dideoxy-2'-fluoro-3'-[N-hydroxy-N-(p-methylbenzylamino)]-α-D-arabinofuranosyl}-5-chlorouracil,
1-{2',3'-Dideoxy-2'-fluoro-3'-[N-hydroxy-N-(p-methylbenzylamino)]-α-D-arabinofuranosyl}-5-bromouracil,
1-{2',3'-Dideoxy-2'-fluoro-3'-[N-hydroxy-N-(p-methylbenzylamino)]-α-D-arabinofuranosyl}-5-iodouracil,
1-{2',3'-Dideoxy-2'-fluoro-3'-[N-hydroxy-N-(p-methylbenzylamino)]-α-D-arabinofuranosyl}-5-ethyluracil,
1-{2',3'-Dideoxy-2'-fluoro-3'-[N-hydroxy-N-(p-methylbenzylamino)]-α-D-arabinofuranosyl}-5-n-propyluracil,
1-{2',3'-Dideoxy-2'-fluoro-3'-[N-hydroxy-N-(p-methylbenzylamino)]-α-D-arabinofuranosyl}-5-i-propyluracil,
1-{2',3'-Dideoxy-2'-fluoro-3'-[N-hydroxy-N-(p-methylbenzylamino)]-α-D-arabinofuranosyl}-5-(E-2-bromo-vinyl)uracil,
1-{2',3'-Dideoxy-2'-fluoro-3'-[N-hydroxy-N-(p-methylbenzylamino)]-α-D-arabinofuranosyl}-5-vinyluracil,
1-{2',3'-Dideoxy-2'-fluoro-3'-[N-hydroxy-N-(p-methylbenzylamino)]-α-D-arabinofuranosyl}-5-carboxyuracil,
1-{2',3'-Dideoxy-2'-fluoro-3'-[N-hydroxy-N-(p-methylbenzylamino)]-α-D-arabinofuranosyl}-5-ethoxycarbonyl-uracil,
1-{2',3'-Dideoxy-2'-fluoro-3'-[N-hydroxy-N-(p-methylbenzylamino)]-α-D-arabinofuranosyl}-5-aminocarbonyl-uracil,
1-{2',3'-Dideoxy-2'-fluoro-3'-[N-hydroxy-N-(p-methylbenzylamino)]-α-D-arabinofuranosyl}-5-cyanouracil,
1-{2',3'-Dideoxy-2'-fluoro-3'-[N-hydroxy-N-(p-methylbenzylamino)]-α-D-arabinofuranosyl}-5-phenyluracil,
1-{2',3'-Dideoxy-2'-fluoro-3'-[N-hydroxy-N-(p-methylbenzylamino)]-α-D-arabinofuranosyl}-5-benzyluracil,
1-{2',3'-Dideoxy-2'-fluoro-3'-[N-hydroxy-N-(p-methylbenzylamino)]-α-D-arabinofuranosyl}-cytosine,
1-{2',3'-Dideoxy-2'-fluoro-3'-[N-hydroxy-N-(p-methylbenzylamino)]-α-D-arabinofuranosyl]-5-fluorocytosine,
1-{2',3'-Dideoxy-2'-fluoro-3'-[N-hydroxy-N-(p-methylbenzylamino)]-α-D-arabinofuranosyl}-5-chlorocytosine,
1-{2',3'-Dideoxy-2'-fluoro-3'-[N-hydroxy-N-(p-methylbenzylamino)]-α-D-arabinofuranosyl}-5-bromocytosine,
1-{2',3'-Dideoxy-2'-fluoro-3'-[N-hydroxy-N-(p-methylbenzylamino)]-α-D-arabinofuranosyl}-5-iodocytosine,
1-{2',3'-Dideoxy-2'-fluoro-3'-[N-hydroxy-N-(p-methylbenzylamino)]-α-D-arabinofuranosyl}-5-ethylcytosine,
1-{2',3'-Dideoxy-2'-fluoro-3'-[N-hydroxy-N-(p-methylbenzylamino)]-α-D-arabinofuranosyl}-5-n-propylcytosine,
1-{2',3'-Dideoxy-2'-fluoro-3'-[N-hydroxy-N-(p-methylbenzylamino)]-α-D-arabinofuranosyl}-5-i-propylcytosine,
1-{2',3'-Dideoxy-2'-fluoro-3'-[N-hydroxy-N-(p-methylbenzylamino)]-α-D-arabinofuranosyl}-5-(E-2-bromovinyl)cytosine, 1-{2',3'-Dideoxy-2'-fluoro-3'-[N-hydroxy-N-(p-methylbenzylamino)]-α-D-arabinofuranosyl}-5-vinylcytosine,
1-{2',3'-Dideoxy-2'-fluoro-3'-[N-hydroxy-N-(p-methylbenzylamino)]-α-D-arabinofuranosyl}-5-carboxycytosine,
1-{2',3'-Dideoxy-2'-fluoro-3'-[N-hydroxy-N-(m-methylbenzylamino)]-α-D-arabinofuranosyl}-5-ethoxycarbonyl-cytosine,
1-{2',3'-Dideoxy-2'-fluoro-3'-[N-hydroxy-N-(p-methylbenzylamino)]-α-D-arabinofuranosyl}-5-aminocarbonyl-cytosine,
1-{2',3'-Dideoxy-2'-fluoro-3'-[N-hydroxy-N-(p-methylbenzylamino)]-α-D-arabinofuranosyl}-5-cyanocytosine,
1-{2',3'-Dideoxy-2'-fluoro-3'-[N-hydroxy-N-(p-methylbenzylamino)]-α-D-arabinofuranosyl}-5-phenylcytosine,
1-{2',3'-Dideoxy-2'-fluoro-3'-[N-hydroxy-N-(p-methylbenzylamino)]-α-D-arabinofuranosyl}-5-benzylcytosine,
1-{2',3'-Dideoxy-2'-fluoro-3'-[N-hydroxy-N-(o-hydroxybenzylamino)]-β-D-arabinofuranosyl}-5-thymine,
1-{2',3'-Dideoxy-2'-fluoro-3'-[N-hydroxy-N-(o-hydroxybenzylamino)]-β-D-arabinofuranosyl}- uracil,
1-{2',3'-Dideoxy-2'-fluoro-3'-[N-hydroxy-N-(o-hydroxybenzylamino)]-β-D-arabinofuranosyl}-5-chlorouracil,
1-{2',3'-Dideoxy-2'-fluoro-3'-[N-hydroxy-N-(o-hydroxybenzylamino)]-β-D-arabinofuranosyl}-5-bromouracil,
1-{2',3'-Dideoxy-2'-fluoro-3'-[N-hydroxy-N-(o-hydroxybenzylamino)]-β-D-arabinofuranosyl}-5-iodouracil,
1-{2',3'-Dideoxy-2'-fluoro-3'-[N-hydroxy-N-(o-hydroxybenzylamino)]-β-D-arabinofuranosyl}-5-ethyluracil,
1-{2',3'-Dideoxy-2'-fluoro-3'-[N-hydroxy-N-(o-hydroxybenzylamino)]-β-D-arabinofuranosyl}-5-n-propyluracil,
1-{2',3'-Dideoxy-2'-fluoro-3'-[N-hydroxy-N-(o-hydroxybenzylamino)]-α-D-arabinofuranosyl}-5-i-propyluracil,
1-{2',3'-Dideoxy-2'-fluoro-3'-[N-hydroxy-N-(o-hydroxybenzylamino)]-α-D-arabinofuranosyl}-5-(E-2-bromo-vinyl)uracil,
1-{2',3'-Dideoxy-2'-fluoro-3'-[N-hydroxy-N-(o-hydroxybenzylamino)]-β-D-arabinofuranosyl}-5-vinyluracil,
1-{2',3'-Dideoxy-2'-fluoro-3'-[N-hydroxy-N-(o-hydroxybenzylamino)]-β-D-arabinofuranosyl}-5-carboxyuracil,
1-{2',3'-Dideoxy-2'-fluoro-3'-[N-hydroxy-N-(o-hydroxybenzylamino)]-β-D-arabinofuranosyl}-5-ethoxycarbonyl-uracil,
1-{2',3'-Dideoxy-2'-fluoro-3'-[N-hydroxy-N-(o-hydroxybenzylamino)]-β-D-arabinofuranosyl}-5-aminocarbonyl-uracil,
1-{2',3'-Dideoxy-2'-fluoro-3'-[N-hydroxy-N-(o-hydroxybenzylamino)]-β-D-arabinofuranosyl}-5-cyanouracil,
1-{2',3'-Dideoxy-2'-fluoro-3'-[N-hydroxy-N-(o-hydroxybenzylamino)]-β-D-arabinofuranosyl}-5-phenyluracil,
1-{2',3'-Dideoxy-2'-fluoro-3'-[N-hydroxy-N-(o-hydroxybenzylamino)]-β-D-arabinofuranosyl}-5-benzyluracil,
1-{2',3'-Dideoxy-2'-fluoro-3'-[N-hydroxy-N-(o-hydroxybenzylamino)]-β-D-arabinofuranosyl}-cytosine,
1-{2',3'-Dideoxy-2'-fluoro-3'-[N-hydroxy-N-(o-hydroxybenzylamino)]-β-D-arabinofuranosyl]-5-fluorocytosine,
1-{2',3'-Dideoxy-2'-fluoro-3'-[N-hydroxy-N-(o-hydroxybenzylamino)]-β-D-arabinofuranosyl}-5-chlorocytosine,
1-{2',3'-Dideoxy-2'-fluoro-3'-[N-hydroxy-N-(o-hydroxybenzylamino)]-β-D-arabinofuranosyl}-5-bromocytosine,
1-{2',3'-Dideoxy-2'-fluoro-3'-[N-hydroxy-N-(o-hydroxybenzylamino)]-β-D-arabinofuranosyl}-5-iodocytosine,
1-{2',3'-Dideoxy-2'-fluoro-3'-[N-hydroxy-N-(o-hydroxybenzylamino)]-β-D-arabinofuranosyl}-5-ethylcytosine,
1-{2',3'-Dideoxy-2'-fluoro-3'-[N-hydroxy-N-(o-hydroxybenzylamino)]-β-D-arabinofuranosyl}-5-n-propylcytosine,
1-{2',3'-Dideoxy-2'-fluoro-3'-[N-hydroxy-N-(o-hydroxybenzylamino)]-β-D-arabinofuranosyl}-5-i-propylcytosine,
1-{2',3'-Dideoxy-2'-fluoro-3'-[N-hydroxy-N-(o-hydroxybenzylamino)]-β-D-arabinofuranosyl}-5-(E-2-bromovinyl)cytosine,
1-{2',3'-Dideoxy-2'-fluoro-3'-[N-hydroxy-N-(o-hydroxybenzylamino)]-β-D-arabinofuranosyl}-5-vinylcytosine,
1-{2',3'-Dideoxy-2'-fluoro-3'-[N-hydroxy-N-(o-hydroxybenzylamino)]-β-D-arabinofuranosyl}-5-carboxycytosine,
1-{2',3'-Dideoxy-2'-fluoro-3'-[N-hydroxy-N-(o-hydroxybenzylamino)]-β-D-arabinofuranosyl}-5-ethoxycarbonyl-cytosine,
1-{2',3'-Dideoxy-2'-fluoro-3'-[N-hydroxy-N-(o-hydroxybenzylamino)]-β-D-arabinofuranosyl}-5-aminocarbonyl-cytosine,
1-{2',3'-Dideoxy-2'-fluoro-3'-[N-hydroxy-N-(o-hydroxybenzylamino)]-β-D-arabinofuranosyl}-5-cyanocytosine,
1-{2',3'-Dideoxy-2'-fluoro-3'-[N-hydroxy-N-(o-hydroxybenzylamino)]-β-D-arabinofuranosyl}-5-phenylcytosine,
1-{2',3'-Dideoxy-2'-fluoro-3'-[N-hydroxy-N-(o-hydroxybenzylamino)]-β-D-arabinofuranosyl}-5-benzylcytosine,
1-{2',3'-Dideoxy-2'-fluoro-3'-[N-hydroxy-N-(o-hydroxybenzylamino)]-α-D-arabinofuranosyl}-thymine,
1-{2',3'-Dideoxy-2'-fluoro-3'-[N-hydroxy-N-(o-hydroxybenzylamino)]-α-D-arabinofuranosyl}-uracil,
1-{2',3'-Dideoxy-2'-fluoro-3'-[N-hydroxy-N-(o-hydroxybenzylamino)]-α-D-arabinofuranosyl}-5-chlorouracil,
1-{2',3'-Dideoxy-2'-fluoro-3'-[N-hydroxy-N-(o-hydroxybenzylamino)]-α-D-arabinofuranosyl}-5-bromouracil,
1-{2',3'-Dideoxy-2'-fluoro-3'-[N-hydroxy-N-(o-hydroxybenzylamino)]-α-D-arabinofuranosyl}-5-iodouracil,
1-{2',3'-Dideoxy-2'-fluoro-3'-[N-hydroxy-N-(o-hydroxybenzylamino)]-α-D-arabinofuranosyl}-5-ethyluracil,
1-{2',3'-Dideoxy-2'-fluoro-3'-[N-hydroxy-N-(o-methylbenzylamino)]-α-D-arabinofuranosyl}-5-n-propyluracil,
1-{2',3'-Dideoxy-2'-fluoro-3'-[N-hydroxy-N-(o-hydroxybenzylamino)]-α-D-arabinofuranosyl}-5-i-propyluracil,
1-{2',3'-Dideoxy-2'-fluoro-3'-[N-hydroxy-N-(o-hydroxybenzylamino)]-α-D-arabinofuranosyl}-5-(E-2-bromo-vinyl)uracil,
1-{2',3'-Dideoxy-2'-fluoro-3'-[N-hydroxy-N-(o-hydroxybenzylamino)]-α-D-arabinofuranosyl}-5-vinyluracil,
1-{2',3'-Dideoxy-2'-fluoro-3'-[N-hydroxy-N-(o-hydroxybenzylamino)]-α-D-arabinofuranosyl}-5-carboxyuracil,
1-{2',3'-Dideoxy-2'-fluoro-3'-[N-hydroxy-N-(o-hydroxybenzylamino)]-α-D-arabinofuranosyl}-5-ethoxycarbonyl-uracil,
1-{2',3'-Dideoxy-2'-fluoro-3'-[N-hydroxy-N-(o-hydroxybenzylamino)]-α-D-arabinofuranosyl}-5-aminocarbonyl-uracil,
1-{2',3'-Dideoxy-2'-fluoro-3'-[N-hydroxy-N-(o-hydroxybenzylamino)]-α-D-arabinofuranosyl}-5-cyanouracil,
1-{2',3'-Dideoxy-2'-fluoro-3'-[N-hydroxy-N-(o-hydroxybenzylamino)]-α-D-arabinofuranosyl}-5-phenyluracil,
1-{2',3'-Dideoxy-2'-fluoro-3'-[N-hydroxy-N-(o-hydroxybenzylamino)]-α-D-arabinofuranosyl}-5-benzyluracil,
1-{2',3'-Dideoxy-2'-fluoro-3'-[N-hydroxy-N-(o-hydroxybenzylamino)]-α-D-arabinofuranosyl}-cytosine,
1-{2',3'-Dideoxy-2'-fluoro-3'-[N-hydroxy-N-(o-hydroxybenzylamino)]-α-D-arabinofuranosyl]-5-fluorocytosine,
1-{2',3'-Dideoxy-2'-fluoro-3'-[N-hydroxy-N-(o-hydroxybenzylamino)]-α-D-arabinofuranosyl}-5-chlorocytosine,
1-{2',3'-Dideoxy-2'-fluoro-3'-[N-hydroxy-N-(o-hydroxybenzylamino)]-α-D-arabinofuranosyl}-5-bromocytosine, 1-{2',3'-Dideoxy-2'-fluoro-3'-[N-hydroxy-N-(o-hydroxybenzylamino)]-α-D-arabinofuranosyl}-5-iodocytosine,
1-{2',3'-Dideoxy-2'-fluoro-3'-[N-hydroxy-N-(o-hydroxybenzylamino)]-α-D-arabinofuranosyl}-5-ethylcytosine,
1-{2',3'-Dideoxy-2'-fluoro-3'-[N-hydroxy-N-(o-hydroxybenzylamino)]-α-D-arabinofuranosyl}-5-n-propylcytosine,
1-{2',3'-Dideoxy-2'-fluoro-3'-[N-hydroxy-N-(o-hydroxybenzylamino)]-α-D-arabinofuranosyl}-5-i-propylcytosine,
1-{2',3'-Dideoxy-2'-fluoro-3'-[N-hydroxy-N-(o-hydroxybenzylamino)]-α-D-arabinofuranosyl}-5-(E-2-bromovinyl)cytosine,
1-{2',3'-Dideoxy-2'-fluoro-3'-[N-hydroxy-N-(o-hydroxybenzylamino)]-α-D-arabinofuranosyl}-5-vinylcytosine,
1-{2',3'-Dideoxy-2'-fluoro-3'-[N-hydroxy-N-(o-hydroxybenzylamino)]-α-D-arabinofuranosyl}-5-carboxycytosine,
1-{2',3'-Dideoxy-2'-fluoro-3'-[N-hydroxy-N-(o-hydroxybenzylamino)]-α-D-arabinofuranosyl}-5-ethoxycarbonyl-cytosine,
1-{2',3'-Dideoxy-2'-fluoro-3'-[N-hydroxy-N-(o-hydroxybenzylamino)]-α-D-arabinofuranosyl}-5-aminocarbonyl-cytosine,
1-{2',3'-Dideoxy-2'-fluoro-3'-[N-hydroxy-N-(o-hydroxybenzylamino)]-α-D-arabinofuranosyl}-5-cyanocytosine,
1-{2',3'-Dideoxy-2'-fluoro-3'-[N-hydroxy-N-(o-hydroxybenzylamino)]-α-D-arabinofuranosyl}-5-phenylcytosine,
1-{2',3'-Dideoxy-2'-fluoro-3'-[N-hydroxy-N-(o-hydroxybenzylamino)]-α-D-arabinofuranosyl}-5-benzylcytosine,
1-{2',3'-Dideoxy-2'-fluoro-3'-[N-hydroxy-N-(p-hydroxybenzylamino)]-β-D-arabinofuranosyl}-thymine,
1-{2',3'-Dideoxy-2'-fluoro-3'-[N-hydroxy-N-(p-hydroxybenzylamino)]-β-D-arabinofuranosyl}uracil,
1-{2',3'-Dideoxy-2'-fluoro-3'-[N-hydroxy-N-(p-hydroxybenzylamino)]-β-D-arabinofuranosyl}-5-chlorouracil,
1-{2',3'-Dideoxy-2'-fluoro-3'-[N-hydroxy-N-(p-hydroxybenzylamino)]-β-D-arabinofuranosyl}-5-bromouracil,
1-{2',3'-Dideoxy-2'-fluoro-3'-[N-hydroxy-N-(p-hydroxybenzylamino)]-β-D-arabinofuranosyl}-5-iodouracil,
1-{2',3'-Dideoxy-2'-fluoro-3'-[N-hydroxy-N-(p-hydroxybenzylamino)]-β-D-arabinofuranosyl}-5-ethyluracil,
1-{2',3'-Dideoxy-2'-fluoro-3'-[N-hydroxy-N-(p-hydroxybenzylamino)]-β-D-arabinofuranosyl}-5-n-propyluracil,
1-{2',3'-Dideoxy-2'-fluoro-3'-[N-hydroxy-N-(p-hydroxybenzylamino)]-β-D-arabinofuranosyl}-5-i-propyluracil,
1-{2',3'-Dideoxy-2'-fluoro-3'-[N-hydroxy-N-(p-hydroxybenzylamino)]-β-D-arabinofuranosyl}-5-(E-2-bromo-vinyl)uracil,
1-{2',3'-Dideoxy-2'-fluoro-3'-[N-hydroxy-N-(p-hydroxybenzylamino)]-β-D-arabinofuranosyl}-5-vinyluracil,
1-{2',3'-Dideoxy-2'-fluoro-3'-[N-hydroxy-N-(p-hydroxybenzylamino)]-β-D-arabinofuranosyl}-5-carboxyuracil,
1-{2',3'-Dideoxy-2'-fluoro-3'-[N-hydroxy-N-(p-hydroxybenzylamino)]-β-D-arabinofuranosyl}-5-ethoxycarbonyluracil,
1-{2',3'-Dideoxy-2'-fluoro-3'-[N-hydroxy-N-(p-hydroxybenzylamino)]-β-D-arabinofuranosyl}-5-aminocarbonyluracil,
1-{2',3'-Dideoxy-2'-fluoro-3'-[N-hydroxy-N-(p-hydroxybenzylamino)]-β-D-arabinofuranosyl}-5-cyanouracil,
1-{2',3'-Dideoxy-2'-fluoro-3'-[N-hydroxy-N-(p-hydroxybenzylamino)]-β-D-arabinofuranosyl}-5-phenyluracil,
1-{2',3'-Dideoxy-2'-fluoro-3'-[N-hydroxy-N-(p-hydroxybenzylamino)]-β-D-arabinofuranosyl}-5-benzyluracil,
1-{2',3'-Dideoxy-2'-fluoro-3'-[N-hydroxy-N-(p-hydroxybenzylamino)]-β-D-arabinofuranosyl}-cytosine,
1-{2',3'-Dideoxy-2'-fluoro-3'-[N-hydroxy-N-(p-hydroxybenzylamino)]-β-D-arabinofuranosyl}-5-fluorocytosine,
1-{2',3'-Dideoxy-2'-fluoro-3'-[N-hydroxy-N-(p-hydroxybenzylamino)]-β-D-arabinofuranosyl}-5-chlorocytosine,
1-{2',3'-Dideoxy-2'-fluoro-3'-[N-hydroxy-N-(p-hydroxybenzylamino)]-β-D-arabinofuranosyl}-5-bromocytosine,
1-{2',3'-Dideoxy-2'-fluoro-3'-[N-hydroxy-N-(p-hydroxybenzylamino)]-β-D-arabinofuranosyl}-5-iodocytosine,
1-{2',3'-Dideoxy-2'-fluoro-3'-[N-hydroxy-N-(p-hydroxybenzylamino)]-β-D-arabinofuranosyl}-5-ethylcytosine,
1-{2',3'-Dideoxy-2'-fluoro-3'-[N-hydroxy-N-(p-hydroxybenzylamino)]-β-D-arabinofuranosyl}-5-n-propylcytosine,
1-{2',3'-Dideoxy-2'-fluoro-3'-[N-hydroxy-N-(p-hydroxybenzylamino)]-β-D-arabinofuranosyl}-5-i-propylcytosine,
1-{2',3'-Dideoxy-2'-fluoro-3'-[N-hydroxy-N-(p-hydroxybenzylamino)]-β-D-arabinofuranosyl}-5-(E-2-bromovinyl)cytosine,
1-{2',3'-Dideoxy-2'-fluoro-3'-[N-hydroxy-N-(p-hydroxybenzylamino)]-β-D-arabinofuranosyl}-5-vinylcytosine,
1-{2',3'-Dideoxy-2'-fluoro-3'-[N-hydroxy-N-(p-hydroxybenzylamino)]-β-D-arabinofuranosyl}-5-carboxycytosine,
1-{2',3'-Dideoxy-2'-fluoro-3'-[N-hydroxy-N-(p-hydroxybenzylamino)]-β-D-arabinofuranosyl}-5-ethoxycarbonylcytosine,
1-{2',3'-Dideoxy-2'-fluoro-3'-[N-hydroxy-N-(p-hydroxybenzylamino)]-β-D-arabinofuranosyl}-5-aminocarbonylcytosine,
1-{2',3'-Dideoxy-2'-fluoro-3'-[N-hydroxy-N-(p-hydroxybenzylamino)]-β-D-arabinofuranosyl}-5-cyanocytosine,
1-{2',3'-Dideoxy-2'-fluoro-3'-[N-hydroxy-N-(p-hydroxybenzylamino)]-β-D-arabinofuranosyl}-5-phenylcytosine,
1-{2',3'-Dideoxy-2'-fluoro-3'-[N-hydroxy-N-(p-hydroxybenzylamino)]-β-D-arabinofuranosyl}-5-benzylcytosine,
1-{2',3'-Dideoxy-2'-fluoro-3'-[N-hydroxy-N-(p-hydroxybenzylamino)]-α-D-arabinofuranosyl}-thymine,
1-{2',3'-Dideoxy-2'-fluoro-3'-[N-hydroxy-N-(p-hydroxybenzylamino)]-α-D-arabinofuranosyl}uracil,
1-{2',3'-Dideoxy-2'-fluoro-3'-[N-hydroxy-N-(p-hydroxybenzylamino)]-α-D-arabinofuranosyl}-5-chlorouracil,
1-{2',3'-Dideoxy-2'-fluoro-3'-[N-hydroxy-N-(p-hydroxylbenzylamino)]-α-D-arabinofuranosyl}-5-bromouracil,
1-{2',3'-Dideoxy-2'-fluoro-3'-[N-hydroxy-N-(p-hydroxybenzylamino)]-α-D-arabinofuranosyl}-5-iodouracil,
1-{2',3'-Dideoxy-2'-fluoro-3'-[N-hydroxy-N-(p-hydroxybenzylamino)]-α-D-arabinofuranosyl}-5-ethyluracil,
1-{2',3'-Dideoxy-2'-fluoro-3'-[N-hydroxy-N-(p-methylbenzylamino)]-α-D-arabinofuranosyl}-5-n-propyluracil,
1-{2',3'-Dideoxy-2'-fluoro-3'-[N-hydroxy-N-(p-hydroxybenzylamino)]-α-D-arabinofuranosyl}-5-i-propyluracil,
1-{2',3'-Dideoxy-2'-fluoro-3'-[N-hydroxy-N-(p-hydroxybenzylamino)]-α-D-arabinofuranosyl}-5-(E-2-bromo-vinyl)uracil,
1-{2',3'-Dideoxy-2'-fluoro-3'-[N-hydroxy-N-(p-hydroxybenzylamino)]-α-D-arabinofuranosyl}-5-vinyluracil,
1-{2',3'-Dideoxy-2'-fluoro-3'-[N-hydroxy-N-(p-hydroxybenzylamino)]-α-D-arabinofuranosyl}-5-carboxyuracil,
1-{2',3'-Dideoxy-2'-fluoro-3'-[N-hydroxy-N-(p-hydroxybenzylamino)]-α-D-arabinofuranosyl}-5-ethoxycarbonyluracil,
1-{2',3'-Dideoxy-2'-fluoro-3'-[N-hydroxy-N-(p-hydroxybenzylamino)]-α-D-arabinofuranosyl}-5-aminocarbonyluracil,
1-{2',3'-Dideoxy-2'-fluoro-3'-[N-hydroxy-N-(p-hydroxybenzylamino)]-α-D-arabinofuranosyl}-5-cyanouracil, 1-{2',3'-Dideoxy-2'-fluoro-3'-[N-hydroxy-N-(p-hydroxybenzylamino)]-α-D-arabinofuranosyl}-5-phenyluracil,
1-{2',3'-Dideoxy-2'-fluoro-3'-[N-hydroxy-N-(p-hydroxybenzylamino)]-α-D-arabinofuranosyl}-5-benzyluracil,
1-{2',3'-Dideoxy-2'-fluoro-3'-[N-hydroxy-N-(p-hydroxybenzylamino)]-α-D-arabinofuranosyl}-cytosine,
1-{2',3'-Dideoxy-2'-fluoro-3'-[N-hydroxy-N-(p-hydroxybenzylamino)]-α-D-arabinofuranosyl]-5-fluorocytosine,
1-{2',3'-Dideoxy-2'-fluoro-3'-[N-hydroxy-N-(p-hydroxybenzylamino)]-α-D-arabinofuranosyl}-5-chlorocytosine,
1-{2',3'-Dideoxy-2'-fluoro-3'-[N-hydroxy-N-(p-hydroxybenzylamino)]-α-D-arabinofuranosyl}-5-bromocytosine,
1-{2',3'-Dideoxy-2'-fluoro-3'-[N-hydroxy-N-(p-hydroxybenzylamino)]-α-D-arabinofuranosyl}-5-iodocytosine,
1-{2',3'-Dideoxy-2'-fluoro-3'-[N-hydroxy-N-(p-hydroxybenzylamino)]-α-D-arabinofuranosyl}-5-ethylcytosine,
1-{2',3'-Dideoxy-2'-fluoro-3'-[N-hydroxy-N-(p-hydroxybenzylamino)]-α-D-arabinofuranosyl}-5-n-propylcytosine,
1-{2',3'-Dideoxy-2'-fluoro-3'-[N-hydroxy-N-(p-hydroxybenzylamino)]-α-D-arabinofuranosyl}-5-i-propylcytosine,
1-{2',3'-Dideoxy-2'-fluoro-3'-[N-hydroxy-N-(p-hydroxybenzylamino)]-α-D-arabinofuranosyl}-5-(E-2-bromovinyl)cytosine,
1-{2',3'-Dideoxy-2'-fluoro-3'-[N-hydroxy-N-(p-hydroxybenzylamino)]-α-D-arabinofuranosyl}-5-vinylcytosine,
1-{2',3'-Dideoxy-2'-fluoro-3'-[N-hydroxy-N-(p-hydroxybenzylamino)]-α-D-arabinofuranosyl}-5-carboxycytosine,
1-{2',3'-Dideoxy-2'-fluoro-3'-[N-hydroxy-N-(p-hydroxybenzylamino)]-α-D-arabinofuranosyl}-5-ethoxycarbonyl-cytosine,
1-{2',3'-Dideoxy-2'-fluoro-3'-[N-hydroxy-N-(p-hydroxybenzylamino)]-α-D-arabinofuranosyl}-5-aminocarbonylcytosine,
1-{2',3'-Dideoxy-2'-fluoro-3'-[N-hydroxy-N-(p-hydroxybenzylamino)]-α-D-arabinofuranosyl}-5-cyanocytosine,
1-{2',3'-Dideoxy-2'-fluoro-3'-[N-hydroxy-N-(p-hydroxybenzylamino)]-α-D-arabinofuranosyl}-5-phenylcytosine,
1-{2',3'-Dideoxy-2'-fluoro-3'-[N-hydroxy-N-(p-hydroxybenzylamino)]-α-D-arabinofuranosyl}-5-benzylcytosine,
1-{2',3'-Dideoxy-2'-fluoro-3'-[N-hydroxy-N-(p-methoxybenzylamino)]-β-D-arabinofuranosyl}-5-thymine,
1-{2',3'-Dideoxy-2'-fluoro-3'-[N-hydroxy-N-(p-methoxybenzylamino)]-β-Darabinofuranosyl}-uracil,
1-{2',3'-Dideoxy-2'-fluoro-3'-[N-hydroxy-N-(p-methoxybenzylamino)]-β-D-arabinofuranosyl}-5-chlorouracil,
1-{2',3'-Dideoxy-2'-fluoro-3'-[N-hydroxy-N-(p-methoxybenzylamino)]-β-D-arabinofuranosyl}-5-bromouracil,
1-{2',3'-Dideoxy-2'-fluoro-3'-[N-hydroxy-N-(p-methoxybenzylamino)]-β-D-arabinofuranosyl}-5-iodouracil,
1-{2',3'-Dideoxy-2'-fluoro-3'-[N-hydroxy-N-(p-methoxybenzylamino)]-β-D-arabinofuranosyl}-5-ethyluracil,
1-{2',3'-Dideoxy-2'-fluoro-3'-[N-hydroxy-N-(p-methoxybenzylamino)]-β-D-arabinofuranosyl}-5-n-propyluracil,
1-{2',3'-Dideoxy-2'-fluoro-3'-[N-hydroxy-N-(p-methoxybenzylamino)]-β-D-arabinofuranosyl}-5-i-propyluracil,
1-{2',3'-Dideoxy-2'-fluoro-3'-[N-hydroxy-N-(p-methoxybenzylamino)]-β-D-arabinofuranosyl}-5-(E-2-bromo-vinyl)uracil,
1-{2',3'-Dideoxy-2'-fluoro-3'-[N-hydroxy-N-(p-methoxybenzylamino)]-β-D-arabinofuranosyl}-5-vinyluracil,
1-{2',3'-Dideoxy-2'-fluoro-3'-[N-hydroxy-N-(p-methoxybenzylamino)]-β-D-arabinofuranosyl}-5-carboxyuracil,
1-{2',3'-Dideoxy-2'-fluoro-3'-[N-hydroxy-N-(p-methoxybenzylamino)]-β-D-arabinofuranosyl}-5-ethoxycarbonyl-uracil,
1-{2',3'-Dideoxy-2'-fluoro-3'-[N-hydroxy-N-(p-methoxybenzylamino)]-β-D-arabinofuranosyl}-5-aminocarbonyluracil,
1-{2',3'-Dideoxy-2'-fluoro-3'-[N-hydroxy-N-(p-methoxybenzylamino)]-β-D-arabinofuranosyl}-5-cyanouracil,
1-{2',3'-Dideoxy-2'-fluoro-3'-[N-hydroxy-N-(p-methoxybenzylamino)]-β-D-arabinofuranosyl}-5-phenyluracil,
1-{2',3'-Dideoxy-2'-fluoro-3'-[N-hydroxy-N-(p-methoxybenzylamino)]-β-D-arabinofuranosyl}-5-benzyluracil,
1-{2',3'-Dideoxy-2'-fluoro-3'-[N-hydroxy-N-(p-methoxybenzylamino)]-β-D-arabinofuranosyl}cytosine,
1-{2',3'-Dideoxy-2'-fluoro-3'-[N-hydroxy-N-(p-methoxybenzylamino)]-β-D-arabinofuranosyl]-5-fluorocytosine,
1-{2',3'-Dideoxy-2'-fluoro-3'-[N-hydroxy-N-(p-methoxybenzylamino)]-β-D-arabinofuranosyl}-5-chlorocytosine,
1-{2',3'-Dideoxy-2'-fluoro-3'-[N-hydroxy-N-(p-methoxybenzylamino)]-β-D-arabinofuranosyl}-5-bromocytosine,
1-{2',3'-Dideoxy-2'-fluoro-3'-[N-hydroxy-N-(p-methoxybenzylamino)]-β-D-arabinofuranosyl}-5-iodocytosine,
1-{2',3'-Dideoxy-2'-fluoro-3'-[N-hydroxy-N-(p-methoxybenzylamino)]-β-D-arabinofuranosyl}-5-ethylcytosine,
1-{2',3'-Dideoxy-2'-fluoro-3'-[N-hydroxy-N-(p-methoxybenzylamino)]-β-D-arabinofuranosyl}-5-n-propylcytosine,
1-{2',3'-Dideoxy-2'-fluoro-3'-[N-hydroxy-N-(p-methoxybenzylamino)]-β-D-arabinofuranosyl}-5-i-propylcytosine,
1-{2',3'-Dideoxy-2'-fluoro-3'-[N-hydroxy-N-(p-methoxybenzylamino)]-β-D-arabinofuranosyl}-5-(E-2-bromovinyl)cytosine,
1-{2',3'-Dideoxy-2'-fluoro-3'-[N-hydroxy-N-(p-methoxybenzylamino)]-β-D-arabinofuranosyl}-5-vinylcytosine,
1-{2',3'-Dideoxy-2'-fluoro-3'-[N-hydroxy-N-(p-methoxybenzylamino)]-β-D-arabinofuranosyl}-5-carboxycytosine,
1-{2',3'-Dideoxy-2'-fluoro-3'-[N-hydroxy-N-(p-methoxybenzylamino)]-β-D-arabinofuranosyl}-5-ethoxycarbonyl-cytosine,
1-{2',3'-Dideoxy-2'-fluoro-3'-[N-hydroxy-N-(p-methoxybenzylamino)]-β-D-arabinofuranosyl}-5-aminocarbonylcytosine,
1-{2',3'-Dideoxy-2'-fluoro-3'-[N-hydroxy-N-(p-methoxybenzylanino)]-β-D-arabinofuranosyl}-5-cyanocytosine,
1-{2',3'-Dideoxy-2'-fluoro-3'-[N-hydroxy-N-(p-methoxybenzylamino)]-β-D-arabinofuranosyl}-5-phenylcytosine,
1-{2',3'-Dideoxy-2'-fluoro-3'-[N-hydroxy-N-(p-methoxybenzylamino)]-β-D-arabinofuranosyl}-5-benzylcytosine,
1-{2',3'-Dideoxy-2'-fluoro-3'-[N-hydroxy-N-(p-methoxybenzylamino)]-α-D-arabinofuranosyl}-thymine,
1-{2',3'-Dideoxy-2'-fluoro-3'-[N-hydroxy-N-(p-methoxybenzylamino)]-α-D-arabinofuranosyl}uracil,
1-{2',3'-Dideoxy-2'-fluoro-3'-[N-hydroxy-N-(p-methoxybenzylamino)]-α-D-arabinofuranosyl}-5-chlorouracil,
1-{2',3'-Dideoxy-2'-fluoro-3'-[N-hydroxy-N-(p-methoxylbenzylamino)]-α-D-arabinofuranosyl}-5-bromouracil,
1-{2',3'-Dideoxy-2'-fluoro-3'-[N-hydroxy-N-(p-methoxybenzylamino)]-α-D-arabinofuranosyl}-5-iodouracil,
1-{2',3'-Dideoxy-2'-fluoro-3'-[N-hydroxy-N-(p-methoxybenzylamino)]-α-D-arabinofuranosyl}-5-ethyluracil,
1-{2',3'-Dideoxy-2'-fluoro-3'-[N-hydroxy-N-(p-methoxybenzylamino)]-α-D-arabinofuranosyl}-5-n-propyluracil,
1-{2',3'-Dideoxy-2'-fluoro-3'-[N-hydroxy-N-(p-methoxybenzylamino)]-α-D-arabinofuranosyl}-5-i-propyluracil, 1-{2',3'-Dideoxy-2'-fluoro-3'-[N-hydroxy-N-(p-methoxybenzylamino)]-α-D-arabinofuranosyl}-5-(E-2-bromo-vinyl)uracil,
1-{2',3'-Dideoxy-2'-fluoro-3'-[N-hydroxy-N-(p-methoxybenzylamino)]-α-D-arabinofuranosyl}-5-vinyluracil,
1-{2',3'-Dideoxy-2'-fluoro-3'-[N-hydroxy-N-(p-methoxybenzylamino)]-α-D-arabinofuranosyl}-5-carboxyuracil,
1-{2',3'-Dideoxy-2'-fluoro-3'-[N-hydroxy-N-(p-methoxybenzylamino)]-α-D-arabinofuranosyl}-5-ethoxycarbonyl-uracil,
1-{2',3'-Dideoxy-2'-fluoro-3'-[N-hydroxy-N-(p-methoxybenzylamino)]-α-D-arabinofuranosyl}-5-aminocarbonyluracil,
1-{2',3'-Dideoxy-2'-fluoro-3'-[N-hydroxy-N-(p-methoxybenzylamino)]-α-D-arabinofuranosyl}-5-cyanouracil,
1-{2',3'-Dideoxy-2'-fluoro-3'-[N-hydroxy-N-(p-methoxybenzylamino)]-α-D-arabinofuranosyl}-5-phenyluracil,
1-{2',3'-Dideoxy-2'-fluoro-3'-[N-hydroxy-N-(p-methoxybenzylamino)]-α-D-arabinofuranosyl}-5-benzyluracil,
1-{2',3'-Dideoxy-2'-fluoro-3'-[N-hydroxy-N-(p-methoxybenzylamino)]-α-D-arabinofuranosyl}5-cytosine,
1-{2',3'-Dideoxy-2'-fluoro-3'-[N-hydroxy-N-(p-methoxybenzylamino)]-α-D-arabinofuranosyl]-5-fluorocytosine,
1-{2',3'-Dideoxy-2'-fluoro-3'-[N-hydroxy-N-(p-methoxybenzylamino)]-α-D-arabinofuranosyl}-5-chlorocytosine,
1-{2',3'-Dideoxy-2'-fluoro-3'-[N-hydroxy-N-(p-methoxybenzylamino)]-α-D-arabinofuranosyl}-5-bromocytosine,
1-{2',3'-Dideoxy-2'-fluoro-3'-[N-hydroxy-N-(p-methoxybenzylamino)]-α-D-arabinofuranosyl}-5-iodocytosine,
1-{2',3'-Dideoxy-2'-fluoro-3'-[N-hydroxy-N-(p-methoxybenzylamino)]-α-D-arabinofuranosyl}-5-ethylcytosine,
1-{2',3'-Dideoxy-2'-fluoro-3'-[N-hydroxy-N-(p-methoxybenzylamino)]-α-D-arabinofuranosyl}-5-n-propylcytosine,
1-{2',3'-Dideoxy-2'-fluoro-3'-[N-hydroxy-N-(p-methoxybenzylamino)]-α-D-arabinofuranosyl}-5-i-propylcytosine,
1-{2',3'-Dideoxy-2'-fluoro-3'-[N-hydroxy-N-(p-methoxybenzylamino)]-α-D-arabinofuranosyl}-5-(E-2-bromovinyl)cytosine,
1-{2',3'-Dideoxy-2'-fluoro-3'-[N-hydroxy-N-(p-methoxybenzylamino)]-α-D-arabinofuranosyl}-5-vinylcytosine,
1-{2',3'-Dideoxy-2'-fluoro-3'-[N-hydroxy-N-(p-methoxybenzylamino)]-α-D-arabinofuranosyl}-5-carboxycytosine,
1-{2',3'-Dideoxy-2'-fluoro-3'-[N-hydroxy-N-(p-methoxybenzylamino)]-α-D-arabinofuranosyl}-5-ethoxycarbonyl-cytosine,
1-{2',3'-Dideoxy-2'-fluoro-3'-[N-hydroxy-N-(p-methoxybenzylamino)]-α-D-arabinofuranosyl}-5-aminocarbonyl-cytosine,
1-{2',3'-Dideoxy-2'-fluoro-3'-[N-hydroxy-N-(p-methoxybenzylamino)]-α-D-arabinofuranosyl}-5-cyanocytosine,
1-{2',3'-Dideoxy-2'-fluoro-3'-[N-hydroxy-N-(p-methoxybenzylamino)]-α-D-arabinofuranosyl}-5-phenylcytosine,
1-{2',3'-Dideoxy-2'-fluoro-3'-[N-hydroxy-N-(p-methoxybenzylamino)]-α-D-arabinofuranosyl}-5-benzylcytosine,
1-{2',3'-Dideoxy-2'-fluoro-3'-[N-hydroxy-N-(4-hydroxy-3-methoxybenzylamino)]-β-D-arabinofuranosyl}thymine,
1-{2',3'-Dideoxy-2'-fluoro-3'-[N-hydroxy-N-(4-hydroxy-3-methoxybenzylamino)]-β-D-arabinofuranosyl}uracil,
1-{2',3'-Dideoxy-2'-fluoro-3'-[N-hydroxy-N-(4-hydroxy-3-methoxybenzylamino)]-β-D-arabinofuranosyl}-5-chlorouracil,
1-{2',3'-Dideoxy-2'-fluoro-3'-[N-hydroxy-N-(4-hydroxy-3-methoxybenzylamino)]-β-D-arabinofuranosyl}-5-bromouracil,
1-{2',3'-Dideoxy-2'-fluoro-3'-[N-hydroxy-N-(4-hydroxy-3-methoxybenzylamino)]-β-D-arabinofuranosyl}-5-iodouracil,
1-{2',3'-Dideoxy-2'-fluoro-3'-[N-hydroxy-N-(4-hydroxy-3-methoxybenzylamino)]-β-D-arabinofuranosyl}-5-ethyluracil,
1-{2',3'-Dideoxy-2'-fluoro-3'-[N-hydroxy-N-(4-hydroxy-3-methoxybenzylamino)]-β-D-arabinofuranosyl}-5-n-propyluracil,
1-{2',3'-Dideoxy-2'-fluoro-3'-[N-hydroxy-N-(4-hydroxy-3-methoxybenzylamino)]-β-D-arabinofuranosyl}-5-i-propyluracil,
1-{2',3'-Dideoxy-2'-fluoro-3'-[N-hydroxy-N-(4-hydroxy-3-methoxybenzylamino)]-β-D-arabinofuranosyl}-5-(E-2-bromo-vinyl)uracil,
1-{2',3'-Dideoxy-2'-fluoro-3'-[N-hydroxy-N-(4-hydroxy-3-methoxybenzylamino)]-β-D-arabinofuranosyl}-5-vinyluracil,
1-{2',3'-Dideoxy-2'-fluoro-3'-[N-hydroxy-N-(4-hydroxy-3-methoxybenzylamino)]-β-D-arabinofuranosyl}-5-carboxyuracil,
1-{2',3'-Dideoxy-2'-fluoro-3'-[N-hydroxy-N-(4-hydroxy-3-methoxybenzylamino)]-β-D-arabinofuranosyl}-5-ethoxycarbonyl-uracil,
1-{2',3'-Dideoxy-2'-fluoro-3'-[N-hydroxy-N-(4-hydroxy-3-methoxybenzylamino)]-β-D-arabinofuranosyl}-5-aminocarbonyl-uracil,
1-{2',3'-Dideoxy-2'-fluoro-3'-[N-hydroxy-N-(4-hydroxy-3-methoxybenzylamino)]-β-D-arabinofuranosyl}-5-cyanouracil,
1-{2',3'-Dideoxy-2'-fluoro-3'-[N-hydroxy-N-(4-hydroxy-3-methoxybenzylamino)]-β-D-arabinofuranosyl}-5-phenyluracil,
1-{2',3'-Dideoxy-2'-fluoro-3'-[N-hydroxy-N-(4-hydroxy-3-methoxybenzylamino)]-β-D-arabinofuranosyl}-5-benzyluracil,
1-{2',3'-Dideoxy-2'-fluoro-3'-[N-hydroxy-N-(4-hydroxy-3-methoxybenzylamino)]-β-D-arabinofuranosyl}cytosine,
1-{2',3'-Dideoxy-2'-fluoro-3'-[N-hydroxy-N-(4-hydroxy-3-methoxybenzylamino)]-β-D-arabinofuranosyl}-5-fluorocytosine,
1-{2',3'-Dideoxy-2'-fluoro-3'-[N-hydroxy-N-(4-hydroxy-3-methoxybenzylamino)]-β-D-arabinofuranosyl}-5-chlorocytosine,
1-{2',3'-Dideoxy-2'-fluoro-3'-[N-hydroxy-N-(4-hydroxy-3-methoxybenzylamino)]-β-D-arabinofuranosyl}-5-bromocytosine,
1-{2',3'-Dideoxy-2'-fluoro-3'-[N-hydroxy-N-(4-hydroxy-3-methoxybenzylamino)]-β-D-arabinofuranosyl}-5-iodocytosine,
1-{2',3'-Dideoxy-2'-fluoro-3'-[N-hydroxy-N-(4-hydroxy-3-methoxybenzylamino)]-β-D-arabinofuranosyl}-5-ethylcytosine,
1-{2',3'-Dideoxy-2'-fluoro-3'-[N-hydroxy-N-(4-hydroxy-3-methoxybenzylamino)]-β-D-arabinofuranosyl}-5-n-propylcytosine,
1-{2',3'-Dideoxy-2'-fluoro-3'-[N-hydroxy-N-(4-hydroxy-3-methoxybenzylamino)]-β-D-arabinofuranosyl}-5-i-propylcytosine,
1-{2',3'-Dideoxy-2'-fluoro-3'-[N-hydroxy-N-(4-hydroxy-3-methoxybenzylamino)]-β-D-arabinofuranosyl}-5-(E-2-bromovinyl)cytosine,
1-{2',3'-Dideoxy-2'-fluoro-3'-[N-hydroxy-N-(4-hydroxy-3-methoxybenzylamino)]-β-D-arabinofuranosyl}-5-vinylcytosine, 1-{2',3'-Dideoxy-2'-fluoro-3'-[N-hydroxy-N-(4-hydroxy-3-methoxybenzylamino)]-β-D-arabinofuranosyl}-5-carboxycytosine,
1-{2',3'-Dideoxy-2'-fluoro-3'-[N-hydroxy-N-(4-hydroxy-3-methoxybenzylamino)]-β-D-arabinofuranosyl}-5-ethoxycarbonyl-cytosine,
1-{2',3'-Dideoxy-2'-fluoro-3'-[N-hydroxy-N-(4-hydroxy-3-methoxybenzylamino)]-β-D-arabinofuranosyl}-5-aminocarbonylcytosine,
1-{2',3'-Dideoxy-2'-fluoro-3'-[N-hydroxy-N-(4-hydroxy-3-methoxybenzylamino)]-β-D-arabinofuranosyl}-5-cyanocytosine,
1-{2',3'-Dideoxy-2'-fluoro-3'-[N-hydroxy-N-(4-hydroxy-3-methoxybenzylamino)]-β-D-arabinofuranosyl}-5-phenylcytosine,
1-{2',3'-Dideoxy-2'-fluoro-3'-[N-hydroxy-N-(4-hydroxy-3-methoxybenzylamino)]-β-D-arabinofuranosyl}-5-benzylcytosine,
1-{2',3'-Dideoxy-2'-fluoro-3'-[N-hydroxy-N-(4-hydroxy-3-methoxybenzylamino)]-α-D-arabinofuranosyl}thymine,
1-{2',3'-Dideoxy-2'-fluoro-3'-[N-hydroxy-N-(4-hydroxy-3-methoxybenzylamino)]-α-D-arabinofuranosyl}uracil,
1-{2',3'-Dideoxy-2'-fluoro-3'-[N-hydroxy-N-(4-hydroxy-3-methoxybenzylamino)]-α-D-arabinofuranosyl}-5-chlorouracil,
1-{2',3'-Dideoxy-2'-fluoro-3'-[N-hydroxy-N-(4-hydroxy-3-methoxybenzylamino)]-α-D-arabinofuranosyl}-5-bromouracil,
1-{2',3'-Dideoxy-2'-fluoro-3'-[N-hydroxy-N-(4-hydroxy-3-methoxybenzylamino)]-α-D-arabinofuranosyl}-5-iodouracil,
1-{2',3'-Dideoxy-2'-fluoro-3'-[N-hydroxy-N-(4-hydroxy-3-methoxybenzylamino)]-α-D-arabinofuranosyl}-5-ethyluracil,
1-{2',3'-Dideoxy-2'-fluoro-3'-[N-hydroxy-N-(4-hydroxy-3-methoxybenzylamino)]-α-D-arabinofuranosyl}-5-n-propyluracil,
1-{2',3'-Dideoxy-2'-fluoro-3'-[N-hydroxy-N-(4-hydroxy-3-methoxybenzylamino)]-α-D-arabinofuranosyl}-5-i-propyluracil,
1-{2',3'-Dideoxy-2'-fluoro-3'-[N-hydroxy-N-(4-hydroxy-3-methoxybenzylamino)]-α-D-arabinofuranosyl}-5-(E-2-bromo-vinyl)uracil,
1-{2',3'-Dideoxy-2'-fluoro-3'-[N-hydroxy-N-(4-hydroxy-3-methoxybenzylamino)]-α-D-arabinofuranosyl}-5-vinyluracil,
1-{2',3'-Dideoxy-2'-fluoro-3'-[N-hydroxy-N-(4-hydroxy-3-methoxybenzylamino)]-α-D-arabinofuranosyl}-5-carboxyuracil,
1-{2',3'-Dideoxy-2'-fluoro-3'-[N-hydroxy-N-(4-hydroxy-3-methoxybenzylamino)]-α-D-arabinofuranosyl}-5-ethoxycarbonyl-uracil,
1-{2',3'-Dideoxy-2'-fluoro-3'-[N-hydroxy-N-(4-hydroxy-3-methoxybenzylamino)]-α-D-arabinofuranosyl}-5-aminocarbonyl-uracil,
1-{2',3'-Dideoxy-2'-fluoro-3'-[N-hydroxy-N-(4-hydroxy-3-methoxybenzylamino)]-α-D-arabinofuranosyl}-5-cyanouracil,
1-{2',3'-Dideoxy-2'-fluoro-3'-[N-hydroxy-N-(4-hydroxy-3-methoxybenzylanino)]-α-D-arabinofuranosyl}-5-phenyluracil,
1-{2',3'-Dideoxy-2'-fluoro-3'-[N-hydroxy-N-(4-hydroxy-3-methoxybenzylamino)]-α-D-arabinofuranosyl}-5-benzyluracil,
1-{2',3'-Dideoxy-2'-fluoro-3'-[N-hydroxy-N-(4-hydroxy-3-methoxybenzylamino)]-α-D-arabinofuranosyl}cytosine,
1-{2',3'-Dideoxy-2'-fluoro-3'-[N-hydroxy-N-(4-hydroxy-3-methoxybenzylamino)]-α-D-arabinofuranosyl]-5-fluorocytosine,
1-{2',3'-Dideoxy-2'-fluoro-3'-[N-hydroxy-N-(4-hydroxy-3-methoxybenzylamino)]-α-D-arabinofuranosyl}-5-chlorocytosine,
1-{2',3'-Dideoxy-2'-fluoro-3'-[N-hydroxy-N-(4-hydroxy-3-methoxybenzylamino)]-α-D-arabinofuranosyl}-5-bromocytosine,
1-{2',3'-Dideoxy-2'-fluoro-3'-[N-hydroxy-N-(4-hydroxy-3-methoxybenzylamino)]-α-D-arabinofuranosyl}-5-iodocytosine,
1-{2',3'-Dideoxy-2'-fluoro-3'-[N-hydroxy-N-(4-hydroxy-3-methoxybenzylamino)]-α-D-arabinofuranosyl}-5-ethylcytosine,
1-{2',3'-Dideoxy-2'-fluoro-3'-[N-hydroxy-N-(4-hydroxy-3-methoxybenzylamino)]-α-D-arabinofuranosyl}-5-n-propylcytosine,
1-{2',3'-Dideoxy-2'-fluoro-3'-[N-hydroxy-N-(4-hydroxy-3-methoxybenzylamino)]-α-D-arabinofuranosyl}-5-i-propylcytosine,
1-{2',3'-Dideoxy-2'-fluoro-3'-[N-hydroxy-N-(4-hydroxy-3-methoxybenzylamino)]-α-D-arabinofuranosyl}-5-(E-2-bromovinyl)cytosine,
1-{2',3'-Dideoxy-2'-fluoro-3'-[N-hydroxy-N-(4-hydroxy-3-methoxybenzylamino)]-α-D-arabinofuranosyl}-5-vinylcyltosine,
1-{2',3'-Dideoxy-2'-fluoro-3'-[N-hydroxy-N-(4-hydroxy-3-methoxybenzylamino)]-α-D-arabinofuranosyl}-5-carboxycytosine,
1-{2',3=-Dideoxy-2'-fluoro-3'-[N-hydroxy-N-(4-hydroxy-3-methoxybenzylamino)]-α-D-arabinofuranosyl}-5-ethoxycarbonyl-cytosine,
1-{2',3'-Dideoxy-2'-fluoro-3'-[N-hydroxy-N-(4-hydroxy-3-methoxybenzylamino)]-α-D-arabinofuranosyl}-5-aminocarbonylcytosine,
1-{2',3'-Dideoxy-2'-fluoro-3'-[N-hydroxy-N-(4-hydroxy-3-methoxybenzylamino)]-α-D-arabinofuranosyl}-5-cyanocytosine,
1-{2',3'-Dideoxy-2'-fluoro-3'-[N-hydroxy-N-(4-hydroxy-3-methoxybenzylamino)]-α-D-arabinofuranosyl}-5-phenylcytosine,
1-{2',3'-Dideoxy-2'-fluoro-3'-[N-hydroxy-N-(4-hydroxy-3-methoxybenzylamino)]-α-D-arabinofuranosyl}-5-benzylcytosine,
1-{2',3'-Dideoxy-2'-fluoro-3'-[N-hydroxy-N-(3,4-methylidenebenzylamino)]-β-D-arabinofuranosyl}thymine,
1-{2',3'-Dideoxy-2'-fluoro-3'-[N-hydroxy-N-(3,4-methylidenebenzylamino)]-β-D-arabinofuranosyl}uracil,
1-{2',3'-Dideoxy-2'-fluoro-3'-[N-hydroxy-N-(3,4-methylidenebenzylamino)]-β-D-arabinofuranosyl}-5-chlorouracil,
1-{2',3'-Dideoxy-2'-fluoro-3'-[N-hydroxy-N-(3,4-methylidenebenzylamino)]-β-D-arabinofuranosyl}-5-bromouraci l,
1-{2',3'-Dideoxy-2'-fluoro-3'-[N-hydroxy-N-(3,4-methylidenebenzylamino)]-β-D-arabinofuranosyl}-5-iodouracil,
1-{2',3'-Dideoxy-2'-fluoro-3'-[N-hydroxy-N-(3,4-methylidenebenzylamino)]-β-D-arabinofuranosyl}-5-ethyluracil,
1-{2',3'-Dideoxy-2'-fluoro-3'-[N-hydroxy-N-(3,4-methylidenebenzylamino)]-β-D-arabinofuranosyl}-5-n-propyluracil,
1-{2',3'-Dideoxy-2'-fluoro-3'-[N-hydroxy-N-(3,4-methylidenebenzylamino)]-β-D-arabinofuranosyl}-5-i-propyluracil, 1-{2',3'-Dideoxy-2'-fluoro-3'-[N-hydroxy-N-(3,4-methylidenebenzylamino)]-β-D-arabinofuranosyl}-5-(E-2-bromo-vinyl)uracil,
1-{2',3'-Dideoxy-2'-fluoro-3'-[N-hydroxy-N-(3,4-methylidenebenzylamino)]-β-D-arabinofuranosyl}-5-vinyluracil,
1-{2',3'-Dideoxy-2'-fluoro-3'-[N-hydroxy-N-(3,4-methylidenebenzylamino)]-β-D-arabinofuranosyl}-5-carboxyuracil,
1-{2',3'-Dideoxy-2'-fluoro-3'-[N-hydroxy-N-(3,4-methylidenebenzylamino)]-β-D-arabinofuranosyl}-5-ethoxycarbonyl-uracil,
1-{2',3'-Dideoxy-2'-fluoro-3'-[N-hydroxy-N-(3,4-methylidenebenzylamino)]-β-D-arabinofuranosyl}-5-aminocarbonyl-uracil,
1-{2',3'-Dideoxy-2'-fluoro-3'-[N-hydroxy-N-(3,4-methylidenebenzylamino)]-β-D-arabinofuranosyl}-5-cyanouracil,
1-{2',3'-Dideoxy-2'-fluoro-3'-[N-hydroxy-N-(3,4-methylidenebenzylamino)]-β-D-arabinofuranosyl}-5-phenyluracil,
1-{2',3'-Dideoxy-2'-fluoro-3'-[N-hydroxy-N-(3,4-methylidenebenzylamino)]-β-D-arabinofuranosyl}-5-benzyluracil,
1-{2',3'-Dideoxy-2'-fluoro-3'-[N-hydroxy-N-(3,4-methylidenebenzylamino)]-β-D-arabinofuranosyl}cytosine,
1-{2',3'-Dideoxy-2'-fluoro-3'-[N-hydroxy-N-(3,4-methylidenebenzylamino)]-β-D-arabinofuranosyl]-5-fluorocytosine,
1-{2',3'-Dideoxy-2'-fluoro-3'-[N-hydroxy-N-(3,4-methylidenebenzylamino)]-β-D-arabinofuranosyl}-5-chlorocytosine,
1-{2',3'-Dideoxy-2'-fluoro-3'-[N-hydroxy-N-(3,4-methylidenebenzylamino)]-β-D-arabinofuranosyl}-5-bromocytosine,
1-{2',3'-Dideoxy-2'-fluoro-3'-[N-hydroxy-N-(3,4-methylidenebenzylamino)]-β-D-arabinofuranosyl}-5-iodocytosine,
1-{2',3'-Dideoxy-2'-fluoro-3'-[N-hydroxy-N-(3,4-methylidenebenzylamino)]-β-D-arabinofuranosyl}-5-ethylcytosine,
1-{2',3'-Dideoxy-2'-fluoro-3'-[N-hydroxy-N-(3,4-methylidenebenzylamino)]-β-D-arabinofuranosyl}-5-n-propylcytosine,
1-{2',3'-Dideoxy-2'-fluoro-3'-[N-hydroxy-N-(3,4-methylidenebenzylamino)]-β-D-arabinofuranosyl}-5-i-propylcytosine,
1-{2',3'-Dideoxy-2'-fluoro-3'-[N-hydroxy-N-(3,4-methylidenebenzylamino)]-β-D-arabinofuranosyl}-5-(E-2-bromovinyl)cytosine,
1-{2',3'-Dideoxy-2'-fluoro-3'-[N-hydroxy-N-(3,4-methylidenebenzylamino)]-β-D-arabinofuranosyl}-5-vinylcytosine,
1-{2',3'-Dideoxy-2'-fluoro-3'-[N-hydroxy-N-(3,4-methylidenebenzylamino)]-β-D-arabinofuranosyl}-5-carboxycytosine,
1-{2',3'-Dideoxy-2'-fluoro-3'-[N-hydroxy-N-(3,4-methylidenebenzylamino)]-β-D-arabinofuranosyl}-5-ethoxycarbonyl-cytosine,
1-{2',3'-Dideoxy-2'-fluoro-3'-[N-hydroxy-N-(3,4-methylidenebenzylamino)]-β-D-arabinofuranosyl -5-aminocarbonylcytosine,
1-{2',3'-Dideoxy-2'-fluoro-3'-[N-hydroxy-N-(3,4-methylidenebenzylamino)]-β-D-arabinofuranosyl}-5-cyanocytosine,
1-{2',3'-Dideoxy-2'-fluoro-3'-[N-hydroxy-N-(3,4-methylidenebenzylamino)]-β-D-arabinofuranosyl}-5-phenylcytosine,
1-{2',3'-Dideoxy-2'-fluoro-3'-[N-hydroxy-N-(3,4-methylidenebenzylamino)]-β-D-arabinofuranosyl}-5-benzylcytosine,
1-{2',3'-Dideoxy-2'-fluoro-3'-[N-hydroxy-N-(3,4-methylidenebenzylamino)]-α-D-arabinofuranosyl}thymine,
1-{2',3'-Dideoxy-2'-fluoro-3'-[N-hydroxy-N-(3,4-methylidenebenzylamino)]-α-D-arabinofuranosyl}uracil,
1-{2',3'-Dideoxy-2'-fluoro-3'-[N-hydroxy-N-(3,4-methylidenebenzylamino)]-α-D-arabinofuranosyl}-5-chlorouracil,
1-{2',3'-Dideoxy-2'-fluoro-3'-[N-hydroxy-N-(3,4-methylidenebenzylamino)]-α-D-arabinofuranosyl}-5-bromouracil,
1-{2',3'-Dideoxy-2'-fluoro-3'-[N-hydroxy-N-(3,4-methylidenebenzylamino)]-α-D-arabinofuranosyl}-5-iodouracil,
1-{2',3'-Dideoxy-2'-fluoro-3'-[N-hydroxy-N-(3,4-methylidenebenzylamino)]-α-D-arabinofuranosyl}-5n-ethyluracil,
1-{2',3'-Dideoxy-2'-fluoro-3'-[N-hydroxy-N-(3,4-methylidenebenzylamino)]-α-D-arabinofuranosyl}-5-n-propyluracil,
1-{2',3'-Dideoxy-2'-fluoro-3'-[N-hydroxy-N-(3,4-methylidenebenzylamino)]-α-D-arabinofuranosyl}-5-i-propyluracil,
1-{2',3'-Dideoxy-2'-fluoro-3'-[N-hydroxy-N-(3,4-methylidenebenzylamino)]-α-D-arabinofuranosyl}-5-(E-2-bromoc-vinyl)uracil,
1-{2',3'-Dideoxy-2'-fluoro-3'-[N-hydroxy-N-(3,4-methylidenebenzylamino)]-α-D-arabinofuranosyl}-5-vinyluracil,
1-{2',3'-Dideoxy-2'-fluoro-3'-[N-hydroxy-N-(3,4-methylidenebenzylamino)]-α-D-arabinofuranosyl}-5-carboxyuracil,
1-{2',3'-Dideoxy-2'-fluoro-3'-[N-hydroxy-N-(3,4-methylidenebenzylamino)]-α-D-arabinofuranosyl}-5-ethoxycarbonyl-uracil,
1-{2',3'-Dideoxy-2'-fluoro-3'-[N-hydroxy-N-(3,4-methylidenebenzylamino)]-α-D-arabinofuranosyl}-5-aminocarbonyl-uracil,
1-{2',3'-Dideoxy-2'-fluoro-3'-[N-hydroxy-N-(3,4-methylidenebenzylamino)]-α-D-arabinofuranosyl}-5-cyanouracil,
1-{2',3'-Dideoxy-2'-fluoro-3'-[N-hydroxy-N-(3,4-methylidenebenzylamino)]-α-D-arabinofuranosyl}-5-phenyluracil,
1-{2',3'-Dideoxy-2'-fluoro-3'-[N-hydroxy-N-(3,4-methylidenebenzylamino)]-α-D-arabinofuranosyl}-5-benzyluracil,
1-{2',3'-Dideoxy-2'-fluoro-3'-[N-hydroxy-N-(3,4-methylidenebenzylamino)]-α-D-arabinofuranosyl}cytosine,
1-{2',3'-Dideoxy-2'-fluoro-3'-[N-hydroxy-N-(3,4-methylidenebenzylamino)]-α-D-arabinofuranosyl]-5-fluorocytosine,
1-{2',3'-Dideoxy-2'-fluoro-3'-[N-hydroxy-N-(3,4-methylidenebenzylamino)]-α-D-arabinofuranosyl}-5-chlorocytosine,
1-{2',3'-Dideoxy-2'-fluoro-3'-[N-hydroxy-N-(3,4-methylidenebenzylamino)]-α-D-arabinofuranosyl}-5-bromocytosine,
1-{2',3'-Dideoxy-2'-fluoro-3'-[N-hydroxy-N-(3,4-methylidenebenzylamino)]-α-D-arabinofuranosyl}-5-iodocytosine, 1-{2',3'-Dideoxy-2'-fluoro-3'-[N-hydroxy-N-(3,4-methylidenebenzylamino)]-α-D-arabinofuranosyl}-5-ethylcytosine,
1-{2',3'-Dideoxy-2'-fluoro-3'-[N-hydroxy-N-(3,4-methylidenebenzylamino)]-α-D-arabinofuranosyl}-5-n-propylcytosine,
1-{2',3'-Dideoxy-2'-fluoro-3'-[N-hydroxy-N-(3,4-methylidenebenzylamino)]-α-D-arabinofuranosyl}-5-i-propylcytosine,
1-{2',3'-Dideoxy-2'-fluoro-3'-[N-hydroxy-N-(3,4-methylidenebenzylamino)]-α-D-arabinofuranosyl}-5-(E-2-bromovinyl)cytosine,
1-{2',3'-Dideoxy-2'-fluoro-3'-[N-hydroxy-N-(3,4-methylidenebenzylamino)]-α-D-arabinofuranosyl}-5-vinylcytosine,
1-{2',3'-Dideoxy-2'-fluoro-3'-[N-hydroxy-N-(3,4-methylidenebenzylamino)]-α-D-arabinofuranosyl}-5-carboxycytosine,
1-{2',3'-Dideoxy-2'-fluoro-3'-[N-hydroxy-N-(3,4-methylidenebenzylamino)]-α-D-arabinofuranosyl}-5-ethoxycarbonyl-cytosine,
1-{2',3'-Dideoxy-2'-fluoro-3'-[N-hydroxy-N-(3,4-methylidenebenzylamino)]-α-D-arabinofuranosyl}-5-aminocarbonylcytosine,
1-{2',3'-Dideoxy-2'-fluoro-3'-[N-hydroxy-N-(3,4-methylidenebenzylamino)]-α-D-arabinofuranosyl}-5-cyanocytosine.
1-{2',3'-Dideoxy-2'-fluoro-3'-[N-hydroxy-N-(3,4-methylidenebenzylamino)]-α-D-arabinofuranosyl}-5-phenylcytosine,
1-{2',3'-Dideoxy-2'-fluoro-3'-[N-hydroxy-N-(3,4-methylidenebenzylamino)]-α-D-arabinofuranosyl}-5-benzylcytosine,
1-{2',3'-Dideoxy-2'-fluoro-3'-[N-hydroxy-N-(3,4-methylidenebenzylamino)]-α-D-arabinofuranosyl}-5-chlorocytosine,
1-{2',3'-Dideoxy-2'-fluoro-3'-[N-hydroxy-N-(3,4-methylidenebenzylamino)]-α-D-arabinofuranosyl}-5-bromocytosine,
1-{2',3'-Dideoxy-2'-fluoro-3'-[N-hydroxy-N-(3,4-methylidenebenzylamino)]-α-D-arabinofuranosyl}-5-iodocytosine,
1-{2',3'-Dideoxy-2'-fluoro-3'-[N-hydroxy-N-(3,4-methylidenebenzylamino)]-α-D-arabinofuranosyl}-5-ethylcytosine,
1-{2',3'-Dideoxy-2'-fluoro-3'-[N-hydroxy-N-(3,4-methylidenebenzylamino)]-α-D-arabinofuranosyl}-5-n-propylcytosine,
1-{2',3'-Dideoxy-2'-fluoro-3'-[N-hydroxy-N-(3,4-methylidenebenzylamino)]-α-D-arabinofuranosyl}-5-i-propylcytosine,
1-{2',3'-Dideoxy-2'-fluoro-3'-[N-hydroxy-N-(3,4-methylidenebenzylamino)]-α-D-arabinofuranosyl}-5-(E-2-bromovinyl)cytosine,
1-{2',3'-Dideoxy-2'-fluoro-3'-[N-hydroxy-N-(3,4-methylidenebenzylamino)]-α-D-arabinofuranosyl}-5-vinylcytosine,
1-{2',3'-Dideoxy-2'-fluoro-3'-[N-hydroxy-N-(3,4-methylidenebenzylamino)]-α-D-arabinofuranosyl}-5-carboxycytosine,
1-{2',3'-Dideoxy-2'-fluoro-3'-[N-hydroxy-N-(3,4-methylidenebenzylamino)]-α-D-arabinofuranosyl}-5-ethoxycarbonyl-cytosine,
1-{2',3'-Dideoxy-2'-fluoro-3'-[N-hydroxy-N-(3,4-methylidenebenzylamino)]-α-D-arabinofuranosyl}-5-aminocarbonylcytosine,
1-{2',3'-Dideoxy-2'-fluoro-3'-[N-hydroxy-N-(3,4-methylidenebenzylamino)]-α-D-arabinofuranosyl}-5-cyanocytosine,
1-{2',3'-Dideoxy-2'-fluoro-3'-[N-hydroxy-N-(3,4-methylidenebenzylamino)]-α-D-arabinofuranosyl}-5-phenylcytosine,
1-{2',3'-Dideoxy-2'-fluoro-3'-[N-hydroxy-N-(3,4-methylidenebenzylamino)]-α-D-arabinofuranosyl}-5-benzylcytosine,
1-{2',3'-Dideoxy-2'-fluoro-3'-[N-hydroxy-N-(3,4-methylidenebenzylamino)]-α-D-arabinofuranosyl}-5-(E-2-bromovinyl)cytosine,
1-{2',3'-Dideoxy-2'-fluoro-3'-[N-hydroxy-N-(3,4-methylidenebenzylamino)]-α-D-arabinofuranosyl}-5-vinylcytosine,
1-{2',3'-Dideoxy-2'-fluoro-3'-[N-hydroxy-N-(3,4-methylidenebenzylamino)]-α-D-arabinofuranosyl}-5-carboxycytosine,
1-{2',3'-Dideoxy-2'-fluoro-3'-[N-hydroxy-N-(3,4-methylidenebenzylamino)]-α-D-arabinofuranosyl}-5-ethoxycarbonyl-cytosine,
1-{2',3'-Dideoxy-2'-fluoro-3'-[N-hydroxy-N-(3,4-methylidenebenzylamino)]-α-D-arabinofuranosyl}-5-aminocarbonylcytosine,
1-{2',3'-Dideoxy-2'-fluoio-3'-[N-hydroxy-N-(3,4-methylidenebenzylamino)]-α-D-arabinofuranosyl}-5-cyanocytosine,
1-{2',3'-Dideoxy-2'-fluoro-3'-[N-hydroxy-N-(3,4-methylidenebenzylamino)]-α-D-arabinofuranosyl}-5-phenylcytosine,
1-{2',3'-Dideoxy-2'-fluoro-3'-[N-hydroxy-N-(3,4-methylidenebenzylamino)]-α-D-arabinofuranosyl}-5-benzylcytosine.

Biological Data

Methodology: The methodologies for identification of the antiviral efficacy of the compounds are standard protocols that are practiced by those skilled in the art. A brief summary of the procedures and the system is outlined below.

System: The most widely used system for the study of anti-HBV agents is the hepatoma cell culture system with the HBV genome. These cells are designated as the 2.2.15 cells, AD38 cells and AD79 cells. The 2.2.15 cells were generated by the transfection of the human hepatoma cells—HepG2 with HBV DNA. (Sells, et al., Proc. Natl. Acad. Sci. USA 84:1005–1009, 1987) HBV viral replication takes place in these cells. The HBV replication can be monitored intracellularly as well as extracellularly in these cells.

Assay for Anti-HBV agents: 2.215 cells are grown in multi-well dishes in RPMI medium supplemented with 4% fetal bovine serum. After 3 to 4 days of growing the cells, they are treated with varying concentrations of the test compound(s). The test compounds are dissolved in DMSO or sterile water. Cultures without the addition of the test compounds serve as controls. The addition of the test compound(s) is repeated at 3-day intervals. The medium is changed and replaced with appropriate concentration of the test compound. At the end of the 9-day treatment period, the culture medium is harvested and processed for viral DNA. The viral DNA thus obtained is analyzed by Southern blot analysis. After the Southern transfer, the blot is subjected to hybridization to an HBV specific probe to detect HBV DNA. The hybridization is carried out overnight. After the hybriodization, free probe is removed by washing of the blots.

The specific hybridization is visualized by autoradiography. Inhibition produced by the test compound is calculated with reference to the levels of HBV DNA in the control samples.

Results of Biological Testing for Anti-HBV, Anti-HIV or Cytotoxicity Activities

Of the various entities evaluated for antiviral activity and cytotoxicity, a number of molecules showed potent antiviral activity with minimal cytotoxicity. In the series 1, compound 20 exhibited moderate activity. In the series 2, compounds 7, 10, 20, 58, 59 and 70 were found to be potent inhibitors of HBV and HIV replications. Compounds 11, 12 and 71 had moderate activities. The results are presented below.

| Compound | Anti-HBV EC$_{50}$ (μM) | Anti-HIV EC$_{50}$ (μM) | Cytotoxicity (IC$_{50}$, μM) | | | |
|---|---|---|---|---|---|---|
| | | | PBM | CEM | Vero | HepG2 |
| Series 1 | | | | | | |
| 1 | >10 | >100 | >100 | ND# | >100 | ND |
| 2 | >10 | 3.3 | >100 | ND | 4.6 | ND |
| 3 | >10 | >100 | >100 | ND | >100 | ND |
| 4 | >10 | 87.7 | >100 | ND | >100 | ND |
| 5 | >10 | >100 | >100 | ND | >100 | ND |
| 20 | 0.23 | 0.8 | >100 | >100 | >100 | ND |
| Series 2 | | | | | | |
| 1 | >10 | >100 | >100 | ND | ND | ND |
| 2 | >10 | >100 | >100 | ND | >100 | ND |
| 5 | >10 | >100 | >100 | ND | ND | ND |
| 6 | >10 | >100 | >100 | >100 | >100 | ND |
| 7 | 0.04 | 2.6 | 48.8 | 5.1 | 56.0 | >100 |
| 10 | 0.13 | 3.3 | >100 | >100 | >100 | >100 |
| 11 | <10 | 112 | >100 | >100 | >100 | ND |
| 12 | <10 | >100 | >100 | >100 | >100 | ND |
| 13 | >10 | >100 | >100 | >100 | >100 | ND |
| 20 | >10 | >100 | >100 | >100 | >100 | ND |
| 21 | >10 | >100 | >100 | >100 | >100 | ND |
| 22 | >10 | >100 | >100 | >100 | >100 | ND |
| 23 | 1.04 | 95.4 | >100 | >100 | >100 | >100 |
| 24 | >10 | >100 | >100 | >100 | >100 | ND |
| 28 | >10 | >100 | >100 | >100 | >100 | ND |
| 33 | >10 | >100 | >100 | >100 | >100 | ND |
| 39 | >10 | >100 | >100 | >100 | >100 | ND |
| 40 | >10 | >100 | >100 | >100 | >100 | ND |
| 55 | >10 | 68 | >100 | >100 | >100 | ND |
| 58 | 0.65 | 0.09 | 7.4 | 40.2 | ~106 | >100 |
| 59 | ≦10 | 0.49 | >100 | 65.3 | >100 | >100 |
| 60 | >10 | >100 | >100 | >100 | >100 | ND |
| 61 | >10 | 52.3 | >100 | >100 | >100 | ND |
| 68 | >10 | >100 | >100 | >100 | >100 | ND |
| 69 | >10 | >100 | >100 | >100 | >100 | ND |
| 70 | ≦10 | 2.4 | >100 | 109 | >100 | ND |
| 71 | <10 | 81.4 | 13 | 30.1 | 68.5 | ND |

ND = not determined

| Series 1 | |
|---|---|
| Compound No. | Structure |
| 1 | 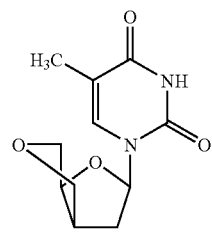 |
| 3 | 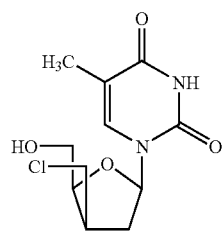 |
| 4 | 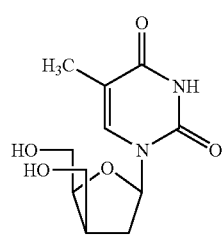 |
| 5 | 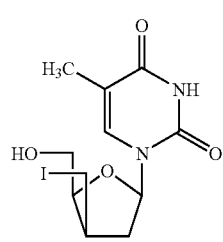 |
| 20 | 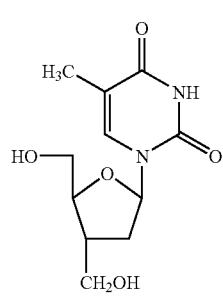 |

| Compound No. | Structure |
|---|---|
| | Series 2 |
| 1 | 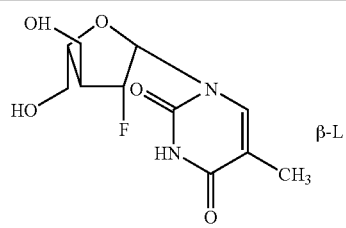 β-L |
| 2 | 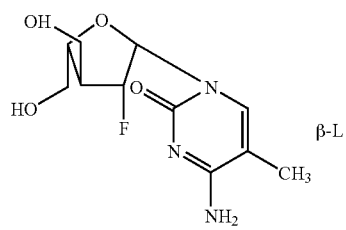 β-L |
| 5 | 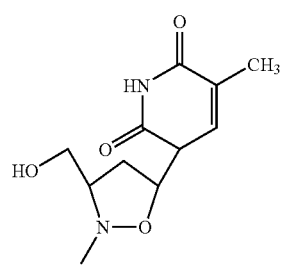 |
| 6 | 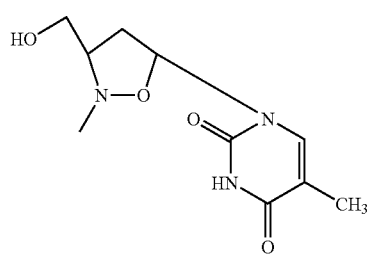 |
| 7 | 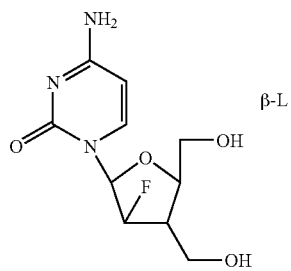 β-L |
| 10 | 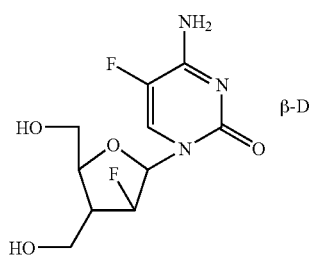 β-D |

-continued
| Series 2 | |
|---|---|
| Compound No. | Structure |
| 11 | 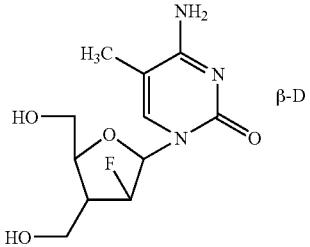 β-D |
| 12 | 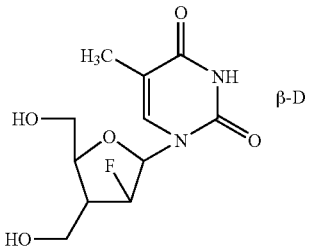 β-D |
| 13 | 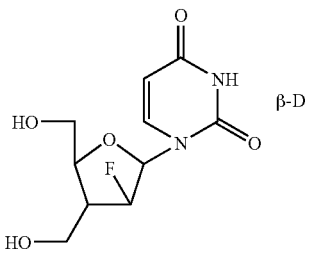 β-D |
| 20 | 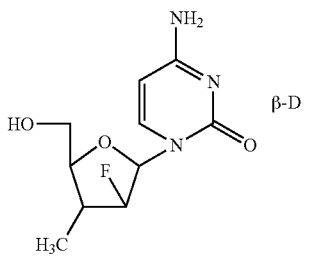 β-D |
| 21 | 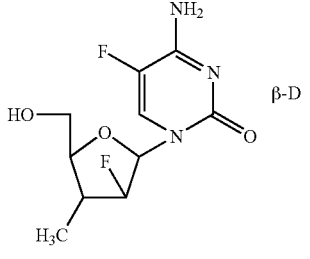 β-D |

-continued
Series 2
| Compound No. | Structure | |
|---|---|---|
| 22 | 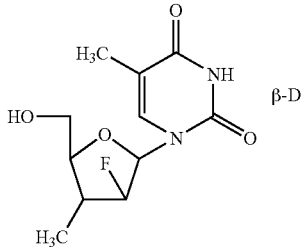 | β-D |
| 23 | 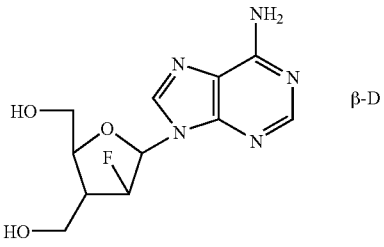 | β-D |
| 24 | 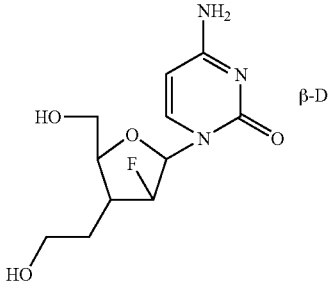 | β-D |
| 28 | 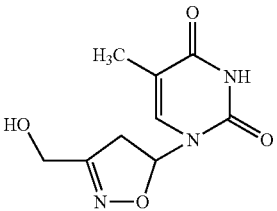 | |
| 33 | 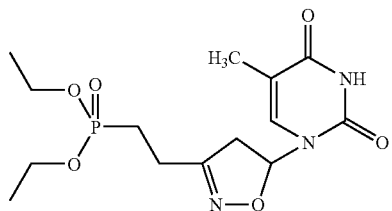 | |
| 39 | 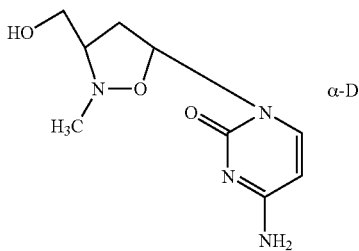 | α-D |

-continued
Series 2
| Compound No. | Structure | |
|---|---|---|
| 40 | 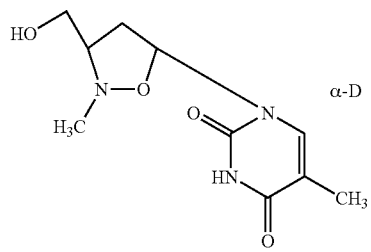 | α-D |
| 55 | 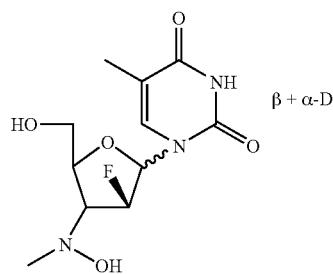 | β + α-D |
| 58 | 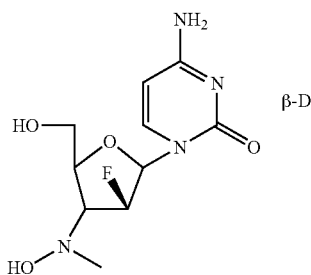 | β-D |
| 59 | 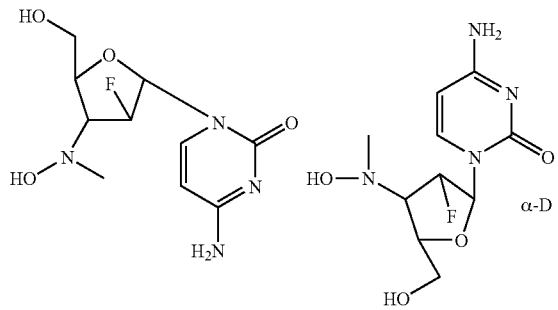 | α-D |
| 60 | 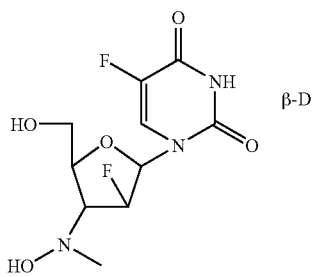 | β-D |

-continued

Series 2

| Compound No. | Structure |
|---|---|
| 61 | 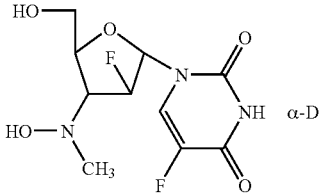 α-D |
| 68 | 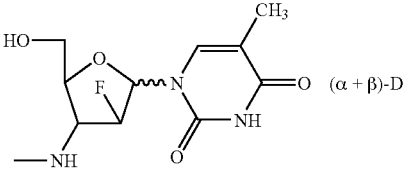 (α + β)-D |
| 69 | 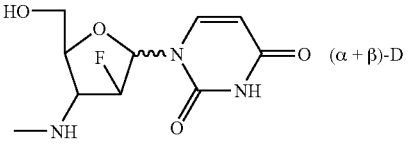 (α + β)-D |
| 70 | 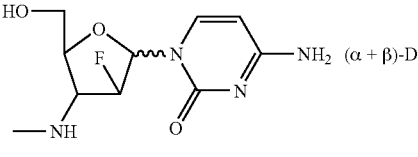 (α + β)-D |
| 71 | 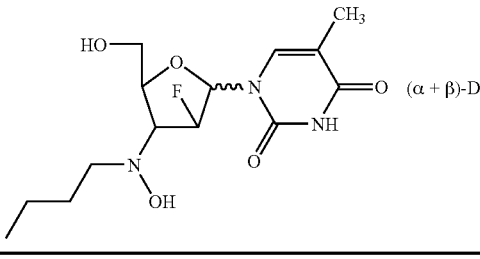 (α + β)-D |

While the invention has been disclosed in its preferred forms, it will be apparent to those of ordinary skill in the art that many modification, additions, and deletions can be made therein without departing from the spirit and scope of the invention and its equivalents as set forth in the following claims.

The invention claimed is:

1. A method for the treatment of hepatitis C virus (HCV) infection comprising administering to a host in need thereof an anti-HCV effective amount of a compound selected from the group consisting of formulas [I]–[IV] below and mixtures of two or more thereof:

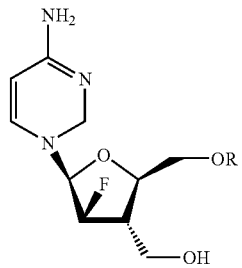

Formula I

Formula II

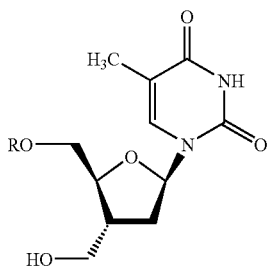

Formula III

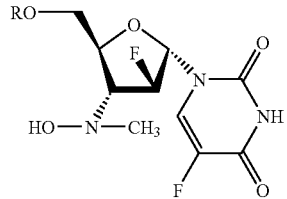

Formula IV

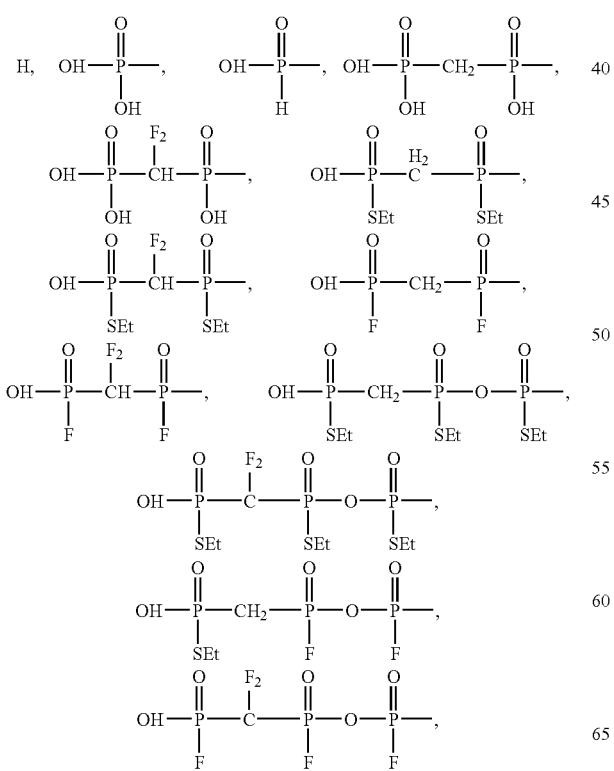

wherein:
R is selected from the group consisting of:

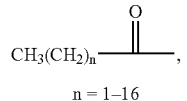

n = 1–16 or a pharmaceutically acceptable salt or prodrug thereof, optionally in combination with a pharmaceutically acceptable carrier.

2. The method of claim 1, further comprising administering the compound in combination or alternation with one or more additional anti-HCV agents.

3. The method of claim 2, wherein the additional HCV agent is selected from the group consisting of interferon, macrokine, heptazyme, ribavarin, amantadine, ofloxacin, zadaxin and reticulose.

4. A method for the treatment of hepatitis D virus (HDV) infection comprising administering to a host in need thereof an anti-HDV effective amount of a compound selected from the group consisting of formulas [I]–[IV] below and mixtures of two or more thereof:

Formula I

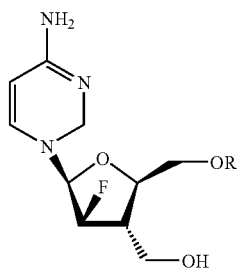

Formula II

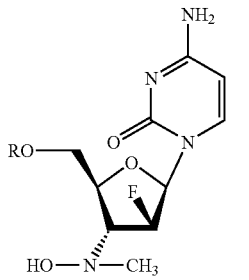

Formula III

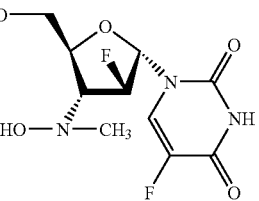

Formula IV wherein:

R is selected from the group consisting of:

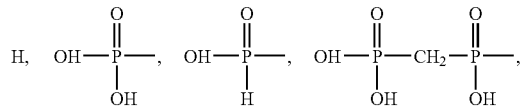
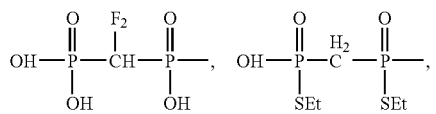
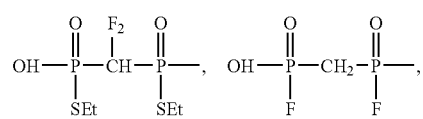
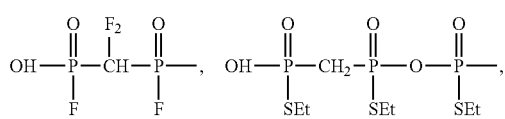
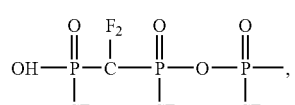
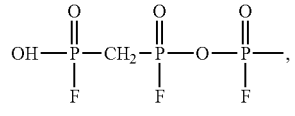
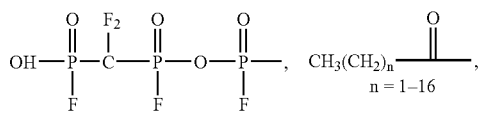

or a pharmaceutically acceptable salt or prodrug thereof, optionally in combination with a pharmaceutically acceptable carrier.

5. The method of claim 4, further comprising administering the compound in combination or alternation with one or more additional anti-HDV agents.

6. The method of claim 5, wherein the additional HDV agent is selected from the group consisting of FTC, L-FMAU, interferon, beta-D-dioxolanyl-guanine (DXG), beta-D-dioxolanyl-2,6-diaminopurine (DAPD), beta-D-dioxolanyl-6-chloropurine (ACP), beta-D-dioxolanyl-2-aminopurine (ADP), famciclovir, penciclovir, bis-POM PMEA (adefovir dipivoxil); lobucavir, ganciclovir, ribavarin, lamivudine (3TC), L-thymidine (L-dT), L-2'-deoxycytidine (L-dT), L-2'-deoxycytidine-3', 5'-diO-valyl (D or L), entecavir (BMS-200475), adefovir, L-D4FC, D-D4FC, and mycophenolic acid (an IMPDH inhibitor).

7. A pharmaceutical composition for the treatment of HCV comprising an anti-HCV agent and an anti-HCV effective amount of a compound selected from the group consisting of formulas [I]–[IV] below and mixtures of two or more thereof:

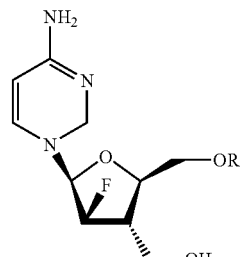

Formula I

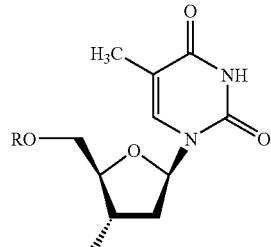

Formula II

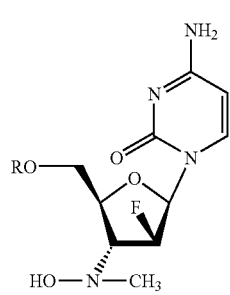

Formula III

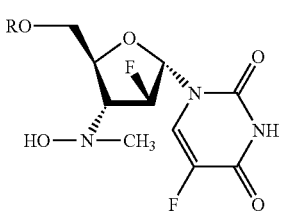

Formula IV wherein:

R is independently selected from the group consisting of:

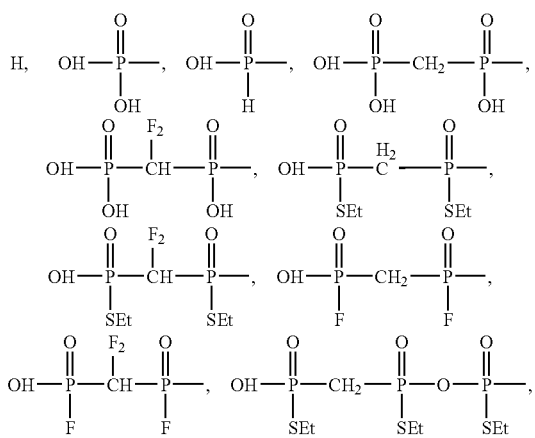

-continued

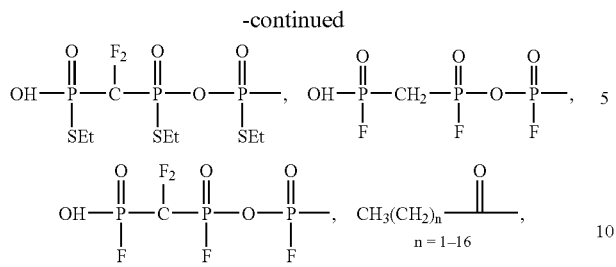

or a pharmaceutically acceptable salt or prodrug thereof, optionally in combination with a pharmaceutically acceptable carrier.

8. A pharmaceutical composition for the treatment of HDV comprising an anti-HDV agent and an anti-HDV effective amount of a compound selected from the group consisting of formulas [I]–[IV] below and mixtures of two or more thereof:

Formula I

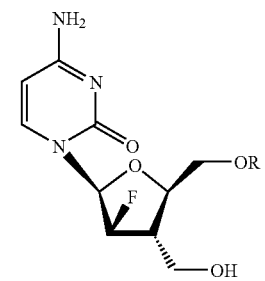

Formula II

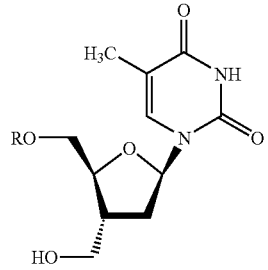

Formula III

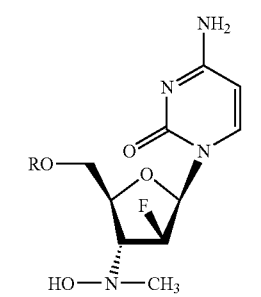

Formula IV

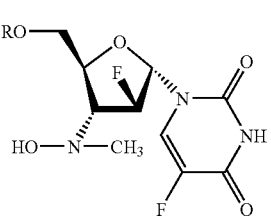

wherein:
R is independently selected from the group consisting of:

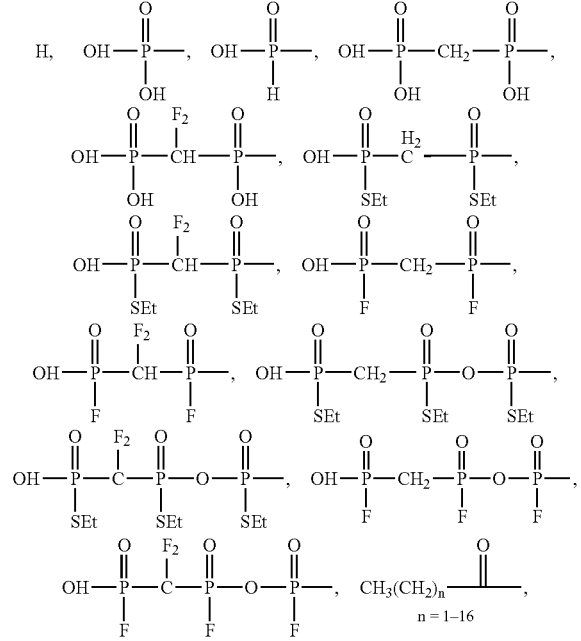

or a pharmaceutically acceptable salt or prodrug thereof, optionally in combination with a pharmaceutically acceptable carrier.

9. A process for stereospecifically preparing a 5'-modified pyrimidine β-nucleoside comprising:
   a. applying the Mitsunobu reaction to a chiral compound of the formula;

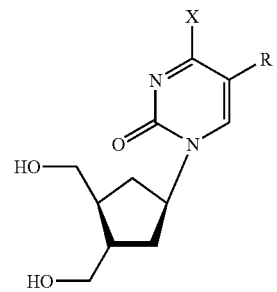

b. selectively protecting the 3'β-position of the resulting nucleoside of step (a) with a benzoyl protecting group or an acid labile protecting group;
   c. subjecting the resulting 3'β-protected anhydro derivative of step (b) to mild alkaline hydrolysis, followed by phosphorylating the ring-opened, 3'β-protected product with a phosphorylating agent;
   d. Saponifiction of the benzoyl group of the resulting product of step (c) to give the desired β-nucleoside 5'-phosphate; and
   e. Optionally oxidizing the 5'-phosphate to obtain the 5'-phosphite.

10. The process of claim 9, wherein the acid labile agent is selected from the group consisting of tetrahydropyranyl (THP), a trityl group, or dimethyl-t-butylsilyl (DBMS).

11. The method of claim 1, wherein the compound is Formula I.

12. The method of claim 1, wherein the compound is Formula II.

13. The method of claim 1, wherein the compound is Formula III.

14. The method of claim 1, wherein the compound is Formula IV.

15. The method of claim 11, wherein R is H.

16. The method of claim 12, wherein R is H.

17. The method of claim 13, wherein R is H.

18. The method of claim 14, wherein R is H.

19. The method of claim 4, wherein the compound is Formula I.

20. The method of claim 4, wherein the compound is Formula II.

21. The method of claim 4, wherein the compound is Formula III.

22. The method of claim 4, wherein the compound is Formula IV.

23. The method of claim 19, wherein R is H.

24. The method of claim 20, wherein R is H.

25. The method of claim 21, wherein R is H.

26. The method of claim 22, wherein R is H.

27. The pharmaceutical composition of claim 7, wherein the compound is Formula I.

28. The pharmaceutical composition of claim 7, wherein the compound is Formula II.

29. The pharmaceutical composition of claim 7, wherein the compound is Formula III.

30. The pharmaceutical composition of claim 7, wherein the compound is Formula IV.

31. The pharmaceutical composition of claim 27, wherein R is H.

32. The pharmaceutical composition of claim 28, wherein R is H.

33. The pharmaceutical composition of claim 29, wherein R is H.

34. The pharmaceutical composition of claim 30, wherein R is H.

35. The pharmaceutical composition of claim 8, wherein the compound is Formula I.

36. The pharmaceutical composition of claim 8, wherein the compound is Formula II.

37. The pharmaceutical composition of claim 8, wherein the compound is Formula III.

38. The pharmaceutical composition of claim 8, wherein the compound is Formula IV.

39. The pharmaceutical composition of claim 35, wherein R is H.

40. The pharmaceutical composition of claim 36, wherein R is H.

41. The pharmaceutical composition of claim 37, wherein R is H.

42. The pharmaceutical composition of claim 38, wherein R is H.

\* \* \* \* \*